United States Patent
Upton et al.

(10) Patent No.: US 10,981,891 B2
(45) Date of Patent: *Apr. 20, 2021

(54) ANTIBACTERIAL COMPOUNDS AND USES THEREOF

(71) Applicants: The Global Alliance for TB Drug Development, Inc., New York, NY (US); Janssen Pharmaceutica NV, Beerse (BE)

(72) Inventors: Anna Marie Upton, New York, NY (US); Christopher Blair Cooper, Lawrenceville, NJ (US); Koenraad Jozef Lodewijk Marcel Andries, Beerse (BE); Jerome Emile Georges Guillemont, Ande (FR); Walter Marcel Mathilde Van den Broeck, Vilvoorde (BE); Brian Desmond Palmer, Auckland (NZ); Zhenkun Ma, Westfield, NJ (US)

(73) Assignees: The Global Alliance for TB Drug Development, Inc., New York, NY (US); Janssen Pharmaceutica NV, Beerse (BE)

( * ) Notice: Subject to any disclaimer, the term of this patent is extended or adjusted under 35 U.S.C. 154(b) by 0 days.

This patent is subject to a terminal disclaimer.

(21) Appl. No.: 16/600,651

(22) Filed: Oct. 14, 2019

(65) Prior Publication Data
US 2020/0039955 A1  Feb. 6, 2020

Related U.S. Application Data

(63) Continuation of application No. 16/079,812, filed as application No. PCT/US2017/021031 on Mar. 7, 2017, now Pat. No. 10,508,097.

(60) Provisional application No. 62/304,661, filed on Mar. 7, 2016.

(51) Int. Cl.
| | | |
|---|---|---|
| C07D 215/00 | (2006.01) |
| C07D 409/12 | (2006.01) |
| C07D 409/14 | (2006.01) |
| A61P 35/02 | (2006.01) |
| C07D 401/06 | (2006.01) |
| C07D 401/14 | (2006.01) |
| C07D 405/14 | (2006.01) |
| C07D 405/06 | (2006.01) |
| C07D 409/06 | (2006.01) |
| C07D 417/14 | (2006.01) |
| A61K 31/4709 | (2006.01) |
| A61P 31/06 | (2006.01) |

(52) U.S. Cl.
CPC ........ *C07D 401/06* (2013.01); *A61K 31/4709* (2013.01); *A61P 31/06* (2018.01); *C07D 401/14* (2013.01); *C07D 405/06* (2013.01); *C07D 405/14* (2013.01); *C07D 409/06* (2013.01); *C07D 409/14* (2013.01); *C07D 417/14* (2013.01)

(58) Field of Classification Search
CPC .. C07D 215/00; C07D 409/12; C07D 409/14; A61P 35/02
USPC .................................................. 546/152, 212
See application file for complete search history.

(56) References Cited

U.S. PATENT DOCUMENTS

| 9,878,982 B2 | 1/2018 | Ding et al. |
| 10,508,097 B2 * | 12/2019 | Upton ................ A61K 31/4709 |

FOREIGN PATENT DOCUMENTS

JP  2006-342109 A  12/2006

OTHER PUBLICATIONS

The English translation of the Chinese Office Action, dated Jun. 1, 2020, in the related Chinese Appl. No. 201780028310.6.
The English translation of the Japanese Office Action, dated Oct. 6, 2020, in the related Japanese Appl. No. 2018-546705.

* cited by examiner

*Primary Examiner* — Niloofar Rahmani

(57) ABSTRACT

The present invention relates to compounds of formula (I) including any stereochemically isomeric form thereof, or pharmaceutically acceptable salts thereof, for the treatment of tuberculosis.

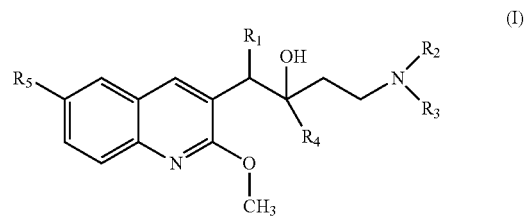

15 Claims, No Drawings

ANTIBACTERIAL COMPOUNDS AND USES THEREOF

CROSS-REFERENCE TO RELATED APPLICATIONS

This application is a Continuation of U.S. patent application Ser. No. 16/079,812, filed Aug. 24, 2018, which in turn is a National Stage Application of PCT/US2017/021031 filed Mar. 7, 2017, which claims priority from U.S. Provisional Patent Application No. 62/304,661, filed on Mar. 7, 2016. Each of the prior mentioned applications is hereby incorporated by reference herein in its entirety.

FIELD OF THE INVENTION

The invention relates generally to diarylquinoline compounds with antibacterial activity and, more specifically, with anti-tuberculosis properties. All documents cited to or relied upon below are expressly incorporated herein by reference.

BACKGROUND OF THE INVENTION

*Mycobacterium tuberculosis* is the causative agent of tuberculosis ("TB"), a devastating infectious disease. It is estimated that about 2 million TB patients die each year globally. Failure to properly treat tuberculosis has caused global drug resistance in *Mycobacterium tuberculosis*, thus rendering some medications ineffective.

A need exists in the art for pharmaceutical compounds that provide advantages over compounds currently used in the art.

SUMMARY OF THE INVENTION

The present invention is directed to a compound of formula (I):

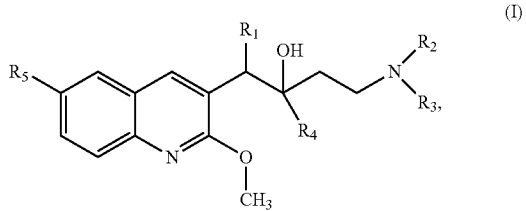

including any stereochemically isomeric form thereof, wherein:
$R_1$ is -phenyl, optionally mono- or bi-substituted independently with lower alkyl, halogen or alkoxy,
   5- or 6-membered heteroaryl, optionally mono-, bi- or tri-substituted independently with lower alkyl, halogen, alkoxy, $-SCH_3$, $SCH_2CH_3$, $-N(CH_2CH_3)_2$ or $-N(CH_3)_2$,
   benzofuranyl,
   2,3-dihydrobenzo[b][1,4]dioxin-5-yl,
   2,3-dihydro-1H-inden-4-yl or
   5,6,7,8-tetrahydro naphthalene-1-yl;
$R_2$ and $R_3$, independently of each other, are hydrogen or lower alkyl;
$R_4$ is -phenyl, optionally mono- or bi-substituted independently with halogen or lower alkyl,
   5- or 6-membered heteroaryl, optionally mono-, bi- or tri-substituted independently with alkoxy, $-O$-cycloalkyl, $-S$-loweralkyl, difluoromethoxy or $-N(CH_3)_2$,
   benzofuranyl,
   benzo[b]thiophenyl or
   2,3-dihydro-1H-indenyl; and
$R_5$ is halogen or cyano,
or a pharmaceutically acceptable salt thereof.

The present invention is also directed to a pharmaceutical composition, comprising a therapeutically effective amount of a compound according to formula I, or a pharmaceutically acceptable salt thereof, and a pharmaceutically acceptable carrier.

The present invention is further directed to a method for the treatment of tuberculosis, comprising the step of administering to a patient in need thereof a therapeutically effective amount of a compound according to formula I, or a pharmaceutically acceptable salt thereof, and a pharmaceutically acceptable carrier.

DETAILED DESCRIPTION OF THE INVENTION

It is to be understood that the descriptions of the present invention have been simplified to illustrate elements that are relevant for a clear understanding of the present invention, while eliminating, for the purpose of clarity, many other elements found in typical pharmaceutical compositions. Those of ordinary skill in the art will recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art. Furthermore, the embodiments identified and illustrated herein are for exemplary purposes only, and are not meant to be exclusive or limited in their description of the present invention.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of pharmacology include Goodman and Gilman's *The Pharmacological Basis of Therapeutics*, 10$^{th}$ Ed., McGraw Hill Companies Inc., New York (2001). Any suitable materials and/or methods known to those of skill can be utilized in carrying out the present invention. However, preferred materials and methods are described. Materials, reagents and the like to which reference are made in the following description and examples are obtainable from commercial sources, unless otherwise noted.

A compound according to the invention is inherently intended to comprise all stereochemically isomeric forms thereof. The term "stereochemically isomeric forms" as used hereinbefore or hereinafter defines all the possible stereoisomeric forms which the compounds of formula (I), and their N-oxides, pharmaceutically acceptable salts or physiologically functional derivatives may possess. Unless otherwise mentioned or indicated, the chemical designation of compounds denotes the mixture of all possible stereochemically isomeric forms. In particular, stereogenic centers may have the R- or S-configuration; substituents on bivalent cyclic (partially) saturated radicals may have either the cisor trans-configuration. Compounds encompassing double bonds can have an E (entgegen) or Z (zusammen)-stereochemistry at said double bond. The terms cis, trans, R, S, E and Z are well known to a person skilled in the art.

Stereochemically isomeric forms of the compounds of formula (I) are obviously intended to be embraced within the scope of this invention. Of special interest are those compounds of formula (I) which are stereochemically pure.

Following CAS-nomenclature conventions, when two stereogenic centers of known absolute configuration are present in a molecule, an R or S descriptor is assigned (based on Cahn-Ingold-Prelog sequence rule) to the lowest-numbered chiral center, the reference center. The configuration of the second stereogenic center is indicated using relative descriptors [R*,R*] or [R*,S*], where R* is always specified as the reference center and [R*,R*] indicates centers with the same chirality and [R*,S*] indicates centers of unlike chirality. For example, if the lowest-numbered chiral center in the molecule has an S configuration and the second center is R, the stereo descriptor would be specified as S—[R*,S*]. If "α" and "β" are used: the position of the highest priority substituent on the asymmetric carbon atom in the ring system having the lowest ring number, is arbitrarily always in the "α" position of the mean plane determined by the ring system. The position of the highest priority substituent on the other asymmetric carbon atom in the ring system relative to the position of the highest priority substituent on the reference atom is denominated "α", if it is on the same side of the mean plane determined by the ring system, or "β", if it is on the other side of the mean plane determined by the ring system.

When a specific stereoisomeric form is indicated, this means that said form is substantially free, i.e. associated with less than 50%, preferably less than 20%, more preferably less than 10%, even more preferably less than 5%, further preferably less than 2% and most preferably less than 1% of the other isomer(s). Thus, when a compound of formula (I) is for instance specified as (R,S), this means that the compound is substantially free of the (S,R) isomer.

Compounds of formula (I) and some of the intermediate compounds invariably have at least two stereogenic centers in their structure which may lead to at least 4 stereochemically different structures.

The compounds of formula (I) may be synthesized in the form of mixtures, in particular racemic mixtures, of enantiomers which can be separated from one another following art-known resolution procedures. The racemic compounds of formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The tautomeric forms of the compounds of formula (I) are meant to comprise those compounds of formula (I) wherein e.g. an enol group is converted into a keto group (keto-enol tautomerism). Tautomeric forms of the compounds of formula (I) or of intermediates of the present invention are intended to be embraced by the ambit of this invention.

The term "alkyl" as used herein denotes an unbranched or branched chain, saturated, monovalent hydrocarbon residue containing 1 to 10 carbon atoms. The term "lower alkyl" denotes a straight or branched chain hydrocarbon residue containing 1 to 6 carbon atoms. "$C_{1-10}$ alkyl" as used herein refers to an alkyl composed of 1 to 10 carbons. Examples of alkyl groups include, but are not limited to, lower alkyl groups include methyl, ethyl, propyl, i-propyl, n-butyl, i-butyl, t-butyl or pentyl, isopentyl, neopentyl, hexyl, heptyl, and octyl.

When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" denotes the radical R'R"—, wherein R' is a phenyl radical, and R" is an alkylene radical as defined herein with the understanding that the attachment point of the phenylalkyl moiety will be on the alkylene radical. Examples of arylalkyl radicals include, but are not limited to, benzyl, phenylethyl, 3-phenylpropyl. The terms "arylalkyl" or "aralkyl" are interpreted similarly except R' is an aryl radical. The terms "(het)arylalkyl" or "(het)aralkyl" are interpreted similarly except R' is optionally an aryl or a heteroaryl radical.

The terms "haloalkyl" or "halo lower alkyl" or "lower haloalkyl" refers to a straight or branched chain hydrocarbon residue containing 1 to 6 carbon atoms wherein one or more carbon atoms are substituted with one or more halogen atoms.

The term "alkoxy" as used herein means an —O-alkyl group, wherein alkyl is as defined above such as methoxy, ethoxy, n-propyloxy, i-propyloxy, n-butyloxy, i-butyloxy, t-butyloxy, pentyloxy, hexyloxy, including their isomers. "Lower alkoxy" as used herein denotes an alkoxy group with a "lower alkyl" group as previously defined. "$C_{1-10}$ alkoxy" as used herein refers to an —O-alkyl wherein alkyl is $C_{1-10}$.

The terms "haloalkoxy" or "halo lower alkoxy" or "lower haloalkoxy" refers to a lower alkoxy group, wherein one or more carbon atoms are substituted with one or more halogen atoms.

The term "hydroxyalkyl" as used herein denotes an alkyl radical as herein defined wherein one to three hydrogen atoms on different carbon atoms is/are replaced by hydroxyl groups.

The term "sulfonyl" as used herein denotes a —$SO_2$— group.

The terms "alkylsulfonyl" and "arylsulfonyl" as used herein refers to a group of formula —$S(=O)_2R$ wherein R is alkyl or aryl respectively and alkyl and aryl are as defined herein. The term "heteroalkylsulfonyl" as used herein refers herein denotes a group of formula —$S(=O)_2R$ wherein R is "heteroalkyl" as defined herein.

The term "lower alkyl sulfonylamido" as used herein refers to a group of formula —$S(=O)_2NR_2$ wherein each R is independently hydrogen or $C_{1-3}$ alkyl, and lower alkyl is as defined herein.

The term "carboxyl" as used herein refers to a group of formula —$C(=O)R_2$ wherein each R is independently hydrogen or $C_{1-3}$ alkyl, and lower alkyl is as defined herein.

The term "cycloalkyl" denotes a monovalent saturated monocyclic or bicyclic hydrocarbon group of 3 to 10 ring carbon atoms. In particular embodiments cycloalkyl denotes a monovalent saturated monocyclic hydrocarbon group of 3 to 8 ring carbon atoms. Bicyclic means consisting of two saturated carbocycles having one or more carbon atoms in common. Particular cycloalkyl groups are monocyclic. Examples for monocyclic cycloalkyl are cyclopropyl, cyclobutanyl, cyclopentyl, cyclohexyl or cycloheptyl. Examples for bicyclic cycloalkyl are bicyclo[2.2.1]heptanyl, or bicyclo[2.2.2]octanyl.

The term "amino" as used herein denotes a group of the formula —NR'R" wherein R' and R" are independently hydrogen, alkyl, alkoxy, cycloalkyl, heterocycloalkyl, aryl or heteroaryl. Alternatively, R' and R", together with the nitrogen to which they are attached, can form a heterocycloalkyl. The term "primary amino" denotes a group wherein both R' and R" are hydrogen. The term "secondary amino" denotes a group wherein R' is hydrogen and R" is not. The term "tertiary amino" denotes a group wherein both R' and R" are not hydrogen. Particular secondary and tertiary amines are methylamine, ethylamine, propylamine, isopropylamine, phenylamine, benzylamine dimethylamine, diethylamine, dipropylamine and diisopropylamine.

The term "heteroaryl" denotes a monovalent aromatic heterocyclic mono- or bicyclic ring system of 5 to 12 ring atoms, comprising 1, 2, 3 or 4 heteroatoms selected from N, O and S, the remaining ring atoms being carbon. Examples of heteroaryl moieties include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl, or quinoxalinyl.

The term "heterocycloalkyl" denotes a monovalent saturated or partly unsaturated mono- or bicyclic ring system of 3 to 9 ring atoms, comprising 1, 2, or 3 ring heteroatoms selected from N, O and S, the remaining ring atoms being carbon. In particular embodiments, heterocycloalkyl is a monovalent saturated monocyclic ring system of 4 to 7 ring atoms, comprising 1, 2, or 3 ring heteroatoms selected from N, O and S, the remaining ring atoms being carbon. Examples for monocyclic saturated heterocycloalkyl are aziridinyl, oxiranyl, azetidinyl, oxetanyl, pyrrolidinyl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, or oxazepanyl. Examples for bicyclic saturated heterocycloalkyl are 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, or 3-thia-9-aza-bicyclo[3.3.1]nonyl. Examples for partly unsaturated heterocycloalkyl are dihydrofuryl, imidazolinyl, dihydro-oxazolyl, tetrahydro-pyridinyl, or dihydropyranyl.

A "patient" is a mammal, e.g., a human, mouse, rat, guinea pig, dog, cat, horse, cow, pig, or non-human primate, such as a monkey, chimpanzee, baboon or rhesus monkey, and the terms "patient" and "subject" are used interchangeably herein.

The term "carrier", as used in this disclosure, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body.

The term "treating", with regard to a subject, refers to improving at least one symptom of the subject's disorder. Treating can be curing, improving, or at least partially ameliorating the disorder.

The term "disorder" is used in this disclosure to mean, and is used interchangeably with, the terms disease, condition, or illness, unless otherwise indicated.

The term "administer", "administering", or "administration" as used in this disclosure refers to either directly administering a compound or pharmaceutically acceptable salt of the compound or a composition to a subject, or administering a prodrug derivative or analog of the compound or pharmaceutically acceptable salt of the compound or composition to the subject, which can form an equivalent amount of active compound within the subject's body.

The term "optionally substituted," as used in this disclosure, means a suitable substituent can replace a hydrogen bound to a carbon, nitrogen, or oxygen. When a substituent is oxo (i.e., =O) then 2 hydrogens on the atom are replaced by a single O. It will be understood by those skilled in the art, with respect to any group containing one or more substituents, that such groups are not intended to introduce any substitution or substitution patterns that are sterically impractical, synthetically non-feasible and/or inherently unstable. Furthermore, combinations of substituents and/or variables within any of the Formulae represented herein are permissible only if such combinations result in stable compounds or useful synthetic intermediates wherein stable implies a reasonable pharmologically relevant half-life at physiological conditions.

Dosage and Administration:

The compounds of the present invention may be formulated in a wide variety of oral administration dosage forms and carriers. Oral administration can be in the form of tablets, coated tablets, dragées, hard and soft gelatin capsules, solutions, emulsions, syrups, or suspensions. Compounds of the present invention are efficacious when administered by other routes of administration including continuous (intravenous drip) topical parenteral, intramuscular, intravenous, subcutaneous, transdermal (which may include a penetration enhancement agent), buccal, nasal, inhalation and suppository administration, among other routes of administration. The preferred manner of administration is generally oral using a convenient daily dosing regimen which can be adjusted according to the degree of affliction and the patient's response to the active ingredient.

A compound or compounds of the present invention, as well as their pharmaceutically useable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. A typical preparation will contain from about 5% to about 95% active compound or compounds (w/w). The term "preparation" or "dosage form" is intended to include both solid and liquid formulations of the active compound and one skilled in the art will appreciate that an active ingredient can exist in different preparations depending on the target organ or tissue and on the desired dose and pharmacokinetic parameters.

The term "excipient" as used herein refers to a compound that is useful in preparing a pharmaceutical composition, generally safe, non-toxic and neither biologically nor otherwise undesirable, and includes excipients that are acceptable for veterinary use as well as human pharmaceutical use. The compounds of this invention can be administered alone but will generally be administered in admixture with one or more suitable pharmaceutical excipients, diluents or carriers selected with regard to the intended route of administration and standard pharmaceutical practice.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

A "pharmaceutically acceptable salt" form of an active ingredient may also initially confer a desirable pharmacokinetic property on the active ingredient which were absent in the non-salt form, and may even positively affect the pharmacodynamics of the active ingredient with respect to its therapeutic activity in the body. The phrase "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like.

Liquid formulations also are suitable for oral administration include liquid formulation including emulsions, syrups, elixirs, aqueous solutions, aqueous suspensions. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well-known suspending agents.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to a skin-adhesive solid support. The compound of interest can also be combined with a penetration enhancer, e.g., Azone (1-dodecylaza-cycloheptan-2-one). Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polylactic acid.

Suitable formulations along with pharmaceutical carriers, diluents and excipients are described in *Remington: The Science and Practice of Pharmacy* 1995, edited by E. W. Martin, Mack Publishing Company, 19th edition, Easton, Pa. A skilled formulation scientist may modify the formulations within the teachings of the specification to provide numerous formulations for a particular route of administration without rendering the compositions of the present invention unstable or compromising their therapeutic activity.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.01 and about 1000 mg/kg body weight per day should be appropriate in monotherapy and/or in combination therapy. A preferred daily dosage is between about 0.1 and about 500 mg/kg body weight, more preferred 0.1 and about 100 mg/kg body weight, and most preferred 1.0 and about 15 mg/kg body weight per day. Thus, for administration to a 70 kg person, the dosage range in one embodiment would be about 70 mg to 0.7 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

EXAMPLES

The following examples further describe and demonstrate particular embodiments within the scope of the present invention. Techniques and formulations generally are found in *Remington's Pharmaceutical Sciences* (Mack Publishing Co., Easton, Pa.). The disclosure is further illustrated by the following examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Melting points were determined on an Electrothermal 2300 melting point apparatus. NMR spectra were obtained on a Bruker Avance 400 spectrometer at 400 MHz for $^1$H and 100 MHz for $^{13}$C spectra and are referenced to Me$_4$Si. Chemical shifts and coupling constants are recorded in units of ppm and Hz, respectively. Low resolution atmospheric pressure chemical ionization mass spectra ([M+H]) of intermediates were measured for methanol solutions on a ThermoFinnigan Surveyor MSQ mass spectrometer. Thin-layer chromatography was carried out on aluminium-backed silica gel plates (Merck 60 F$_{254}$) with visualization of components by UV light (254 nm) and/or exposure to I$_2$. Column chromatography was carried out on silica gel (Merck 230-

400 mesh) unless stated otherwise. Alumina for column chromatography was Merck aluminium oxide 90 (standardised). Analysis of the final test compounds was carried out on an Agilent 1200-6110 LCMS system, using the following conditions; Column: Sunfire C-18, 4.6×50 mm; Mobile phase: ACN (0.05% TFA)-water (0.05% TFA); Gradient: 5% ACN to 95% ACN in 1.0 min, hold 1.0 min, total 2.5 min; flow rate: 1.8 mL/min; LC detector: UV 214 nm, 254 nm; MS ([M+H]): atmospheric pressure electrospray ionisation; MS cone voltage: (V) Positive 4000, Negative 3000. All test compounds were determined to have >95% purity.

Abbreviations

ACN acetonitrile
aq. aqueous
bd broad doublet
bs broad singlet
n-BuLi n-butyllithium
d doublet
DCM dichloromethane
dd doublet of doublets
ddd doublet of doublet of doublets
dist. distilled
DMAP 4-(dimethylamino)pyridine
DMF dimethylformamide
DMSO dimethylsulfoxide
DPPP 1,3-bis(diphenylphosphino)propane
dq doublet of quartets
dt doublet of triplets
Et$_2$O diethyl ether
EtOAc ethyl acetate
h hour
HPLC high pressure liquid chromatography
HOAc acetic acid
m.p. melting point
MeOH methanol
mesyl methanesulfonyl
min minutes
p pentet
pd pentet of doublets
q quartet
qt quartet of triplets
r.t. room temperature
s singlet
sat. saturated
sp septet
t triplet
TFA trifluoroacetic acid
TFAA trifluoroacetic anhydride
THF tetrahydrofuran I. Preparation of Representative Intermediates of the Invention (6-Bromo-2-methoxyquinolin-3-yl)boronic Acid (1)

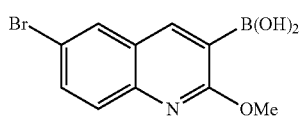

(1)

A solution of 2,2,6,6-tetramethylpiperidine (14.4 mL, 84.8 mmol) in THF (100 mL, dist. Na) at −78° C. was treated with n-BuLi (33 mL, 2.5 M in hexanes, 82.5 mmol), the solution was then warmed to −20° C. for 20 min and then cooled to −78° C. A solution of 6-bromo-2-methoxyquinoline (10.0 g, 42.0 mmol) and triisopropylborate (20.0 mL, 87.2 mmol) in THF (100 mL, dist. Na) was added dropwise and the orange solution was stirred for 3 h at −78° C., warmed to −40° C. and then quenched with sat. aq. NH$_4$Cl (500 mL). The mixture was diluted with water (1 L) and the white precipitate was filtered, triturated with hexanes and dried to give 1 (11.17 g, 94%) as a white solid. $^1$H NMR (DMSO-d$_6$) δ 8.44 (s, 1H), 8.15-8.18 (m, 3H), 7.76 (dd, J=8.8, 2.3 Hz, 1H), 7.68 (d, J=8.9 Hz, 1H), 3.99 (s, 3H). Found: [M−OH+OMe]=296.2.

2,6-Diethoxyisonicotinic Acid (2)

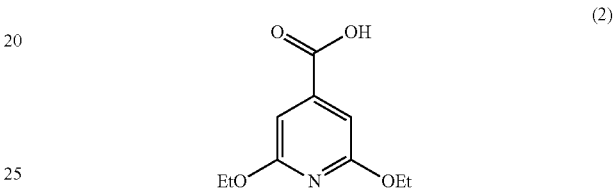

(2)

Sodium (4.08 g, 177 mmol) was added to anhydrous ethanol (75 mL) and after the sodium had completely reacted the resulting solution was added to 2,6-dichloroisonicotinic acid (5.00 g, 29.6 mmol) in a steel reactor. The mixture was heated to 130° C. for 18 h, cooled and evaporated. The residue was dissolved in a minimal amount of water and acidified to pH 3 with 2M HCl. The solid was filtered and dried to give 2 as a white solid (4.12 g, 66%). $^1$H NMR (CDCl$_3$) δ 6.80 (s, 2H), 4.28 (q, J=6.8 Hz, 2H), 3.85 (br, 1H), 1.36 (s, 3H). Found: [M+H]=212.2.

2,6-Diethoxy-N-methoxy-N-methylisonicotinamide (3)

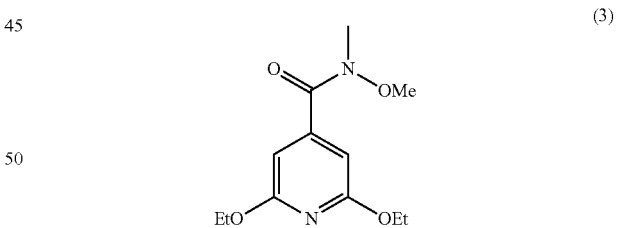

(3)

Oxalyl chloride (0.73 mL, 8.6 mmol) was added to a suspension of 2 (1.52 g, 7.20 mmol) in DCM (50 mL, anhydrous) and DMF (0.20 mL, 2.6 mmol) at r.t. The mixture was stirred at r.t. for 1 h to give a colourless solution, which was then cooled to 0° C. N,O-dimethylhydroxylamine hydrochloride (0.77 g, 17.89 mmol) and pyridine (1.92 mL, 23.7 mmol) were added sequentially and the mixture was stirred at r.t. for 18 h, then partitioned between EtOAc and sat. aq. NaHCO$_3$. Column chromatography using 3:1 hexanes:EtOAc gave 3 (1.26 g, 69%). $^1$H NMR (CDCl$_3$) δ 6.43 (s, 2H), 4.33 (q, J=7.1 Hz, 2H), 3.59 (br s, 3H), 3.32 (s, 3H), 1.39 (t, J=7.1 Hz, 3H). Found: [M+H]= 255.1.

1-(2,6-Diethoxypyridin-4-yl)-3-(dimethylamino)propan-1-one (4)

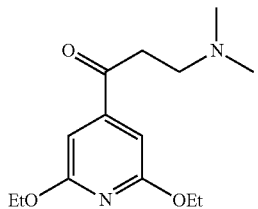

(4)

Vinylmagnesium bromide (14.6 mL of a 1N solution in THF, 14.6 mmol) was added to a solution of 3 (1.23 g, 4.85 mmol) in dry THF (50 mL) at 0° C. The brown solution was warmed to r.t. for 1 h then a solution of 2N dimethylamine in THF (14.6 mL, 29.2 mmol) and water (10 mL) were added. The solution was stirred at r.t. for 1 h, then partitioned between EtOAc and water. The solution was dried and evaporated to give 4 as a brown oil (1.24 g, 96%). $^1$H NMR (CDCl$_3$) δ 6.71 (s, 2H), 4.34 (q, J=7.1 Hz, 2H), 3.05 (t, J=7.0 Hz, 2H), 2.72 (t, J=7.0 Hz, 2H), 2.26 (s, 6H), 1.40 (t, J=7.0 Hz, 3H). Found: [M+H]=267.2.

N,2,6-Trimethoxy-N-methylisonicotinamide (5)

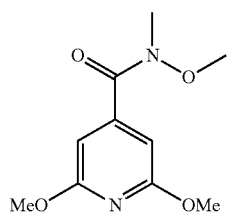

(5)

Oxalyl chloride (1.34 mL, 15.8 mmol) was added to a suspension of 2,6-dimethoxyisonicotinic acid (2.41 g, 13.2 mmol) in DCM (70 mL) and DMF (0.20 mL, 2.6 mmol) at r.t. The mixture was stirred for 1 h to give a colourless solution which was cooled to 0° C. N,O-dimethylhydroxylamine hydrochloride (1.42 g, 14.6 mmol) and pyridine (3.51 mL, 28.9 mmol) were added sequentially and the mixture was stirred at r.t. for 18 h, then partitioned between EtOAc and sat. aq. NaHCO$_3$. Column chromatography with hexanes:EtOAc (2:1) gave 5 (2.49 g, 83%). $^1$H NMR (CDCl$_3$) δ 6.47 (s, 2H), 3.93 (s, 6H), 3.58 (br s, 3H), 3.32 (s, 3H). Found: [M+H]=227.2.

1-(2,6-Dimethoxypyridin-4-yl)-3-(dimethylamino)propan-1-one (6)

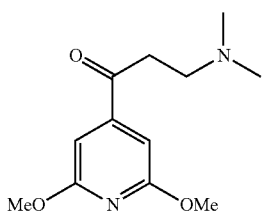

(6)

Vinylmagnesium bromide (32 mL of a 1N solution in THF, 32 mmol) was added to a solution of 5 (2.45 g, 10.8 mmol) in dry THF (100 mL) at 0° C. The brown solution was warmed to r.t. for 1 h then dimethylamine (32 mL of a 2N solution in THF, 64 mmol) and water (30 mL) were added. The solution was stirred at r.t. for 1 h, then partitioned between EtOAc and water. The solution was dried and evaporated and column chromatography with DCM:MeOH (95:5) eluted impurities while DCM:MeOH (9:1) gave 6 as an oil (0.81 g, 31%). $^1$H NMR (CDCl$_3$) δ 6.74 (s, 2H), 3.95 (s, 6H), 3.06 (t, J=7.0 Hz, 2H), 2.72 (t, J=7.0 Hz, 2H), 2.27 (s, 6H). Found: [M+H]=239.1.

3-((2,4-Dimethoxybenzyl)(methyl)amino)-1-(2,6-dimethoxypyridin-4-yl)propan-1-one (7)

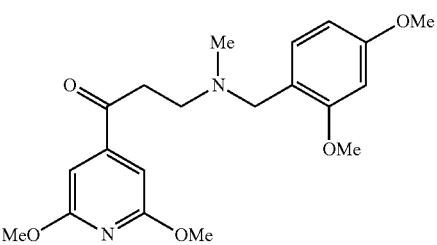

(7)

Vinylmagnesium bromide (17.7 mL of a 1N solution in THF, 17.7 mmol) was added to a solution of 5 (2.00 g, 8.84 mmol) in dry THF (30 mL) at 0° C. The brown solution was warmed to r.t. for 1 h then a solution of N-methyl-2,4-dimethoxybenzylamine (4.00 g, 22.0 mmol) in THF (10 mL), and water (10 mL) were added. The solution was stirred at r.t. for 1 h, then partitioned between EtOAc and water. The solution was dried and evaporated to give a brown oil, which was chromatographed. Elution with EtOAc/hexanes gave fore fractions, then elution with EtOAc gave 7 (2.27 g, 68%) as a light yellow oil. $^1$H NMR (CDCl$_3$) δ 7.13 (d, J=8.9 Hz, 1H), 6.73 (s, 2H), 6.44-6.41 (m, 2H), 3.59 (s, 6H), 3.88 (s, 3H), 3.53 (s, 3H), 3.50 (s, 2H), 3.12 (t, J=7.0 Hz, 1H), 2.84 (t, J=7.0 Hz, 2H), 2.26 (s, 3H). Found: [M+H]=375.3.

6-Bromo-3-(2-fluoro-3-methoxybenzyl)-2-methoxyquinoline (8)

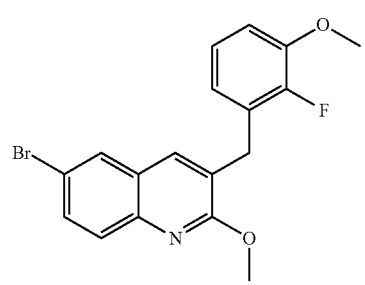

(8)

To a mixture of 1 (1.50 g, 5.32 mmol) and 2-fluoro-3-methoxybenzyl bromide (5.59 mmol) in 1,2-dimethoxyethane (25 mL) in a sealed tube was added 2M Na$_2$CO$_3$ solution (5 mL) and the mixture was degassed under N$_2$ for 15 min, then Pd(PPh₃)₄ (0.307 g, 0.27 mmol) was added and the mixture heated at 90° C. for 4 h. The reaction mixture was cooled to r.t., water (100 mL) was added followed by extraction with EtOAc (2×125 mL). The organic layer was washed with brine, dried (Na₂SO₄) and concentrated to give a yellow residue. Purification by flash column chromatography using hexanes-EtOAc (100:0 to 95:5) gave 8 as a colourless oil which solidified to give a white powder (1.16 g, 58%). ¹H NMR (CDCl₃) δ 7.75 (d, J=2.2 Hz, 1H), 7.68 (d, J=8.9 Hz, 1H), 7.61 (dd, J=8.9, 2.2 Hz, 1H), 7.01 (dt, J=8.1, 1.5 Hz, 1H), 6.88 (dt, J=8.1, 1.5 Hz, 1H), 6.78 (dt, J=8.1, 1.5 Hz, 1H), 4.09 (s, 3H), 4.05 (s, 2H), 3.90 (s, 3H). Found: [M+H]=376.2.

6-Bromo-3-(3-fluorobenzyl)-2-methoxyquinoline (9)

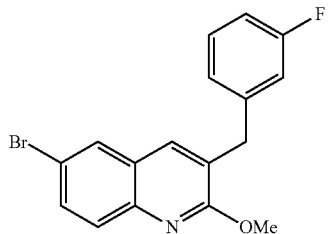

(9)

Reaction of 1 with 3-fluorobenzyl bromide as described above for preparation of 8 gave 9 as a white solid after chromatography (88%). ¹H NMR (CDCl₃) δ 7.77 (d, J=2.2 Hz, 1H), 7.69 (d, J=8.9 Hz, 1H), 7.63 (dd, J=8.9, 2.2 Hz, 1H), 7.52 (br s, 1H), 7.30-7.24 (m, 1H), 7.01 (bd d, J=7.7 Hz, 1H), 6.96-6.90 (m, 2H), 4.07 (s, 3H), 3.98 (s, 2H). Found: [M+H]=346.2.

6-Bromo-2-methoxy-3-(3-methylbenzyl)quinoline (10)

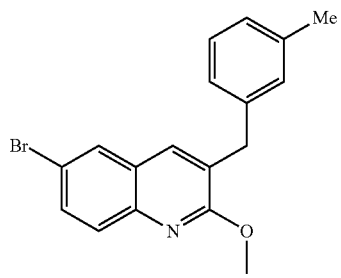

(10)

Reaction of 1 with 3-methylbenzyl bromide as described above for preparation of 8 gave 10 as a white solid after chromatography (73%). ¹H NMR (CDCl₃) δ 7.76 (d, J=2.2 Hz, 1H), 7.69 (d, J=6.8 Hz, 1H), 7.60 (dd, J=8.8, 2.2 Hz, 1H), 7.48 (br s, 1H), 7.21 (dd, J=7.7, 7.8 Hz, 1H), 7.09-7.02 (m, 3H), 4.08 (s, 3H), 3.99 (s, 2H). Found: [M+H]=342.1.

6-Bromo-3-(2,3-dimethoxybenzyl)-2-methoxyquinoline (11)

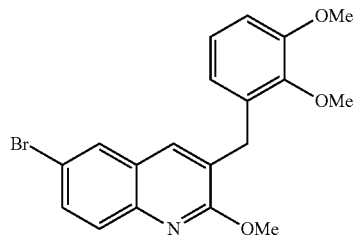

(11)

A stirred mixture of 1 (1.63 g, 5.79 mmol), 2,3-dimethoxybenzyl bromide (1.60 g, 6.95 mmol) and Cs₂CO₃ (3.78 g, 11.50 mmol)) in toluene (20 mL) and DMF (10 mL) was deoxygenated by bubbling nitrogen gas through it for 10 min. Pd(PPh₃)₄ (0.33 g, 0.29 mmol) was then added and the mixture was stirred under an atmosphere of nitrogen at 90° C. for 5 h. The mixture was diluted with EtOAc and washed with water, then brine. The extract was dried over Na₂SO₄ and the solvent was removed under reduced pressure. The product was chromatographed. Elution with 0-4% EtOAc/hexanes gave the product 11 as a white solid (1.26 g, 56%), which crystallised from methanol as colourless microneedles, m.p. 93° C. ¹H NMR (CDCl₃) δ 7.72 (d, J=2.2 Hz, 1H), 7.68 (d, J=8.9 Hz, 1H), 7.59 (dd, J=8.9, 2.2 Hz, 1H), 7.44 (br s, 1H), 7.01 (t, J=7.0 Hz, 1H), 6.86 (dd, J=8.2, 1.4 Hz, 1H), 6.75 (dd, J=7.7, 1.4 Hz, 1H), 4.10 (s, 3H), 4.04 (s, 2H), 3.89 (s, 3H), 3.77 (s, 3H). Found: [M+H]=388.3.

2,5-Dimethylthiophene-3-carbaldehyde (12)

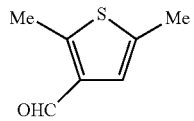

(12)

A solution of 2,5-dimethylthiophene (7.80 g, 69.5 mmol) in DCM (15 mL) and a solution of dichloromethoxymethane (10.40 g, 90.5 mmol) in DCM (15 mL) were added simultaneously to a solution of TiCl₄ (19.1 mL, 174 mmol) in DCM (20 mL) keeping the temperature of the solution below 5° C. The mixture was stirred at 0° C. for 2 h, warmed to r.t. over 30 min then poured onto ice acidified with conc. HCl (20 mL). The mixture was partitioned between DCM and water, and the organic layer was washed with water, dried and evaporated. Kugelrohr distillation (membrane pump, kugelrohr set to approximately 175° C.) gave 12 as a colourless liquid (5.81 g, 60%). ¹H NMR (CDCl₃) δ 9.93 (s, 1H), 7.00 (d, J=1.1 Hz, 1H), 2.70 (s, 3H), 2.40 (d, J=0.4 Hz, 3H). Found: [M+H]=141.1.

(6-Bromo-2-methoxyquinolin-3-yl)(2,5-dimethylthiophen-3-yl)methanol (13)

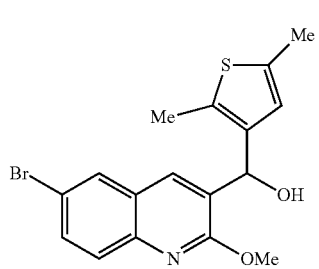

A solution of 2,2,6,6-tetramethylpiperidine (1.89 mL, 11.1 mmol) in dry THF (12 mL) was cooled to −40° C., and n-BuLi (4.45 mL of a 2.5N solution in hexane, 11.1 mmol) was added and the solution was stirred at −40° C. for 15 min, then cooled to −78° C. A solution of 6-bromo-2-methoxyquinoline (2.20 g, 9.28 mmol) in THF (10 mL) was added dropwise, and the orange solution was stirred at −78° C. for 1.5 h, then a solution of 12 (1.30 g, 9.27 mmol) in THF (10 mL) was added. The mixture was stirred at −78° C. for 3 h, then acetic acid (1.60 mL, 28.0 mmol) was added and the solution was allowed to warm to r.t. The mixture was partitioned between EtOAc and water, and the organic fraction was dried and evaporated. Chromatography with DCM:hexanes (1:3) eluted starting materials, then elution with DCM:hexanes (1:1) gave 13 as a white solid (1.97 g, 56%). $^1$H NMR (CDCl$_3$) δ 7.93 (s, 1H), 7.88 (d, J=2.1 Hz, 1H), 7.70 (d, J=8.4 Hz, 1H), 7.65 (dd, J=8.4, 2.1 Hz, 1H), 6.51 (d, J=1.0 Hz, 1H), 6.04 (dd, J=3.3, 0.8 Hz, 1H), 4.07 (s, 3H), 2.67 (d, J=3.4 Hz, 1H), 2.43 (s, 3H), 2.34 (s, 3H). Found: [M+H]=378.2.

6-Bromo-3-((2,5-dimethylthiophen-3-yl)methyl)-2-methoxyquinoline (14)

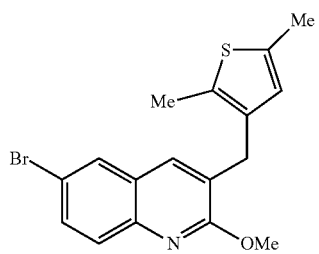

Triethylsilane (6.8 mL, 42.1 mmol) was added to a solution of 13 (1.99 g, 5.26 mmol) and TFA (3.9 mL, 52.5 mmol) in DCM (50 mL) at 0° C., and the solution was stirred for 0.5 h at 0° C. then at r.t. for 2 h. The solution was cooled to 0° C., quenched with sat. aq. NaHCO$_3$ and partitioned between DCM and water. Column chromatography (1:3 DCM:hexanes) gave 14 as a white solid (1.70 g, 89%). $^1$H NMR (CDCl$_3$) δ 7.76 (d, J=2.2 Hz, 1H), 7.69 (d, J=8.9 Hz, 1H), 7.61 (dd, J=8.9, 2.2 Hz, 1H), 7.40 br s, 1H), 6.42 (s, 1H), 4.10 (s, 3H), 3.83 (s, 2H), 2.39 (s, 3H), 2.31 (s, 3H). Found: [M+H]=362.2.

(6-Bromo-2-methoxyquinolin-3-yl)(5-methylthiophen-2-yl)methanol (15)

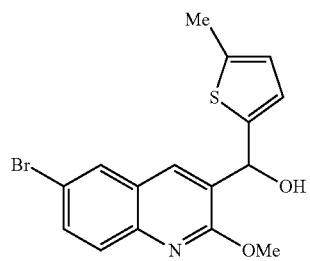

A solution of 2,2,6,6-tetramethylpiperidine (3.5 mL, 20.6 mmol) in dry THF (20 mL) was cooled to −40° C., and n-BuLi (8.0 mL of a 2.5N solution in hexanes, 20 mmol) was added and the solution was stirred at −40° C. for 15 min, then cooled to −78° C. A solution of 6-bromo-2-methoxyquinoline (4.00 g, 16.8 mmol) in THF (20 mL) was added dropwise and the orange solution was stirred at −78° C. for 1.5 h. A solution of 5-methylthiophene-2-carbaldehyde (1.12 g, 16.8 mmol) in THF (10 mL) was added. The mixture was stirred at −78° C. for 3 h, then acetic acid (2.9 mL, 50.7 mmol) was added and the solution was allowed to warm to r.t. The mixture was partitioned between EtOAc and water and the organic fraction was dried and evaporated. Chromatography with DCM:hexanes (1:3) eluted unreacted starting materials, then elution with DCM:hexanes (1:1) gave 15 as a white solid (3.37 g, 55%). $^1$H NMR (CDCl$_3$) δ 8.00 (s, 1H), 7.88 (d, J=2.1 Hz, 1H), 7.71 (d, J=8.9 Hz, 1H), 7.66 (dd, J=8.9, 2.1 Hz, 1H), 6.72 (d, J=3.4 Hz, 1H), 6.59 (dd, J=3.4, 1.0 Hz, 1H), 6.18 (s, 1H), 4.07 (s, 3H), 3.03 (bs, 1H), 2.44 (s, 3H). Found: [M+H]=364.1.

6-Bromo-2-methoxy-3-((5-methylthiophen-2-yl)methyl)quinoline (16)

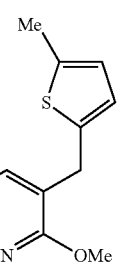

Triethylsilane (13.6 mL, 84 mmol) was added to a solution of 15 (3.75 g, 10.3 mmol) and TFA (7.70 mL, 104 mmol) in DCM (100 mL) at 0° C., then the solution was stirred for 0.5 h at r.t. and ice water was added. The solution was partitioned between sat. aq. NaHCO$_3$ and DCM and the aqueous fraction was extracted with DCM, the organic fractions were combined and evaporated. Chromatography (1:3 DCM:hexanes to 1:1 DCM:hexanes) gave 16 as a white solid (2.83 g, 79%). $^1$H NMR (CDCl$_3$) δ 7.78 (d, J=2.2 Hz, 1H), 7.69 (d, J=8.8 Hz, 1H), 7.62 (br s, 1H), 7.61 (dd, J=8.8, 2.2 Hz, 1H), 6.65 (d, J=3.3 Hz, 1H), 6.59 (d, J=3.3 Hz, 1H), 4.13 (br s, 2H), 4.10 (s, 3H), 2.44 (s, 3H). Found: [M+H]=348.2.

6-Bromo-2-methoxy-3-((2-methoxypyridin-3-yl)methyl)quinolone (17)

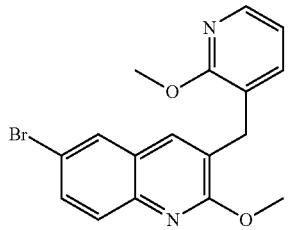

A mixture of 1 (1.00 g, 3.55 mmol), 3-(chloromethyl)-2-methoxypyridine (0.68 g, 4.31 mmol) and $Cs_2CO_3$ (2.31 g, 7.09 mmol) in toluene:DMF (60 mL, 2:1) was degassed under $N_2$, then $Pd(PPh_3)_4$ (0.082 g, 0.071 mmol) was added, and the mixture heated at 80° C. for 4 h. The reaction mixture was cooled to r.t., filtered through a plug of Celite, water (150 mL) was added and extracted with EtOAc (3×100 mL). The combined organic layers were washed with brine (100 mL), dried over $Na_2SO_4$, filtered and concentrated under reduced pressure to obtain a yellow residue. Purification by flash column chromatography using hexanes:EtOAc (9:1) gave 17 as white solid (0.94 g, 74%). $^1H$ NMR ($CDCl_3$) δ 8.08 (dd, J=5.0, 1.9 Hz, 1H), 7.77 (d, J=2.2 Hz, 1H), 7.68 (d, J=8.9 Hz, 1H), 7.61 (dd, J=8.9, 2.2 Hz, 1H), 7.53 (s, 1H), 7.38 (dd, J=7.2, 1.9 Hz, 1H), 6.83 (dd, J=7.2, 5.0 Hz, 1H), 4.07 (s, 3H), 3.96 (s, 2H), 3.95 (s, 3H). Found: [M+H]=359.6.

N-Methoxy-N-methyl-2,3-dihydro-1H-indene-4-carboxamide (18)

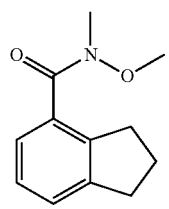

To a solution of 2,3-dihydro-1H-indene-4-carboxylic acid (4.40 g, 27.5 mmol) in DCM (250 mL) was added DMF (0.426 mL) followed by dropwise addition of oxalyl chloride (4.19 g, 33.0 mmol). The reaction mixture was stirred for 1 h, cooled to 0° C., then N,O-dimethylhydroxylamine hydrochloride (2.95 g, 30.3 mmol) and pyridine (7.32 mL, 90.7 mmol) were added and the reaction was stirred at r.t. for 18 h. The mixture was poured onto sat. aqueous $NaHCO_3$ (150 mL) and extracted with DCM (3×100 mL). The combined organic layers were dried over $Na_2SO_4$, filtered and concentrated under reduced pressure to obtain a yellowish residue. The crude product 18 was used in the next step without further purification (5.64 g, 100%). $^1H$ NMR ($CDCl_3$) δ 7.21-7.13 (m, 3H), 3.56 (s, 3H), 3.31 (s, 3H), 2.98-2.91 (m, 4H), 2.11-2.04 (m, 2H). Found: [M+H]=206.5.

1-(2,3-Dihydro-1H-inden-4-yl)-3-(dimethylamino)propan-1-one (19)

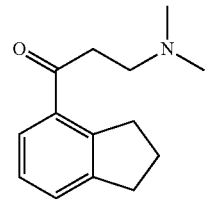

To a solution of 18 (5.64 g, 27.5 mmol) in THF (150 mL) at 0° C. was added vinylmagnesium bromide (1M solution in THF, 57.7 mL, 57.7 mmol) and the solution was stirred for 3.5 h at 0° C. Dimethylamine (2M solution in THF, 57.7 mL, 115.5 mmol) was added to the reaction mixture followed by water (60 mL). After 30 minutes stirring at r.t., the reaction mixture was concentrated under reduced pressure to obtain a brownish residue. This was extracted with EtOAc (3×200 mL). The combined organic layers were washed with brine (100 mL), dried over $Na_2SO_4$, filtered and concentrated under reduced pressure to obtain 19 as brown oil (5.66 g, 95%). $^1H$ NMR ($CDCl_3$) δ 7.66 (d, J=7.8 Hz, 1H), 7.34 (d, J=7.4 Hz, 1H), 7.20 (t, J=7.6 Hz, 1H), 3.24 (t, J=7.5 Hz, 2H), 3.11 (t, J=7.3 Hz, 2H), 2.88 (t, J=7.5 Hz, 2H), 2.72 (t, J=7.3 Hz, 2H), 2.27 (s, 6H), 2.04 (t, J=7.5 Hz, 2H). Found: [M+H]=218.6.

(2,3-Dihydrobenzo[b][1,4]dioxin-5-yl)methanol (20)

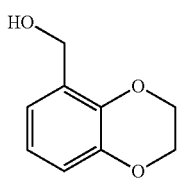

To a solution of 2,3-dihydrobenzo[b][1,4]dioxine-5-carboxylic acid (5.00 g, 28.0 mmol) in THF (150 mL) at 0° C. was added lithium aluminium hydride (2.13 g, 56.0 mmol) in small portions. The reaction mixture was stirred at 0° C. for 10 min and stirred for a further 18 h at r.t. Water (150 mL) was added to the reaction mixture which was extracted with EtOAc (2×100 mL). The combined organic layers were washed with brine (100 mL), dried over $Na_2SO_4$, filtered and concentrated under reduced pressure to obtain 20 as yellow oil (3.22 g, 99%). $^1H$ NMR ($CDCl_3$) δ 6.87-6.79 (m, 3H), 4.66 (s, 2H), 4.32-4.30 (m, 2H), 4.28-4.25 (m, 2H), 2.19 (bs, 1H). Found: [M+H−18]=149.5.

5-(Bromomethyl)-2,3-dihydrobenzo[b][1,4]dioxine (21)

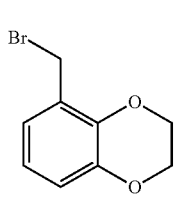

A solution of 20 (3.75 g, 32.3 mmol) in diethyl ether (80 mL) was cooled to 0° C. and phosphorous tribromide (3.67 mL, 38.8 mmol) was added dropwise. The solution was stirred at 0° C. for 10 min, then at r.t. for 1 h. Water (10 mL) was added cautiously to quench the excess of reagent and the mixture was diluted with diethyl ether and washed with water (3×50 mL). The combined organic layers were washed with brine (100 mL), dried over $Na_2SO_4$, filtered and concentrated under reduced pressure to obtain 21 as a brown solid (4.61 g, 62%). $^1$H NMR ($CDCl_3$) δ 6.91-6.77 (m, 3H), 4.52 (s, 2H), 4.35-4.33 (m, 2H), 4.29-4.27 (m, 2H). Found: [M+H–Br]=149.5.

6-Bromo-3-((2,3-dihydrobenzo[b][1,4]dioxin-5-yl)methyl)-2-methoxyquinoline (22)

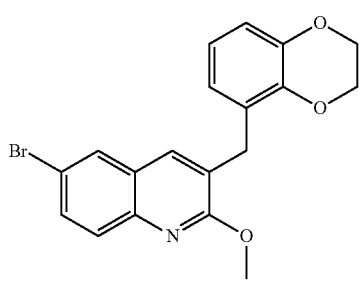

A mixture of 1 (4.42 g, 15.4 mmol), 21 (4.6 g, 20.0 mmol) and $Cs_2CO_3$ (11.54 g, 0.77 mmol) in toluene:DMF (60 mL, 2:1) was degassed under $N_2$, then $Pd(PPh_3)_4$ (0.890 g, 0.77 mmol) was added, and the mixture heated at 110° C. for 4 h. The mixture was cooled to r.t., filtered through a plug of Celite, water (150 mL) was added and extracted with EtOAc (3×100 mL). The combined organic layers were washed with brine (100 mL), dried over $Na_2SO_4$, filtered and concentrated under reduced pressure to obtain a yellow residue. Purification by flash column chromatography using hexanes:EtOAc (9:1) gave 22 as white solid (3.1 g, 52%). $^1$H NMR ($CDCl_3$) δ 7.75 (d, J=2.2 Hz, 1H), 7.73-7.70 (m, 1H), 7.61-7.59 (m, 1H), 7.43 (s, 1H), 6.84-6.78 (m, 2H), 6.72-6.70 (m, 1H), 4.27-4.22 (m, 4H), 4.10 (s, 3H), 3.98 (s, 2H). Found: [M+H]=386.6.

3-Benzyl-6-iodo-2-methoxyquinoline (23)

A solution of 3-benzyl-6-bromo-2-methoxyquinoline (3.00 g, 9.14 mmol) in THF (7 mL) was cooled to −78° C., then n-BuLi (2M solution in cyclohexane, 5.48 mL, 11.0 mmol) was added to give a deep purple solution. After 60 seconds, iodine (1.74 g, 7.31 mmol) in THF (23 mL) was added and the red solution was stirred at −78° C. for 10 min. Water (20 mL) was added to the resultant solution which was extracted with EtOAc (3×30 mL), dried with $MgSO_4$, filtered and the solvent was evaporated to give orange oil. MeOH (10 mL) was added to the mixture which was sonicated until a white solid formed. The solid was filtered to give 23 as a white solid (1.77 g, 52%). $^1$H NMR ($CDCl_3$) δ 7.96 (d, J=2.0 Hz, 1H), 7.77 (dd, J=8.8, 2.0 Hz, 1H), 7.55 (d, J=8.8 Hz, 1H), 7.46 (s, 1H), 7.34-7.22 (m, 5H), 4.08 (s, 3H), 4.02 (s, 2H). Found: [M+H]=376.6.

2,6-Bis(ethylthio)isonicotinic Acid (24)

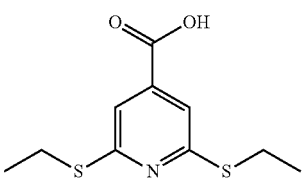

To a suspension of sodium hydride (1.82 g, 45.5 mmol) in DMF (20 mL) at 0° C. was added ethanethiol (3.29 mL, 45.5 mmol) dropwise. The milky foamy solution was stirred at 0° C. for 10 min 2,6-Dichloroisonicotinic acid (3.17 g, 13.0 mmol) in DMF (5 mL) was added dropwise to the solution. The mixture was warmed to 50° C. and stirred for 18 h. Water (40 mL) was added to the resultant solution and the pH was adjusted to ~3 using 2M HCl solution. The aqueous solution was extracted with EtOAc (3×30 mL), dried with $MgSO_4$, filtered and the solvent was evaporated to give 24 as a yellow solid which was used for the next step without further purification (2.82 g, 89%). $^1$H NMR ($CDCl_3$) δ 7.40 (s, 2H), 3.19 (q, J=7.3 Hz, 4H), 1.39 (t, J=7.3 Hz, 6H). Found: [M+H]=244.5.

2,6-Bis(ethylthio)-N-methoxy-N-methylisonicotinamide (25)

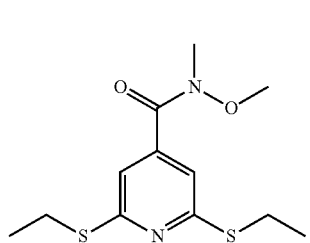

(25)

To a solution of 24 (3.24 g, 13.3 mmol) in DCM (150 mL) was added DMF (0.206 mL), followed by dropwise addition of oxalyl chloride (1.37 mL, 16.0 mmol). The mixture was stirred at r.t. for 2 h, then cooled to 0° C. and N,O-dimethylhydroxylamine hydrochloride (1.43 g, 14.6 mmol) followed by pyridine (3.55 mL, 43.9 mmol) were added and resulting mixture was stirred at r.t. for 18 h. The mixture was poured onto sat. NaHCO$_3$ (150 mL), extracted with DCM (150 mL) and EtOAc (100 mL). The combined organic phase was dried with Na$_2$SO$_4$ and concentrated to give a yellow residue. Purification by flash column chromatography using hexanes:EtOAc (1:1) gave 25 as colourless oil (3.65 g, 96%). $^1$H NMR (CDCl$_3$) δ 7.02 (s, 2H), 3.56 (s, 3H), 3.32 (s, 3H), 3.19 (q, J=7.3 Hz, 4H), 1.37 (t, J=7.3 Hz, 6H). Found: [M+H]=287.5.

1-(2,6-Bis(ethylthio)pyridin-4-yl)-3-(dimethylamino)propan-1-one (26)

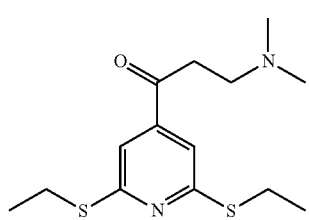

(26)

To a solution of 25 (3.65 g, 12.7 mmol) in THF (150 mL) at 0° C. was added vinylmagnesium bromide (1M solution in THF, 31.5 mL, 31.5 mmol) which was then stirred at 0° C. for 4 h. Dimethylamine (2M solution in THF, 31.5 mL, 63.0 mmol) was added followed by water (60 mL). After 30 minutes stirring at r.t., the reaction mixture was concentrated under reduced pressure to obtain a brownish residue. This was extracted with EtOAc (3×200 mL). The combined organic layers were washed with brine (100 mL), dried over Na$_2$SO$_4$, filtered and concentrated under reduced pressure to give a brown oil. Purification by flash column chromatography using EtOAc:MeOH (9:1) gave 26 as a yellow oil (2.51 g, 66%). $^1$H NMR (CDCl$_3$) δ 7.24 (s, 2H), 3.20 (q, J=7.4 Hz, 4H), 3.03 (t, J=7.1 Hz, 2H), 2.71 (t, J=7.2 Hz, 2H), 2.26 (s, 6H), 1.38 (t, J=7.4 Hz, 6H). Found: [M+H]=299.6.

2,6-Bis(methylthio)isonicotinic acid (27)

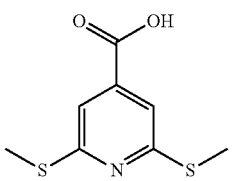

(27)

To a solution of 2,6-dichloroisonicotinic acid (4.00 g, 20.8 mmol) in DMF (40 mL) at 0° C. was added sodium thiomethoxide (4.38 g, 65.5 mmol). The reaction mixture was stirred at 150° C. for 18 h. Water (40 mL) was added to the resultant solution and the pH was adjusted to ~3 using 2M HCl solution. The aqueous solution was extracted with EtOAc (3×40 mL), dried with MgSO$_4$, filtered and concentrated under reduced pressure to give 27 as an orange solid, which was recrystallized from methanol (4.01 g, 90%). $^1$H NMR (CDCl$_3$) δ 7.44 (s, 2H), 2.61 (s, 6H). Found: [M+H]=216.5.

N-Methoxy-N-methyl-2,6-bis(methylthio)isonicotinamide (28)

(28)

To a solution of 27 (5.03 g, 23.4 mmol) in DCM (200 mL) was added DMF (0.362 mL), followed by dropwise addition of oxalyl chloride (2.41 mL, 28.0 mmol). The mixture was stirred at r.t. for 2 h, cooled to 0° C. and N,O-dimethylhydroxylamine hydrochloride (2.51 g, 25.7 mmol) followed by pyridine (6.22 mL, 77.1 mmol) were added and resulting mixture was stirred at r.t. for 18 h. The mixture was poured onto sat NaHCO$_3$ (150 mL), extracted with DCM (150 mL) and EtOAc (100 mL). The organic phase was dried with Na$_2$SO$_4$ and concentrated to give 28 as yellow oil, which was used without further purification for the next step (4.96 g, 82%). $^1$H NMR (CDCl$_3$) δ 7.04 (s, 2H), 3.56 (s, 3H), 3.33 (s, 3H), 2.60 (s, 6H). Found: [M+H]=259.5.

1-(2,6-Bis(methylthio)pyridin-4-yl)-3-(dimethylamino)propan-1-one (29)

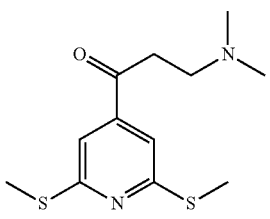

(29)

To a solution of 28 (4.96 g, 19.2 mmol) in THF (90 mL) at 0° C. was added vinylmagnesium bromide (1M solution in THF, 40.3 mL, 40.3 mmol) and the solution was stirred at 0° C. for 1 h. Dimethylamine (2M solution in THF, 40.3 mL, 80.6 mmol) was added followed by water (60 mL). After 30 minutes stirring at r.t., the reaction mixture was concentrated under reduced pressure to obtain a brownish residue. This was extracted with EtOAc (3×200 mL). The combined organic layers were washed with brine (100 mL), dried over $Na_2SO_4$, filtered and concentrated under reduced pressure to give 29 as a brown oil (4.87 g, 94%). $^1$H NMR ($CDCl_3$) δ 7.26 (s, 2H), 3.04 (t, J=7.0 Hz, 2H), 2.70 (t, J=7.2 Hz, 2H), 2.61 (s, 6H), 2.26 (s, 6H). Found: [M+H]=271.6.

6-Bromo-3-(2-fluoro-3-methylbenzyl)-2-methoxy-quinoline (30)

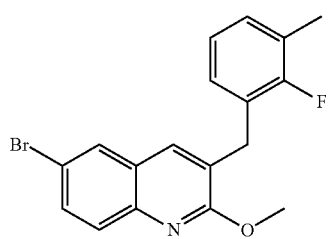

A mixture of 1 (3.00 g, 10.5 mmol), 1-(bromomethyl)-2-fluoro-3-methylbenzene (4.24 g, 20.9 mmol) and $Cs_2CO_3$ (7.87 g, 24.2 mmol) in toluene:DMF (60 mL, 2:1) was degassed under $N_2$, then $Pd(PPh_3)_4$ (0.607 g, 0.525 mmol) was added, and the mixture was heated at 90° C. for 2 h. The reaction mixture was cooled to r.t., filtered through a plug of Celite, water (150 mL) was added and the mixture was extracted with EtOAc (3×100 mL). The organic layer was washed with brine (100 mL), dried over $Na_2SO_4$, filtered and concentrated under reduced pressure to obtain a yellow residue. Purification by flash column chromatography using hexanes:EtOAc (9:1) gave 30 as a white solid (2.87 g, 76%). $^1$H NMR ($CDCl_3$) δ 7.75 (d, J=2.2 Hz, 1H), 7.67 (d, J=8.8 Hz, 1H), 7.60 (dd, J=8.9, 2.2 Hz, 1H), 7.50 (s, 1H), 7.11-6.96 (m, 3H), 4.09 (s, 3H), 4.03 (s, 2H), 2.28 (d, J=2.1 Hz, 3H). Found: [M+H]=360.6.

2-Methoxy-6-(methylthio)isonicotinic acid (31)

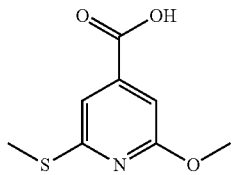

To a mixture of methyl 2-methoxy-6-(methylthio)isonicotinate (WO 2010/036632) (2.07 g, 9.71 mmol) in MeOH:THF:$H_2O$ (60 mL, 1:1:1) was added lithium hydroxide (0.697 g, 29.1 mmol). The reaction mixture was stirred at r.t. for 24 h. The solvent was removed under reduced pressure, water (50 mL) was added and the mixture was washed with EtOAc (50 mL) which was discarded. 2M HCl (50 mL) was added to the aqueous layer, which was extracted with EtOAc (3×50 mL). The combined organic layers were washed with brine (100 mL), dried over $Na_2SO_4$, filtered and concentrated under reduced pressure to obtain 31 as a white solid (1.70 g, 88%). $^1$H NMR (DMSO-$d_6$) δ 13.67 (s, 1H), 7.22 (d, J=0.92 Hz, 1H), 6.86 (d, J=0.92 Hz, 1H), 3.90 (s, 3H), 2.55 (s, 3H). Found: [M+H]=200.5.

N,2-Dimethoxy-N-methyl-6-(methylthio)isonicotinamide (32)

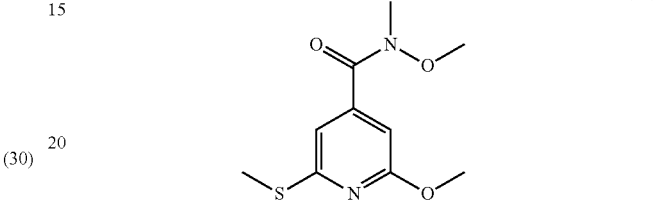

To a solution of 31 (1.70 g, 8.53 mmol) in DCM (200 mL) was added DMF (0.13 mL), followed by dropwise addition of oxalyl chloride (0.88 mL, 10.2 mmol). The mixture was stirred at r.t. for 2 h. The reaction mixture was cooled to 0° C. and N,O-dimethylhydroxylamine hydrochloride (0.915, 9.38 mmol) followed by pyridine (2.27 mL, 28.2 mmol) were added and resulting mixture was stirred at r.t. for 18 h. The mixture was poured onto sat. $NaHCO_3$ (150 mL) and extracted with DCM (150 mL) and EtOAc (100 mL). The combined organic phase was dried with $Na_2SO_4$ and concentrated to give a yellow residue. Purification by flash column chromatography using hexanes:EtOAc (4:1) gave 32 as yellow oil (2.07 g, 99%). $^1$H NMR ($CDCl_3$) δ 6.93 (d, J=0.72 Hz, 1H), 6.59 (s, 1H), 3.97 (s, 3H), 3.57 (s, 3H), 3.32 (s, 3H), 2.57 (s, 3H). Found: [M+H]=243.5.

3-(Dimethylamino)-1-(2-methoxy-6-(methylthio)pyridin-4-yl)propan-1-one (33)

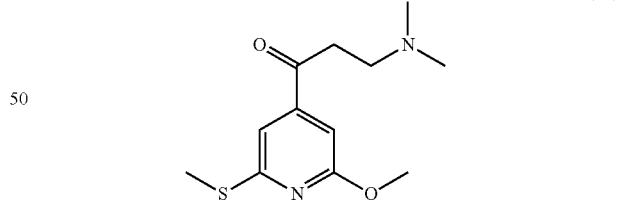

To a solution of 32 (2.07 g, 8.54 mmol) in THF (100 mL) at 0° C. was added vinylmagnesium bromide (1M solution in THF, 17.9 mL, 17.9 mmol) and the solution was stirred at 0° C. for 3 h. Dimethylamine (2M solution in THF, 17.9 mL, 35.9 mmol) was added followed by water (40 mL). After 30 minutes stirring at r.t. the reaction mixture was concentrated under reduced pressure to obtain a brownish residue. This was extracted with EtOAc (3×200 mL). The combined organic layers were washed with brine (100 mL), dried over $Na_2SO_4$, filtered and concentrated under reduced pressure to give 33 as a brown oil (2.17 g, 99%). $^1$H NMR ($CDCl_3$) δ 7.19 (d, J=1.2 Hz, 1H), 6.82 (d, J=1.1 Hz, 1H), 3.98 (s, 3H), 3.04 (t, J=7.0 Hz, 2H), 2.72 (t, J=7.3 Hz, 2H), 2.58 (s, 3H), 2.27 (s, 6H). Found: [M+H]=255.6.

Methyl 2-(difluoromethoxy)-6-methoxyisonicotinate (34)

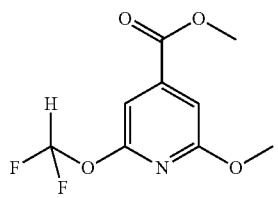

(34)

To a solution of methyl 2-hydroxy-6-methoxyisonicotinate (WO 2009/083553) (3.00 g, 16.4 mmol) in DMF (40 mL) was added sodium chlorodifluoroacetate (7.50 g, 49.2 mmol) and $K_2CO_3$ (2.73 g, 21.3 mmol). The reaction mixture was stirred at 80° C. for 72 h, then washed with water (50 mL) and extracted with EtOAc (3×30 mL). The combined organic layers were washed with brine (50 mL), dried over $Na_2SO_4$, filtered and concentrated under reduced pressure to obtain a yellow residue. Purification by flash column chromatography using hexanes:EtOAc (1:1) gave 34 as a white solid (2.02 g, 52%). $^1$H NMR (CDCl$_3$) δ 7.40 (t, J=73.0, 1H), 7.10 (d, J=1.0 Hz, 1H), 7.00 (d, J=1.0 Hz, 1H), 3.94 (s, 3H), 3.93 (s, 3H). Found: [M+H]=234.5.

2-(Difluoromethoxy)-6-methoxyisonicotinic Acid (35)

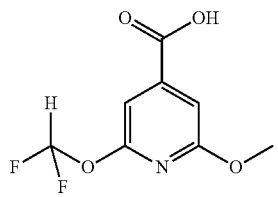

(35)

To a solution of 34 (2.02 g, 8.66 mmol) in MeOH:THF:H$_2$O (60 mL, 1:1:1) was added lithium hydroxide (0.62 g, 26.0 mmol) and the reaction mixture was stirred at r.t. for 72 h. The solvent was removed under reduced pressure, water (50 mL) was added and the mixture was washed with EtOAc (50 mL) which was discarded. 2M HCl (50 mL) was added to the aqueous layer, which was extracted with EtOAc (3×50 mL). The combined organic layers were washed with brine (100 mL), dried over Na$_2$SO$_4$, filtered and concentrated under reduced pressure to obtain 35 as a white solid (1.90 g, 99%). $^1$H NMR (DMSO-d$_6$) δ 13.85 (bs, 1H), 7.76 (t, J=72.5 Hz, 1H), 7.03 (d, J=0.96 Hz, 1H), 6.95 (d, J=0.92 Hz, 1H), 3.91 (s, 3H). Found: [M+H]=220.6.

2-(Difluoromethoxy)-N,6-dimethoxy-N-methylisonicotinamide (36)

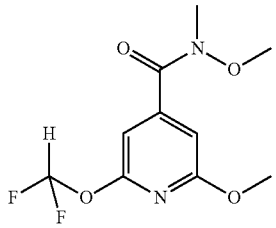

(36)

To a solution of 35 (1.70 g, 8.53 mmol), hydroxybenzotriazole (1.29 g, 9.54 mmol), N,O-dimethylhydroxylamine hydrochloride (1.27 g, 13.0 mmol) and 1-ethyl-3-(3-dimethylaminopropyl)carbodiimide (1.48 g, 9.54 mmol) in DCM (50 mL) was added DMF (4.83 mL, 34.7 mmol). The reaction mixture was stirred at r.t for 24 h. The reaction mixture was washed with water (100 mL) and extracted with DCM (3×50 mL). The organic phase was dried with Na$_2$SO$_4$ and concentrated to give a yellow residue. Purification by flash column chromatography using hexanes:EtOAc (1:1) gave 36 as a yellow oil (1.85 g, 81%). $^1$H NMR (CDCl$_3$) δ 7.41 (t, J=73.1 Hz, 1H), 6.73 (d, J=0.68 Hz, 1H), 6.65 (d, J=0.64 Hz, 1H), 3.92 (s, 3H), 3.58 (s, 3H), 3.34 (s, 3H). Found: [M+H]=263.5.

1-(2-(Difluoromethoxy)-6-methoxypyridin-4-yl)-3-(dimethylamino)propan-1-one (37)

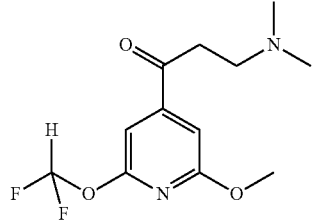

(37)

To a solution of 36 (1.85 g, 7.06 mmol) in THF (100 mL) at 0° C. was added vinylmagnesium bromide (1M solution in THF, 14.8 mL, 14.8 mmol) and the solution stirred at 0° C. for 3 h. Dimethylamine (2M solution in THF, 14.8 mL, 29.7 mmol) was added followed by water (40 mL). After 30 minutes stirring at r.t., the reaction mixture was concentrated under reduced pressure to obtain a brownish residue. This was extracted with EtOAc (3×200 mL). The combined organic layers were washed with brine (100 mL), dried over Na$_2$SO$_4$, filtered and concentrated under reduced pressure to give 37 as a brown oil (1.92 g, 99%). $^1$H NMR (CDCl$_3$) δ 7.40 (t, J=73.0 Hz, 1H), 6.97 (d, J=1.1 Hz, 1H), 6.89 (d, J=1.1 Hz, 1H), 3.95 (s, 3H), 3.07 (t, J=7.0 Hz, 2H), 2.73 (t, J=7.3 Hz, 2H), 2.27 (s, 6H). Found: [M+H]=275.6.

(2,6-Bis(methylthio)pyridin-4-yl)methanol (38)

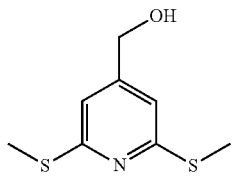

To a solution of 27 (6.12 g, 28.4 mmol) in THF (100 mL, dist. Na) at 0° C. was added borane dimethyl sulfide complex (8.09 mL, 85.3 mmol) followed by trimethyl borate (9.68 mL, 85.3 mmol). The reaction mixture was warmed to r.t. and stirred for 21 h. The reaction mixture was cooled to 0° C., MeOH (50 mL) was added to quench the reaction and solvent was removed under reduced pressure. The residue was washed with water (100 mL), extracted with EtOAc (3×50 mL) and the organic phase was dried with $Na_2SO_4$ and concentrated to give a yellow residue. Purification by flash column chromatography using hexanes:EtOAc (4:1) gave 38 as a white solid (4.56 g, 80%). $^1$H NMR ($CDCl_3$) δ 6.87 (t, J=0.7 Hz, 2H), 4.61 (s, 2H), 2.58 (s, 6H). Found: [M+H]=202.5.

4-(Bromomethyl)-2,6-bis(methylthio)pyridine (39)

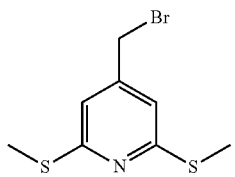

To a solution of 38 (5.26 g, 26.1 mmol) in DCM (300 mL) at 0° C. was added phosphorous tribromide (2.97 mL, 31.4 mmol). The reaction mixture was stirred at r.t. for 18 h and solvent was removed under reduced pressure. The residue was diluted with DCM (100 mL) and quenched with ice-water (100 mL), then the organic phase was washed with sat. aq. $NaHCO_3$, dried with $Na_2SO_4$ and concentrated to give a yellow residue. Purification by flash column chromatography using hexanes:EtOAc (6:1) gave 39 as white solid (3.44 g, 50%). $^1$H NMR ($CDCl_3$) δ 6.86 (s, 2H), 4.23 (s, 2H), 2.58 (s, 6H). Found: [M+H]=264.4.

3-((2,6-Bis(methylthio)pyridin-4-yl)methyl)-6-bromo-2-methoxyquinoline (40)

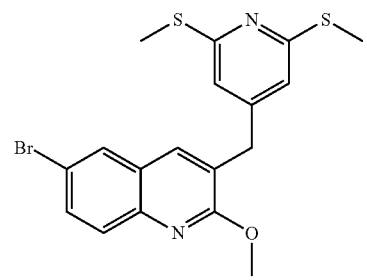

A mixture of 1 (4.31 g, 15.0 mmol), 39 (3.44 g, 15.0 mmol) and $Cs_2CO_3$ (11.24 g, 34.5 mmol) in toluene:DMF (60 mL, 2:1) was degassed under $N_2$, then $Pd(PPh_3)_4$ (0.867 g, 0.75 mmol) was added and the mixture was heated at 90° C. for 2 h. The reaction mixture was cooled to r.t., filtered through a plug of Celite, water (150 mL) was added and the mixture was extracted with EtOAc (3×100 mL). The combined organic layers were washed with brine (100 mL), dried over $Na_2SO_4$, filtered and concentrated under reduced pressure to obtain a yellow residue. Purification by flash column chromatography using hexanes:EtOAc (9:1) gave 40 as a white solid (2.91 g, 46%). $^1$H NMR ($CDCl_3$) δ 7.80 (d, J=2.1 Hz, 1H), 7.69 (d, J=8.9 Hz, 1H), 7.64 (dd, J=8.9, 2.2 Hz, 1H), 7.57 (s, 1H), 6.72 (s, 2H), 4.05 (s, 3H), 3.87 (s, 2H), 2.57 (s, 6H). Found: [M+H]=421.8.

(2,3-Dihydro-1H-inden-4-yl)methanol (41)

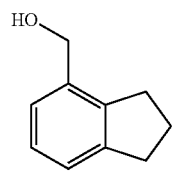

To a solution of 2,3-dihydro-1H-indene-4-carboxylic acid (6.12 g, 28.4 mmol) in THF (100 mL, dist. Na) at 0° C. was added lithium aluminium hydride (8.09 mL, 85.3 mmol) in small portions. The reaction mixture was stirred at 0° C. for 30 min and then at r.t. for a further 24 h. The reaction mixture was washed with water (100 mL) and extracted with EtOAc (3×50 mL). The organic phase was dried with $Na_2SO_4$ and concentrated under reduced pressure to obtain 41 as a yellow oil (2.45 g, 99%). $^1$H NMR ($CDCl_3$) δ 7.22-7.12 (m, 3H), 4.67 (s, 2H), 2.93 (t, J=7.6 Hz, 2H), 2.91 (t, J=7.4 Hz, 2H), 2.09 (p, J=7.6 Hz, 2H). Found: [M+H-18]=131.5.

4-(Chloromethyl)-2,3-dihydro-1H-indene (42)

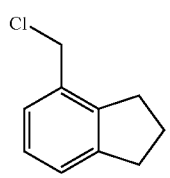

(42)

To a solution of 41 (4.33 g, 36.4 mmol) in DCM (50 mL) at 0° C. was added thionyl chloride (2.45 g, 16.5 mmol). The reaction mixture was stirred at r.t. for 24 h and solvent was removed under reduced pressure. The residue was diluted with DCM (100 mL) and quenched with ice-water (100 mL). The organic phase was washed with sat. aq. $NaHCO_3$, dried with $Na_2SO_4$ and concentrated to give a yellow residue. Purification by flash column chromatography using hexanes:EtOAc (1:1) gave 42 as a colourless oil (2.36 g, 86%). $^1$H NMR ($CDCl_3$) δ 7.22-7.13 (m, 3H), 4.59 (s, 2H), 2.99 (t, J=7.5 Hz, 2H), 2.94 (t, J=7.5 Hz, 2H), 2.11 (p, J=7.6 Hz, 2H). Found: [M+H]=167.5.

6-Bromo-3-((2,3-dihydro-1H-inden-4-yl)methyl)-2-methoxyquinoline (43)

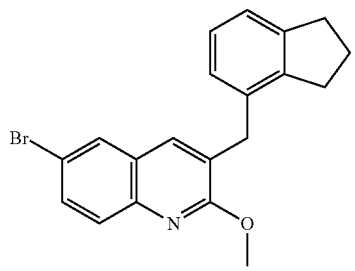

(43)

A mixture of 1 (3.69 g, 12.9 mmol), 42 (2.36 g, 14.2 mmol) and $Cs_2CO_3$ (9.67 g, 29.7 mmol) in toluene:DMF (60 mL, 2:1) was degassed under $N_2$, then $Pd(PPh_3)_4$ (0.745 g, 0.645 mmol), was added and the mixture was heated at 90° C. for 3 h. The reaction mixture was cooled to r.t., filtered through a plug of Celite, water (150 mL) was added the mixture was extracted with EtOAc (3×100 mL). The combined organic layers were washed with brine (100 mL), dried over $Na_2SO_4$, filtered and concentrated under reduced pressure to obtain a yellow residue. Purification by flash column chromatography using hexanes:EtOAc (9:1) gave 43 as a yellow oil (4.70 g, 99%). $^1$H NMR ($CDCl_3$) δ 7.71 (d, J=2.2 Hz, 1H), 7.68 (d, J=8.9 Hz, 1H), 7.60 (dd, J=8.9, 2.2 Hz, 1H), 7.33 (s, 1H), 7.18-7.11 (m, 2H), 6.95 (d, J=7.2 Hz, 1H), 4.11 (s, 3H), 3.98 (s, 2H), 2.96 (t, J=7.5 Hz, 2H), 2.79 (t, J=7.4 Hz, 2H), 2.04 (p, J=7.6 Hz, 2H). Found: [M+H]=368.5.

(5,6,7,8-Tetrahydronaphthalen-1-yl)methanol (44)

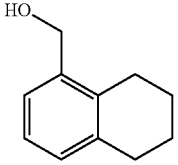

(44)

To a solution of 1-tetrahydronaphthoic acid (5.70 g, 32.3 mmol) in THF (100 mL, dist. Na) at 0° C. was added lithium aluminium hydride (2.46 g, 64.7 mmol) in small portions. The reaction mixture was stirred at 0° C. for 30 min and then stirred for further 24 h at r.t. The reaction mixture was washed with water (100 mL) and extracted with EtOAc (3×50 mL). The organic phase was dried with $Na_2SO_4$ and concentrated under reduced pressure to obtain 44 as colourless oil (5.23 g, 99%). $^1$H NMR ($CDCl_3$) δ 7.18 (d, J=7.4 Hz, 1H), 7.11 (d, J=7.5 Hz, 1H), 7.05 (d, J=7.6 Hz, 1H), 4.67 (s, 2H), 2.80 (t, J=6.2 Hz, 2H), 2.76 (t, J=6.4 Hz, 2H), 1.88-1.77 (m, 4H). Found: [M+H-18]=145.5.

5-(Chloromethyl)-1,2,3,4-tetrahydronaphthalene (45)

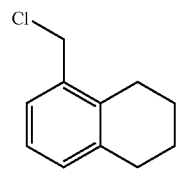

(45)

To a solution of 44 (5.24 g, 32.3 mmol) in DCM (200 mL) at 0° C. was added thionyl chloride (8.45 g, 71.1 mmol). The reaction mixture was stirred at r.t. for 24 h, then solvent was removed under reduced pressure. The residue was diluted with DCM (100 mL) and quenched with ice-water (100 mL). The organic phase was washed with sat. aq. $NaHCO_3$, dried with $Na_2SO_4$ and concentrated to give 45 as a brown oil (3.25 g, 56%). $^1$H NMR ($CDCl_3$) δ 7.16-7.05 (m, 3H), 4.59 (s, 2H), 2.86 (t, J=6.3 Hz, 2H), 2.79 (t, J=6.4 Hz, 2H), 1.88-1.77 (m, 4H). Found: [M+H]=181.6.

6-Bromo-2-methoxy-3-((5,6,7,8-tetrahydronaphthalen-1-yl)methyl)quinolone (46)

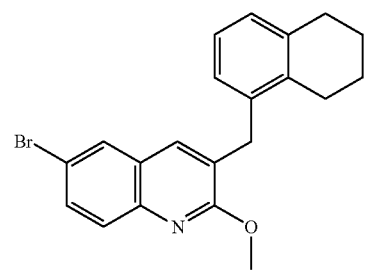

(46)

A mixture of 1 (4.69 g, 16.4 mmol), 45 (3.25 g, 18.0 mmol) and Cs$_2$CO$_3$ (12.29 g, 37.7 mmol) in toluene:DMF (60 mL, 2:1) was degassed under N$_2$, then Pd(PPh$_3$)$_4$ (0.948 g, 0.82 mmol) was added and the mixture was heated at 90° C. for 3 h. The reaction mixture was cooled to r.t., filtered through a plug of Celite, water (150 mL) was added and the mixture was extracted with EtOAc (3×100 mL). The combined organic layers were washed with brine (100 mL), dried over Na$_2$SO$_4$, filtered and concentrated under reduced pressure to obtain a yellow residue. Purification by flash column chromatography using hexanes:EtOAc (9:1) gave 46 as a white solid (4.64 g, 74%). $^1$H NMR (CDCl$_3$) δ 7.71-7.69 (m, 2H), 7.60 (dd, J=8.9, 2.2 Hz, 1H), 7.23 (s, 1H), 7.12-7.04 (m, 2H), 6.92 (d, J=6.9 Hz, 1H), 4.11 (s, 3H), 3.96 (s, 2H), 2.83 (bs, 2H), 2.57 (bs, 2H), 1.76 (p, J=3.5 Hz, 4H). Found: [M+H]=382.1.

6-Fluoro-N-methoxy-N-methylnicotinamide (47)

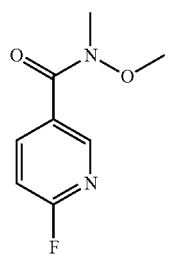

(47)

To a suspension of 6-fluoronicotinic acid (2.00 g, 14.20 mmol) in anhydrous DCM (56 mL) was added 8 drops of anhydrous DMF under nitrogen flow. Oxalyl chloride (1.4 mL, 17.0 mmol) was added slowly. Effervescence was observed throughout addition. The resultant mixture was stirred at room temperature for 1.5 hours by which time it had become clear. The mixture was cooled to 2° C., N,O-dimethylhydroxylamine hydrochloride (1.52 g, 15.60 mmol) was added, followed by anhydrous pyridine (2.5 mL, 31.2 mmol). The mixture was stirred from 2° C. to r.t. overnight. The mixture was treated with sat. aq. NaHCO$_3$ solution until gas evolution ceased. The organic layer was collected. The aqueous phase was further extracted with EtOAc (2×). The organic extract was washed with brine, dried (MgSO$_4$) and concentrated in vacuo to furnish the crude product. Flash chromatography of the crude product using 1-3% MeOH in DCM as eluents afforded the product 47 as a light brown oil. Yield=1.96 g, 75%. $^1$H NMR (CDCl$_3$) δ 8.66 (1H, d, J=2.4 Hz), 8.19 (1H, ddd, J=2.4, 3.6, 8.8 Hz), 7.0 (1H, ddd, J=0.4, 2.8, 8.8 Hz), 3.57 (3H, s), 3.40 (3H, s).

6-(Diethylamino)nicotinaldehyde (48)

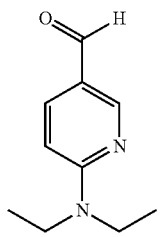

(48)

To a glass pressure tube was charged a solution of 47 (2.13 g, 11.60 mmol) and diethylamine (2.4 mL, 23.20 mmol) in anhydrous acetonitrile (12 mL). The mixture was sealed in the tube and refluxed for 3 hours. The solvent was removed and the residue was treated with sat. aq. NaHCO$_3$ solution and extracted with DCM (5×). The combined extract was washed with brine, dried (MgSO$_4$) and concentrated to yield the crude product as a brown oil. $^1$H NMR analysis of the crude product indicated a 10:7 mixture of product and starting material. The mixture was submitted to the above reaction conditions again and the reaction left to proceed overnight. Work up as above gave the crude product as a brown oil (2.58 g), which was used directly in the next step. $^1$H NMR analysis confirmed the identity and purity of the diethylaminopyridine intermediate. $^1$H NMR (CDCl$_3$) δ 8.70 (1H, d, J=2.4 Hz), 7.90 (1H, dd, J=2.4, 9.1 Hz), 6.44 (1H, d, J=9.1 Hz), 3.62 (3H, s), 3.56 (4H, q, J=7.1 Hz), 3.35 (3H, s), 1.20 (6H, t, J=7.1 Hz). The intermediate adduct (2.58 g) was dissolved in freshly distilled THF (40 mL). To the solution was added at −78° C. under nitrogen lithium aluminium hydride (0.31 g, 8.15 mmol) in one portion. The mixture was maintained at −78° C. for 30 min, then at 2° C. for 75 min. The mixture was quenched with water dropwise, until gas evolution ceased. 1M Sodium hydroxide solution (16 mL) was added, the resultant yellow mixture was stirred for 30 min. The aqueous mixture was extracted with EtOAc (2×), and the combined extract was washed with brine, dried (MgSO$_4$) and concentrated in vacuo to give the crude product as a yellow oil. Flash chromatography of the crude product using 4:1 then 3:1 mixtures of hexanes/EtOAc as eluent afforded the product 48 as a colourless oil. Yield=1.42 g, 75%. $^1$H NMR (CDCl$_3$) δ 9.74 (1H, d, J=0.3 Hz), 8.53 (1H, dd, J=0.04, 2.3 Hz), 7.88 (1H, dd, J=0.4, 2.3 Hz), 6.51 (1H, d, J=9.2 Hz), 3.60 (4H, q, J=7.0 Hz), 1.23 (6H, t, J=7.1 Hz). Found: [M+H]=179.6.

(6-Bromo-2-methoxyquinolin-3-yl)(6-(diethylamino)pyridin-3-yl)methanol (49)

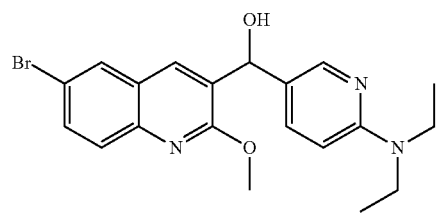

(49)

n-BuLi (4.4 mL, 8.760 mmol) was added at −30° C. under nitrogen to a solution of freshly distilled 2,2,6,6-tetramethylpiperidine (1.6 mL, 9.557 mmol) in freshly distilled THF (13 mL). The mixture was maintained at about −30° C. for 15 min, then cooled to −78° C. A solution of 6-bromo-2-methoxyquinoline (1.90 g, 7.964 mmol) in dry THF (15 mL) was added dropwise at −78° C. and the mixture was stirred at this temperature for 75 min A solution of 48 (1.42 g, 7.964 mmol) in dry THF (6 mL) was added dropwise at −78° C., the reaction mixture remained orange brown and was stirred at −78° C. for 2.5 hours. The mixture was quenched with acetic acid (0.68 mL) at −65° C. Water was added, the aqueous mixture was extracted with EtOAc (2×), and the combined extract was washed with brine, dried (MgSO$_4$) and concentrated in vacuo to give the crude product as a yellow solid. Flash chromatography of the product using 10-100% EtOAc in hexanes as eluent afforded the product 49 as an off-white solid. Yield=1.90 g, 57%. ¹H NMR (CDCl₃) δ 8.15 (1H, d, J=2.4 Hz), 8.01 (1H, s), 7.88 (1H, d, J=2.1 Hz), 7.69 (1H, d, J=8.9 Hz), 7.65 (1H, dd, J=2.1, 9.0 Hz), 7.40 (1H, dd, J=2.5, 9.0 Hz), 6.42 (1H, d, J=8.9 Hz), 5.94 (1H, d, J=3.7 Hz), 4.04 (3H, s), 3.50 (4H, dq, J=1.7, 7.1 Hz), 2.65 (1H, d, J=3.9 Hz), 1.17 (6H, t, J=7.0 Hz).

5-((6-Bromo-2-methoxyquinolin-3-yl)methyl)-N,N-diethylpyridin-2-amine (50)

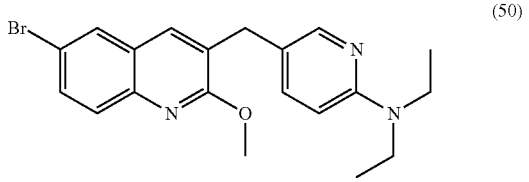 [SMILES: CCN(CC)c1ccc(Cc2cc3cc(Br)ccc3nc2OC)cn1]
(50)

To a solution of 49 (1.90 g, 4.56 mmol) in freshly distilled THF (19 mL) was added at 2° C. under nitrogen sodium borohydride (0.86 g, 23.0 mmol) in 3 portions over 10 min. The mixture was stirred at 2-4° C. for 1 hour. The mixture was cooled to 2° C. again and aluminium trichloride (1.83 g, 13.70 mmol) was added in 4 batches over 15 min. The mixture was stirred at 2° C. for 10 min, then refluxed for 2 hours. The mixture was then quenched with water cautiously at 2° C., until gas evolution ceased. The white slurry was filtered through Celite. The milky white filtrate was diluted in water, and the organic phase was collected. The aqueous phase was extracted with EtOAc (3×). The organic extract was washed with brine, dried (MgSO₄) and concentrated in vacuo to furnish the crude product as a brownish residue. Flash chromatography of the crude product using 10% EtOAc in hexanes as eluent afforded the product 50 as a white solid. Yield=1.39 g, 76%. ¹H NMR (CDCl₃) δ 8.06 (1H, d, J=2.1 Hz), 7.75 (1H, d, J=2.2 Hz), 7.68 (1H, d, J=8.8 Hz), 7.60 (1H, dd, J=2.2, 8.8 Hz), 7.52 (1H, s), 7.27 (1H, dd, J=2.4, 8.7 Hz), 6.43 (1H, dd, J=0.3, 8.7 Hz), 4.09 (3H, s), 3.85 (2H, s), 3.50 (4H, q, 7.0 Hz), 1.18 (6H, t, J=7.0 Hz). Found: [M+H]=400.8.

2,3-Difluoroisonicotinic Acid (51)

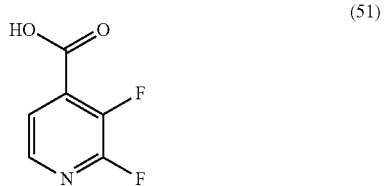 [SMILES: O=C(O)c1ccnc(F)c1F]
(51)

To a solution of n-BuLi (26.1 mL, 52.09 mmol) in THF (70 mL, dist. Na) at −78° C. was added consecutively N,N-diisopropylamine (7.30 mL, 52.09 mmol) and 2,3-difluoropyridine (5.00 g, 43.41 mmol). The resultant mixture was stirred at −78° C. for 1 hour, and then poured on crushed dry ice (excess). The reaction was allowed to warm to r.t. for 1 hour, and after evaporation of excess dry ice and THF, the residue was taken up into water (100 mL) and washed with EtOAc (2×50 mL). The aqueous layer was then acidified to pH 1 and extracted with EtOAc (2×100 mL). The combined organic extracts were dried and evaporated to afford the product 51. Yield=2.39 g, 35%. ¹H NMR (CDCl₃) δ 15.3-13.2 (1H, br s), 8.14 (1H, dd, J=1.2, 5.0 Hz), 7.70 (1H, dd, J=4.8, 4.8 Hz). Found: [M−H]=158.5.

3-Fluoro-2-methoxyisonicotinic Acid (52)

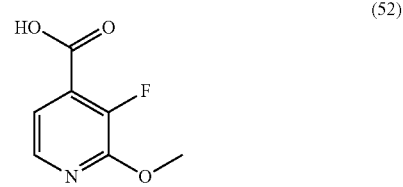
(52)

Sodium (0.79 g, 33.09 mmol) was added portion wise to MeOH (60 mL) over 0.5 h. 51 (2.39 g, 15.04 mmol) was then added and the reaction refluxed for 2 hours. The solution was cooled and the solvent evaporated. The residue was taken up into water (100 mL) and washed with EtOAc (2×50 mL). The aqueous layer was then acidified to pH 1 and extracted with EtOAc (2×100 mL). The combined organic extracts were dried and evaporated to afford the product 52. Yield=2.23 g, 87%. ¹H NMR (DMSO-d₆) δ 14.6-12.8 (1H, br s), 8.05 (1H, d, J=5.2 Hz), 7.28 (1H, dd, J=4.7, 4.9 Hz), 3.97 (3H, s). Found: [M−H]=170.5.

(3-Fluoro-2-methoxypyridin-4-yl)methanol (53)

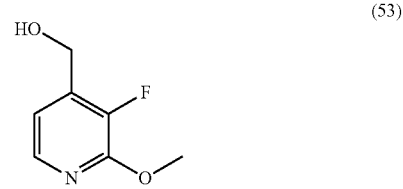
(53)

Borane-dimethylsulfide complex (2.47 mL, 26.07 mmol) and trimethyl borate (2.96 mL, 26.07 mmol) were added to a solution of 52 (13.03 mmol) in THF (80 mL, dist. Na) at 0° C., and the solution warmed to r.t. and stirred overnight. The mixture was then cooled to 0° C., and quenched with methanol (10 mL). The solvent was then evaporated and the residue was partitioned between EtOAc and water. The organic layer was then dried and evaporated to afford the product 53. Yield=1.89 g, 92%. ¹H NMR (CDCl₃) δ 7.92 (1H, d, J=5.2 Hz), 7.02 (1H, dd, J=4.5, 5.1 Hz), 4.81 (2H, s), 4.03 (3H, s). Found: [M+H]=158.5.

4-(Bromomethyl)-3-fluoro-2-methoxypyridine (54)

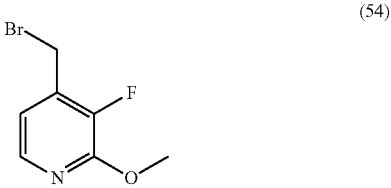
(54)

To a solution of 53 (1.89 g, 12.03 mmol) and triethylamine (2.52 mL, 18.05 mmol) in DCM (30 mL, anhydrous) at r.t. was added mesyl chloride (1.12 mL, 14.44 mmol) dropwise. After 15 min, the reaction was diluted with DCM (20 mL) and the organic layer washed with sat. NaHCO$_3$, dried and evaporated. The residue was dissolved in acetone (60 mL, anhydrous), lithium bromide (excess) added, and the mixture heated at reflux for 30 min. The solution was then cooled and the solvent evaporated, and the residue partitioned between EtOAc and water. The aqueous layer was extracted twice with EtOAc and the organic layer was dried and evaporated to give the product 54. Yield=2.20 g, 83% $^1$H NMR (CDCl$_3$) δ 7.90 (1H, d, J=5.2 Hz), 6.90 (1H, dd, J=4.8, 4.9 Hz), 4.43 (2H, s), 4.02 (3H, s). Found: [M+H]=220.2.

6-Bromo-3-((3-fluoro-2-methoxypyridin-4-yl)methyl)-2-methoxyquinoline (55)

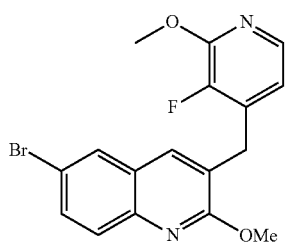

A mixture of 1 (2.56 g, 9.09 mmol), 54 (2.20 g, 10.00 mmol) and cesium carbonate (5.92 g, 18.18 mmol) in toluene (45 mL, anhydrous) and DMF (22.5 mL, anhydrous) was purged with nitrogen. Pd(PPh$_3$)$_4$ (0.42 g, 0.363 mmol) was then added, the mixture purged with nitrogen, then heated to 80° C. under nitrogen for 4 hours. The reaction was partitioned between EtOAc and water and the organic fraction was dried and evaporated. Column chromatography (19:1 hexanes/EtOAc) gave the product 55. Yield=1.76 g, 51%. $^1$H NMR (CDCl$_3$) δ 7.82 (1H, d, J=5.2 Hz), 7.79 (1H, d, J=2.1 Hz), 7.69 (1H, d, J=8.8 Hz), 7.6 4 (1H, dd, J=2.2, 8.9 Hz), 7.60 (1H, s), 6.69 (1H, dd, J=4.8, 5.0 Hz), 4.07 (3H, s), 4.06 (2H, s), 4.03 (3H, s). Found: [M+H]=377.2.

(2,6-Dimethoxypyridin-3-yl)boronic Acid (56)

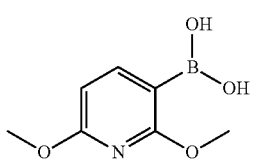

To a solution of 2,6-dimethoxypyridine (10 g, 71.84 mmol) and N,N-diisopropylamine (0.50 mL, 3.59 mmol) in THF (200 mL, dist. Na) at −40° C. under nitrogen was added n-BuLi (43.10 mL, 86.21 mmol) dropwise. The resultant solution was stirred at −40° C. for 5 min, and then warmed to 0° C. and stirred at this temperature for a further 3 hours. The solution was then again cooled to −40° C., and triisopropylborate (24.87 mL, 107.76 mmol) was added dropwise, and the mixture stirred at r.t. for another 1 hour. Water (50 mL) was added and the solvent was removed in vacuo. To the residue was added 1M NaOH (100 mL) and the aqueous layer washed with EtOAc (2×100 mL). The aqueous layer was then acidified to pH 3 and a solid precipitated. This solid was filtered and dried to afford the product 56. Yield=8.10 g, 61%. $^1$H NMR (DMSO-d$_6$) δ 7.87 (1H, d, J=7.9 Hz), 6.36 (1H, d, J=7.9 Hz), 3.90 (3H, s), 3.87 (3H, s).

2,6-Dimethoxypyridin-3-ol (57)

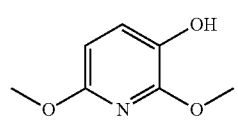

To a solution of 56 (8.00 g, 43.49 mmol) in THF (150 mL, dist. Na) at 0° C. was added dropwise 32% peracetic acid in acetic acid (21.53 mL, 86.98 mmol) over 10 min. The resultant solution was stirred at r.t. for 2 h. A 10% solution of sodium sulfite (75 mL) was then added and the mixture stirred at r.t. for 0.5 hour. The solvent was evaporated and the residue partitioned between EtOAc and water. The aqueous layer was extracted twice and the organic layer dried and evaporated. Column chromatography with 9:1 hexanes/EtOAc afforded the product 57. Yield=6.05 g, 90%. $^1$H NMR (CDCl$_3$) δ 7.12 (1H, d, J=8.3 Hz), 6.21 (1H, d, J=8.2 Hz), 4.90 (1H, s), 7.00 (3H, s), 3.86 (3H, s). Found: [M+H]=156.7.

3-(Ethoxymethoxy)-2,6-dimethoxypyridine (58)

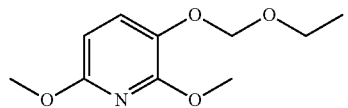

To a solution of 57 (6.45 g, 40.97 mmol) in DMF (70 mL, anhydrous) at 0° C. was added 60% sodium hydride in mineral oil (41.97 g, 9.16 mmol) in portions. The mixture was warmed to r.t. and stirred for 1 hour. 1-Chloro-2-methoxyethane (4.37 mL, 47.11 mmol) was then added, and the resultant mixture stirred at r.t. for a further 2 hours. The reaction was diluted with brine (100 mL) and extracted with EtOAc three times. The organic layer was washed with brine three times, dried and evaporated. Column chromatography with 19:1 hexanes/EtOAc afforded the product 58. Yield: 8.14 g, 93%. $^1$H NMR (CDCl$_3$) δ 7.41-7.33 (1H, m), 6.26-6.17 (1H, m), 5.15 (2H, d, J=1.9 Hz), 3.98 (3H, d, J=1.8 Hz), 3.87 (3H, d, J=2.0 Hz), 3.77 (2H, dq, J=1.8, 7.1 Hz), 1.22 (3H, dt, J=2.9, 7.0 Hz).

3-Hydroxy-2,6-dimethoxyisonicotinic Acid (59)

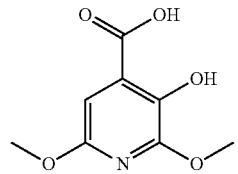

To a solution of 58 (4.95 g, 23.24 mmol) and N,N-diisopropylamine (0.16 mL, 1.16 mmol) in THF (80 mL, dist. Na) at −40° C. under nitrogen was added n-BuLi (17.43 mL, 34.86 mmol) dropwise. The resultant solution was stirred at −40° C. for 5 min, and then warmed to 0° C. and stirred at this temperature for a further 3 hours. The solution was then again cooled to −40° C., and dry ice (20 g, excess) was added, and the mixture stirred at r.t. for another 1 hour. Water (25 mL) was added and the solvent was removed in vacuo. To the residue was added 1M NaOH (100 mL) and the aqueous layer washed with EtOAc (2×100 mL). The aqueous layer was then acidified to pH 1 using conc. hydrochloric acid and a solid precipitated. This solid was filtered and dried to afford the product 59. Yield=3.85 g, 83%. $^1$H NMR (DMSO-d$_6$) δ 6.52 (1H, s), 3.90 (3H, s), 3.79 (3H, s). Found: [M+H]=200.5.

Methyl 2,3,6-trimethoxyisonicotinate (60)

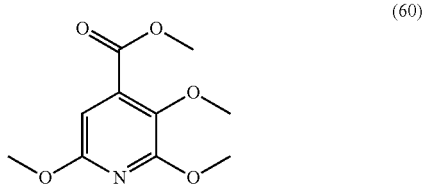

A mixture of 59 (3.85 g, 19.34 mmol) and potassium carbonate (10.70 g, 7.39 mmol) in DMF (100 mL, anhydrous) was heated at 50° C. for 15 min. Methyl iodide (3.61 mL, 58.03 mmol) was then added and the mixture stirred at this temperature for 2 hours. The resultant solution was diluted with EtOAc and washed with brine three times. The organic layer was dried and evaporated. Column chromatography with 9:1 hexanes/EtOAc afforded the product 60. Yield=3.63 g, 96%. $^1$H NMR (CDCl$_3$) δ 6.51 (1H, s), 4.01 (3H, s), 3.92 (3H, s), 3.89 (3H, s), 3.83 (3H, s).

2,3,6-Trimethoxyisonicotinic Acid (61)

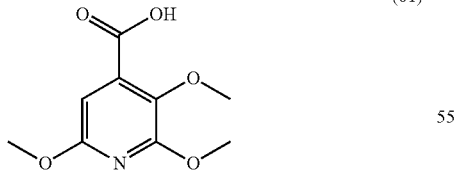

A solution of 60 (3.60 g, 55.86 mmol) in 1M NaOH (100 mL) was heated at 50° C. for 2 hours. The reaction was cooled and washed with EtOAc (2×50 mL). The aqueous layer was then acidified to pH 1 and the solid filtered and dried to afford the product 61. Yield=3.04 g, 90%. $^1$H NMR (DMSO-d$_6$) δ 14.3-12.2 (1H, br s), 6.42 (1H, s), 3.93 (3H, s), 3.83 (3H, s), 3.69 (3H, s). Found: [M+H]=214.5.

N,2,3,6-Tetramethoxy-N-methylisonicotinamide (62)

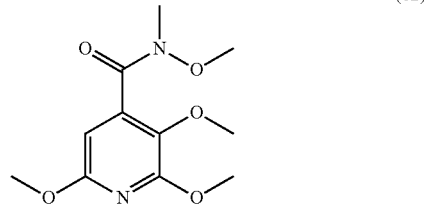

Oxalyl chloride (1.46 mL, 16.90 mmol) was added to a solution of 61 (3.00 g, 14.08 mmol) in DCM (60 mL, anhydrous) and DMF (0.22 mL, 2.82 mmol) at r.t. The mixture was stirred at r.t. for 1 hour, and then the solvent was evaporated and the residue washed with benzene (2×50 mL). The residue was redissolved in DMF (60 mL, anhydrous) and cooled to 0° C. N,O-dimethylhydroxylamine hydrochloride (1.51 g, 15.49 mmol) and pyridine (3.75 mL, 46.46 mmol) were added sequentially and the mixture was stirred at r.t. for 2 hours, then partitioned between EtOAc and sat. aq. NaHCO$_3$. Column chromatography with 9:1 hexanes/EtOAc gave the product 62. Yield=2.89 g, 80%. $^1$H NMR (CDCl$_3$) δ 6.18 (1H, s), 4.01 (3H, s), 3.89 (3H, s), 3.80 (3H, s), 3.60-3.47 (3H, br s), 3.42-3.26 (3H, s). Found: [M+H]=257.6.

3-(Dimethylamino)-1-(2,3,6-trimethoxypyridine-4-yl)propan-1-one (63)

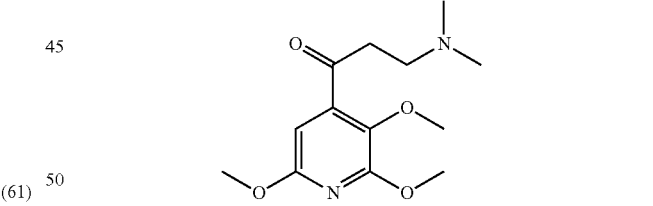

Vinylmagnesium bromide in THF (1N, 22.13 mL, 22.13 mmol) was added to a solution of 62 (2.70 g, 10.54 mmol) in THF (80 mL, dist. Na) at 0° C., then the yellow/orange solution was warmed to r.t. for 1 hour. Dimethylamine in THF (2N, 22.13 mL, 44.27 mmol) then water (30 mL) were added. The solution was stirred at r.t. for 1 hour, the solvent removed in vacuo, and the resultant mixture then partitioned between EtOAc and water. The solution was dried and evaporated to afford the product 63. Yield=2.81 g, 99%. $^1$H NMR (CDCl$_3$) δ 6.32 (1H, s), 4.01 (3H, s), 3.89 (3H, s), 3.81 (3H, s), 3.08 (2H, t, J=7.2 Hz), 2.68 (2H, t, J=7.2 Hz), 2.24 (6H, s). Found: [M-Me$_2$N]=224.5.

(3-Fluoro-4-methoxyphenyl)methanol (64)

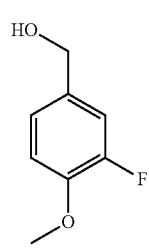

(64)

Borane-dimethylsulfide complex (2.79 mL, 29.40 mmol) and trimethyl borate (3.34 mL, 29.40 mmol) were added to a solution of 3-fluoro-4-methoxybenzoic acid (2.50 g, 14.69 mmol) in THF (80 mL, dist. Na) at 0° C., and the solution warmed to r.t. and stirred overnight. The mixture was then cooled to 0° C., and quenched with MeOH (10 mL). The solvent was then evaporated and the residue was partitioned between EtOAc and water. The organic layer was then dried and evaporated to afford the product 64. Yield=2.35 g, 100%. $^1$H NMR (CDCl$_3$) δ 7.11 (1H, dd, J=2.0, 11.9 Hz), 7.06 (1H, ddd, J=0.9, 2.0, 9.1 Hz), 6.94 (1H, dd, J=8.4, 8.4 Hz), 4.61 (2H, s), 3.89 (3H, s), 1.73 (1H, s). Found: [M−OH]=139.7.

4-(Bromomethyl)-2-fluoro-1-methoxybenzene (65)

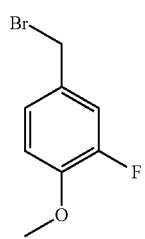

(65)

To a solution of 64 (2.35 g, 15.05 mmol) and triethylamine (3.15 mL, 22.58 mmol) in DCM (50 mL, anhydrous) at r.t. was added mesyl chloride (1.41 mL, 18.06 mmol) dropwise. After 15 min, the reaction was diluted with DCM (50 mL) and the organic layer washed with sat. aq. NaHCO$_3$, dried and evaporated. The residue was dissolved in acetone (100 mL, anhydrous), lithium bromide (excess) added, and the mixture heated at reflux for 30 min. The solution was then cooled and the solvent evaporated, and the residue partitioned between EtOAc and water. The aqueous layer was extracted twice with EtOAc and the organic layer was dried and evaporated to afford the product 65. Yield=3.00 g, 91%. $^1$H NMR (CDCl$_3$) δ 7.16-7.07 (2H, m), 6.90 (1H, dd, J=8.3, 8.4 Hz), 4.45 (2H, s), 3.89 (3H, s).

6-Bromo-3-(3-fluoro-4-methoxybenzyl)-2-methoxyquinoline (66)

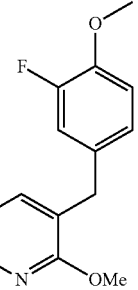

(66)

A mixture of 1 (3.51 g, 12.45 mmol), 65 (3.00 g, 13.69 mmol) and cesium carbonate (8.93 g, 27.40 mmol) in toluene (60 mL, anhydrous) and DMF (30 mL, anhydrous) was purged with nitrogen. Pd(PPh$_3$)$_4$ (0.58 g, 0.50 mmol) was then added, the mixture purged with nitrogen then heated to 80° C. under nitrogen for 5 hours. The reaction was partitioned between EtOAc and water and the organic fraction was dried and evaporated. Column chromatography (19:1 hexanes/EtOAc) gave the product 66. Yield=2.10 g, 41%. $^1$H NMR (CDCl$_3$) δ 7.76 (1H, d, J=2.2 Hz), 7.69 (1H, d, J=12.3 Hz), 7.62 (1H, dd, J=2.2, 8.9 Hz), 7.49 (1H, s), 7.00-6.86 (3H, m), 4.07 (3H, s), 3.95 (2H, s), 3.88 (3H, s). Found: [M+H]=376.0.

3-(Ethoxymethoxy)-2,6-dimethoxyisonicotinaldehyde (67)

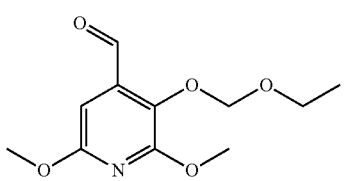

(67)

To a solution of 58 (4.00 g, 18.78 mmol) and N,N-diisopropylamine (0.13 mL, 0.94 mmol) in THF (60 mL, dist. Na) at −40° C. under nitrogen was added n-BuLi (14.09 mL, 28.17 mmol) dropwise. The resultant solution was stirred at −40° C. for 5 min, and then warmed to 0° C. and stirred at this temperature for a further 3 hours. The solution was then again cooled to −40° C., and 1-formylpiperidine (3.75 mL, 33.80 mmol) was added dropwise, and the mixture stirred at r.t. for another 1 hour. Acetic acid (7.5 mL) was added and the solvent was removed in vacuo. The resultant mixture was partitioned between EtOAc and water, and the organic fraction dried and evaporated. Column chromatography with 19:1 hexanes/EtOAc afforded the product 67. Yield=2.30 g, 51%. $^1$H NMR (CDCl$_3$) δ 10.39 (1H, s), 6.61 (1H, s), 6.19 (2H, s), 4.02 (3H, s), 3.88 (3H, s), 3.78 (2H, q, J=10.1 Hz), 1.21 (3H, t, J=7.1 Hz).

3-Hydroxy-2,6-dimethoxyisonicotinaldehyde (68)

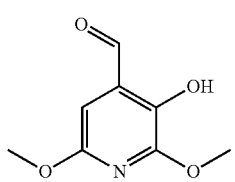
(68)

A solution of 67 (2.30 g, 9.54 mmol) and 3M hydrochloric acid (60 mL) in THF (30 mL, dist. Na) was heated at 40° C. for 1.5 hours. The solution was then cooled, diluted with water, and the pH adjusted to 7 using NaHCO$_3$. The aqueous layer was then extracted with EtOAc three times, and the organic layer dried and evaporated. Column chromatography with 19:1 hexanes/EtOAc afforded the product 68. Yield=1.36 g, 78%. $^1$H NMR (CDCl$_3$) δ 9.96 (1H, s), 9.61 (1H, s), 6.46 (1H, s), 4.06 (3H, s), 3.91 (3H, s).

2,3,6-Trimethoxyisonicotinaldehyde (69)

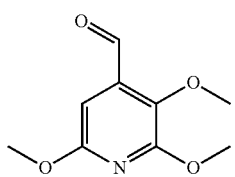
(69)

A mixture of 68 (1.35 g, 7.38 mmol) and potassium carbonate (1.53 g, 11.07 mmol) in DMF (40 mL, anhydrous) was heated at 50° C. for 10 min. Methyl iodide (0.56 mL, 8.86 mmol) was then added and the mixture stirred at this temperature for 2 hours. The resultant solution was diluted with EtOAc and washed with brine three times. The organic layer was dried and evaporated to afford the product 69. Yield=1.40 g, 96%. $^1$H NMR (CDCl$_3$) δ 10.40 (1H, s), 6.58 (1H, s), 4.04 (3H, s), 3.93 (3H, s), 3.91 (3H, s).

(2,3,6-Trimethoxypyridin-4-yl)methanol (70)

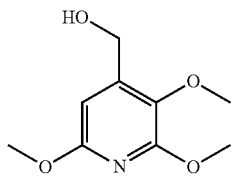
(70)

A mixture of 69 (1.40 g, 7.11 mmol) and sodium borohydride (0.54 g, 14.21 mmol) in MeOH (30 mL, anhydrous) was stirred at r.t. for 1 hour. The solvent was then removed and the residue partitioned between EtOAc and water. The organic layer was dried and evaporated to afford the product 70. Yield=1.35 g, 95%. $^1$H NMR (CDCl$_3$) δ 6.30 (1H, s), 4.68 (2H, d, J=5.6 Hz), 3.99 (3H, s), 3.88 (3H, s), 3.79 (3H, s), 2.21 (1H, t, J=5.9 Hz).

4-(Bromomethyl)-2,3,6-trimethoxypyridine (71)

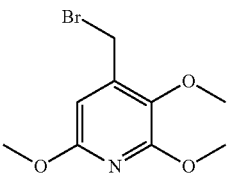
(71)

To a solution of 70 (1.35 g, 6.78 mmol) and triethylamine (1.42 mL, 10.78 mmol) in DCM (20 mL, anhydrous) at r.t. was added mesyl chloride (0.63 mL, 8.14 mmol) dropwise. After 15 min, the reaction was diluted with DCM (20 mL) and the organic layer washed with sat. aq. NaHCO$_3$, dried and evaporated. The residue was dissolved in acetone (40 mL, anhydrous), lithium bromide (excess) added, and the mixture heated at reflux for 30 min. The solution was then cooled and the solvent evaporated, and the residue partitioned between EtOAc and water. The aqueous layer was extracted twice with EtOAc and the organic layer was dried and evaporated to give the product 71. Yield=1.69 g, 95%. $^1$H NMR (CDCl$_3$) δ 6.27 (1H, s), 4.40 (2H, s), 3.98 (3H, s), 3.87 (3H, s), 3.87 (3H, s). Found: [M+H]=262.5.

6-Bromo-2-methoxy-3-((2,3,6-trimethoxypyridin-4-yl)methyl)quinolone (72)

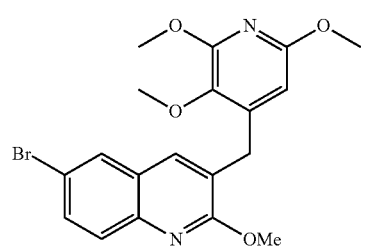
(72)

A mixture of 1 (1.89 g, 6.69 mmol), 71 (1.67 g, 6.37 mmol) and cesium carbonate (4.15 g, 12.74 mmol) in toluene (40 mL, anhydrous) and DMF (20 mL, anhydrous) was purged with nitrogen. Pd(PPh$_3$)$_4$ (0.29 g, 0.26 mmol) was then added, the mixture purged with nitrogen then heated to 80° C. under nitrogen for 4 hours. The reaction was partitioned between EtOAc and water and the organic fraction was dried and evaporated. Column chromatography (19:1 hexanes/EtOAc) gave the product 72. Yield=1.44 g, 54%. $^1$H NMR (CDCl$_3$) δ 7.76 (1H, d, J=2.2 Hz), 7.68 (1H, d, J=8.9 Hz), 7.61 (1H, dd, J=2.2, 8.8 Hz), 7.54 (1H, s), 6.04 (1H, s), 4.07 (3H, s), 4.00 (3H, s), 4.39 (2H, s), 3.85 (3H, s), 3.72 (3H, s). Found: [M+H]=420.0.

Methyl 2-(dimethylamino)-6-(ethylthio)isonicotinate (73)

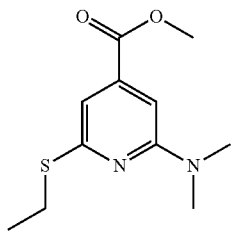

To a glass tube was charged methyl 2-chloro-6-(dimethylamino)isonicotinate (WO 2010/100475) (2.44 g, 11.40 mmol), rac-bis(diphenylphosphino)-1,1'-binaphthol (0.71 g, 1.140 mmol) and cesium carbonate (4.43 g, 13.60 mmol) under continuous nitrogen flow. Anhydrous toluene (30 mL) was added. The mixture was purged with nitrogen for 5 min Palladium acetate (0.26 g, 1.158 mmol) was added and the mixture was purged again with nitrogen. Ethanethiol (1.0 mL, 13.60 mmol) was added and the mixture was sealed in the tube and heated at 150° C. for 22 hours. The mixture was filtered through Celite, washing with EtOAc. The filtrate was concentrated in the fume hood by heating the solution while purging with air. A crude orange solid was obtained. Flash chromatography of the product using 2-5% diethyl ether in hexanes provided the product 73 as a yellow crystalline solid. Yield=2.42 g, 88%. %. $^1$H NMR (CDCl$_3$) δ 6.96 (1H, d, J=1.0 Hz), 6.73 (1H, d, J=1.0 Hz), 3.89 (3H, s), 3.15 (2H, q, 7.3 Hz), 3.12 (6H, s), 1.38 (3H, t, J=7.3 Hz). Found: [M+H]=241.5.

(2-(Dimethylamino)-6-(ethylthio)pyridin-4-yl)methanol (74)

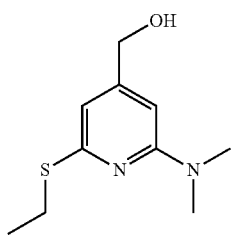

To a solution of 73 (1.64 g, 6.824 mmol) in freshly distilled THF (66 mL) was added at 2° C. under nitrogen lithium aluminium hydride (0.31 g, 8.189 mmol) in 3 batches. The mixture was stirred at 2° C. for 15 min then at r.t. for 1 hour. The mixture was quenched cautiously with water at 2° C. until gas evolution ceased. 1M NaOH (20 mL) was added. The mixture was stirred for 5 min, then decanted leaving the aluminium salts which were filtered through Celite. The aqueous mixture was partitioned between water and EtOAc. The aqueous phase was extracted with EtOAc (3×). The combined organic extract was washed with brine, dried (Na$_2$SO$_4$) and concentrated to give the crude product as a brown oil. The crude product was purified by flash chromatography using a 4:1 mixture of hexanes/EtOAc to afford the product 74 as a brown oil. Yield=1.30 g, 90%. $^1$H NMR (CDCl$_3$) δ 6.43 (1H, s), 6.18 (1H, d, J=0.8 Hz), 4.56 (2H, d, J=5.0 Hz), 3.14 (2H, q, 7.4 Hz), 3.08 (6H, s), 1.67 (1H, br t, J=5.8 Hz), 1.57 (3, s), 1.37 (3H, t, J=7.3 Hz). Found: [M+H]=213.5.

4-(Bromomethyl)-6-(ethylthio)-N,N-dimethylpyridin-2-amine (75)

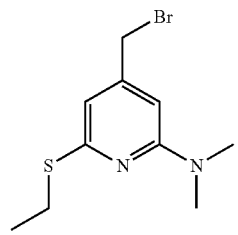

To a solution of 74 (0.60 g, 2.84 mmol) in anhydrous DCM (10 mL) was added at 2° C. under nitrogen triethylamine (0.59 mL, 4.26 mmol) dropwise, followed by mesyl chloride (0.26 mL, 3.41 mmol). The mixture was stirred from 2° C. to 5° C. over 1 hour. The mixture was quenched with sat. aq. NaHCO$_3$ solution. The aqueous mixture was extracted with DCM (3×). The combined extract was washed with brine, dried (MgSO$_4$) and concentrated to afford the crude product as a light brown oil. The crude intermediate was dissolved in acetone (20 mL). Lithium bromide (0.99 g, 11.36 mmol) was added and the suspension was stirred at r.t. for 2.5 hours. Flash chromatography using 98:2 hexanes/Et$_2$O furnished the product 75 as a brown solid. The reaction was repeated on a 3.29 mmol scale and the products were combined. Total yield=1.39 g, 82%. $^1$H NMR (CDCl$_3$) δ 6.46 (1H, d, J=1.2 Hz), 6.15 (1H, d, J=0.8 Hz), 4.24 (2H, s), 3.13 (2H, q, J=7.2 Hz), 3.08 (6H, s), 1.37 (3H, t, J=7.2 Hz). Found: [M+H]=275.5.

4-((6-Bromo-2-methoxyquinolin-3-yl)methyl)-6-(ethylthio)-N,N-dimethylpyridin-2-amine (76)

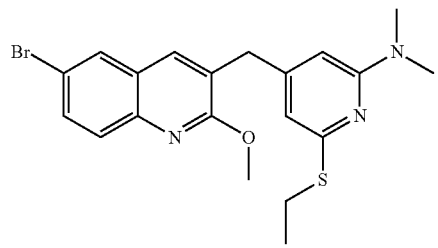

A mixture of 1 (1.42 g, 5.05 mmol), 75 (1.39 g, 5.05 mmol) and cesium carbonate (3.29 g, 10.09 mmol) in a mixture of toluene (14 mL) and DMF (7 mL) was purged with nitrogen. Pd(PPh$_3$)$_4$ (0.29 g) was added. The mixture was purged again with nitrogen and heated at 85° C. under nitrogen for 2.5 hours. The mixture was partitioned between water and EtOAc. The aqueous mixture was extracted with EtOAc (2×). The extract was washed with water, brine, dried (MgSO4) and concentrated to afford the crude product as an orange oil which was chromatographed using 2-5% Et$_2$O in hexanes as eluent to yield the product 76 as a light yellow solid. Recrystallisation from DCM/MeOH provided a white solid. Yield=1.25 g, 57%. $^1$H NMR (CDCl$_3$) δ 7.79 (1H, d, J=2.4 Hz), 7.70 (1H, d, J=8.8 Hz), 7.64 (1H, dd, J=2.4, 9.2 Hz), 7.56 (1H, s), 6.34 (1H, s), 6.06 (1H, s), 4.09 (3H, s), 3.86 (2H, s), 6.15 (2H, q, J=7.2 Hz), 3.07 (6H, s), 1.39 (3H, t, J=7.2 Hz). Found [M+H]=432.1.

2,5-Dimethoxynicotinaldehyde (77)

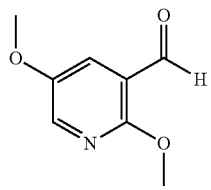

A mixture of 5-hydroxy-2-methoxynicotinaldehyde (Organic & Biomolecular Chemistry, 6(8), 1364-1376; 2008) (3.20 g, 20.89 mmol) and potassium carbonate (4.33 g, 31.34 mmol) in DMF (100 mL, anhydrous) was heated at 50° C. for 10 min. Methyl iodide (1.56 mL, 25.08 mmol) was then added and the mixture stirred at this temperature for 2 hours. The resultant solution was diluted with EtOAc and washed with brine three times. The organic layer was dried and evaporated to afford the product 77, identical to the compound reported in Organic & Biomolecular Chemistry, 6(8), 1364-1376; 2008. Yield=2.70 g, 77%.

(2,5-Dimethoxypyridin-3-yl)methanol (78)

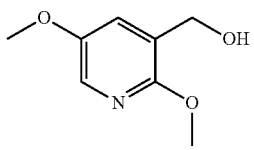

A mixture of 77 (2.70 g, 16.15 mmol) and sodium borohydride (1.22 g, 32.30 mmol) in methanol (60 mL, anhydrous) was stirred at r.t. for 1 h. The solvent was then removed and the residue partitioned between EtOAc and water. The organic layer was dried and evaporated to afford the product 78. Yield: 2.74 g, 99%. $^1$H NMR (CDCl$_3$) δ 7.72 (1H, d, J=3.0 Hz), 7.26 (1H, d, J=3.0 Hz), 4.62 (2H, d, J=6.3 Hz), 3.94 (3H, s), 3.81 (3H, s), 2.37 (1H, t, J=6.4 Hz).

3-(Bromomethyl)-2,5-dimethoxypyridine (79)

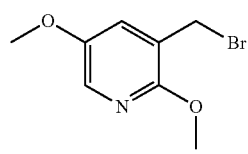

To a solution of 78 (2.65 g, 15.66 mmol) and triethylamine (3.27 mL, 23.49 mmol) in DCM (45 mL, anhydrous) at r.t. was added mesyl chloride (13.46 mL, 18.79 mmol) dropwise. After 15 min, the reaction was diluted with DCM (25 mL) and the organic layer washed with sat. NaHCO$_3$, dried and evaporated. The residue was dissolved in acetone (90 mL, anhydrous), lithium bromide (excess) was added, and the mixture heated at reflux for 30 min. The solution was then cooled and the solvent evaporated, and the residue partitioned between EtOAc and water. The aqueous layer was extracted twice with EtOAc and the organic layer was dried and evaporated to afford the product 79. Yield=3.08 g, 85%. $^1$H NMR (CDCl$_3$) δ 7.78 (1H, d, J=3.0 Hz), 7.25 (1H, d, J=3.6 Hz), 4.46 (2H, s), 3.97 (3H, s), 3.82 (3H, s).

6-Bromo-3-((2,5-dimethoxypyridin-3-yl)methyl)-2-methoxyquinoline (80)

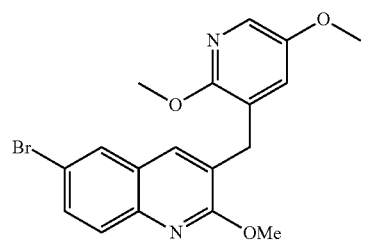

A mixture of 1 (3.40 g, 12.06 mmol), 79 (3.08 g, 13.27 mmol) and cesium carbonate (7.86 g, 24.12 mmol) in toluene (60 mL, anhydrous) and DMF (30 mL, anhydrous) was purged with nitrogen. Pd(PPh$_3$)$_4$ (0.057 g, 0.48 mmol) was then added, the mixture purged with nitrogen then heated to 80° C. under nitrogen for 4 hours. The reaction was partitioned between EtOAc and water and the organic fraction was dried and evaporated. Column chromatography (19:1 hexanes/EtOAc) gave the product 80. Yield=3.60 g, 69%. $^1$H NMR (CDCl$_3$) δ 7.77 (1H, d, J=2.2 Hz), 7.71 (1H, d, J=3.0 Hz), 7.68 (1H, d, J=8.9 Hz), 7.61 (1H, dd, J=2.2, 8.9 Hz), 7.55 (1H, s), 7.04 (1H, d, J=3.0 Hz), 4.07 (3H, s), 3.94 (2H, s), 3.90 (3H, s), 3.78 (3H, s). Found: [M+H]=389.8.

2,6-Dimethoxy-3-((triisopropylsilyl)oxy)pyridine (81)

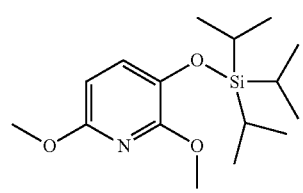

To a mixture of 57 (8.05 g, 51.9 mmol) and imidazole (7.42 g, 108.99 mmol) in DMF (130 mL) at r.t. was added triisopropylsilyl chloride (13.33 mL, 62.23 mmol), and the resultant mixture stirred at r.t. for 2 hours. The solution was then partitioned between EtOAc and water, and the aqueous layer extracted three times. The combined organic layers were washed with brine three times, dried and evaporated. Column chromatography with 19:1 hexanes/EtOAc afforded the product 81. Yield: 15.59 g, 96%. $^1$H NMR (CDCl$_3$) δ 7.07 (1H, d, J=8.2 Hz), 6.13 (1H, d, J=8.2 Hz), 3.92 (3H, s), 3.86 (3H, s), 1.27-1.18 (3H, m), 1.08 (18H, d, J=7.1 Hz). Found: [M+H]=312.8.

2,6-Dimethoxy-5-((triisopropylsilyl)oxy)nicotinaldehyde (82)

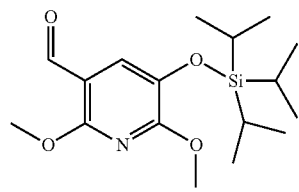

To a solution of 81 (8.00 g, 25.69 mmol) and N,N-diisopropylamine (0.18 mL, 1.28 mmol) in THF (100 mL, dist. Na) at −40° C. under nitrogen was added n-BuLi (15.41 mL, 30.83 mmol) dropwise. The resultant solution was stirred at −40° C. for 5 min, and then warmed to 0° C. and stirred at this temperature for a further 3 hours. The solution was then again cooled to −40° C., and formylpiperidine (4.28 mL, 38.54 mmol) was added dropwise, and the mixture stirred at r.t. for another 1 hour. Acetic acid (8 mL) was added and the solvent was removed in vacuo. The resultant mixture was partitioned between EtOAc and water, and the organic fraction dried and evaporated. Column chromatography with 49:1 hexanes/EtOAc afforded the product 82. Yield=7.55 g, 87%. $^1$H NMR (CDCl$_3$) δ 10.17 (1H, s), 7.51 (1H, s), 4.02 (3H, s), 4.01 (3H, s), 1.30-1.19 (3H, m), 1.08 (18H, d, J=7.3 Hz). Found: [M−CHO]$^+$=312.8.

5-Hydroxy-2,6-dimethoxynicotinaldehyde (83)

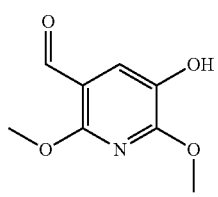

Tetrabutylammonium fluoride in THF (1N, 33.36 mL, 33.36 mmol) was added to a solution of 82 (7.55 g, 22.24 mmol) in THF (35 mL, dist. Na) at 0° C. The reaction was then warmed to r.t. and stirred for 4 hours. The solvent was removed and the residue partitioned between EtOAc and water. The aqueous layer was extracted with EtOAc three times, and the organic layer dried and evaporated. Column chromatography with DCM followed by 3:1 DCM/EtOAc afforded the product 83. Yield=3.15 g, 77%. $^1$H NMR (CDCl$_3$) δ 10.20 (1H, s), 7.59 (1H, s), 5.15-4.80 (1H, br s), 4.10 (3H, s), 4.01 (3H, s).

2,5,6-Trimethoxynicotinaldehyde (84)

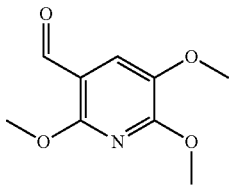

A mixture of 83 (3.15 g, 17.20 mmol) and potassium carbonate (3.57 g, 25.80 mmol) in DMF (80 mL, anhydrous) was heated at 50° C. for 10 min. Methyl iodide (1.29 mL, 20.64 mmol) was then added and the mixture stirred at this temperature for 2 hours. The resultant solution was diluted with EtOAc and washed with brine three times. The organic layer was dried and evaporated to afford the product 84. Yield=3.39 g, 100%. $^1$H NMR (CDCl$_3$) δ 10.21 (1H, 7.53 (1H, s), 4.10 (3H, s), 4.02 (3H, s), 3.87 (3H, s).

(6-Bromo-2-methoxyquinolin-3-yl)(2,5,6-trimethoxypyridin-3-yl)methanol (85)

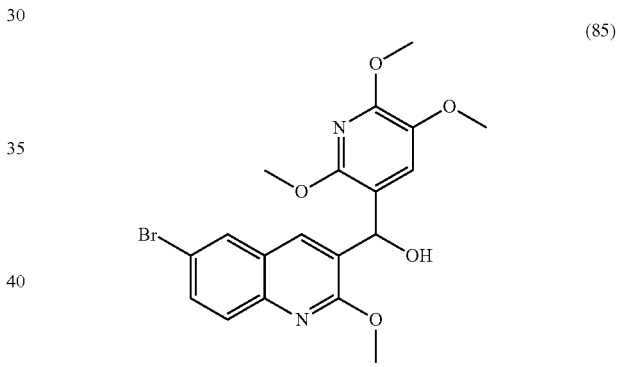

A solution of 2,2,6,6-tetramethylpiperidine (3.59 mL, 21.03 mmol) in THF (40 mL, dist. Na) was cooled to −40° C., n-BuLi (10.52 mL, 21.03 mmol) was added and the solution was stirred at −40° C. for 15 min, then cooled to −78° C. A solution of 6-bromo-2-methoxyquinoline (17.53 mmol) in THF (40 mL, dist. Na) was added dropwise, the orange solution was stirred at −78° C. for 1.5 hours, then a solution of 84 (3.42 g, 17.53 mmol) in THF (40 mL, dist. Na) was added. The mixture was stirred at −78° C. for 2 hours, then acetic acid (2.5 mL) was added and the solution was allowed to warm to r.t. The solvent was removed and the residue partitioned between EtOAc and water, and the organic fraction was dried and evaporated. Column chromatography with 9:1 hexanes/EtOAc followed by 4:1 hexanes/EtOAc gave the product as a white solid. Yield=5.50 g, 72%. $^1$H NMR (CDCl$_3$) δ 7.85 (1H, d, J=2.1 Hz), 7.79 (1H, s), 7.70 (1H, d, J=8.9 Hz), 7.65 (1H, dd, J=2.1, 8.9 Hz), 7.15 (1H, s), 6.14 (1H, d, J=5.2 Hz), 4.08 (3H, s), 4.02 (3H, s), 3.90 (3H, s), 3.78 (3H, s), 3.48 (1H, d, J=5.4 Hz). Found: [M+H]=436.1.

6-Bromo-2-methoxy-3-((2,5,6-trimethoxypyridin-3-yl)methyl)quinolone (86)

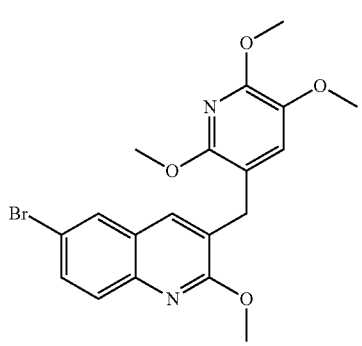

Trifluoroacetic acid (11.30 mL, 148.2 mmol) and triethylsilane (17.76 mL, 111.2 mmol) were added sequentially to a solution of 85 (5.35 g, 12.35 mmol) in DCM (125 mL) and the solution was stirred for 1 hour at r.t., then ice water was added. The solution was partitioned between sat. aq. NaHCO$_3$ and DCM and the aqueous fraction was extracted with DCM. The organic fractions were combined, dried and evaporated. Column chromatography with 9:1 hexanes/EtOAc gave the product 86 as a white solid. Yield=4.45 g, 86%. $^1$H NMR (CDCl$_3$) δ 7.76 (1H, d, J=2.2 Hz), 7.68 (1H, d, J=8.9 Hz), 7.60 (1H, dd, J=2.2, 8.4 Hz), 7.49 (1H, s), 7.05 (1H, s), 4.09 (3H, s), 4.01 (3H, s), 3.89 (5H, s), 3.79 (3H, s). Found: [M+H]=419.0.

Ethyl 2-(dimethylamino)-6-methoxyisonicotinate (87)

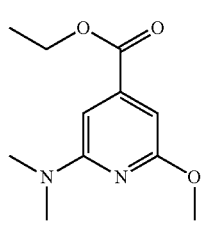

To a glass tube was charged ethyl 2-chloro-6-methoxyisonicotinate (WO 2009/024905) (4.01 g, 18.60 mmol), diphenylphosphino-1,1'-binaphthol (1.85 g, 2.976 mmol) and cesium carbonate (8.49 g, 26.10 mmol) under continuous nitrogen flow. Anhydrous toluene (72 mL) was added. The mixture was purged with nitrogen for 5 min. Palladium acetate (0.33 g, 1.488 mmol) was added, the mixture was purged again with nitrogen. Dimethylamine in tetrahydrofuran (2N, 11.2 mL, 22.3 mmol) was added and the mixture was sealed in the tube and heated at 80° C. for 19.5 hours. The mixture was filtered through Celite, washing with EtOAc. The filtrate was concentrated in vacuo to yield the crude product as a dark red liquid. Flash column chromatography of the crude product using 3-10% Et$_2$O in hexanes provided the product 87 as a yellow crystalline solid. Yield=3.36 g, 80%. $^1$H NMR (CDCl$_3$) δ 6.61 (1H, d, J=0.96 Hz), 6.52 (1H, d, J=0.88 Hz), 4.35 (2H, q, J=7.1 Hz), 3.90 (3H, s), 3.1 (6H, s), 1.38 (3H, t, J=7.2 Hz). Found: [M+H]=225.5.

(2-(Dimethylamino)-6-methoxypyridin-4-yl)methanol (88)

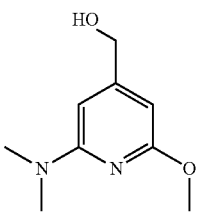

To a solution of 87 (3.31 g, 14.8 mmol) in freshly distilled THF (70 mL) was added at 2° C. under nitrogen lithium aluminium hydride (0.73 g, 19.3 mmol) in 3 batches. The mixture was stirred at 2° C. for 10 min then at r.t. for 1 hour. The mixture was quenched cautiously with water at 2° C. until gas evolution ceased. 1M NaOH (30 mL) was added and the mixture was stirred for 1 hour, then the aqueous mixture was diluted in water and extracted with EtOAc (3×). The combined organic extract was washed with brine, dried (Na$_2$SO$_4$) and concentrated to give the product 88 as a light-yellow oil, which was used without further purification. Yield=2.69 g, >99%. $^1$H NMR (CDCl$_3$) δ 6.05 (1H, d, J=0.4 Hz), 5.97 (1H, d, J=0.4 Hz), 4.59 (2H, d, J=4.8 Hz), 3.88 (3H, s), 3.06 (6H, s), 1.70 (1H, t, J=5.6 Hz).

4-(Bromomethyl)-6-methoxy-N,N-dimethylpyridin-2-amine (89)

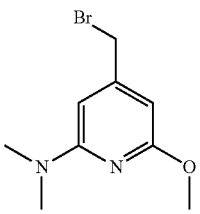

To a solution of 88 (3.30 g, 18.1 mmol) in anhydrous DCM (54 mL) was added at 2° C. under nitrogen triethylamine (3.8 mL, 27.2 mmol) dropwise, followed by mesyl chloride (1.7 mL, 21.7 mmol). The mixture was stirred from 2° C. for 10 min, then at r.t. for 2 hours. The mixture was quenched with sat. aq. NaHCO$_3$ solution. The aqueous mixture was extracted with DCM (2×) and the combined extract was washed with brine, dried (MgSO$_4$) and concentrated to afford the crude product as a beige solid. The crude intermediate was dissolved in acetone (60 mL). Lithium bromide (1.53 g, 36.2 mmol) was added and the suspension was refluxed for 2 hours. Flash chromatography using a mixture of 3-5% Et$_2$O in hexanes as eluent gave the product 89 as a mobile yellow oil. Yield=3.78 g, 85%. $^1$H NMR (CDCl$_3$) δ 6.02 (1H, d, J=0.8 Hz), 6.00 (1H, d, J=0.4 Hz), 4.27 (2H, s), 3.88 (3H, s), 3.06 (6H, s).

4-((6-Bromo-2-methoxyquinolin-3-yl)methyl)-6-methoxy-N,N-dimethylpyridin-2-amine (90)

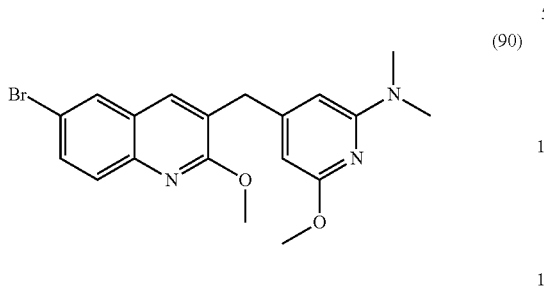

(90)

A mixture of 1 (4.34 g, 15.4 mmol), 89 (3.77 g, 115.4 mmol) and cesium carbonate (10.03 g, 30.8 mmol) in a mixture of toluene (40 mL) and DMF (20 mL) was purged with nitrogen. Pd(PPh$_3$)$_4$ (0.890 g, 0.774 mmol) was added and the mixture was purged again with nitrogen and heated at 85° C. under nitrogen for 3.5 hours. The mixture was partitioned between water and EtOAc and the mixture was extracted with EtOAc (2×). The extract was washed with water (2×), brine, dried (MgSO$_4$) and concentrated to afford the crude product as a brown solid which was chromatographed using 3-10% Et$_2$O in hexanes as eluent to yield the product 90 as a light yellow solid. Yield=3.69 g, 60%. $^1$H NMR (CDCl$_3$) δ 7.76 (1H, d, J=2 Hz), 7.68 (1H, d, J=8.8 Hz), 7.61 (1H, dd, J=2, 8.8 Hz), 7.55 (1H, s), 5.92 (1H, s), 5.86 (1H, s), 4.07 (3H, s), 3.87 (5H, s), 3.04 (6H, s). Found: [M+H]=402.0.

2-(Dimethylamino)-6-methoxyisonicotinic Acid (91)

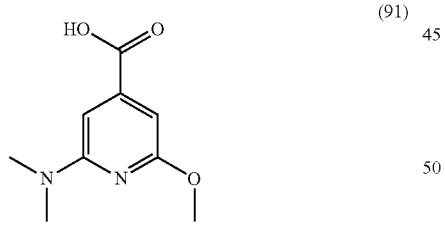

(91)

To a solution of 87 (6.77 g, 30.2 mmol) in EtOH (150 mL) was added at r.t. NaOH (30.2 mL, 60.4 mmol). The mixture was stirred at r.t. for 2 hours and then concentrated in vacuo to a light yellow solution, which was further diluted in water. The aqueous mixture was acidified to pH with 2M HCl, when bright yellow solids precipitated out. These were collected by filtration, washed with water and dried under ambient conditions to yield 91 as a bright yellow powder. Yield=5.60 g, 95%. $^1$H NMR (DMSO-d$_6$) δ 13.25 (1H, br s), 6.54 (1H, d, J=0.9 Hz), 6.33 (1H, d, J=0.8 Hz), 3.82 (3H, s), 3.04 (6H, s).

2-(Dimethylamino)-N,6-dimethoxy-N-methylisonicotinamide (92)

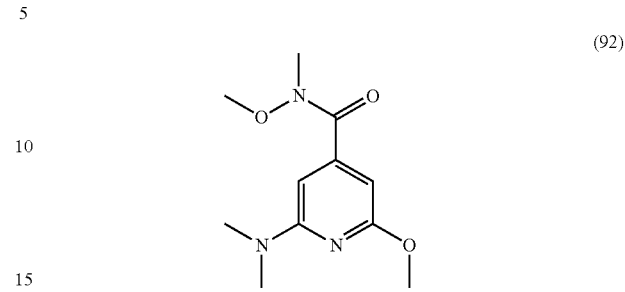

(92)

To a suspension of 91 (0.75 g, 3.81 mmol) in anhydrous DMF (22 mL) was added triethylamine (1.6 mL, 11.4 mmol), the mixture was cooled to 2° C. Ethyl chloroformate (0.62 mL, 4.19 mmol) was added dropwise and fumes were evolved. The mixture was stirred from 2° C. to r.t. for 2.5 hours and then treated with N,O-dimethylhydroxylamine hydrochloride (0.557 g, 5.71 mmol) at 2° C. under nitrogen. The mixture was stirred to r.t. overnight. The mixture was diluted in water, and the aqueous mixture was extracted with EtOAc (4×) and the organic extract was washed with water, brine, dried (MgSO$_4$) and concentrated to afford the crude product. This was purified by repeated flash chromatography eluting with mixtures of 4:1 then 2:1 hexanes/EtOAc as eluent, yielding the product 92 as a yellow oil. Yield=0.70 g, 77%. $^1$H NMR (CDCl$_3$) δ 6.17 (1H, s), 6.11 (1H, s), 3.89 (3H, s), 3.62 (3H, br s), 3.31 (3H, s), 3.08 (6H, s).

3-(Dimethylamino)-1-(2-(dimethylamino)-6-methoxypyridin-4-yl)propan-1-one (93)

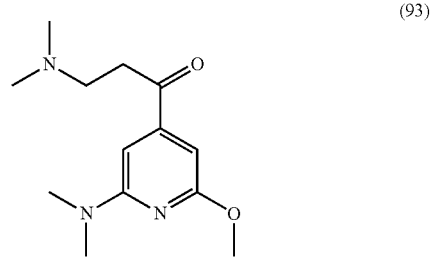

(93)

To a solution of 92 (2.53 g, 10.60 mmol) in freshly distilled THF (96 mL) was added at 2° C. under nitrogen vinylmagnesium bromide in THF (1N, 21.1 mL, 21.10 mmol) dropwise. The mixture was stirred at 2° C. for 20 min, then at r.t. for 75 min. Dimethylamine in THF (2N, 21.1 mL, 42.20 mmol) was added, followed by water (40 mL). The mixture was stirred at r.t. for 1 hour. The aqueous mixture was partitioned between water and EtOAc and the organic phase was separated and the aqueous phase was extracted with EtOAc (2×). The organic extract was washed with brine, dried (Na$_2$SO$_4$) and concentrated in vacuo to give the crude product as a yellow-brown oil. Flash chromatography of the product using 2-8% MeOH in DCM as eluent gave 93 as a yellow oil which crystallised at −20° C. Yield=1.91 g, 72%. $^1$H NMR (CDCl$_3$) δ 6.47 (1H, d, J=1.0 Hz), 6.39 (1H, d, J=1.0 Hz), 3.91 (3H, s), 3.10 (6H, s), 3.06 (2H, t, J=7.0 Hz), 2.72 (2H, t, J=7.1 Hz), 2.27 (6H, s).

Ethyl 2-(dimethylamino)-6-ethoxyisonicotinate (94)

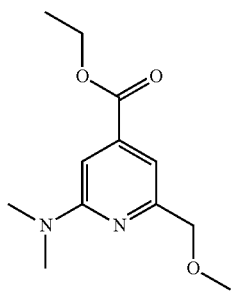

To a glass tube was charged ethyl 2-chloro-6-ethoxyisonicotinate (WO 2010/080864) (1.00 g, 4.37 mmol), diphenylphosphino-1,1'-binaphthol (0.44 g, 0.70 mmol) and cesium carbonate (1.99 g, 6.12 mmol) under continuous nitrogen flow. Anhydrous toluene (24 mL) was added. The mixture was purged with nitrogen 5 min. Palladium acetate (0.079 g, 0.35 mmol) was added, the mixture was purged again with nitrogen. Dimethylamine in THF (2N, 2.6 mL, 5.246 mmol) was added and the mixture was sealed in the tube and heated at 80° C. overnight. The mixture was filtered through Celite, washing with EtOAc and the filtrate was concentrated in vacuo to yield the crude product as a dark red liquid. Flash chromatography using 2-4% Et$_2$O in hexanes gave the product 94 as a light yellow oil. Yield=0.85 g, 82%. $^1$H NMR (CDCl$_3$) δ 6.60 (1H, d, J=0.8 Hz), 6.51 (1H, d, J=0.8 Hz), 4.35 (2H, q, J=7.0 Hz), 4.33 (2H, q, J=7.1 Hz), 3.09 (6H, s), 1.38 (31-1, t, J=7.2 Hz), 1.37 (3H, t, J=7.2 Hz).

4-(Bromomethyl)-6-ethoxy-N,N-dimethylpyridin-2-amine (95)

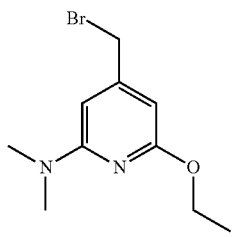

To a solution of 94 (4.40 g, 18.50 mmol) in freshly distilled THF (90 mL) was added at −78° C. under nitrogen lithium aluminium hydride (0.91 g, 24.0 mmol) in 3 batches. The mixture was stirred at −78° C. for 15 min then at r.t. for 1 hour. The mixture was quenched cautiously with water at 2° C. until gas evolution ceased. 1M NaOH (32 mL) was added and the mixture was stirred for 1 hour, then the aqueous mixture was diluted with water and extracted with EtOAc (3×). The combined organic extract was washed with brine, dried (Na$_2$SO$_4$) and concentrated to give the product, which was purified via flash chromatography eluting with mixtures of 6:1 then 4:1 hexanes/EtOAc to give the alcohol intermediate as a light yellow oil. Yield=3.27 g, 90%. The material was used directly in the next step without further characterisation.

To a solution of the alcohol intermediate (3.27 g, 16.7 mmol) in anhydrous DCM (50 mL) was added at 2° C. under nitrogen triethylamine (3.5 mL, 25.0 mmol) dropwise, followed by mesyl chloride (1.6 mL, 20.0 mmol). The mixture was stirred from 2° C. for 10 min, then at r.t. for 0.5 hour. The mixture was quenched with sat. aq. NaHCO$_3$ solution. The aqueous mixture was extracted with DCM (3×) and the combined extract was washed with brine, dried and concentrated to afford the crude product as a brown oil. This was diluted in acetone (60 mL), lithium bromide (1.42 g) was added. And the suspension was refluxed for 2 hours. Flash chromatography using a mixture of 2-3% Et$_2$O in hexanes as eluent gave the product 95 as a mobile yellow oil. Yield=3.84 g, 89%. $^1$H NMR (CDCl$_3$) δ 6.011 (1H, s), 5.99 (1H, s), 4.30 (2H, q, J=6.8 Hz), 4.27 (2H, s), 3.05 (6H, s), 1.37 (3H, t, J=7.2 Hz).

4-((6-Bromo-2-methoxyquinolin-3-yl)methyl)-6-ethoxy-N,N-dimethylpyridin-2-amine (96)

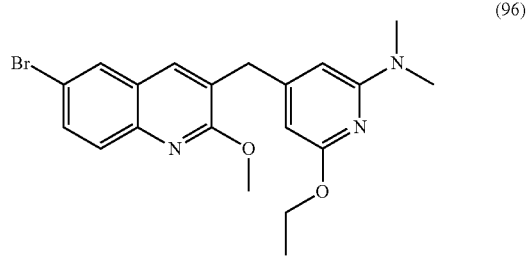 [SMILES: CCSc1cc(Cc2cc3cc(Br)ccc3nc2OC)cc(N(C)C)n1]

A mixture of 1 (4.13 g, 14.7 mmol), 95 (3.80 g, 14.7 mmol) and cesium carbonate (9.58 g, 29.4 mmol) in a mixture of toluene (40 mL) and DMF (20 mL) was purged with nitrogen. Pd(PPh$_3$)$_4$ (0.68 g) was added. The mixture was purged again with nitrogen and heated at 85° C. under nitrogen for 3 hours. The mixture was partitioned between water and EtOAc and the aqueous mixture was extracted with EtOAc (2×). The extract was washed with water (2×), brine, dried and concentrated to afford the crude product as a brown oil. This was chromatographed using 3-10% Et$_2$O in hexanes as eluent to yield the product 96 as a yellow solid (3.83 g), which was triturated in diethyl ether to afford the clean product as a pale yellow solid. Yield=3.51 g, 57%. $^1$H NMR (CDCl$_3$) δ 7.76 (1H, d, J=2.2 Hz), 7.68 (1H, d, J=8.8 Hz), 7.61 (1H, dd, J=2.2, 8.8 Hz), 7.55 (1H, s), 5.91 (1H, s), 5.84 (1H, s), 4.30 (2H, q, J=7.1 Hz), 4.07 (3H, s), 3.87 (2H, s), 3.03 (6H, s), 1.36 (3H, t, J=7.1 Hz).

5-Isopropoxy-2-methoxynicotinaldehyde (97)

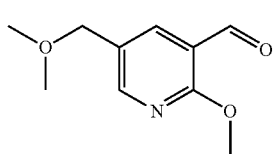

A mixture of 5-hydroxy-2-methoxynicotinaldehyde (Organic & Biomolecular Chemistry, 6(8), 1364-1376; 2008) (1.00 g, 6.53 mmol) and potassium carbonate (1.35 g, 9.80 mmol) in DMF (30 mL, anhydrous) was heated at 50° C. for 10 min Isopropyl iodide (0.78 mL, 7.84 mmol) was then added and the mixture stirred at this temperature for 2 hours. The resultant solution was diluted with EtOAc and washed with brine three times. The organic layer was dried and evaporated to afford the product 97. Yield=0.90 g, 71%. $^1$H NMR (CDCl$_3$) δ 10.34 (1H, s), 8.07 (1H, d, J=3.2 Hz), 7.66 (1H, d, J=3.2 Hz), 4.48 (1H, sp, J=6.1 Hz), 4.03 (3H, s), 1.33 (6H, d, J=4.8 Hz).

(5-Isopropoxy-2-methoxypyridin-3-yl)methanol (98)

(98)

A mixture of 97 (0.90 g, 4.61 mmol) and sodium borohydride (0.35 g, 9.22 mmol) in MeOH (15 mL, anhydrous) was stirred at r.t. for 1 hour. The solvent was then removed and the residue partitioned between EtOAc and water. The organic layer was dried and evaporated. Column chromatography with 9:1 hexanes/EtOAc afforded the product 98. Yield=0.68 g, 75%. $^1$H NMR (CDCl$_3$) δ 7.72 (1H, s), 7.25 (1H, d, J=3 Hz), 4.61 (2H, s), 4.42 (1H, sp), 3.93 (3H, s), 2.92-2.19 (1H, br s), 1.32 (6H, d, J=6.1 Hz).

3-(Bromomethyl)-5-isopropoxy-2-methoxypyridine (99)

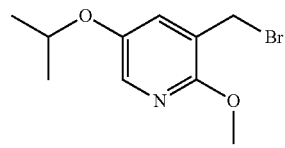

(99)

To a solution of 98 (0.68 g, 3.45 mmol) and triethylamine (0.72 mL, 5.18 mmol) in DCM (10 mL, anhydrous) at r.t. was added mesyl chloride (0.32 mL, 4.14 mmol) dropwise. After 15 min, the reaction was diluted with DCM (10 mL) and the organic layer washed with sat. NaHCO$_3$, dried and evaporated. The residue was redissolved in acetone (20 mL, anhydrous), lithium bromide (excess) added, and the mixture heated at reflux for 30 min. The solution was then cooled and the solvent evaporated, and the residue partitioned between EtOAc and water. The aqueous layer was extracted twice with EtOAc and the organic layer was dried and evaporated to afford the product 99. Yield=0.70 g, 78%. $^1$H NMR (CDCl$_3$) δ 7.76 (1H, dd, J=2.6, 3.4 Hz), 7.25 (1H, dd, J=2.4, 2.4 Hz), 4.5 (2H, d, J=2.2 Hz), 4.42 (1H, sp, J=2.6, 6.0 Hz), 3.96 (3H, d, J=2.9 Hz), 1.32 (6H, dd, J=3.0, 6.1 Hz).

6-Bromo-3-((5-isopropoxy-2-methoxypyridin-3-yl)methyl)-2-methoxyquinoline (100)

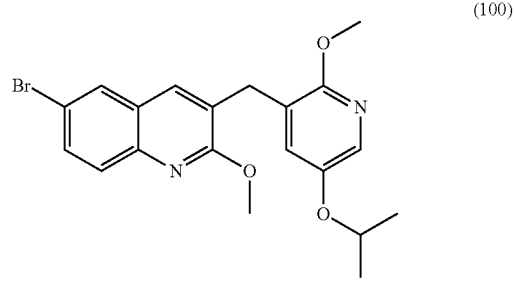 [SMILES: COc1ncc(OC(C)C)cc1Cc1cc2cc(Br)ccc2nc1OC]

(100)

A mixture of 1 (0.80 g, 2.82 mmol), 99 (0.70 g, 2.69 mmol) and cesium carbonate (1.75 g, 5.38 mmol) in toluene (10 mL, anhydrous) and DMF (5 mL, anhydrous) was purged with nitrogen. Pd(PPh$_3$)$_4$ (0.12 g, 0.11 mmol) was then added, and the mixture then heated to 80° C. under nitrogen for 4 hours. The reaction was partitioned between EtOAc and water and the organic fraction was dried and evaporated. Column chromatography (19:1 hexanes/EtOAc) gave the product 100. Yield=0.57 g, 48%. $^1$H NMR (CDCl$_3$) δ 7.77 (1H, d, J=2.2 Hz), 7.71 (1H, d, J=2.9 Hz), 7.69 (1H, d, J=8.9 Hz), 7.62 (1H, dd, J=2.2, 8.9 Hz), 7.56 (1H, s), 7.02 (1H, d, J=2.9 Hz), 4.38 (1H, sp, J=6.0 Hz), 4.08 (3H, s), 3.92 (2H, s), 3.90 (3H, s), 1.29 (6H, d, J=6.1 Hz).

1-(6-Bromo-2-methoxyquinolin-3-yl)-4-((2,4-dimethoxybenzyl)(methyl)amino)-2-(2,6-dimethoxypyridin-4-yl)-1-(3-fluorophenyl)butan-2-ol (101)

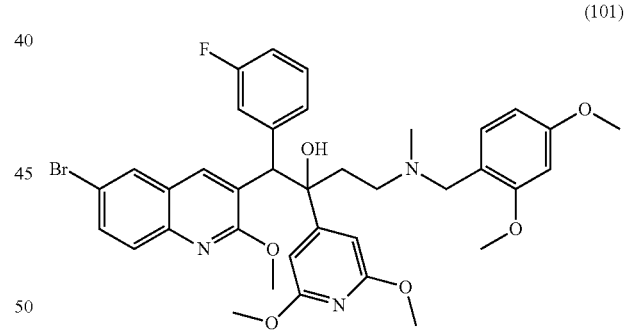

(101)

The product was prepared from 9 and 7 (using the General Coupling Procedure below). Flash chromatography of the crude product using mixtures of hexanes/EtOAc in increasing eluent strength provided a 1:1 mixture of diastereomers 101 as a light yellow foam (65%). $^1$H NMR (CDCl$_3$) δ 8.71 (1H, s), 8.69 (1H, s), 8.12 (1H, bs), 7.81 (2H, m), 7.65 (1H, d, J=8.9 Hz), 7.59 (1H, dd, J=2.2, 8.9 Hz), 7.53 (1H, dd, J=2.0, 8.8 Hz), 7.50 (1H, d, J=8.81 Hz), 7.43 (1H, dt, J=2.4, 10.5 Hz), 7.39 (1H, d, J=7.8 Hz), 7.25-7.17 (2H, m), 7.07 (1H, d, J=7.8 Hz), 7.0 (1H, d, J=8.0 Hz), 6.98-6.92 (2H, m), 6.87 (1H, dt, J=1.8, 8.4 Hz), 6.67 (1H, dt, J=1.8, 9.2 Hz), 6.55-6.31 (8H, m), 4.82 (1H, s), 4.71 (1H, s), 4.10 (3H, s), 3.89 (3H, s), 3.87 (3H, s), 3.85 (6H, s), 3.83 (3H, s), 3.82 (3H, s), 3.81 (3H, s), 3.79 (6H, s), 3.29-3.17 (4H, m), 2.46 (2H, br t, J=2.4 Hz), 2.16-2.02 (4H, m), 1.93 (3H, s), 1.91

(3H, s), 1.69 (1H, t, J=4.7 Hz), 1.58-1.50 (1H, m, partially obscured by water peak). One OH not evident. Found: [M+H]=720.1.

1-(6-Bromo-2-methoxyquinolin-3-yl)-2-(2,6-dimethoxypyridin-4-yl)-1-(3-fluorophenyl)-4-(methylamino)butan-2-ol (102)

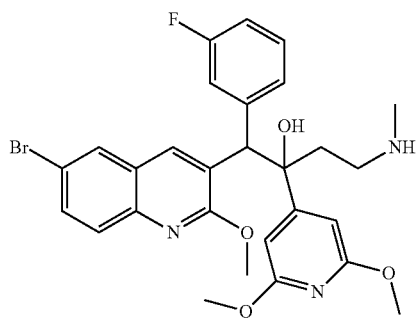

To a solution of 101 (2.50 g, 3.471 mmol) and in anhydrous DCM (80 mL) was added at 2° C. under nitrogen triethylamine (1.1 mL) and trifluoroacetic anhydride (0.97 mL) sequentially. The mixture was stirred at r.t. for 2 hours. The mixture was washed with sat. aq. NaHCO$_3$ (2×), dried (MgSO$_4$) and concentrated in vacuo to afford the crude trifluoroacetamide intermediate, which was dissolved in MeOH (55 mL). A solution of cesium carbonate (2.83 g, 8.678 mmol) in water (5.5 mL) was added. The resultant brown solution was stirred at r.t. for 10 min, then stored at 4° C. overnight. The mixture was subsequently diluted in water and extracted with EtOAc (3×). The combined extract was washed with brine, dried (MgSO$_4$) and concentrated in vacuo to furnish the crude product, which was purified by column chromatography using 0-5% MeOH in DCM as eluent. The product 102 was eluted as a 1:1 mixture of diastereomers. $^1$H NMR (CDCl$_3$) δ 8.66 (1H, s), 8.57 (1H, s), 7.89 (1H, d, J=2.1 Hz), 7.82 (1H, d, J=1.9 Hz), 7.67 (1H, d, J=8.9 Hz), 7.61 (1H, dd, J=2.1, 8.8 Hz), 7.53 (1H, dd, J=2.0, 8.9 Hz), 7.50 (1H, d, J=8.8 Hz), 7.38-7.31 (2H, m), 7.26-7.20 (2H, m), 7.11 (1H, d, J=7.8 Hz), 7.03-6.95 (1H, m), 6.90 (1H, dt, J=2.6, 8.5 Hz), 6.69 (1H, dt, J=2.6, 8.4 Hz), 6.47 (4H, bs), 4.88 (1H, s), 4.72 (1H, s), 4.12 (3H, s), 3.90 (3H, s), 3.87 (6H, s), 3.81 (6H, s), 2.67-2.58 (2H, m), 2.42-2.31 (2H, m), 2.25 (3H, s), 2.21 (3H, s), 1.89 (1H, br t, J=12.1 Hz), 1.84-1.78 (2H, m), 1.67 (1H, br d, J=14.8 Hz). Found: [M+H]=569.9.

2,4-Dichlorothiazole (103)

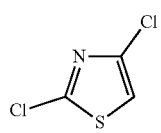

To a mixture of thiazolidine-2,4-dione (5.00 g, 42.69 mmol) in phosphorous oxychloride (25 mL) at 0° C. was added pyridine (3.80 mL, 46.96 mmol) dropwise. The mixture was then stirred at reflux for 3 hours, then cooled and poured onto ice-water. The aqueous layer was then extracted by DCM, and the combined organic layers dried and evaporated. Column chromatography with 19:1 hexanes/EtOAc afforded the product 103. Yield=0.94 g, 14%. $^1$H NMR (CDCl$_3$) δ 7.02 (1H, s). Found: [M+H]= 133.3.

6-Bromo-2-methoxyquinoline-3-carbaldehyde (104)

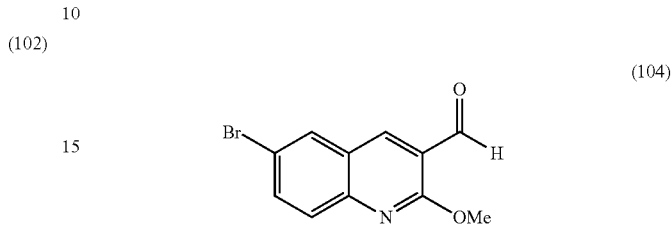

A solution of 2,2,6,6-tetramethylpiperidine (4.28 mL, 25.2 mmol) in THF (50 mL, dist. Na) was cooled to −40° C., n-BuLi (12.60 mL, 25.2 mmol) was added and the solution was stirred at −40° C. for 15 min, then cooled to −78° C. A solution of 6-bromo-2-methoxyquinoline (5.00 g, 21 mmol) in THF (50 mL, dist. Na) was added dropwise, the orange solution was stirred at −78° C. for 1.5 hours, then DMF (2.19 mL, 31.5 mmol) was added and the solution was warmed to r.t. Acetic acid (3 mL) was added and the solvent removed, and the residue partitioned between EtOAc and water, and the organic fraction was dried and evaporated. Column chromatography with 4:1 hexanes/DCM followed by 1:1 hexanes/DCM followed by 1:4 hexanes/DCM gave the product 104 as a white solid. Yield=3.00 g, 53%. $^1$H NMR (CDCl$_3$) δ 10.46 (1H, s), 8.49 (1H, s), 7.99 (1H, d, J=2.1 Hz), 7.79 (1H, dd, J=2.2, 8.9 Hz), 7.74 (1H, d, J=8.9 Hz), 4.18 (3H, s).

(6-Bromo-2-methoxyquinolin-3-yl)(2,4-dichlorothiazol-5-yl)methanol (105)

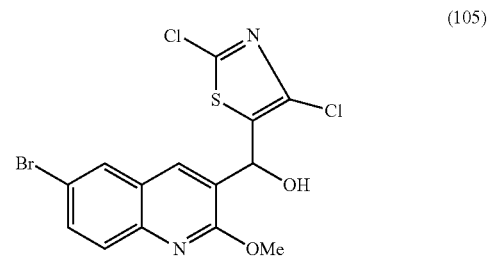 [SMILES: COc1nc2ccc(Br)cc2cc1C(O)c1sc(Cl)nc1Cl]

A solution of N,N-diisopropylamine (0.93 mL, 6.65 mmol) in THF (30 mL, dist. Na) was cooled to −40° C., n-BuLi (3.33 mL, 6.65 mmol) was added and the solution was stirred at −40° C. for 15 min, then cooled to −78° C. A solution of 103 (0.98 g, 6.043 mmol) in THF (20 mL, dist. Na) was added dropwise, the orange solution was stirred at −78° C. for 2 hours, then a solution of 104 (1.78 g, 6.043 mmol) in THF (20 mL, dist. Na) was added. The mixture was stirred at −78° C. for 2 hours, then water (20 mL) was added and the solution was allowed to warm to r.t. The solvent was removed and the residue partitioned between EtOAc and water, and the organic fraction was dried and evaporated. Column chromatography with 9:1 hexanes/EtOAc gave the product 105 as a white solid. Yield=1.98 g, 78%. ¹H NMR (CDCl₃) δ 7.92-7.87 (2H, m), 7.74-7.68 (2H, m), 6.25 (1H, dd, 0.8, 4.8 Hz), 4.11 (3H, s), 3.43 (1H, d, J=4.8 Hz). Found: [M+H]=421.9.

5-((6-Bromo-2-methoxyquinolin-3-yl)methyl)-2,4-dichlorothiazole (106)

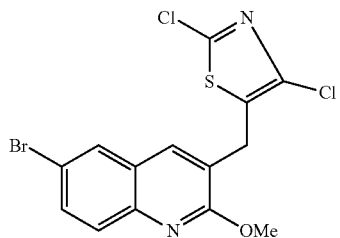

(106)

Trifluoroacetic acid (3.35 mL, 43.80 mmol) and triethylsilane (5.74 mL, 39.92 mmol) were added sequentially to a solution of 105 (1.84 g, 4.38 mmol) in DCM (50 mL), the solution was stirred for 3 hours at reflux, and then the solution was cooled and added to ice water. The solution was partitioned between sat. aq. NaHCO₃ and DCM and the aqueous fraction was extracted with DCM, the organic fractions were combined, dried and evaporated. Column chromatography with 19:1 hexanes/EtOAc gave the product 106. Yield=1.10 g, 62%. ¹H NMR (CDCl₃) δ 7.84 (1H, d, J=2.0 Hz), 7.75 (1H, s), 7.70 (1H, d, J=8.9 Hz), 7.66 (1H, dd, J=2.1, 8.8 Hz), 4.13 (2H, s), 4.12 (3H, s).

5-((6-Bromo-2-methoxyquinolin-3-yl)methyl)-4-chloro-2-methoxythiazole (107)

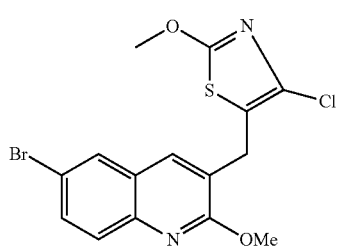

(107)

Sodium methoxide (0.20 g, 3.71 mmol) was added to a suspension of 106 (1.00 g, 2.78 mmol) in MeOH (50 mL, anhydrous), and the mixture stirred at reflux for 18 hours. The solution was then cooled and the solvent removed, and the residue partitioned between EtOAc and water. The organic fraction was dried and evaporated. Column chromatography with 19:1 hexanes/EtOAc gave the product 106. Yield=0.50 g, 45%. ¹H NMR (CDCl₃) δ 7.83 (1H, d, J=2.1 Hz), 7.70 (1H, d, J=3.6 Hz), 7.69 (1H, s), 7.64 (1H, dd, J=2.2, 9.0 Hz), 4.11 (3H, s), 4.05 (3H, s), 4.03 (2H, d, J=0.8 Hz). Found: [M+H]=399.1.

1-(6-Bromo-2-methoxyquinolin-3-yl)-1-(2,3-dihydrobenzo[b][1,4]dioxin-5-yl)-4-((2,4-dimethoxybenzyl)(methyl)amino)-2-(2,6-dimethoxypyridin-4-yl)butan-2-ol (108)

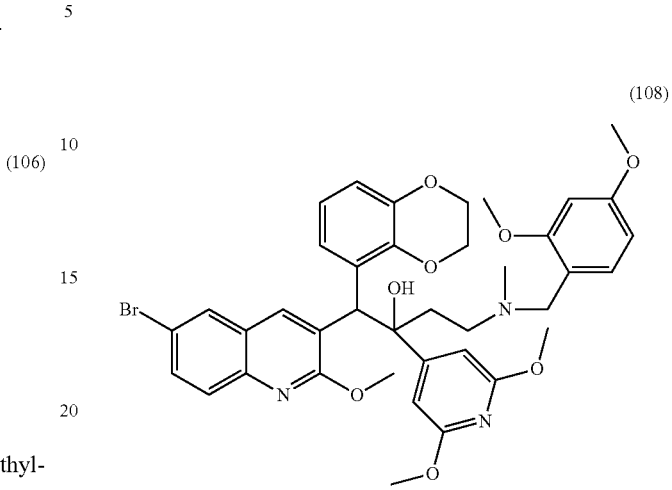

(108)

The product was prepared from 22 and 7 using the General Coupling Procedure below. Column chromatography with EtOAc:hexanes (1:1) gave fore fractions, then 108 as a mixture of isomers (66%), as a yellow foam. ¹H NMR (CDCl₃, 400 MHz) δ 8.69 (s, 1H), 8.46 (s, 1H), 7.93 (bs, 2H), 7.79 (d, J=2.0 Hz, 2H), 7.64 (d, J=8.9 Hz, 1H), 7.59-7.50 (m, 4H), 7.16 (dd, J=5.9, 3.6 Hz, 1H), 7.00 (d, J=8.6 Hz, 1H), 6.89 (d, J=8.3 Hz, 1H), 6.70-6.60 (m, 3H), 6.58-6.45 (m, 4H), 6.46-6.39 (m, 4H), 6.37-6.34 (m, 1H), 5.37 (s, 1H), 5.35 (s, 1H), 4.41-4.29 (m, 4H), 4.12 (s, 3H), 4.02-3.91 (m, 4H), 3.85 (s, 6H), 3.84 (s, 3H), 3.83 (s, 3H), 3.82-3.80 (m, 12H), 3.79 (s, 3H), 3.25-3.19 (m, 4H), 2.49-2.41 (m, 2H), 2.15-1.95 (m, 4H), 1.90 (s, 3H), 1.88 (s, 3H), 1.77-1.66 (m, 2H). Found: [M+H]=760.2.

1-(6-Bromo-2-methoxyquinolin-3-yl)-1-(2,3-dihydrobenzo[b][1,4]dioxin-5-yl)-2-(2,6-dimethoxypyridin-4-yl)-4-(methylamino)butan-2-ol (109)

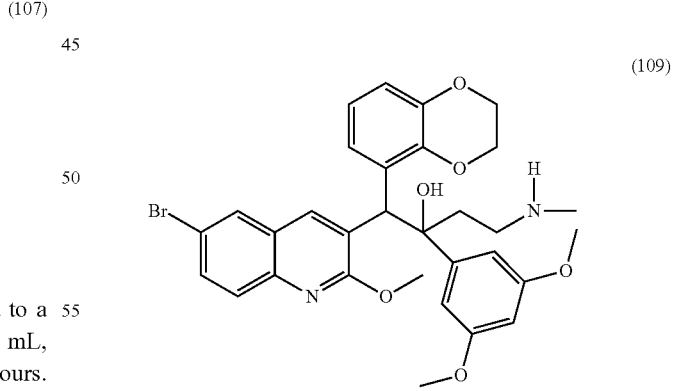

(109)

To a solution of 108 (4.13 g, 5.43 mmol) in DCM (100 mL) cooled to 0° C., was added triethylamine (1.67 mL, 11.9 mmol) and trifluoroacetic anhydride (1.51 mL, 10.9 mmol). The reaction mixture was stirred for 1 h, poured onto sat. aq. NaHCO₃ (150 mL), extracted with DCM (3×100 mL). The combined organic layers were dried over Na₂SO₄, filtered and concentrated under reduced pressure to obtain a yellowish residue. The crude material was dissolved in MeOH (150 mL) and cooled to −78° C. Cesium carbonate (4.42 g, 13.6 mmol) in water (3 mL) was added and the reaction mixture was stirred at −20° C. for 72 h. Reaction mixture was added water (150 mL) and extracted with EtOAc (3×100 mL). The combined organic layers washed with brine (100 mL), dried over $Na_2SO_4$, filtered and concentrated under reduced pressure to obtain a yellow residue. Column chromatography with EtOAc gave fore fractions, followed by racemate A of 109 (35%). Elution with EtOAc: MeOH (6:1) gave racemate B of 109 (28%).

Racemate A, white solid. $^1$H NMR ($CDCl_3$, 400 MHz) δ 8.33 (s, 1H), 7.84 (d, J=2.2 Hz, 1H), 7.67 (d, J=8.9 Hz, 1H), 7.62-7.58 (m, 2H), 6.63 (t, J=8.0 Hz, 1H), 6.58-6.51 (m, 3H), 5.40 (s, 1H), 4.14 (s, 3H), 4.03-3.95 (m, 4H), 3.87 (s, 6H), 2.57 (dt, J=12.5, 3.1 Hz, 1H), 2.31 (td, J=12.6, 2.1 Hz, 1H), 2.16 (s, 3H), 1.85 (dt, J=15.2, 3.3 Hz, 1H), 1.72 (td, J=12.7, 2.9 Hz, 1H). (no OH, NH observed) Found: [M+H]=610.1.

Racemate B, white solid. $^1$H NMR ($CDCl_3$, 400 MHz) δ 8.75 (s, 1H), 7.80 (d, J=1.3 Hz, 1H), 7.52-7.48 (m, 2H), 7.04 (dd, J=6.7, 2.7 Hz, 1H), 6.72-6.67 (m, 2H), 6.58 (bs, 2H), 5.37 (s, 1H), 4.42-4.28 (m, 4H), 3.84 (s, 3H), 3.83 (s, 6H), 2.59 (dt, J=12.4, 3.3 Hz, 1H), 2.34-2.89 (m, 1H), 2.21 (s, 3H), 1.85-1.80 (m, 2H). Found: [M+H]=610.1. (no OH, NH observed). Found: [M+H]=610.1.

1-(6-Bromo-2-methoxyquinolin-3-yl)-4-((2,4-dimethoxybenzyl)(methyl)amino)-2-(2,6-dimethoxypyridin-4-yl)-1-(5-methylthiophen-2-yl)butan-2-ol (110)

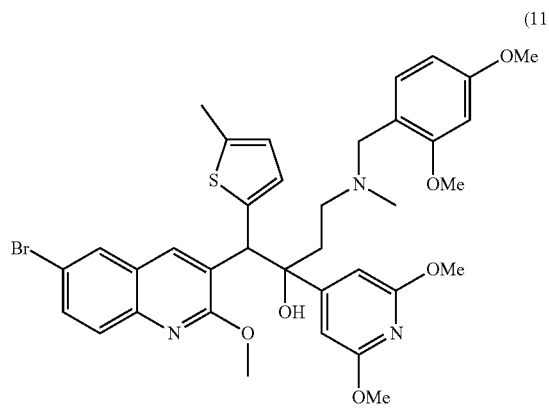

(110)

The product was prepared from 16 and 7 using the General Coupling Procedure below. Column chromatography with 9:1 hexanes:EtOAc eluted unreacted quinolone 16, while chromatography with 3:1 hexanes:EtOAc gave 110 (67%) as a white foam, as a mixture of diastereomers in a ratio of 1:0.95. $^1$H NMR ($CDCl_3$) δ 8.60 (s, 1H), 8.53 (s, 0.95H), 8.05-8.25 (bs, 1.7H), 7.81 (dd, J=11.6, 2.2 Hz, 2H), 7.66 (d, J=8.9 Hz, 1H), 7.59 (dd, J=8.8, 2.2 Hz, 1H), 7.47-7.54 (m, 1.95H), 7.09 (d, J=8.4 Hz, 1H), 6.90-6.95 (m, 1.95H), 6.48-6.55 (m, 3.8H), 6.38-6.40 (m, 4.1H), 6.35 (bs, 1.4H), 6.28-6.31 (m, 1.4H), 5.15 (s, 1H), 5.08 (s, 0.95H), 4.09-4.15 (m, 3.5H), 3.88-3.92 (m, 8.6H), 3.75 (bs, 2.7H), 2.40-2.54 (m, 2.4H), 2.39 (d, J=0.9 Hz, 3H), 2.29 (d, J=0.9 Hz, 3H), 2.08-2.19 (m, 1.6H), 2.04-2.07 (m, 3.7H), 1.79-1.89 (m, 4.2H), 1.59-1.59 (m, 2H plus additional water-obscured signals). Found: [M+H]=722.4.

1-(6-Bromo-2-methoxyquinolin-3-yl)-2-(2,6-dimethoxypyridin-4-yl)-4-(methylamino)-1-(5-methylthiophen-2-yl)butan-2-ol (111)

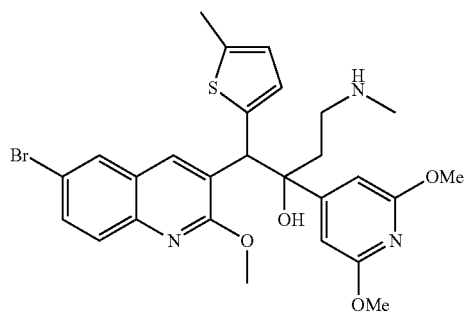

(111)

Triethylamine (0.63 mL, 4.5 mmol) and trifluoroacetic anhydride (0.54 mL, 4.1 mmol) were added sequentially to a solution of 110 (1.459 g, 2.02 mmol) in DMF (30 mL) at 0° C. The solution was stirred at r.t. for 1 h and then partitioned between DCM and sat. aq. $NaHCO_3$, the organic fraction was dried and evaporated to give an oil which was dissolved in MeOH (50 mL) and cooled to 0° C. $Cs_2CO_3$ (1.64 g, 5.03 mmol) in water (10 mL) was added and the mixture was stirred at 4° C. for 16 h. The mixture was diluted with water then extracted with EtOAc, column chromatography (EtOAc) gave 111 (0.876 g, 76%) as a white foam as a mixture diastereomers, in a ratio of 1:0.7. $^1$H NMR ($CDCl_3$) δ 8.54 (s, 1H), 8.51 (s, 0.7H), 7.89 (d, J=2.2 Hz, 1H), 7.81 (d, J=1.6 Hz, 0.7H), 7.68 (d, J=8.9 Hz, 1H), 7.62 (dd, J=8.8, 2.2 Hz, 1H), 7.47-7.53 (m, 1.5H), 6.91 (d, J=3.4 Hz, 0.7H), 6.51-6.56 (m, 3.6H), 6.38-6.43 (m, 1.4H), 6.29-6.33 (m, 1H), 5.18 (s, 1H), 5.09 (s, 0.7H), 4.13 (s, 3.8H), 3.92 (s, 2.1H), 3.91 (s, 5.6H), 3.78 (m, 4.2H), 2.67 (dt, J=9.2, 3.3 Hz, 1H), 2.55 (dt, J=12.6, 3.0 Hz, 1H), 2.34-2.45 (m, 3.1H), 2.18-2.33 (m, 6.7H), 2.16 (s, 3H), 1.67-1.82 (m, 2.6H), 1.42-1.62 (m, 4H plus additional water-obscured signals). Found: [M+H]=572.1.

1-(Benzofuran-7-yl)ethan-1-ol (112)

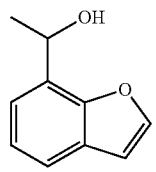

(112)

A solution of 7-bromobenzofuran (2.05 g, 10.4 mmol) in dry THF (20 mL) was prepared. Approximately 4 mL of this solution was added to a flask containing magnesium (0.75 g, 30.9 mmol) and the mixture was agitated until an exothermic reaction occurred. The remaining solution was added and the mixture was refluxed for 1 h, cooled and transferred by cannula to a dry flask. The solution was cooled to 0° C. and acetaldehyde (0.70 mL, 12.3 mmol) was added, the mixture was stirred at 0° C. for 1 h then partitioned between EtOAc and water, the organic fractions were dried and evaporated. Column chromatography with hexanes:DCM (1:1) eluted non polar impurities, elution with DCM gave 112 (1.21 g, 72%). $^1$H NMR (CDCl$_3$) δ 7.64 (d, J=2.2 Hz, 1H), 7.52 (dd, J=7.7, 1.2 Hz, 1H), 7.34 (bd, J=7.3 Hz, 1H), 7.24 (t, J=7.6 Hz, 1H), 6.79 (d, J=2.2 Hz, 1H), 5.38 (td, J=6.5, 4.8 Hz, 1H), 2.16 (d, J=4.8 Hz, 1H), 1.67 (d, J=6.5 Hz, 3H). Found: [M−H$_2$O]=145.

1-(Benzofuran-7-yl)ethan-1-one (113)

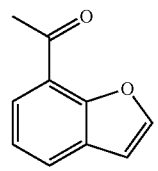

A mixture of 112 (1.16 g, 7.15 mmol) and MnO$_2$ (3.10 g, 35.6 mmol) in benzene (40 mL) was refluxed for 1 h, filtered through Celite and the solvent was evaporated. Column chromatography with hexanes:DCM (3:1 to 1:1) gave 113 (0.98 g, 86%). $^1$H NMR (CDCl$_3$) δ 7.92 (dd, J=7.6, 1.2 Hz, 1H), 7.81 (dd, J=7.7, 1.2 Hz, 1H), 7.75 (d, J=2.2 Hz, 1H), 7.33 (t, J=7.7 Hz, 1H), 6.87 (d, J=2.2 Hz, 1H), 2.86 (s, 3H). Found: [M+H]=161.1.

1-(Benzofuran-7-yl)-3-(dimethylamino)propan-1-one (114)

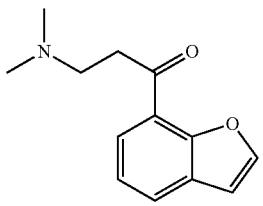

A mixture of 113 (4.95 g, 30.9 mmol), dimethylamine HCl (3.78 g, 46.4 mmol) and paraformaldehyde (1.39 g, 46.3 mmol) in EtOH (50 mL) and HCl (0.5 mL, 12 M, 6 mmol) was refluxed in a sealed tube for 18 h. The solvent was evaporated and the solid residue was triturated with Et$_2$O and filtered. The solid was washed with Et$_2$O, dissolved in water and basified with 2M NaOH, then extracted with EtOAc (3×100 mL). The organic fractions were dried and evaporated to give 114 (4.63 g, 69%). $^1$H NMR (CDCl$_3$) δ 7.93 (dd, J=7.6, 1.1 Hz, 1H), 7.81 (dd, J=7.7, 1.3 Hz, 1H), 7.74 (d, J=2.2 Hz, 1H), 7.33 (t, J=7.7 Hz, 1H), 6.87 (d, J=2.2 Hz, 1H), 3.46 (t, J=7.5 Hz, 2H), 2.82 (t, J=7.5 Hz, 2H), 2.32 (s, 6H). Found: [M+H]=218.2.

(5,6-Dimethoxypyridin-3-yl)methanol (115)

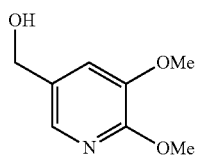

n-BuLi (4.90 mL, 2.0 M in cyclohexanes, 35.2 mmol) was added to a solution of 5-bromo-2,3-dimethoxypyridine (7.00 g, 32.1 mmol) in dry THF (100 mL) at −35° C., the cream coloured precipitate was stirred at −35° C. for 0.5 h then DMF (4.90 mL, 63.7 mmol) was added. The mixture was stirred at −35° C. for 1 h, then quenched with water and partitioned between EtOAc and water, the organic fraction was dried and evaporated. The crude aldehyde was dissolved in MeOH (50 mL) and cooled to −40° C., NaBH$_4$ (1.20 g, 32 mmol) was added and the mixture was stirred at −40° C. for 1 h and then quenched with water. The mixture was partitioned between EtOAc and water, the organic fractions were dried and evaporated. Column chromatography using hexanes:EtOAc (2:1) gave 115 (4.02 g, 74%). $^1$H NMR (CDCl$_3$) δ 7.67 (d, J=1.9 Hz, 1H), 7.13 (d, J=1.9 Hz, 1H), 4.63 (d, J=5.4 Hz, 2H), 4.02 (s, 3H), 3.90 (s, 3H), 1.77 (t, J=5.4 Hz, 1H). Found: [M+H]=170.2.

(5-Bromomethyl)-2,3-dimethoxypyridine (116)

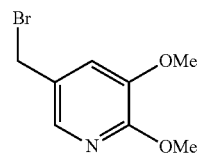

A solution of 115 (3.98 g, 23.6 mmol) in DCM (anhydrous, 80 mL) at 0° C. was treated with triethylamine (6.6 mL, 47.4 mmol) and then mesyl chloride (2.73 mL, 35.3 mmol), the mixture was stirred at 0° C. for 1 h and then partitioned between DCM and water. The organic fraction was dried and evaporated and the residue was dissolved in acetone (100 mL), LiBr (117 mmol) was added and the mixture was refluxed for 1 h and then evaporated. The residue was partitioned between DCM and water; the organic fraction was dried and evaporated. Column chromatography (DCM) gave 116 (3.36 g, 61%) which was contaminated with the corresponding chloro derivative (0.30 g, 7%). $^1$H NMR (CDCl$_3$) δ 7.73 (d, J=2.0 Hz, 1H), 7.07 (d, J=2.0 Hz, 1H), 4.47 (s, 2H), 4.02 (s, 3H), 3.90 (s, 3H). Found: [M−H]=232.4.

6-Bromo-3-((5,6-dimethoxypyridin-3-yl)methyl)-2-methoxyquinoline (117)

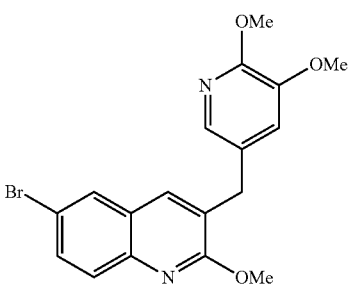

A mixture of 1 (4.02 g, 14.3 mmol), 116 (3.34 g, 14.4 mmol) and Cs$_2$CO$_3$ (9.3 g, 28.5 mmol) in toluene (80 mL, anhydrous) and DMF (40 mL, anhydrous) was purged with nitrogen. Pd(PPh$_3$)$_4$ (0.33 g, 0.3 mmol) was added, the mixture was purged with nitrogen, then heated to 80° C. under nitrogen for 4 h. The reaction was partitioned between EtOAc and water and the organic fraction was dried and evaporated. Column chromatography (95:5 DCM:EtOAc) gave the product which was recrystallized from MeOH to give 117 (3.85 g, 69%). $^1$H NMR (CDCl$_3$) δ 7.77 (d, J=2.2 Hz, 1H), 7.70 (d, J=8.9 Hz, 1H), 7.65 (d, J=1.9 Hz, 1H), 7.63 (dd, J=8.9, 2.2 Hz, 1H), 7.52 (s, 1H), 6.92 (d, J=1.9 Hz, 1H), 4.09 (s, 3H), 4.02 (s, 3H), 3.95 (s, 2H), 3.83 (s, 3H). Found: [M+H]=389.1.

(2,3-Dimethoxypyridin-4-yl)methanol (118)

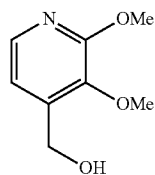

A warm solution of 2,3-dimethoxyisonicotinaldehyde (0.68 g, 4.10 mmol) in EtOH (5 mL) was added dropwise to a suspension of NaBH$_4$ (0.08 g, 2.04 mmol) in EtOH (10 mL) at −40° C., gas evolution occurred and the mixture was stirred at −40° C. for 45 min The mixture was quenched with brine (10 mL) and diluted with water (10 mL), then extracted with ether (3×50 mL). Column chromatography (1:1 hexanes:EtOAc) gave 118 (0.69 g, 98%). $^1$H NMR (CDCl$_3$) δ 7.89 (d, J=5.1 Hz, 1H), 6.93 (d, J=5.1 Hz, 1H), 4.73 (d, J=6.1 Hz, 2H), 4.01 (s, 3H), 3.88 (s, 3H), 2.15 (t, J=6.1 Hz, 1H). Found: [M+H]=170.2.

4-(Bromomethyl)-2,3-dimethoxypyridine (119)

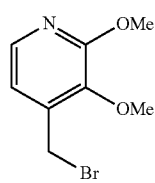

A solution of 118 (2.83 g, 16.8 mmol) and triethylamine (4.70 mL, 33.7 mmol) in DCM (50 mL, anhydrous) was cooled to 0° C., then treated with mesyl chloride (1.95 mL, 25.2 mmol). The cloudy suspension was stirred at 0° C. for 1 h and partitioned between DCM and water. The organic fraction was dried and evaporated to give the crude mesylate. The crude mesylate was dissolved in acetone (100 mL) and LiBr (14.5 g, 167 mmol) was added. The mixture was refluxed for 1 h, evaporated and the residue was partitioned between DCM and water. The organic fraction was dried and evaporated. Column chromatography (DCM) gave 119 (3.53 g, 91%). $^1$H NMR (CDCl$_3$) δ 7.85 (d, J=5.2 Hz, 1H), 6.87 (d, J=5.2 Hz, 1H), 4.45 (s, 2H), 4.01 (s, 3H), 3.95 (s, 3H). Found: [M+H]=232.4.

6-Bromo-3-((2,3-dimethoxypyridin-4-yl)methyl)-2-methoxyquinoline (120)

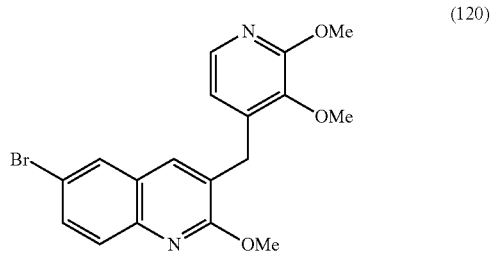 [SMILES: COc1nc2ccc(Br)cc2cc1Cc1ccnc(OC)c1OC]

A mixture of 1 (10.28 g, 36.5 mmol), 119 (8.64 g, 36.5 mmol) and Cs$_2$CO$_3$ (24.0 g, 73.7 mmol) in DMF:toluene (1:2, 200 mL) was purged with nitrogen. Pd(PPh$_3$)$_4$ (0.84 g, 0.73 mmol) was added and the mixture was heated to 80° C. for 3 h under nitrogen. The mixture was partitioned between EtOAc and water and the aqueous layer was extracted with EtOAc. The organic fraction was dried and evaporated, column chromatography using a gradient of 3:1 hexanes: DCM to 95:5 DCM:EtOAc gave 120 (8.65 g, 61%). $^1$H NMR (CDCl$_3$) δ 7.80 (d, J=5.2 Hz, 1H), 7.77 (d, J=2.2 Hz, 1H), 7.69 (d, J=8.9 Hz, 1H), 7.62 (dd, J=8.9, 2.2 Hz, 1H), 7.53 (s, 1H), 6.66 (d, J=5.2 Hz, 1H), 4.07 (s, 3H), 4.03 (s, 2H), 4.02 (s, 3H), 3.80 (s, 3H). Found: [M+H]=389.1.

N-Methoxy-N-methylbenzofuran-2-carboxamide (121)

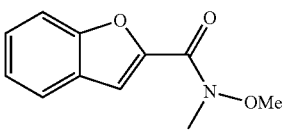

Oxalyl chloride (3.13 mL, 3.70 mmol) was added to a suspension of benzofuran-2-carboxylic acid (5.00 g, 3.08 mmol) in DCM (100 mL, anhydrous) and DMF (0.1 mL, 1.3 mmol) at r.t. The mixture was stirred at r.t. for 1 h to give a colourless solution which was cooled to 0° C. N,O-Dimethylhydroxylamine hydrochloride (3.31 g, 3.39 mmol) and pyridine (7.5 mL, 9.27 mmol) were added sequentially and the mixture was stirred at r.t. for 18 h, then partitioned between EtOAc and sat. aq. NaHCO$_3$. Column chromatography (3:1 hexanes:EtOAc) gave 121 (6.32 g, 100%). $^1$H NMR (CDCl$_3$) δ 7.69 (ddd, 7.9, 1.2, 0.7 Hz, 1H), 7.61 (ddd, J=8.4, 1.7, 0.9 Hz, 1H), 7.51 (d, J=1.0 Hz, 1H), 7.48 (ddd, J=7.9, 7.2, 1.3 Hz, 1H), 7.30 (ddd, J=7.5, 7.3, 0.9 Hz, 1H), 3.84 (s, 3H), 3.43 (s, 3H). Found: [M+H]=206.2.

1-(Benzofuran-2-yl)-3-(dimethylamino)propan-1-one (122)

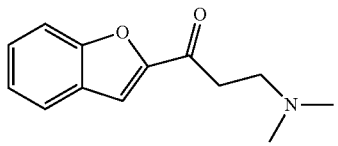
(122)

Vinylmagnesium bromide (58 mL, 58 mmol, 1 M in THF) was added to a solution of 121 (3.95 g, 19.2 mmol) in THF (200 mL, anhydrous) at 0° C., the brown solution was warmed to r.t. for 1 h then dimethylamine (58 mL, 116 mmol, 2 M in THF) and water (40 mL) were added. The solution was stirred at r.t. for 1 h, and then partitioned between EtOAc and water. The solution was dried and evaporated to give 122 (4.17 g, 100%). $^1$H NMR (CDCl$_3$) δ 7.72 (ddd, J=7.9, 1.0, 0.8 Hz, 1H), 7.59 (dd, J=8.4, 0.8 Hz, 1H), 7.53 (d, J=0.9 Hz, 1H), 7.48 (ddd, J=7.8, 7.2, 1.2 Hz, 1H), 7.32 (ddd, J=7.5, 7.2, 1.0 Hz, 1H), 3.14 (t, J=7.5 Hz, 2H), 2.81 (t, J=7.5 Hz, 2H), 2.31 (s, 6H). Found: [M+H]= 218.2.

Methyl benzofuran-5-carboxylate (123)

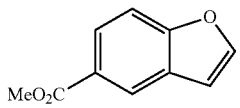
(123)

A mixture of 5-bromobenzofuran (4.00 g, 20.3 mmol), DPPP (0.42 g, 1 mmol), triethylamine (6.3 mL, 45 mmol) and Pd(OAc)$_2$ (0.23 g, 1 mmol) in DMSO (30 mL) and MeOH (30 mL) in a Berghof pressure reactor was evacuated then purged three times with carbon monoxide. The mixture was heated to 80° C. for 18 h under 60 psi of carbon monoxide pressure, cooled and partitioned between EtOAc and water. Column chromatography with 3:1 hexanes:DCM eluted traces of impurities while elution with DCM gave 123 (2.77 g, 78%). $^1$H NMR (CDCl$_3$) δ 8.35 (d, J=1.4 Hz, 1H), 8.03 (dd, J=8.7, 1.7 Hz, 1H), 7.69 (d, J=2.2 Hz, 1H), 7.53 (dt, J=8.7, 0.8 Hz, 1H), 6.84 (dd, J=2.2, 1.0 Hz, 1H), 3.94 (s, 3H).

Benzofuran-5-carboxylic Acid (124)

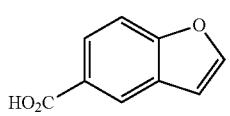
(124)

A solution of LiOH (1.13 g, 47.2 mmol) in water (20 mL) was added to a solution of 123 (2.77 g, 15.7 mmol) in THF (40 mL) and MeOH (40 mL) and the solution was stirred at r.t. for 18 h and then evaporated. The residue was dissolved in water (50 mL) and acidified with conc. HCl to pH 2. The precipitate was dissolved in EtOAc, the organic fraction was dried and evaporated to give 124 (2.49 g, 98%). $^1$H NMR (DMSO-d$_6$) δ 12.86 (s, 1H), 8.30 (d, J=1.4 Hz, 1H), 8.10 (d, J=2.2 Hz, 1H), 7.92 (dd, J=8.6, 1.8 Hz, 1H), 7.68 (dt, J=8.6, 0.7 Hz, 1H), 7.08 (dd, J=2.2, 0.9 Hz, 1H).

N-methoxy-N-methylbenzofuran-5-carboxamide (125)

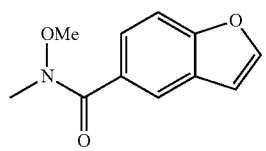
(125)

Oxalyl chloride (1.55 mL, 18.3 mmol) was added to a suspension of 124 (2.48 g, 15.3 mmol) in DCM (100 mL, anhydrous) and DMF (0.05 mL, 0.64 mmol) at r.t. The mixture was stirred at r.t. for 1 h to give a colourless solution which was cooled to 0° C. N,O-Dimethylhydroxylamine hydrochloride (1.64 g, 16.8 mmol) and pyridine (3.71 mL, 45.9 mmol) were added sequentially and the mixture was stirred at r.t. for 18 h, then partitioned between EtOAc and sat. aq. NaHCO$_3$. Column chromatography with 95:5 DCM: EtOAc gave 125 (2.28 g, 73%) as a pale brown oil. $^1$H NMR (CDCl$_3$) δ 7.99 (d, J=1.4 Hz, 1H), 7.65-7.69 (m, 2H), 7.52 (dt, J=8.6, 0.6 Hz, 1H), 6.82 (dd, J=2.2, 0.9 Hz, 1H), 3.56 (s, 3H), 3.39 (s, 3H). Found: [M+H]=206.2.

1-(Benzofuran-5-yl)-3-(dimethylamino)propan-1-one (126)

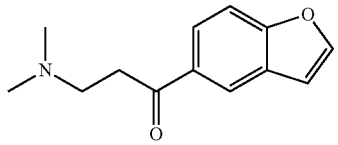
(126)

Vinylmagnesium bromide (33.2 mL, 1 M in THF, 33.2 mmol) was added to a solution of 125 (2.27 g, 11.1 mmol) in THF (100 mL, dist. Na) at 0° C., the brown solution was stirred at 0° C. for 1 h then dimethylamine (33.2 mL, 2 M in THF, 66.4 mmol) and water (20 mL) were added. The solution was stirred at r.t. for 1 h, and then partitioned between EtOAc and water. The solution was dried and evaporated to give 126 (2.33 g, 97%). $^1$H NMR (CDCl$_3$) δ 8.27 (d, J=1.8 Hz, 1H), 7.98 (dd, J=8.7, 1.8 Hz, 1H), 7.70 (d, J=2.2 Hz, 1H), 7.55 (d, J=8.7 Hz, 1H), 6.84 (dd, J=2.2, 0.8 Hz, 1H), 3.22 (t, J=7.1 Hz, 2H), 2.80 (t, J=7.1 Hz, 2H), 2.31 (s, 6H). Found: [M−H]=218.2.

(2,6-Diethoxypyridin-4-yl)methanol (127)

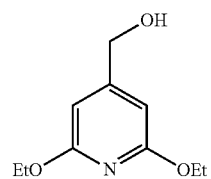
(127)

Trimethylborate (3.88 mL, 34.2 mmol) and borane-dimethylsulfide (3.25 mL, 34.3 mmol) were added sequentially to a solution of 2,6-diethoxyisonicotinic acid (2) (2.41 g, 11.4 mmol) in THF (100 mL, dist. Na) at 0° C. and the mixture was stirred at r.t. for 18 hr. The solution was cooled to 0° C. and methanol was cautiously added to quench excess borane. Removal of the solvent gave a solid which was partitioned between EtOAc and water, the organic fraction was dried and evaporated. Column chromatography (3:1 hexanes:EtOAc) gave 127 (2.13 g, 95%). $^1$H NMR (DMSO-d$_6$) δ 6.27 (d, J=0.6 Hz, 2H), 4.62 (d, J=6.2 Hz, 2H), 4.31 (q, J=7.1 Hz, 4H), 1.72 (t, J=6.2 Hz, 1H), 1.38 (t, J=7.1 Hz, 6H). Found: [M+H]=198.1.

4-(Bromomethyl)-2,6-diethoxypyridine (128)

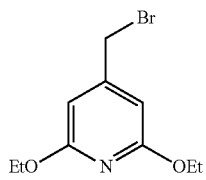

A solution of 127 (2.07 g, 10.5 mmol) in DCM (100 mL, anhydrous) at 0° C. was treated sequentially with triethylamine (2.93 mL, 21.0 mmol) and mesyl chloride (1.22 mL, 15.8 mmol), the mixture was stirred at 0° C. for 1 h then partitioned between DCM and water. The organic fraction was dried and evaporated and the residue was dissolved in acetone (100 mL), LiBr (9.15 g, 105 mmol) was added and the mixture was refluxed for 1 h then evaporated. The residue was partitioned between DCM and water and the organic fraction was dried and evaporated. Column chromatography (DCM) gave 128 (2.63 g, 92%). $^1$H NMR (CDCl$_3$) δ 6.28 (s, 2H), 4.31 (q, J=7.1 Hz, 4H), 4.28 (s, 2H), 1.38 (t, J=7.1 Hz, 6H). Found: [M+H]=260.5.

6-Bromo-3-(2,6-diethoxypyridin-4-yl)methyl)-2-methoxyquinoline (129)

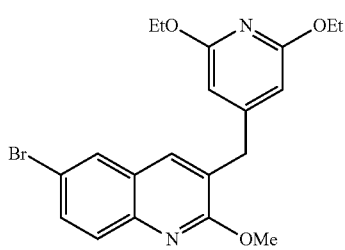

A mixture of 1 (2.20 g, 7.80 mmol), 128 (2.13 g, 8.20 mmol) and Cs$_2$CO$_3$ (5.13 g, 15.6 mmol) in toluene (40 mL) and DMF (20 mL) was purged with nitrogen. Pd(PPh$_3$)$_4$ (0.18 g, 0.156 mmol) was added, the mixture was purged with nitrogen, then heated to 80° C. under nitrogen for 3 h. The reaction was partitioned between EtOAc and water and the organic fraction was dried and evaporated. Column chromatography with 3:1 hexanes:DCM eluted non polar impurities, elution with 1:1 hexanes:DCM gave 129 (2.35 g, 72%). $^1$H NMR (CDCl$_3$) δ 7.77 (d, J=2.2 Hz, 1H), 7.69 (d, J=8.0 Hz, 1H), 7.62 (dd, J=8.8, 2.2 Hz, 1H), 7.58 (s, 1H), 6.13 (s, 2H), 4.29 (q, J=7.1 Hz, 4H), 4.06 (s, 3H), 3.90 (s, 2H), 1.36 (t, J=7.1 Hz, 6H). Found: [M+H]=417.1.

Benzofuran-4-yl Trifluoromethanesulfonate (130)

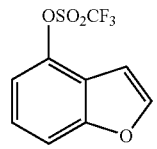

A solution of benzofuran-4-ol (2.61 g, 19.5 mmol), DMAP (0.060 g, 0.49 mmol) and pyridine (2.37 mL, 29.3 mmol) in DCM (60 mL, anhydrous) at 0° C. was treated with TFAA (4.92 mL, 29.2 mmol) and then stirred at 0° C. for 2 h. The mixture was partitioned between DCM and water; the organic fractions were dried and evaporated. Column chromatography (hexanes) gave 130 (3.93 g, 76%). $^1$H NMR (CDCl$_3$) δ 7.70 (d, J=2.3 Hz, 1H), 7.56 (d, J=8.2 Hz, 1H), 7.35 (t, J=8.2 Hz, 1H), 7.20 (d, J=8.1 Hz, 1H), 6.90 (dd, J=1.9, 1.0 Hz, 1H). Found: [M+H]=267.0.

Methyl benzofuran-4-carboxylate (131)

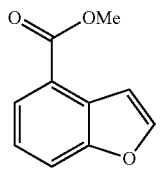

A mixture of 130 (3.88 g, 14.6 mmol), DPPP (0.180 g, 0.44 mmol), triethylamine (4.07 mL, 29.2 mmol) and Pd(OAc)$_2$ (0.098 g, 0.44 mmol) in DMSO (50 mL) and MeOH (50 mL) in a Berghof pressure reactor was evacuated then purged three times with carbon monoxide. The mixture was heated to 80° C. for 18 h under 60 psi of carbon monoxide pressure, cooled and partitioned between EtOAc and water. Column chromatography with 3:1 hexanes:DCM eluted traces of impurities while elution with DCM gave 131 (2.08 g, 81%). $^1$H NMR (CDCl$_3$) δ 7.99 (dd, J=7.7, 0.9 Hz, 1H), 7.74 (d, J=2.2 Hz, 1H), 7.70 (dt, J=8.2, 0.9 Hz, 1H), 7.33-7.39 (m, 2H), 3.99 (s, 3H).

Benzofuran-4-caroxylic Acid (132)

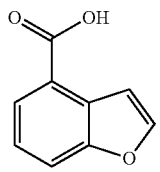

A solution of LiOH (1.44 g, 34.3 mmol) in water (20 mL) was added to a solution of 131 (2.02 g, 11.4 mmol) in THF (20 mL) and MeOH (20 mL) and the solution was stirred at r.t. for 16 h and then evaporated. The residue was dissolved in water (50 mL) and acidified with conc. HCl and the precipitate was filtered and dried to give 132 (1.83 g, 99%). $^1$H NMR (DMSO-$d_6$) δ 13.10 (s, 1H), 8.14 (d, J=2.1 Hz, 1H), 7.85-7.91 (m, 2H), 7.43 (t, J=7.9 Hz, 1H), 7.33 (dd, J=2.1, 1.0 Hz, 1H). Found: [M−H]=161.1.

N-Methoxy-N-methylbenzofuran-4-carboxamide (133)

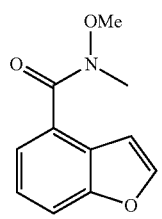

Oxalyl chloride (1.14 mL, 13.5 mmol) was added to a suspension of 132 (1.82 g, 11.2 mmol) in DCM (100 mL, anhydrous) and DMF (0.2 mL, 2.5 mmol) at r.t. The mixture was stirred at r.t. for 1 h to give a colourless solution which was cooled to 0° C. N,O-Dimethylhydroxylamine hydrochloride (1.31 g, 13.5 mmol) and pyridine (2.72 mL, 33.6 mmol) were added sequentially and the mixture was stirred at r.t. for 18 h, then partitioned between DCM and water. Column chromatography with 95:5 DCM:EtOAc gave 133 (2.13 g, 93%). $^1$H NMR (CDCl$_3$) δ 7.68 (d, J=2.2 Hz, 1H), 7.59 (dt, J=8.3, 0.8 Hz, 1H), 7.51 (dd, J=7.5, 0.9 Hz, 1H), 7.32 (t, J=7.9 Hz, 1H), 6.95 (dd, J=2.2, 0.9 Hz, 1H), 3.56 (s, 3H). 3.40 (s, 3H). Found: [M+H]=206.2.

1-(Benzofuran-4-yl)-3-(dimethylamino)propan-1-one (134)

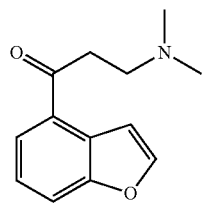

Vinylmagnesium bromide (20.5 mL, 20.5 mmol) was added to a solution of 133 (2.11 g, 10.3 mmol) in THF (100 mL, dist. Na) at 0° C., the brown solution was warmed to r.t. for 1 h, then dimethylamine in THF (20.5 mL, 2 M, 41 mmol) and water (20 mL) were added. The solution was stirred at r.t. for 1 h, then partitioned between EtOAc and water. The solution was dried and evaporated to give 134 (1.83 g, 82%). $^1$H NMR (CDCl$_3$) δ 7.86 (dd, J=7.6, 0.6 Hz, 1H), 7.76 (d, J=2.1 Hz, 1H), 7.71 (dt, J=8.2, 0.8 Hz, 1H), 7.55 (dd, J=2.2, 1.0 Hz, 1H), 7.37 (t, J=7.9 Hz, 1H), 3.27 (t, J=7.1 Hz, 2H), 2.82 (t, J=7.1 Hz, 2H), 2.32 (s, 6H). Found: [M+H]=218.2.

Methyl benzo[b]thiophene-7-carboxylate (135)

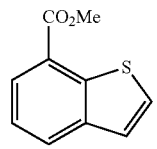

A suspension of 2-mercaptobenzoic acid (10.00 g, 6.49 mmol) in EtOH (50 mL) was treated with 2-bromo-1,1,-dimethoxyethane (10 mL, 8.5 mmol) and NaOH (5.70 g, 14.3 mmol) and the mixture was refluxed for 3 h. The solvent was evaporated and the residue was dissolved in DMF (100 mL), MeI (6.0 mL, 9.6 mmol) and K$_2$CO$_3$ (27.0 g, 19.5 mmol) were added and the mixture was stirred at r.t. for 1 h, then partitioned between EtOAc and water, the organic layer was washed with water and brine, dried and evaporated. The residue was dissolved in chlorobenzene (50 mL), polyphosphoric acid (33 g) was added and the mixture was heated to 130° C. for 2 h. The gummy residue was poured onto ice and extracted with EtOAc, the organic fractions were washed with water, brine, dried and evaporated. Column chromatography with 10:1 hexanes:EtOAc gave 135 (6.46 g, 52%). $^1$H NMR (CDCl$_3$) δ 8.12 (ddd, J=6.9, 1.0, 0.4 Hz, 1H), 8.03 (dd, J=7.9, 1.2 Hz, 1H), 7.58 (dd, J=5.6, 0.3 Hz, 1H), 7.46 (t, J=7.6 Hz, 1H), 7.40 (d, J=5.6 Hz, 1H), 4.03 (s, 3H).

Benzo[b]thiophene-7-carboxylic Acid (136)

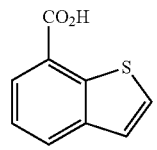

A solution of LiOH (2.10 g, 87.7 mmol) in water (25 mL) was added to a solution of 135 (5.61 g, 29.2 mmol) in THF (50 mL) and MeOH (50 mL) and the solution was stirred at r.t. for 18 h then evaporated. The residue was dissolved in water (150 mL) and acidified to pH 2 with conc. HCl. The precipitate was extracted into EtOAc, the organic fractions were dried and evaporated to give 136 (4.69 g, 90%). $^1$H NMR (DMSO-$d_6$) δ 13.42 (s, 1H), 8.16 (d, J=7.8 Hz, 1H), 8.04 (d, J=7.4 Hz, 1H), 7.86 (d, J=5.6 Hz, 1H), 7.50-7.56 (m, 2H). Found: [M−H]=177.1.

N-Methoxy-N-methylbenzo[b]thiophene-7-carboxamide (137)

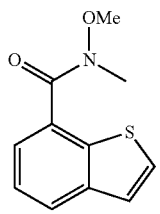

Oxalyl chloride (2.67 mL, 31.6 mmol) was added to a suspension of 136 (4.69 g, 26.3 mmol) in DCM (200 mL, anhydrous) and DMF (0.5 mL, 6.5 mmol) at r.t. The mixture was stirred at r.t. for 1 h then cooled to 0° C. N,O-Dimethylhydroxylamine hydrochloride (3.08 g, 31.6 mmol) and pyridine (6.38 mL, 78.9 mmol) were added sequentially and the mixture was stirred at r.t. for 18 h, then partitioned between EtOAc and sat. aq. NaHCO$_3$. Column chromatography with DCM gave 137 (5.48 g, 94%). $^1$H NMR (CDCl$_3$) δ 7.92 (dd, J=7.9, 1.0 Hz, 1H), 7.81 (dd, J=7.5, 0.5 Hz, 1H), 7.53 (dd, J=5.5, 0.3 Hz, 1H), 7.41 (t, J=7.8 Hz, 1H), 7.37 (d, J=5.5 Hz, 1H), 3.61 (s, 3H), 3.43 (s, 3H). Found: [M+H]= 222.1.

1-(Benzo[b]thiophen-7-yl)-3-(dimethylamino)propan-1-one (138)

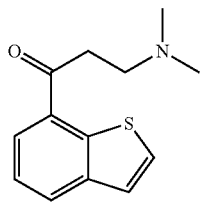
(138)

Vinylmagnesium bromide (49 mL, 1 M, 49 mmol) was added to a solution of 137 (5.38 g, 24.3 mmol) in THF (250 mL, dist. Na) at 0° C., the brown solution was warmed to r.t. for 1 h and then dimethylamine in THF (49 mL, 2 M, 98 mmol) and water (25 mL) were added. The solution was stirred at r.t. for 1 h, then partitioned between EtOAc and water. The solution was dried and evaporated to give 138 (5.45 g, 96%). $^1$H NMR (CDCl$_3$) δ 8.07 (d, J=7.8 Hz, 2H), 7.64 (d, J=5.6 Hz, 1H), 7.50 (t, J=7.6 Hz, 1H), 7.41 (d, J=5.6 Hz, 1H), 3.34 (t, J=7.7 Hz, 2H), 2.87 (t, J=7.7 Hz, 2H), 2.33 (s, 6H). Found: [M+H]=234.1.

Methyl 2-hydroxy-6-methoxyisonicotinate (139)

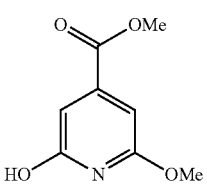
(139)

A suspension of 2,6-dihydroxyisonicotinic acid (10.00 g, 64.5 mmol) in MeOH (60 mL) was treated dropwise with H$_2$SO$_4$ (10 mL, 18.4 M, 184 mmol). The solution was refluxed for 72 h and then evaporated. The residue was treated with sat. aq. NaHCO$_3$ to pH 8 and extracted with EtOAc (3×200 mL). The organic extracts were washed with sat. aq. NaHCO$_3$ and brine, then dried and evaporated to give 139 (3.55 g, 30%). $^1$H NMR (DMSO-d$_6$) δ 11.2 (bs, 1H), 6.61 (bs, 2H), 3.84 (s, 3H), 3.83 (s, 3H). Found: [M+H]=184.2.

Methyl 2-isopropoxy-6-methoxyisonicotinate (140)

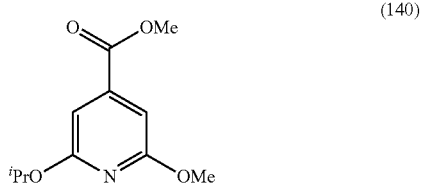 [SMILES: COC(=O)c1cc(OC)nc(OC(C)C)c1]
(140)

A solution of 139 (5.04 g, 27.5 mmol) in DMF (100 mL, anhydrous) was treated with K$_2$CO$_3$ (4.75 g, 34.4 mmol) and then 2-iodopropane (3.43 mL, 34.4 mmol). The mixture was stirred at r.t. for 24 h, more 2-iodopropane (3.43 mL, 34.3 mmol) was added and the mixture was stirred for a further 72 h then partitioned between EtOAc and water and the aqueous layer was extracted further with EtOAc. The organic fractions were washed with water, dried and evaporated. Chromatography (DCM) gave 140 (6.21 g, 100%). $^1$H NMR (CDCl$_3$) δ 6.81 (s, 2H), 5.24 (sp, J=6.2 Hz, 1H), 3.92 (s, 3H), 3.90 (s, 3H), 1.36 (d, J=6.2 Hz, 6H). Found: [M+H]=226.2.

2-Isopropoxy-6-methoxyisonicotinic Acid (141)

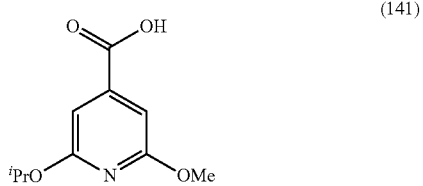 [SMILES: COc1cc(C(=O)O)cc(OC(C)C)n1]
(141)

A solution of LiOH (1.98 g, 82.7 mmol) in water (60 mL) was added to a solution of 140 (6.20 g, 27.5 mmol) in MeOH (60 mL) and THF (60 mL) and the solution was stirred at r.t. for 18 h and then evaporated. The residue was dissolved in water (150 mL) and acidified to pH 3 with 2 M HCl. The precipitate was filtered and dried to give 141 (5.33 g, 92%) as a white solid. $^1$H NMR (DMSO-d$_6$) δ 13.50 (bs, 1H), 6.70 (d, J=1.0 Hz, 1H), 6.66 (d, J=1.0 Hz, 1H), 5.20 (sp, J=6.2 Hz, 1H), 3.86 (s, 3H), 1.31 (d, J=6.2 Hz, 6H). Found: [M+H]= 212.1.

2-Isopropoxy-N,6-dimethoxy-N-methylisonicotinamide (142)

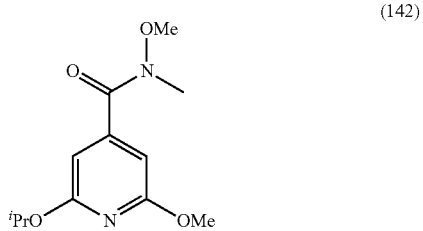 [SMILES: COc1cc(C(=O)N(C)OC)cc(OC(C)C)n1]
(142)

Oxalyl chloride (1.75 mL, 20.7 mmol) was added to 141 (3.65 g, 17.3 mmol) in DCM (100 mL, anhydrous) and DMF (0.3 mL) at r.t. The mixture was stirred at r.t. for 1 h to give a colourless solution which was cooled to 0° C. N,O-Dimethylhydroxylamine hydrochloride (2.03 g, 20.8 mmol) and pyridine (4.2 mL, 51.9 mmol) were added sequentially and the mixture was stirred at r.t. for 18 h, then partitioned between EtOAc and water. Column chromatography with 3:1 hexanes:EtOAc gave 142 (4.58 g, 100%) which was used directly in the subsequent synthesis of 143. $^1$H NMR (CDCl$_3$) δ 6.42 (s, 1H), 6.41 (s, 1H), 5.24 (sp, J=6.2 Hz, 1H), 3.90 (s, 3H), 3.60 (bs, 3H), 3.32 (bs, 3H), 1.35 (d, J=6.2 Hz, 6H). Found: [M+H]=255.2.

3-(Dimethylamino)-1-(2-isopropoxy-6-methoxypyridin-4-yl)propan-1-one (143)

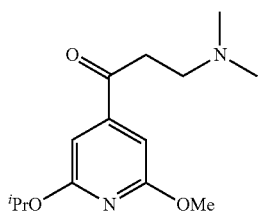

(143)

Vinylmagnesium bromide (36 mL, 1 M, 36 mmol) was added to a solution of 142 (4.54 g, 17.9 mmol) in THF (200 mL, dist. Na) at 0° C., the brown solution was warmed to r.t. for 1 h, then dimethylamine in THF (36 mL, 2 M, 72 mmol) and water (30 mL) were added. The solution was stirred at r.t. for 1 h and then partitioned between EtOAc and water. Column chromatography using a gradient of 97.5:2.5 DCM:MeOH to 95:5 DCM:MeOH gave 143 (3.58 g, 75%). $^1$H NMR (CDCl$_3$) δ 6.70 (d, J=1.0 Hz, 1H), 6.69 (d, J=1.0 Hz, 1H), 5.25 (sp, J=6.2 Hz, 1H), 3.92 (s, 3H), 3.05 (t, J=7.4 Hz, 2H), 2.72 (t, J=7.4 Hz, 2H), 2.26 (s, 6H), 1.36 (d, J=6.2 Hz, 6H). Found: [M+H]=267.2.

Methyl 2-ethoxy-6-methoxyisonicotinate (144)

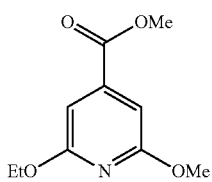

(144)

A solution of 139 (6.96 g, 38.0 mmol) in DMF (100 mL, anhydrous) was treated with K$_2$CO$_3$ (6.57 g, 47.6 mmol) and then iodoethane (3.85 mL, 47.6 mmol). The mixture was stirred at r.t. for 24 h, partitioned between EtOAc and water and the aqueous layer was extracted with EtOAc. The organic fractions were washed with water, dried and evaporated, chromatography (DCM) gave 144 (6.20 g, 77%). $^1$H NMR (CDCl$_3$) δ 6.84 (s, 2H), 4.35 (q, J=7.1 Hz, 2H), 3.93 (s, 3H), 3.91 (s, 3H), 1.40 (t, J=7.1 Hz, 3H). Found: [M+H]=212.1.

2-Ethoxy-6-methoxyisonicotinic Acid (145)

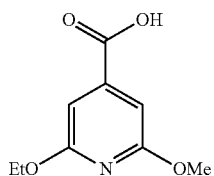

(145)

A solution of LiOH (2.10 g, 87.7 mmol) in water (60 mL) was added to a solution of 144 (6.20 g, 29.4 mmol) in MeOH (60 mL) and THF (60 mL), the solution was stirred at r.t. for 18 h and then evaporated. The residue was dissolved in water (150 mL) and acidified to pH 3 with 2 M HCl. The precipitate was filtered and dried to give 145 (5.61 g, 97%) as a white solid. $^1$H NMR (DMSO-d$_6$) δ 13.54 (bs, 1H), 6.73 (d, J=1.0 Hz, 1H), 6.71 (d, J=1.0 Hz, 1H), 4.32 (q, J=7.0 Hz, 2H), 3.87 (s, 3H), 1.33 (t, J=7.0 Hz, 3H). Found: [M+H]=198.2.

2-Ethoxy-N,6-dimethoxy-N-methylisonicotinamide (146)

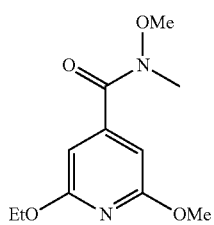

(146)

Oxalyl chloride (2.18 mL, 25.8 mmol) was added to a suspension of 145 (4.23 g, 21.5 mmol) in DCM (100 mL, anhydrous) and DMF (0.3 mL) at r.t. The mixture was stirred at r.t. for 1 h to give a colourless solution which was cooled to 0° C. N,O-Dimethylhydroxylamine hydrochloride (2.51 g, 25.8 mmol) and pyridine (5.2 mL, 64.3 mmol) were added sequentially and the mixture was stirred at r.t. for 18 h, then partitioned between DCM and sat. aq. NaHCO$_3$. Column chromatography with 3:1 hexanes:EtOAc gave 146 (5.02 g, 97%). $^1$H NMR (CDCl$_3$) δ 6.46 (s, 1H), 6.45 (s, 1H), 4.35 (q, J=7.1 Hz, 2H), 3.92 (s, 3H), 3.59 (bs, 3H), 3.32 (s, 3H), 1.40 (t, J=7.1 Hz, 3H). Found: [M+H]=241.1.

3-(Dimethylamino)-1-(2-ethoxy-6-methoxypyridin-4-yl)propan-1-one (147)

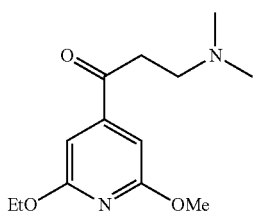

(147)

Vinylmagnesium bromide (16.6 mL, 1 M, 16.6 mmol) was added to a solution of 146 (2.00 g, 8.30 mmol) in THF (100 mL, dist. Na) at 0° C., the brown solution was warmed to r.t. for 1 h then dimethylamine in THF (2M, 16.6 mL, 33.2 mmol) and water (25 mL) were added. The solution was stirred at r.t. for 1 h, then partitioned between EtOAc and water. The solution was dried and evaporated, column chromatography of the residue (95:5 DCM:MeOH) gave 147 (1.40 g, 67%). ¹H NMR (CDCl₃) δ 6.73 (s, 1H), 6.72 (s, 1H), 4.37 (q, J=7.0 Hz, 2H), 3.93 (s, 3H), 3.06 (t, J=7.4 Hz, 2H), 2.72 (t, J=7.4 Hz, 2H), 2.27 (s, 6H), 1.41 (t, J=7.0 Hz, 3H). Found: [M+H]=253.2.

(2-Isopropoxy-6-methoxypyridin-4-yl)methanol (148)

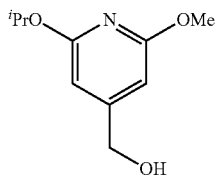

Trimethylborate (6.81 mL, 59.6 mmol) and borane dimethylsulfide complex (5.66 mL, 59.7 mmol) were added sequentially to a solution of 141 (6.30 g, 29.8 mmol) in THF (100 mL, dist. Na) at 0° C., the mixture was stirred at r.t. for 18 hr. The solution was cooled to 0° C. and quenched with methanol. Removal of the solvent gave a white solid, which was partitioned between EtOAc and water, the organic fraction was dried and evaporated to give 148 (5.86 g, 99%). ¹H NMR (CDCl₃) δ 6.26 (t, J=0.8 Hz, 1H), 6.25 (t, J=0.8 Hz, 1H), 5.23 (sp, J=6.2 Hz, 1H), 4.61 (d, J=6.2 Hz, 2H), 3.88 (s, 3H), 1.73 (t, J=6.2 Hz, 1H), 1.34 (d, J=6.2 Hz, 6H). Found: [M+H]=212.2 (M−OH+MeO).

4-(Bromomethyl)-2-isopropoxy-6-methoxypyridine (149)

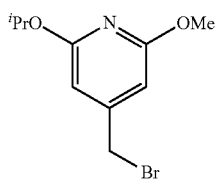

A solution of 148 (5.86 g, 29.9 mmol) in DCM (100 mL, anhydrous) at 0° C. was treated with triethylamine (8.3 mL, 59.5 mmol) and then mesyl chloride (3.47 mL, 44.8 mmol), the mixture was stirred at 0° C. for 1 h then partitioned between DCM and water. The organic fraction was dried and evaporated and the residue was dissolved in acetone (200 mL), LiBr (25.9 g, 299 mmol) was added and the mixture was refluxed for 1 h then evaporated. The residue was partitioned between DCM and water; the organic fraction was dried and evaporated. Column chromatography (DCM) gave 149 (6.98 g, 90%). ¹H NMR (CDCl₃) δ 6.28 (s, 1H), 6.27 (s, 1H), 5.23 (sp, J=6.2 Hz, 1H), 4.27 (s, 2H), 3.88 (s, 3H), 1.35 (d, J=6.3 Hz, 6H). Found: [M+H]=260.1.

6-Bromo-3-((2-isopropoxy-6-methoxypyridin-4-yl)methyl)-2-methoxyquinoline (150)

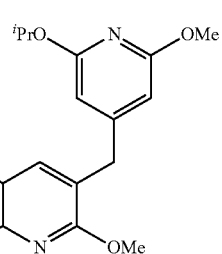

A mixture of 1 (7.45 g, 26.4 mmol), 149 (6.84 g, 26.4 mmol) and Cs₂CO₃ (17.3 g, 52.7 mmol) in toluene (100 mL) and DMF (50 mL) was purged with nitrogen. Pd(PPh₃)₄ (0.61 g, 0.528 mmol) was added, the mixture was purged with nitrogen and then heated to 80° C. under nitrogen for 3 h. The reaction mixture was partitioned between EtOAc and water and the organic fraction was dried and evaporated. Column chromatography with 3:1 hexanes:DCM eluted impurities, then elution with 1:1 hexanes:DCM gave 150 (8.59 g, 78%). ¹H NMR (CDCl₃) δ 7.78 (d, J=2.1 Hz, 1H), 7.69 (d, J=8.9 Hz, 1H), 7.62 (dd, J=8.9, 2.2 Hz, 1H), 7.58 (s, 1H), 6.14 (d, J=0.9 Hz, 1H), 6.10 (d, J=0.9 Hz, 1H), 5.22 (sp, J=6.2 Hz, 1H), 4.06 (s, 3H), 3.90 (s, 2H), 3.87 (s, 3H), 1.33 (d, J=6.2 Hz, 6H). Found: [M+H]=417.1.

(2-Ethoxy-6-methoxypyridin-4-yl)methanol (151)

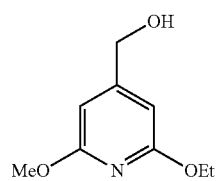

Trimethylborate (6.06 mL, 53.1 mmol) and then borane-dimethylsulfide (5.04 mL, 53.1 mmol) were added to a solution of 145 (5.24 g, 26.6 mmol) in THF (100 mL, dist. Na) at 0° C. and the mixture was stirred at r.t. for 18 hr. The solution was cooled to 0° C. and quenched with methanol. Removal of the solvent gave a solid which was partitioned between EtOAc and water, the organic fraction was dried and evaporated to give 151 (4.79 g, 98%). ¹H NMR (CDCl₃) 6.29 (bd, J=0.7 Hz, 1H), 6.28 (bd, J=0.7 Hz, 1H), 4.63 (d, J=6.2 Hz, 2H), 4.32 (q, J=7.1 Hz, 2H), 3.90 (s, 3H), 1.76 (t, J=6.2 Hz, 1H), 1.39 (t, J=7.1 Hz, 3H). Found: [M+H]=184.2.

4-(Bromomethyl)-2-ethoxy-6-methoxypyridine (152)

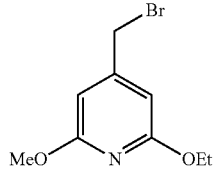
(152)

A solution of 151 (4.72 g, 25.9 mmol) in DCM (100 mL, anhydrous) at 0° C. was treated sequentially with triethylamine (7.22 mL, 51.8 mmol) and mesyl chloride (3.00 mL, 38.8 mmol), the mixture was stirred at 0° C. for 1 h then partitioned between DCM and water. The organic fraction was dried and evaporated and the residue was dissolved in acetone (200 mL), LiBr (22.5 g, 259 mmol) was added and the mixture was refluxed for 1 h then evaporated. The residue was partitioned between DCM and water; the organic fraction was dried and evaporated. Column chromatography (DCM) gave 152 (5.78 g, 91%). $^1$H NMR (CDCl$_3$) δ 6.30 (s, 2H), 4.33 (q, J=7.1 Hz, 2H), 4.28 (s, 2H), 3.90 (s, 3H), 1.39 (t, J=7.1 Hz, 3H). Found: [M+H]=246.0.

6-Bromo-3-((2-ethoxy-6-methoxypyridin-4-yl)methyl)-2-methoxyquinoline (153)

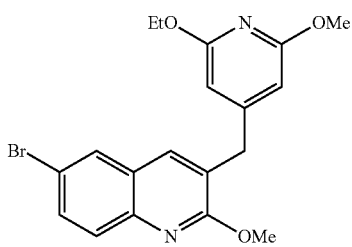
(153)

A mixture of 1 (6.61 g, 23.4 mmol), 152 (5.77 g, 23.4 mmol) and Cs$_2$CO$_3$ (15.25 g, 46.5 mmol) in toluene (100 mL) and DMF (50 mL) was purged with nitrogen. Pd(PPh$_3$)$_4$ (0.54 g, 0.465 mmol) was added, the mixture was purged with nitrogen then heated to 80° C. under nitrogen for 3 h. The reaction mixture was partitioned between EtOAc and water and the organic fraction was dried and evaporated. Column chromatography with 3:1 hexanes:DCM eluted impurities, then elution with 1:1 hexanes:DCM gave 153 (6.69 g, 71%). $^1$H NMR (CDCl$_3$) δ 7.78 (d, J=2.1 Hz, 1H), 7.69 (d, J=8.9 Hz, 1H), 7.63 (dd, J=8.9, 2.2 Hz, 1H), 7.57 (s, 1H), 6.15 (d, J=8.0 Hz, 2H), 4.31 (q, J=7.1 Hz, 2H), 4.06 (s, 3H), 3.91 (s, 2H), 3.88 (s, 3H), 1.37 (t, J=7.1 Hz, 3H). Found: [M+H]=403.1.

Ethyl 2-ethoxy-6-hydroxyisonicotinate (154)

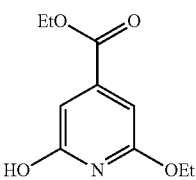
(154)

A suspension of 2,6-dihydroxyisonicotinic acid (40.00 g, 258 mmol) in EtOH (300 mL) was treated dropwise with H$_2$SO$_4$ (40 mL, 18.4 M, 752 mmol). The solution was refluxed for 72 h then evaporated; the residue was treated with sat. aq. NaHCO$_3$ to pH 8 and then extracted with EtOAc (3×500 mL). The organic extracts were washed with sat. aq. NaHCO$_3$, brine, then dried and evaporated to give 154 (10.86 g, 20%). $^1$H NMR (DMSO-d$_6$) δ 11.15 (bs, 1H), 6.59 (d, J=1.0 Hz, 1H), 6.57 (bs, 1H), 4.29 (q, J=7.1 Hz, 2H), 4.25 (q, J=7.1 Hz, 2H), 1.298 (t, J=7.1 Hz, 3H), 1.296 (t, J=7.1 Hz, 3H). Found: [M+H]=212.2.

Ethyl 2-ethoxy-6-isopropoxyisonicotinate (155)

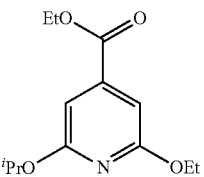
(155)

A solution of 154 (10.82 g, 51.2 mmol) in DMF (125 mL, anhydrous) was treated with K$_2$CO$_3$ (8.65 g, 62.5 mmol) and then 2-iodopropane (6.4 mL, 64 mmol). The mixture was stirred at r.t. for 48 h, K$_2$CO$_3$ (8.65 g, 62.5 mmol) and 2-iodopropane (6.4 mL, 64 mmol) were added and the mixture was stirred for a further 24 h, partitioned between EtOAc and water and the aqueous layer was extracted with EtOAc. The organic fractions were washed with water, dried and evaporated. Chromatography (DCM) gave 155 (11.56 g, 89%). $^1$H NMR (DMSO-d$_6$) δ 6.81 (s, 2H), 5.23 (sp, J=6.2 Hz, 1H), 4.20-4.38 (m, 4H), 1.35-1.42 (m, 12H). Found: [M+H]=254.1.

2-Ethoxy-6-isopropoxyisonicotinic Acid (156)

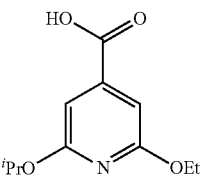
(156)

A solution of LiOH (3.25 g, 136 mmol) in water (60 mL) was added to a solution of 155 (11.42 g, 45.1 mmol) in THF (60 mL) and MeOH (60 mL), the solution was stirred at r.t. for 18 h and then evaporated. The residue was dissolved in water (150 mL) and acidified to pH 3 with 2 M HCl. The precipitate was filtered and dried to give 156 (10.03 g, 99%). ¹H NMR (DMSO-d₆) δ 13.48 (bs, 1H), 6.66 (d, J=0.9 Hz, 1H), 6.64 (d, J=0.9 Hz, 1H), 5.17 (sp, J=6.2 Hz, 1H), 4.29 (q, J=7.0 Hz, 2H), 1.32 (t, J=7.0 Hz, 3H), 1.30 (d, J=6.2 Hz, 6H). Found: [M+H]=226.1.

2-Ethoxy-6-isopropoxy-N-methoxy-N-methylisonicotinamide (157)

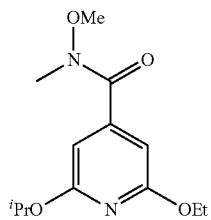

(157)

Oxalyl chloride (3.13 mL, 37 mmol) was added to 156 (6.95 g, 30.8 mmol) in DCM (100 mL, anhydrous) and DMF (5.2 mmol) at r.t. The mixture was stirred at r.t. for 1 h to give a colourless solution which was cooled to 0° C. N,O-Dimethylhydroxylamine hydrochloride (3.61 g, 37.0 mmol) and pyridine (7.5 mL, 92.7 mmol) were added sequentially and the mixture was stirred at r.t. for 18 h, then partitioned between EtOAc and water. The organic fractions were washed with water, dried and evaporated. Column chromatography with 95:5 DCM:EtOAc gave 157 (7.98 g, 97%). ¹H NMR (CDCl₃) δ 6.40 (s, 1H), 6.39 (s, 1H), 5.22 (sp, J=6.2 Hz, 1H), 4.33 (q, J=7.1 Hz, 2H), 3.60 (bs, 3H), 3.31 (s, 3H), 1.39 (t, J=6.2 Hz, 3H), 1.34 (d, J=7.1 Hz, 6H). Found: [M+H]=269.2.

3-(Dimethylamino)-1-(2-ethoxy-6-isopropoxypyridin-4-yl)propan-1-one (158)

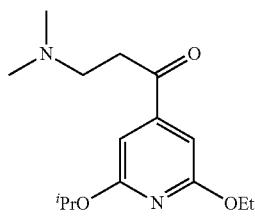

(158)

Vinylmagnesium bromide (40 mL, 1 M in THF, 40 mmol) was added to a solution of 157 (5.33 g, 19.9 mmol) in THF (100 mL, dist. Na) at 0° C., the brown solution was stirred at 0° C. for 1 h and then dimethylamine (40 mL, 2 M in THF, 80 mmol) and water (40 mL) were added. The solution was stirred at r.t. for 1 h then partitioned between EtOAc and water. The solution was dried and evaporated, to give 158 (5.57 g, 100%) as a brown oil. ¹H NMR (CDCl₃) δ 6.68 (d, J=1.0 Hz, 1H), 6.67 (d, J=1.0 Hz, 1H), 5.22 (sp, J=6.2 Hz, 1H), 4.33 (q, J=7.0 Hz, 2H), 3.05 (t, J=7.5 Hz, 2H), 2.72 (t, J=7.5 Hz, 2H), 2.26 (s, 6H), 1.40 (t, J=6.2 Hz, 3H), 1.36 (d, J=7.0 Hz, 6H). Found: [M+H]=281.7.

Methyl 2-methoxy-6-propoxyisonicotinate (159)

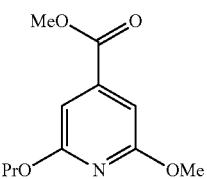

(159)

A solution of 139 (6.00 g, 32.8 mmol) in DMF (100 mL, anhydrous) was treated with K₂CO₃ (6.80 g, 49.2 mmol) and then 1-iodopropane (4.8 mL, 49.2 mmol). The mixture was stirred at r.t. for 48 h, partitioned between EtOAc and water and the aqueous layer was extracted with EtOAc. The organic fractions were washed with water, dried and evaporated. Column chromatography (DCM) gave 159 (6.59 g, 89%). ¹H NMR (CDCl₃) δ 6.85 (d, J=1.0 Hz, 1H), 6.83 (d, J=1.0 Hz, 1H), 4.24 (t, J=6.7 Hz, 2H), 3.93 (s, 3H), 3.91 (s, 3H), 1.80 (qt, J=7.4, 6.7 Hz, 2H), 1.02 (t, J=7.4 Hz, 3H). Found: [M+H]=226.1.

2-Methoxy-6-propoxyisonicotinic Acid (160)

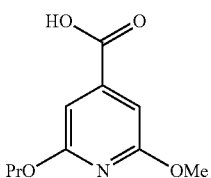

(160)

A solution of LiOH (2.04 g, 85.2 mmol) in water (60 mL) was added to a solution of 159 (6.40 g, 28.4 mmol) in THF (60 mL) and MeOH (60 mL), the solution was stirred at r.t. for 18 h and then evaporated. The residue was dissolved in water (200 mL) and acidified to pH 3 with 2 M HCl. The precipitate was filtered and dried to give 160 (5.39 g, 90%). ¹H NMR (DMSO-d₆) δ 13.53 (bs, 1H), 6.73 (d, J=1.0 Hz, 1H), 6.72 (d, J=1.0 Hz, 1H), 4.23 (t, J=6.6 Hz, 2H), 3.87 (s, 3H), 1.73 (qt, J=7.4, 6.6 Hz, 2H), 0.96 (t, J=7.4 Hz, 3H). Found: [M+H]=212.1.

(2-Methoxy-6-propoxypyridin-4-yl)methanol (161)

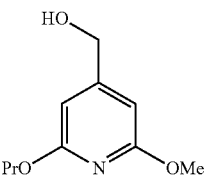

(161)

Trimethylborate (5.8 mL, 50.8 mmol) and borane dimethylsulfide complex (4.8 mL, 50.6 mmol) were added sequentially to a solution of 160 (5.39 g, 25.5 mmol) in THF (100 mL, dist. Na) at 0° C., and the mixture was stirred at r.t. for 16 hr. The solution was cooled to 0° C. and methanol was cautiously added to quench the reaction. Removal of the solvent gave a solid which was partitioned between EtOAc and water, the organic fraction was dried and evaporated. Column chromatography (3:1 hexanes:EtOAc) gave 161 (5.04 g, 100%). $^1$H NMR (CDCl$_3$) δ 6.28 (d, J=0.8 Hz, 1H), 6.26 (d, J=0.8 Hz, 1H), 4.62 (d, J=6.2 Hz, 2H), 4.31 (q, J=7.1 Hz, 2H), 4.20 (t, J=6.8 Hz, 2H), 1.72-1.83 (m, 3H), 1.38 (t, J=7.0 Hz, 3H), 1.00 (t, J=7.4 Hz, 3H). Found: [M+H]=198.2.

4-(Bromomethyl)-2-methoxy-6-propoxypyridine (162)

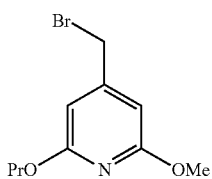
(162)

A solution of 161 (5.00 g, 25.4 mmol) in DCM (100 mL, anhydrous) at 0° C. was treated with triethylamine (7.07 mL, 50.7 mmol) and then mesyl chloride (2.94 mL, 38.0 mmol), the mixture was stirred at 0° C. for 1 h then partitioned between DCM and water. The organic fraction was dried and evaporated and the residue was dissolved in acetone (150 mL), LiBr (22.0 g, 253 mmol) was added and the mixture was refluxed for 1 h then evaporated. The residue was partitioned between DCM and water; the organic fraction was dried and evaporated. Column chromatography (DCM) gave 162 (6.15 g, 93%) as a colourless oil. $^1$H NMR (CDCl$_3$) δ 6.31 (d, J=1.0 Hz, 1H), 6.30 (d, J=1.0 Hz, 1H), 4.28 (s, 2H), 4.22 (t, J=6.7 Hz, 2H), 3.90 (s, 3H), 1.79 (qt, J=7.4, 6.7 Hz, 2H), 1.02 (t, J=7.4 Hz, 3H). Found: [M+H]=260.5.

6-Bromo-2-methoxy-3-((2-methoxy-6-propoxypyridin-4-yl)methyl)quinoline (163)

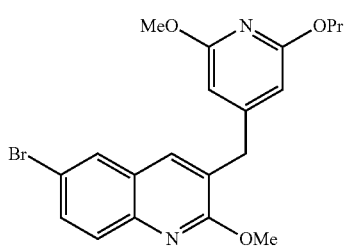
(163)

A mixture of 1 (6.62 g, 23.5 mmol), 162 (6.11 g, 23.5 mmol) and Cs$_2$CO$_3$ (15.3 g, 47.0 mmol) in toluene (66 mL) and DMF (33 mL) was purged with nitrogen. Pd(PPh$_3$)$_4$ (0.54 g, 0.47 mmol) was added, the mixture was purged with nitrogen then heated to 80° C. under nitrogen for 3 h. The reaction was partitioned between EtOAc and water and the organic fraction was dried and evaporated. Column chromatography with 1:1 DCM:hexanes gave an impure product which was rechromatographed using a gradient of 2:1 hexanes:DCM to 1:1 hexanes:DCM to give 163 (6.63 g, 68%). $^1$H NMR (CDCl$_3$) δ 7.78 (d, J=2.2 Hz, 1H), 7.69 (d, J=8.9 Hz, 1H), 7.63 (dd, J=8.9, 2.2 Hz, 1H), 7.58 (s, 1H), 6.15 (s, 1H), 6.14 (s, 1H), 4.21 (t, J=6.8 Hz, 2H), 4.06 (s, 3H), 3.91 (s, 2H), 3.88 (s, 3H), 1.79 (qt, J=7.4, 6.8 Hz, 2H), 1.00 (t, J=7.4 Hz, 3H). Found: [M+H]=417.1.

6-Chloro-2-methoxyquinoline (164)

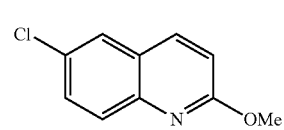
(164)

A mixture of 2,6-dichloroquinoline (12.92 g, 65.3 mmol) and sodium methoxide (17.63 g, 326 mmol) in MeOH (200 mL) was refluxed for 18 h. The solvent was removed in vacuo and the residue was partitioned between EtOAc and water. Recrystallisation from MeOH gave 164 (11.63 g, 92%). $^1$H NMR (CDCl$_3$) δ 7.89 (d, J=8.9 Hz, 1H), 7.78 (d, J=8.9 Hz, 1H), 7.69 (d, J=2.3 Hz, 1H), 7.55 (dd, J=8.9, 2.4 Hz, 1H), 6.92 (d, J=8.9 Hz, 1H), 4.06 (s, 3H). Found: [M+H]=194.0.

(6-Chloro-2-methoxyquinolin-3-yl)1 (165)

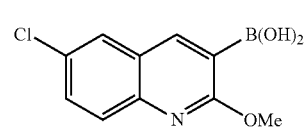
(165)

A solution of anhydrous 2,2,6,6,-tetramethylpiperidine (6.7 mL, 39.7 mmol) in THF (70 mL, dist. Na) at −40° C. was treated with n-BuLi (19.8 mL, 2 M in cyclohexane, 39.7 mmol), the solution was then stirred at −40° C. for 5 min and then cooled to −78° C. A solution of 164 (6.35 g, 32.9 mmol) and triisopropylborate (9.1 mL, 39.7 mmol) in THF (50 mL, dist. Na) was added dropwise and the orange solution was stirred for 3 h at −78° C., then quenched with sat. aq. NH$_4$Cl and ice. The precipitate was filtered, triturated with hexanes and dried to give 165 (5.84 g, 75%). $^1$H NMR (DMSO-d$_6$) δ 8.35 (s, 1H), 8.17 (s, 2H), 8.02 (d, J=2.4 Hz, 1H), 7.76 (d, J=8.9 Hz, 1H), 7.65 (dd, J=8.9, 2.5 Hz, 1H), 3.99 (s, 3H). Found: [M−OH+OMe]=252.2.

6-Chloro-3-(2-fluoro-3-methoxybenzyl)-2-methoxyquinoline (166)

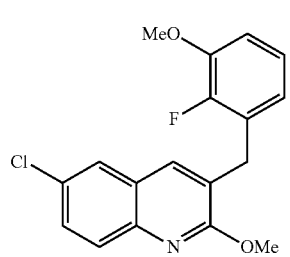
(166)

A mixture of 165 (5.00 g, 21.1 mmol), 1-(bromomethyl)-2-fluoro-3-methoxybenzene (4.61 g, 21.0 mmol) and Cs$_2$CO$_3$ (13.7 g, 42.0 mmol) in toluene (100 mL) and DMF (50 mL) was purged with nitrogen. Pd(PPh₃)₄ (0.49 g, 0.42 mmol) was added, the mixture was purged with nitrogen then heated to 80° C. under nitrogen for 3 h. The reaction was partitioned between EtOAc and water and the organic fraction was dried and evaporated. Column chromatography with 3:1 hexanes:DCM eluted impurities, then elution with 1:1 hexanes:DCM gave 166 (3.40 g, 57%). ¹H NMR (CDCl₃) δ 7.74 (d, J=8.8 Hz, 1H), 7.58 (d, J=2.4 Hz, 1H), 7.52 (s, 1H), 7.48 (dd, J=8.9, 2.4 Hz, 1H), 7.01 (td, J=8.0, 1.5 Hz, 1H), 6.88 (td, J=8.1, 1.5 Hz, 1H), 6.78 (td, J=7.0, 1.5 Hz, 1H), 4.09 (s, 3H), 4.05 (s, 2H), 3.90 (s, 3H). Found: [M+H]=332.1.

N,2-Dimethoxy-N-methyl-6-propoxyisonicotinamide (167)

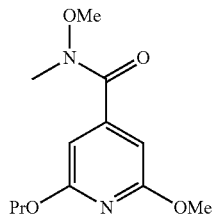

(167)

Oxalyl chloride (2.76 mL, 32.6 mmol) was added to 160 (5.74 g, 27.2 mmol) in DCM (100 mL, anhydrous) and DMF (0.4 mL, 5.2 mmol) at r.t. The mixture was stirred at r.t. for 1 h to give a colourless solution which was cooled to 0° C. N,O-Dimethylhydroxylamine hydrochloride (3.18 g, 32.6 mmol) and pyridine (6.6 mL, 81.6 mmol) were added sequentially and the mixture was stirred at r.t. for 18 h, then partitioned between DCM and water. Column chromatography on alumina with DCM gave 167 (6.29 g, 91%). ¹H NMR (CDCl₃) δ 6.42 (s, 1H), 6.41 (s, 1H), 5.24 (sp, J=6.2 Hz, 1H), 3.90 (s, 3H), 3.59 (bs, 3H), 3.32 (s, 3H), 1.35 (d, J=6.2 Hz, 6H). Found: [M+H]=255.1.

3-(Dimethylamino)-1-(2-methoxy-6-propoxypyridin-4-yl)propan-1-one (168)

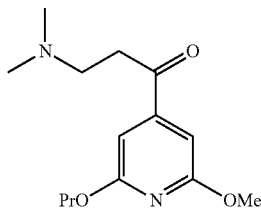

(168)

Vinylmagnesium bromide (43 mL, 1 M in THF, 43 mmol) was added to a solution of 167 (5.78 g, 21.7 mmol) in THF (100 mL, dist. Na) at 0° C., the brown solution was stirred at 0° C. for 1 h and then dimethylamine (43 mL, 2 M in THF, 86 mmol) and water (40 mL) were added. The solution was stirred at r.t. for 1 h then partitioned between EtOAc and water. The solution was dried and evaporated to give 168 (5.75 g, 100%). ¹H NMR (CDCl₃) δ 6.73 (d, J=1.1 Hz, 1H), 6.72 (d, J=1.1 Hz, 1H), 4.26 (t, J=6.7 Hz, 2H), 3.93 (s, 3H), 3.06 (t, J=7.4 Hz, 2H), 2.72 (J=7.4 Hz, 2H), 2.27 (s, 6H), 1.80 (qt, J=7.4, 6.7 Hz, 2H), 1.03 (t, J=7.4 Hz, 3H). Found: [M+H]=267.2.

Benzofuran-7-ylmethanol (169)

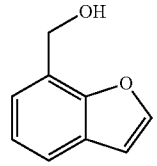

(169)

A solution of methyl benzofuran-7-carboxylate (3.59 g, 20.4 mmol) in Et₂O (100 mL, dist. Na) at 0° C. was treated with LiAlH₄ (1.54 g, 40.6 mmol) then stirred at r.t. for 3 h and quenched with ice. The mixture was partitioned between Et₂O and sat. aq. sodium potassium tartrate and then filtered through Celite. The aqueous layer was extracted with Et₂O and the organic phases were combined and dried. Column chromatography (0-5% EtOAc:DCM) gave 169 (2.60 g, 86%). ¹H NMR (CDCl₃) δ 7.65 (d, J=2.2 Hz, 1H), 7.56 (dd, J=7.7, 1.2 Hz, 1H), 7.31 (dd, J=7.3, 0.6 Hz, 1H), 7.23 (t, J=7.5 Hz, 1H), 6.80 (d, J=2.2 Hz, 1H), 5.02 (d, J=6.2 Hz, 2H), 1.93 (t, J=6.2 Hz, 1H).

7-(Bromomethyl)benzofuran (170)

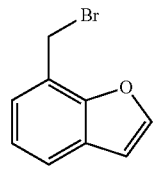

(170)

A solution of 169 (4.72 g, 31.8 mmol) in DCM (100 mL, anhydrous) at 0° C. was treated sequentially with triethylamine (8.9 mL, 63.9 mmol) then mesyl chloride (3.70 mL, 47.8 mmol), the mixture was stirred at 0° C. for 1 h then partitioned between DCM and water. The organic fraction was dried and evaporated and the residue was dissolved in acetone (200 mL), LiBr (27.6 g, 318 mmol) was added and the mixture was refluxed for 0.5 h and then evaporated. The residue was partitioned between DCM and water; the organic fraction was dried and evaporated. Column chromatography (DCM) gave 170 (6.08 g, 90%). ¹H NMR (CDCl₃) δ 7.69 (d, J=2.2 Hz, 1H), 7.57 (dd, J=7.7, 1.2 Hz, 1H), 7.32 (dd, J=7.4, 0.7 Hz, 1H), 7.22 (t, J=7.6 Hz, 1H), 6.80 (d, J=2.2 Hz, 1H), 4.81 (s, 2H).

3-(Benzofuran-7-ylmethyl)-6-bromo-2-methoxyquinoline (171)

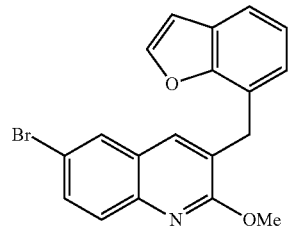

(171)

A mixture of 1 (8.00 g, 28.4 mmol), 170 (5.99 g, 28.4 mmol) and Cs$_2$CO$_3$ (18.5 g, 56.7 mmol) in toluene (100 mL) and DMF (50 mL) was purged with nitrogen. Pd(PPh$_3$)$_4$ (0.66 g, 0.57 mmol) was added, the mixture was purged with nitrogen then heated to 80° C. under nitrogen for 3 h. The reaction was partitioned between EtOAc and water and the organic fraction was dried and evaporated. Column chromatography with 3:1 hexanes:DCM eluted impurities, then elution with 1:1 hexanes:DCM then DCM gave 171 (6.95 g, 67%). $^1$H NMR (CDCl$_3$) δ 7.71 (d, J=2.2 Hz, 1H), 7.68 (d, J=8.8 Hz, 1H), 7.58-7.62 (m, 2H), 7.50-7.54 (m, 2H), 7.20 (t, J=7.4 Hz, 1H), 7.13 (dd, J=7.4, 0.6 Hz, 1H), 6.79 (d, J=2.2 Hz, 1H), 4.32 (s, 2H), 4.10 (s, 3H). Found: [M+H]=368.8.

Methyl 2-cyclobutoxy-6-methoxyisonicotinate (172)

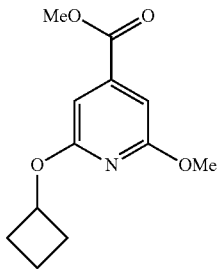

(172)

A solution of 139 (3.00 g, 16.4 mmol) in DMF (50 mL, anhydrous) was treated with K$_2$CO$_3$ (4.52 g, 32.7 mmol) and then bromocyclobutane (2.00 mL, 25.0 mmol). The mixture was stirred at r.t. for 48 h, partitioned between EtOAc and water and the aqueous layer was extracted with EtOAc. The organic fractions were washed with water, dried and evaporated. Column chromatography (DCM) gave 172 (2.21 g, 57%). $^1$H NMR (CDCl$_3$) δ 6.84 (d, J=1.0 Hz, 1H), 6.79 (d, J=1.0 Hz, 1H), 5.08 (pd, J=7.4, 0.8 Hz, 1H), 3.91 (s, 3H), 3.90 (s, 3H), 2.42-2.52 (m, 2H), 2.12-2.24 (m, 2H), 1.80-1.90 (m, 1H), 1.62-1.75 (m, 1H). Found: [M+H]=238.2.

2-Cyclobutoxy-6-methoxyisonicotinic Acid (173)

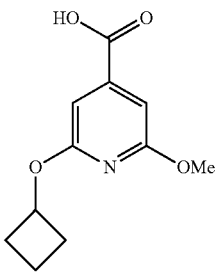

(173)

A solution of LiOH (0.71 g, 29.6 mmol) in water (20 mL) was added to a solution of 172 (2.20 g, 9.29 mmol) in MeOH (20 mL) and THF (20 mL); the solution was stirred at r.t. for 18 h and then evaporated. The residue was dissolved in water (80 mL) and acidified to pH 3 with 2 M HCl. The precipitate was filtered and dried to give 173 (2.02 g, 97%). $^1$H NMR (DMSO-d$_6$) δ 13.56 (bs, 1H), 6.74 (d, J=1.0 Hz, 1H), 6.67 (d, J=1.0 Hz, 1H), 5.07 (pd, J=7.1, 0.7 Hz, 1H), 3.85 (s, 3H), 2.37-2.46 (m, 2H), 2.14-2.22 (m, 2H), 1.74-1.83 (m, 1H), 1.59-1.72 (m, 1H). Found: [M+H]=224.2.

2-Cyclobutoxy-N,6-dimethoxy-N-methylisonicotinamide (174)

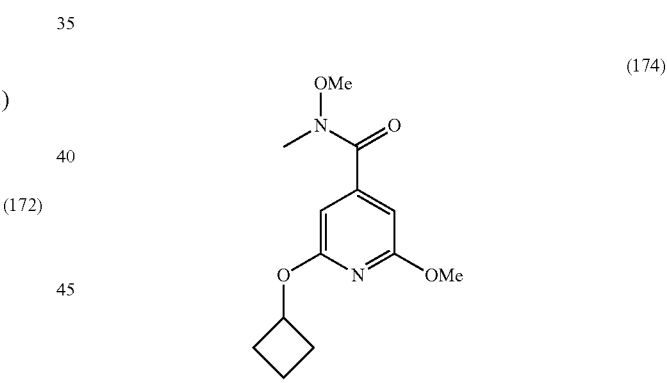

(174)

Oxalyl chloride (0.45 mL, 5.32 mmol) was added to a suspension of 173 (1.00 g, 4.48 mmol) in DCM (50 mL, anhydrous) and DMF (0.2 mL) at r.t. The mixture was stirred at r.t. for 1 h to give a colourless solution which was cooled to 0° C. N,O-Dimethylhydroxylamine hydrochloride (0.52 g, 5.33 mmol) and pyridine (1.09 mL, 13.5 mmol) were added sequentially and the mixture was stirred at r.t. for 18 h, then partitioned between DCM and sat. aq. NaHCO$_3$. Column chromatography on alumina with DCM gave 174 (1.01 g, 85%). $^1$H NMR (CDCl$_3$) δ 6.46 (s, 1H), 6.40 (d, J=0.6 Hz, 1H), 5.08 (pd, J=7.4, 0.9 Hz, 1H), 3.90 (s, 3H), 3.58 (bs, 3H), 3.32 (s, 3H), 2.41-2.51 (m, 2H), 2.12-2.23 (m, 2H), 1.80-1.90 (m, 1H), 1.62-1.74 (m, 1H). Found: [M+H]=267.2.

1-(2-cyclobutoxy-6-methoxypyridin-4-yl)-3-(dimethylamino)propan-1-one (175)

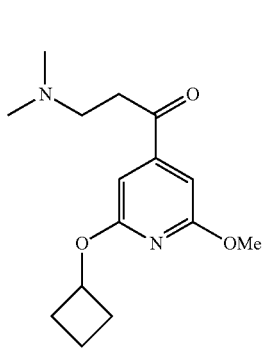

(175)

Vinylmagnesium bromide (8.0 mL, 1 M, 8.0 mmol) was added to a solution of 174 (1.02 g, 3.84 mmol) in THF (50 mL, dist. Na) at 0° C., the brown solution was warmed to r.t. for 1 h then dimethylamine in THF (8.0 mL, 2M, 16.0 mmol) and water (10 mL) were added. The solution was stirred at r.t. for 1 h, and then partitioned between EtOAc and water. The solution was dried and evaporated, column chromatography (95:5 DCM:MeOH) gave 175 (1.05 g, 97%). $^1$H NMR (CDCl$_3$) δ 6.73 (d, J=1.1 Hz, 1H), 6.68 (d, J=1.2 Hz, 1H), 5.10 (pd, J=7.4, 1.1 Hz, 1H), 3.91 (s, 3H), 3.05 (t, J=7.0 Hz, 2H), 2.72 (t, J=7.0 Hz, 2H), 2.42-2.50 (m, 2H), 2.27 (s, 6H), 2.13-2.23 (m, 2H), 1.80-1.90 (m, 1H), 1.62-1.74 (m, 1H). Found: [M+H]=279.2.

(2-Ethoxy-6-isopropoxypyridin-4-yl)methanol (176)

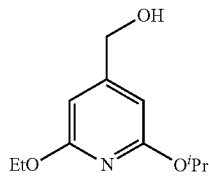

(176)

Trimethylborate (3.03 mL, 26.7 mmol) and then borane-dimethylsulfide (2.53 mL, 26.7 mmol) were added to a solution of 156 (3.00 g, 13.3 mmol) in THF (50 mL, dist. Na) at 0° C. and the mixture was stirred at r.t. for 18 hr. The solution was cooled to 0° C. and methanol was cautiously added to quench the reaction. Removal of the solvent gave a solid, this was partitioned between EtOAc and water, the organic fraction was dried and evaporated. Column chromatography (3:1 hexanes:EtOAc) gave 176 (2.72 g, 97%). $^1$H NMR (CDCl$_3$) δ 6.24 (s, 1H), 6.23 (s, 1H), 5.21 (sp, J=6.2 Hz, 1H), 4.60 (d, J=6.2 Hz, 2H), 4.30 (q, J=7.0 Hz, 2H), 1.70 (t, J=6.2 Hz, 1H), 1.38 (t, J=7.0 Hz, 3H), 1.34 (d, J=6.2 Hz, 6H). Found: [M+H]=212.2.

4-(Bromomethyl)-2-ethoxy-6-isopropoxypyridine (177)

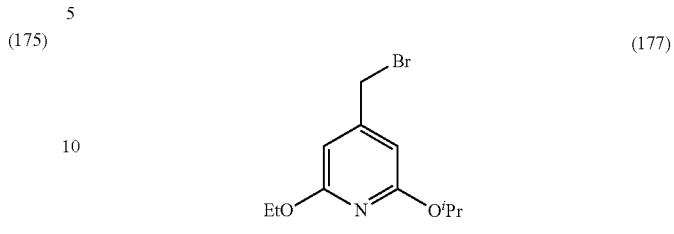

(177)

A solution of 176 (2.60 g, 12.3 mmol) in DCM (50 mL, anhydrous) at 0° C. was treated sequentially with triethylamine (3.43 mL, 24.6 mmol) then mesyl chloride (1.43 mL, 18.5 mmol), the mixture was stirred at 0° C. for 1 h then partitioned between DCM and water. The organic fraction was dried and evaporated and the residue was dissolved in acetone (100 mL), LiBr (10.7 g, 123 mmol) was added and the mixture was refluxed for 1 h and then evaporated. The residue was partitioned between DCM and water; the organic fraction was dried and evaporated. Column chromatography (DCM) gave 177 (3.04 g, 100%). $^1$H NMR (CDCl$_3$) δ 6.26 (s, 1H), 6.25 (s, 1H), 5.20 (sp, J=6.2 Hz, 1H), 4.26-4.33 (m, 4H), 1.38 (t, J=7.0 Hz, 3H), 1.34 (d, J=6.2 Hz, 6H). Found: [M+H]=274.1.

6-Bromo-3-((2-ethoxy-6-isopropoxypyridin-4-yl)methyl)-2-methoxyquinoline (178)

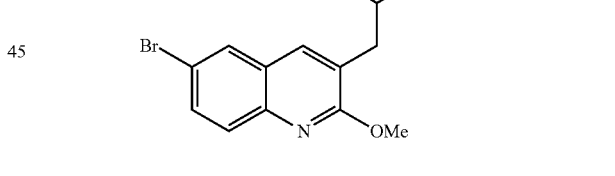

(178)

A mixture of 1 (11.6 mmol), 177 (3.18 g, 11.6 mmol) and Cs$_2$CO$_3$ (7.56 g, 23.2 mmol) in toluene (66 mL) and DMF (33 mL) was purged with nitrogen. Pd(PPh$_3$)$_4$ (0.27 g, 0.23 mmol) was added, the mixture was purged with nitrogen then heated to 80° C. under nitrogen for 3 h. The reaction was partitioned between EtOAc and water and the organic fraction was dried and evaporated. Column chromatography with 3:1 hexanes:DCM eluted impurities, then elution with DCM gave 178 (3.42 g, 68%) as white solid. $^1$H NMR (CDCl$_3$) δ 7.77 (d, J=2.1 Hz, 1H), 7.68 (d, J=8.8 Hz, 1H), 7.62 (dd, J=8.8, 2.2 Hz, 1H), 7.58 (s, 1H), 6.11 (s, 1H), 6.10 (s, 1H), 5.20 (sp, J=6.2 Hz, 1H), 4.28 (q, J=7.1 Hz, 2H), 4.06 (s, 3H), 3.89 (s, 2H), 1.36 (t, J=7.1 Hz, 3H), 1.32 (d, J=6.2 Hz, 6H). Found: [M+H]=431.1.

(6-Chloro-2-methoxyquinolin-3-yl)(m-tolyl)methanol (179)

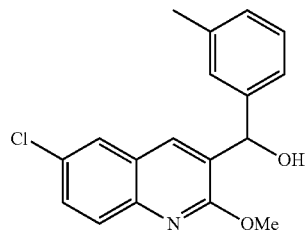
(179)

n-BuLi (12.4 mL, 2 M in cyclohexanes, 24.8 mmol) was added to a solution of 2,2,6,6,-tetramethylpiperidine (4.18 mL, 24.8 mmol) in THF (50 mL, dist. Na) at −40° C. and the solution was stirred for 5 min then cooled to −78° C. A solution of 164 (4.00 g, 20.7 mmol) in THF (40 mL, dist. Na) was added and the solution was stirred at −78 for 1.5 h, then a solution of m-tolualdehyde (2.49 g, 20.7 mmol) in THF (10 mL, dist, Na) was added. The solution was stirred at −78° C. for 3 h then acetic acid (3.55 mL, 62.0 mmol) was added, the mixture was partitioned between EtOAc and water and the aqueous was extracted with EtOAc, the organic fractions were combined and evaporated. Column chromatography (3:1 hexanes:DCM to 2:1 hexanes:DCM to DCM and then 95:5 DCM:EtOAc) gave 179 (3.39 g, 55%) as a white solid. $^1$H NMR (CDCl$_3$) δ 7.88 (s, 1H), 7.76 (d, J=8.9 Hz, 1H), 7.69 (d, J=2.4 Hz, 1H), 7.53 (dd, J=8.9, 2.4 Hz, 1H), 7.16-7.25 (m, 2H), 7.11 (d, J=7.4 Hz, 1H), 6.03 (d, J=3.8 Hz, 1H), 4.05 (s, 3H), 2.86 (d, J=4.3 Hz, 1H), 2.34 (s, 3H). Found: [M+H]=314.1.

6-Chloro-2-methoxy-3-(3-methylbenzyl)quinoline (180)

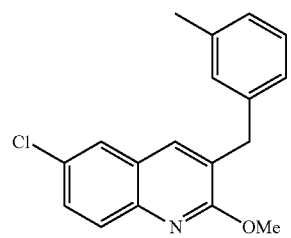
(180)

A solution of 179 (3.36 g, 113 mmol) in DCM (60 mL) was treated with trifluoroacetic acid (8.4 mL, 113 mmol) and then triethylsilane (14.5 mL, 89.9 mmol). The solution was refluxed for 18 h, neutralised with sat. aq. NaHCO$_3$ and partitioned with water. The organic phase was dried and evaporated, column chromatography (3:1 hexanes:DCM) gave 180 (2.27 g, 67%). $^1$H NMR (CDCl$_3$) δ 7.75 (d, J=8.9 Hz, 1H), 7.58 (d, J=2.4 Hz, 1H), 7.46-7.50 (m, 2H), 7.21 (t, J=7.8 Hz, 1H), 7.01-7.08 (m, 3H), 4.08 (s, 3H), 3.99 (s, 2H), 2.33 (s, 3H). Found: [M+H]=298.1.

(2,6-Dimethoxypyridin-4-yl)methanol (279)

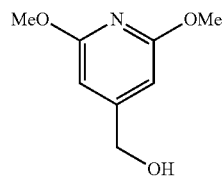
(279)

Borane-dimethylsulfide (4.60 mL, 48.5 mmol) and trimethylborate (5.58 mL, 49.1 mmol) were added to a solution of 2,6-dimethoxyisonicotinic acid (3.00 g, 16.4 mmol) in THF (100 mL, dist. Na) at 0° C., the solution was then stirred at r.t. for 18 h, cooled to 0° C., quenched with MeOH and evaporated. The residue was partitioned between EtOAc and water and the organic fraction was dried and evaporated. Column chromatography (2:1 hexanes:EtOAc) gave 279 (2.72 g, 98%). $^1$H NMR (CDCl$_3$) δ 6.30 (s, 2H), 4.64 (d, J=5.8 Hz, 2H), 3.91 (s, 6H), 1.75 (t, J=6.1 Hz, 1H). Found: [M+H]=170.1.

4-(Bromomethyl)-2,6-dimethoxypyridine (280)

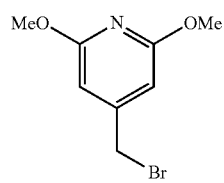
(280)

A solution of 279 (1.57 g, 9.30 mmol) in DCM (40 mL, anhydrous) at 0° C. was treated with triethylamine (2.60 mL, 18.6 mmol) then mesyl chloride (1.08 mL, 13.9 mmol), the mixture was stirred at 0° C. for 1 h then partitioned between DCM and water. The organic fraction was dried and evaporated and the residue was dissolved in acetone (50 mL). LiBr (4.04 g, 46.5 mmol) was added and the mixture was refluxed for 1 h then evaporated. The residue was partitioned between DCM and water and the organic fraction was dried and evaporated. Column chromatography (DCM) gave 280 (1.96 g, 91%). $^1$H NMR (CDCl$_3$) δ 6.32 (s, 2H), 4.29 (s, 2H), 3.91 (s, 6H). Found: [M+H]=232.0.

6-Bromo-3-((2,6-dimethoxypyridin-4-yl)methyl)-2-methoxyquinoline (281)

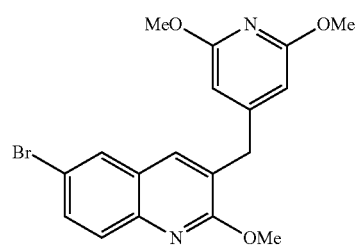
(281)

A mixture of 1 (2.20 g, 7.80 mmol), 280 (1.93 g, 8.30 mmol), $Cs_2CO_3$ (5.10 g, 15.7 mmol) and $Pd(PPh_3)_4$ (0.45 g, 0.39 mmol) in DMF (10 mL) and toluene (20 mL) was purged with nitrogen, then heated to 80° C. for 4 h under nitrogen. The mixture was partitioned between EtOAc and water and the organic fraction was dried and evaporated. Column chromatography (3:1 hexanes:DCM) eluted non polar impurities, elution with DCM gave 281 (1.95 g, 64%). $^1$H NMR ($CDCl_3$) δ 7.78 (d, J=2.1 Hz, 1H), 7.69 (d, J=8.9 Hz, 1H), 7.63 (dd, J=8.9, 2.2 Hz, 1H), 7.57 (s, 1H), 6.17 (s, 2H), 4.06 (s, 3H), 3.92 (s, 2H), 3.89 (s, 6H). Found: [M+H]=389.1.

N-Methoxy-N,2,6-trimethylisonicotinamide (282)

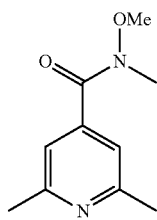

(282)

Oxalyl chloride (1.46 mL, 17.3 mmol) was added to a suspension of 2,6-dimethylisonicotinic acid (2.38 g, 15.7 mmol) in DCM (100 mL, anhydrous) and DMF (1.3 mmol) at r.t. The mixture was stirred at r.t. for 1 h to give a colorless solution which was cooled to 0° C. N,O-Dimethylhydroxylamine hydrochloride (1.46 mL, 17.3 mmol) and pyridine (3.82 mL, 47.2 mmol) were added sequentially and the mixture was stirred at r.t. for 18 h, then partitioned between EtOAc and sat. aq. $NaHCO_3$. Column chromatography with hexanes:EtOAc 1:1 gave 282 as an oil (1.50 g, 49%). $^1$H NMR ($CDCl_3$) δ 7.15 (s, 2H), 3.56 (s, 3H), 3.35 (s, 3H), 2.57 (s, 6H). Found: [M+H]=195.1.

3-(Dimethylamino)-1-(2,6-dimethylpyridin-4-yl)propan-1-one (283)

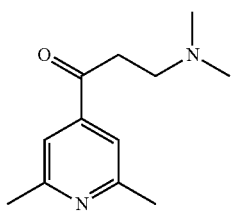

(283)

Vinylmagnesium bromide solution in THF (1N, 22.0 mL, 22 mmol) was added to a solution of 282 (1.43 g, 7.37 mmol) in THF (100 mL, dist. Na) at 0° C., the brown solution was warmed to r.t. for 1 h then dimethylamine in THF (2N, 22.0 mL, 44 mmol) and water (20 mL) were added. The solution was stirred at r.t. for 1 h, then partitioned between EtOAc and water. The solution was dried and evaporated to give 283 as a yellow oil (1.54 g, 99%). $^1$H NMR ($CDCl_3$) δ 7.38 (s, 2H), 3.10 (t, J=7.2 Hz, 2H), 2.74 (t, J=7.2 Hz, 2H), 2.61 (s, 6H), 2.28 (s, 6H). Found: [M+H]=207.2.

II. Preparation of Representative Embodiments of the Invention

Example 1

1-(6-Bromo-2-methoxyquinolin-3-yl)-2-(2,6-dimethoxypyridin-4-yl)-4-(dimethylamino)-1-(m-tolyl)butan-2-ol (181)

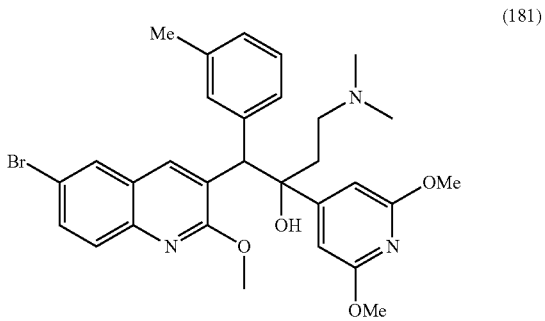 [SMILES: COc1cc(C(O)(CCN(C)C)C(c2cccc(C)c2)c2cc3cc(Br)ccc3nc2OC)cc(OC)n1]

(181)

General Coupling Procedure:

n-BuLi (2.63 mL of a 2N solution in cyclohexane, 5.26 mmol) was added at −30° C. under dry nitrogen to a solution of dry diisopropylamine (0.74 mL, 5.26 mmol) in dry THF (6 mL) and the solution was stirred at this temperature for 10 min, then cooled to −78° C. A solution of 10 (1.50 g, 4.38 mmol) in dry THE (6 mL) was added dropwise and the mixture was stirred at −78° C. for 90 min, to give a dark, wine-red colored solution. A solution of dry 6 (1.15 g, 4.82 mmol) in dry THF (7 mL) was added and the reaction mixture was stirred at this temperature for 4 h. HOAc (0.90 mL) was added and the reaction mixture was warmed to r.t. Water (100 mL) was added and the mixture was extracted with EtOAc (2×). The combined organic extract was washed with sat. aq. $NaHCO_3$ solution, and brine, then dried ($Na_2SO_4$) and the solvent removed under reduced pressure. The residue was purified by flash column chromatography. Elution with 0-10% MeOH/DCM gave fore fractions of unreacted 10, followed by the product 181 as a 1:1 mixture of diastereomers (0.91 g, 36%). Found: [M+H]=580.1.

The following compounds were synthesised using the General Coupling Procedure. Each coupled product was resolved into its four optical isomers using preparative chiral HPLC.

Example 2

2-(Benzofuran-7-yl)-1-(6-bromo-2-methoxyquinolin-3-yl)-4-(dimethylamino)-1-phenylbutan-2-ol (182)

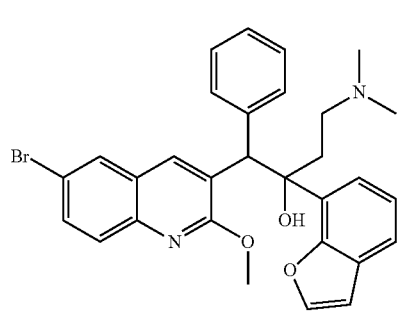
(182)

From coupling of 3-benzyl-6-bromo-2-methoxyquinoline and (114). Column chromatography of the crude product with 0-5% MeOH:DCM gave fore fractions, followed by 182. Found: [M+H]=544.9.

Example 3

1-(6-Bromo-2-methoxyquinolin-3-yl)-1-(5,6-dimethoxypyridin-3-yl)-4-(dimethylamino)-2-(3-fluorophenyl)butan-2-ol (183)

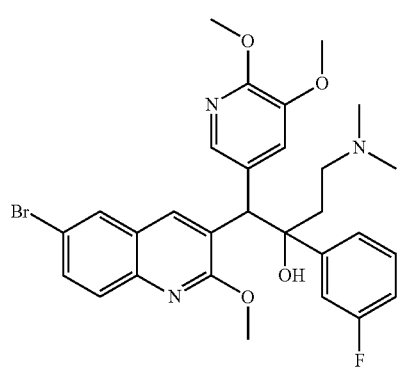
(183)

From coupling of 117 and 3-(dimethylamino)-1-(3-fluorophenyl)propan-1-one. Column chromatography of the crude product with 0-5% MeOH:DCM gave fore fractions, followed by 183. Found: [M+H]=583.9.

Example 4

1-(6-Bromo-2-methoxyquinolin-3-yl)-1-(2,3-dimethoxypyridin-4-yl)-4-(dimethylamino)-2-(m-tolyl)butan-2-ol (184)

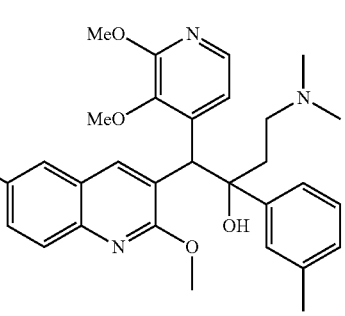
(184)

From coupling of 120 and 3-(dimethylamino)-1-(m-tolyl)propan-1-one. Column chromatography of the crude product with 0-5% MeOH:DCM gave fore fractions, followed by 184. Found: [M+H]=580.0.

Example 5

1-(6-Bromo-2-methoxyquinolin-3-yl)-2-(2,6-diethoxypyridin-4-yl)-4-(dimethylamino)-1-(2-fluoro-3-methoxyphenyl)butan-2-ol (185)

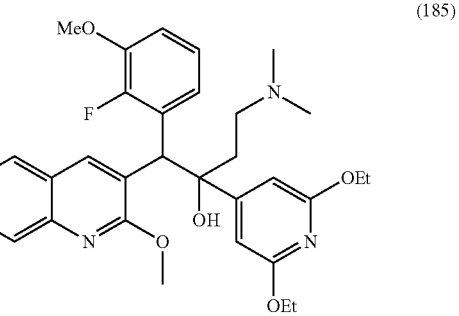
(185)

From coupling of 8 and 4. Column chromatography of the crude product with 0-5% MeOH:DCM gave fore fractions, followed by 185. Found: [M+H]=642.1.

Example 6

2-(Benzofuran-2-yl)-1-(6-bromo-2-methoxyquino-lin-3-yl)-4-(dimethylamino)-1-(3-fluorophenyl)bu-tan-2-ol (186)

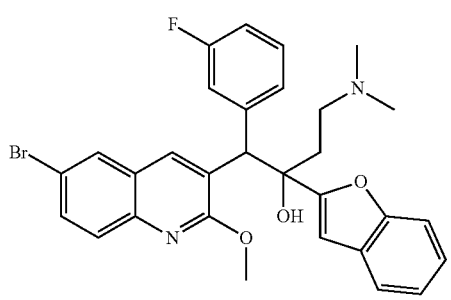

(186)

From coupling of 9 and 122. Column chromatography of the crude product with 0-5% MeOH:DCM gave fore fractions, followed by 186. Found: [M+H]=562.9.

Example 7

2-(Benzofuran-2-yl)-1-(6-bromo-2-methoxyquino-lin-3-yl)-1-(2,3-dimethoxypyridin-4-yl)-4-(dimethyl-amino)butan-2-ol (187)

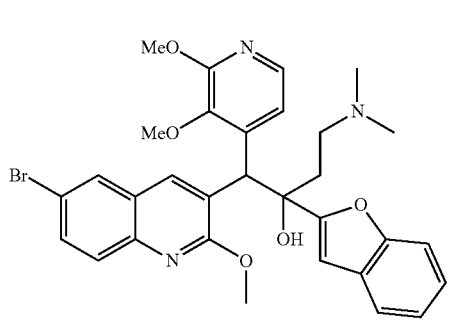

(187)

From coupling of 120 and 122. Column chromatography of the crude product with 0-5% MeOH:DCM gave fore fractions, followed by 187. Found: [M+H]=606.1.

Example 8

2-(Benzofuran-7-yl)-1-(6-bromo-2-methoxyquino-lin-3-yl)-4-(dimethylamino)-1-(3-fluorophenyl)bu-tan-2-ol (188)

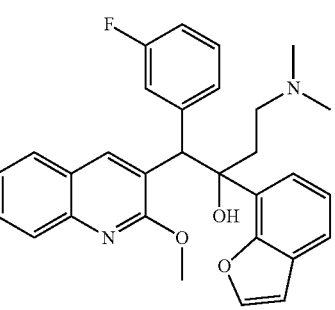

(188)

From coupling of 9 and 114. Column chromatography of the crude product with 0-5% MeOH:DCM gave fore fractions, followed by 188. Found: [M+H]=562.9.

Example 9

1-(6-Bromo-2-methoxyquinolin-3-yl)-1-(2,3-dime-thoxypyridin-4-yl)-2-(2,6-dimethoxypyridin-4-yl)-4-(dimethylamino)butan-2-ol (189)

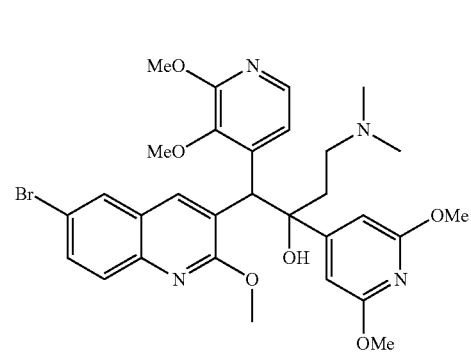

(189)

From coupling of 120 and 6. Column chromatography of the crude product with 0-5% MeOH:DCM gave fore fractions, followed by 189. Found: [M+H]=627.1.

Example 10

2-(Benzofuran-5-yl)-1-(6-bromo-2-methoxyquinolin-3-yl)-1-(2,3-dimethoxypyridin-4-yl)-4-(dimethylamino)butan-2-ol (190)

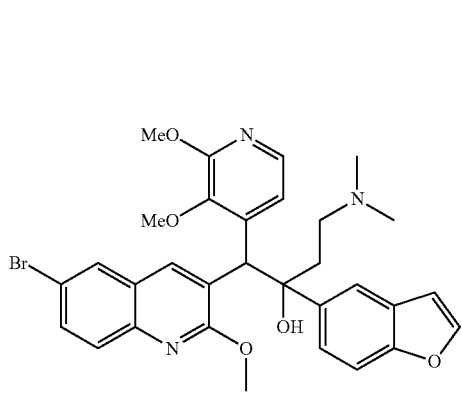
(190)

From coupling of 120 and 126. Column chromatography of the crude product with 0-5% MeOH:DCM gave fore fractions, followed by 190. Found: [M+H]=606.1.

Example 11

1-(6-Bromo-2-methoxyquinolin-3-yl)-2-(2,6-dimethoxypyridin-4-yl)-4-(dimethylamino)-1-(5-methylthiophen-2-yl)butan-2-ol (191)

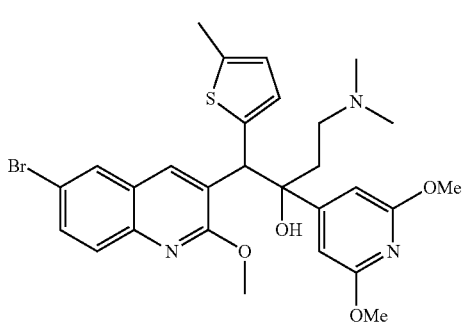
(191)

From coupling of 16 and 6. Column chromatography of the crude product with 0-5% MeOH:DCM gave fore fractions, followed by 191. Found: [M+H]=586.1.

Example 12

2-(Benzofuran-7-yl)-1-(6-bromo-2-methoxyquinolin-3-yl)-1-(2,6-diethoxypyridin-4-yl)-4-(dimethylamino)butan-2-ol (192)

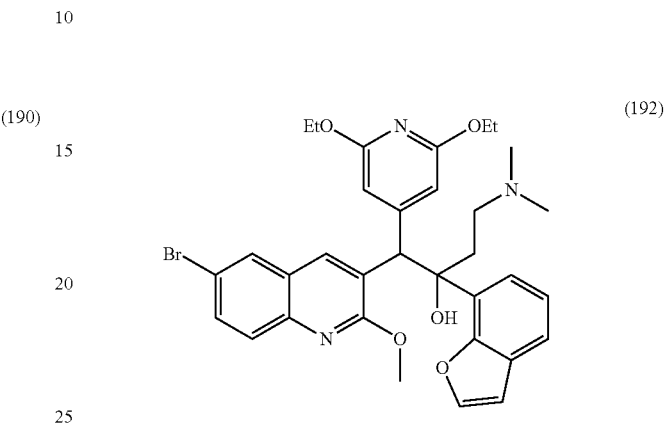
(192)

From coupling of 129 and 114. Column chromatography of the crude product with 0-5% MeOH:DCM gave fore fractions, followed by 192. Found: [M+H]=634.2.

Example 13

1-(6-Bromo-2-methoxyquinolin-3-yl)-2-(2,6-dimethoxypyridin-4-yl)-4-(dimethylamino)-1-(2-fluoro-3-methoxyphenyl)butan-2-ol (193)

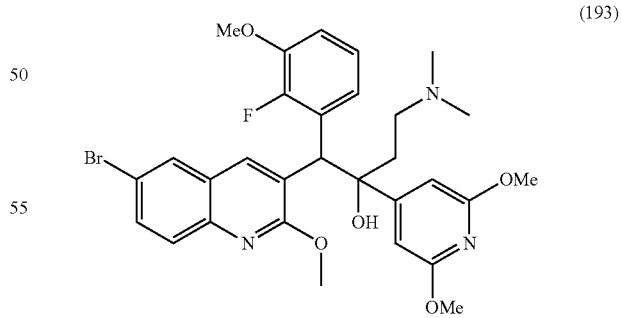
(193)

From coupling of 8 and 6. Column chromatography of the crude product with 0-5% MeOH:DCM gave fore fractions, followed by 193. Found: [M+H]=614.0.

Example 14

2-(Benzofuran-4-yl)-1-(6-bromo-2-methoxyquinolin-3-yl)-4-(dimethylamino)-1-phenylbutan-2-ol (194)

Example 16

1-(6-Bromo-2-methoxyquinolin-3-yl)-4-(dimethylamino)-1-(2-fluoro-3-methoxyphenyl)-2-(2-isopropoxy-6-methoxypyridin-4-yl)butan-2-ol (196)

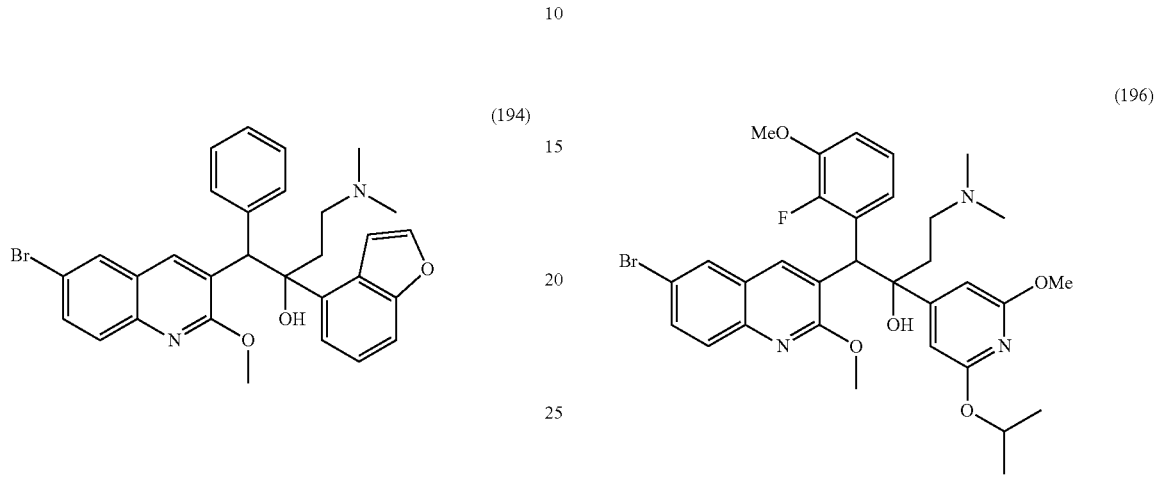

From coupling of 3-benzyl-6-bromo-2-methoxyquinoline and 134. Column chromatography of the crude product with 0-5% MeOH:DCM gave fore fractions, followed by 194. Found: [M+H]=544.5.

From coupling of 8 and 143. Column chromatography of the crude product with 0-5% MeOH:DCM gave fore fractions, followed by 196. Found: [M+H]=642.1.

Example 15

2-(Benzo[b]thiophen-7-yl)-1-(6-bromo-2-methoxyquinolin-3-yl)-4-(dimethylamino)-1-phenylbutan-2-ol (195)

Example 17

1-(6-Bromo-2-methoxyquinolin-3-yl)-4-(dimethylamino)-2-(2-ethoxy-6-methoxypyridin-4-yl)-1-(2-fluoro-3-methoxyphenyl)butan-2-ol (197)

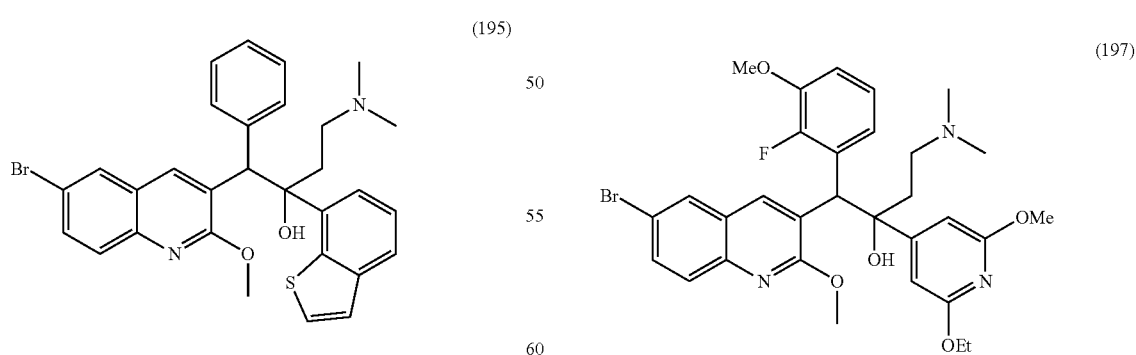

From coupling of 3-benzyl-6-bromo-2-methoxyquinoline and 138. Column chromatography of the crude product with 0-5% MeOH:DCM gave fore fractions, followed by 195. Found: [M+H]=561.0.

From coupling of 8 and 147. Column chromatography of the crude product with 0-5% MeOH:DCM gave fore fractions, followed by 197. Found: [M+H]=627.7.

Example 18

1-(6-Bromo-2-methoxyquinolin-3-yl)-1-(2,3-dimethoxypyridin-4-yl)-4-(dimethylamino)-2-(2-isopropoxy-6-methoxypyridin-4-yl)butan-2-ol (198)

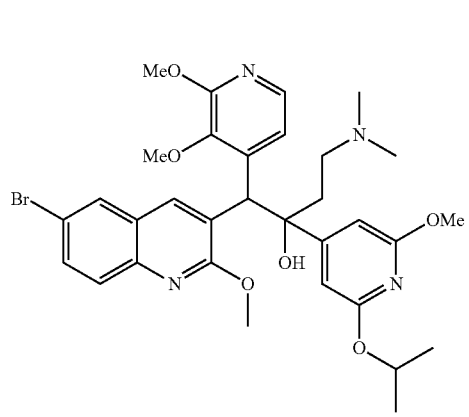

From coupling of 120 and 143. Column chromatography of the crude product with 0-5% MeOH:DCM gave fore fractions, followed by 198. Found: [M+H]=655.1.

Example 19

1-(6-Bromo-2-methoxyquinolin-3-yl)-2-(2,6-dimethoxypyridin-4-yl)-4-(dimethylamino)-1-(2-isopropoxy-6-methoxypyridin-4-yl)butan-2-ol (199)

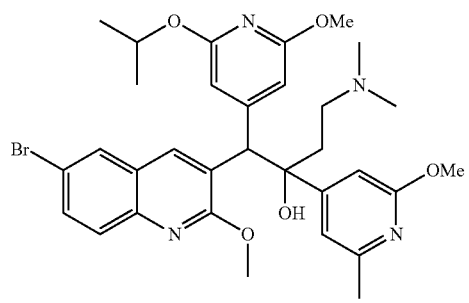

From coupling of 150 and 6. Column chromatography of the crude product with 0-5% MeOH:DCM gave fore fractions, followed by 199. Found: [M+H]=655.0.

Example 20

1-(6-Bromo-2-methoxyquinolin-3-yl)-1-(2,3-dimethoxypyridin-4-yl)-4-(dimethylamino)-2-(2-ethoxy-6-methoxypyridin-4-yl)butan-2-ol (200)

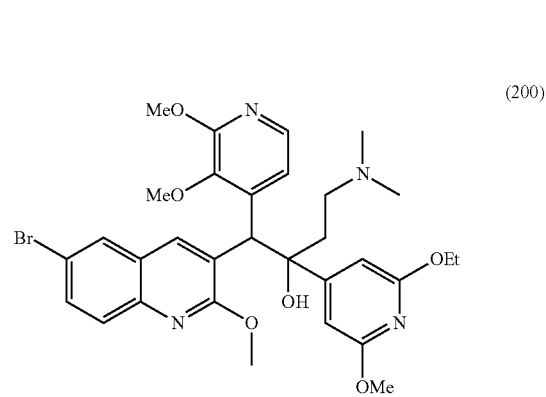 [SMILES: CCOc1cc(C(O)(CCN(C)C)C(c2cc3cc(Br)ccc3nc2OC)c2ccnc(OC)c2OC)cc(OC)n1]

From coupling of 120 and 147. Column chromatography of the crude product with 0-5% MeOH:DCM gave fore fractions, followed by 200. Found: [M+H]=641.2.

Example 21

2-(Benzofuran-7-yl)-1-(6-bromo-2-methoxyquinolin-3-yl)-4-(dimethylamino)-1-(2-isopropoxy-6-methoxypyridin-4-yl)butan-2-ol (201)

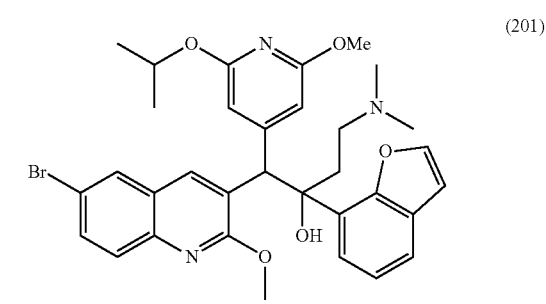 [SMILES: COc1cc(C(c2cc3cc(Br)ccc3nc2OC)C(O)(CCN(C)C)c2cccc3ccoc23)cc(OC(C)C)n1]

From coupling of 150 and 114. Column chromatography of the crude product with 0-5% MeOH:DCM gave fore fractions, followed by 2012 Found: [M+H]=634.1.

Example 22

2-(Benzofuran-7-yl)-1-(6-bromo-2-methoxyquinolin-3-yl)-4-(dimethylamino)-1-(2-ethoxy-6-methoxypyridin-4-yl)butan-2-ol (202)

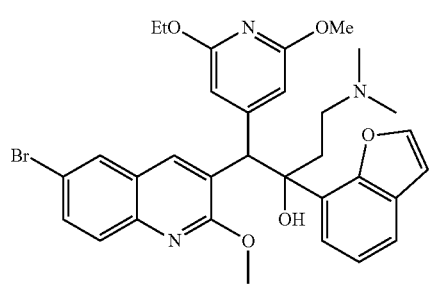

(202)

From coupling of 153 and 114. Column chromatography of the crude product with 0-5% MeOH:DCM gave fore fractions, followed by 202. Found: [M+H]=620.1.

Example 23

1-(6-Bromo-2-methoxyquinolin-3-yl)-1-(2,3-dimethoxypyridin-4-yl)-4-(dimethylamino)-2-(2-ethoxy-6-isopropoxypyridin-4-yl)butan-2-ol (203)

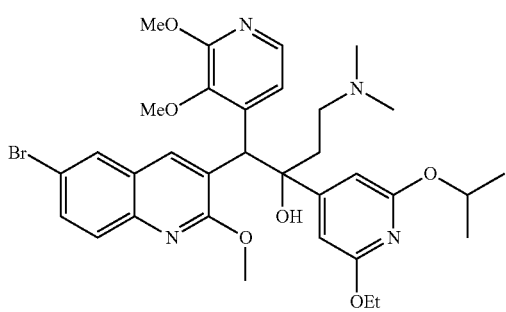

(203)

From coupling of 120 and 158. Column chromatography of the crude product with 0-5% MeOH:DCM gave fore fractions, followed by 203. Found: [M+H]=669.0.

Example 24

1-(6-Bromo-2-methoxyquinolin-3-yl)-1-(2,6-dimethoxypyridin-4-yl)-4-(dimethylamino)-2-(2-ethoxy-6-isopropoxypyridin-4-yl)butan-2-ol (204)

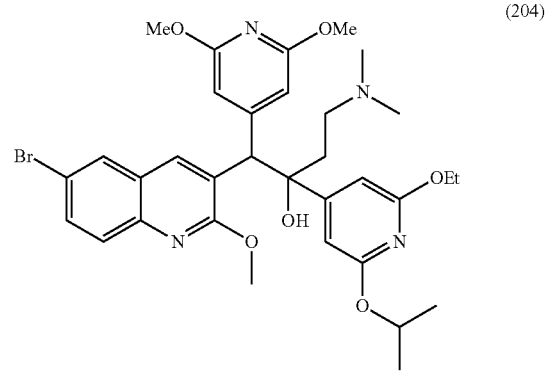 [SMILES: CCOc1cc(C(O)(CCN(C)C)C(c2cc(OC)nc(OC)c2)c2cc3cc(Br)ccc3nc2OC)cc(OC(C)C)n1]

(204)

From coupling of 281 and 158. Column chromatography of the crude product with 0-5% MeOH:DCM gave fore fractions, followed by 204. Found: [M+H]=669.0.

Example 25

1-(6-Bromo-2-methoxyquinolin-3-yl)-4-(dimethylamino)-2-(2-isopropoxy-6-methoxypyridin-4-yl)-1-(m-tolyl)butan-2-ol (205)

(205)

From coupling of 10 and 143. Column chromatography of the crude product with 0-5% MeOH:DCM gave fore fractions, followed by 205. Found: [M+H]=607.7.

Example 26

1-(6-Bromo-2-methoxyquinolin-3-yl)-2-(2,6-dimethoxypyridin-4-yl)-4-(dimethylamino)-1-(2-methoxy-6-propoxypyridin-4-yl)butan-2-ol (206)

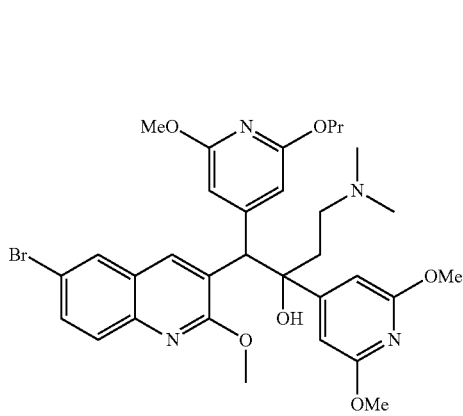
(206)

From coupling of 163 and 6. Column chromatography of the crude product with 0-5% MeOH:DCM gave fore fractions, followed by 206. Found: [M+H]=654.7.

Example 27

1-(6-Chloro-2-methoxyquinolin-3-yl)-2-(2,6-diethoxypyridin-4-yl)-4-(dimethylamino)-1-(2-fluoro-3-methoxyphenyl)butan-2-ol (207)

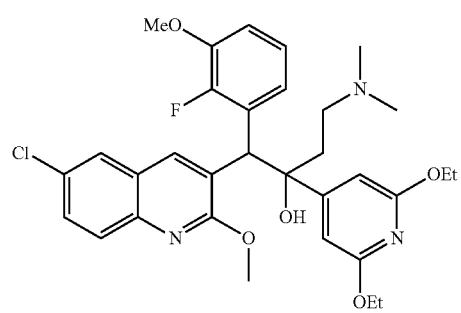
(207)

From coupling of 166 and 4. Column chromatography of the crude product with 0-3% MeOH:DCM gave fore fractions, followed by 207. Found: [M+H]=597.8.

Example 28

1-(6-Bromo-2-methoxyquinolin-3-yl)-1-(2,3-dimethoxypyridin-4-yl)-4-(dimethylamino)-2-(2-methoxy-6-propoxypyridin-4-yl)butan-2-ol (208)

(208)

From coupling of 120 and 168. Column chromatography of the crude product with 0-5% MeOH:DCM gave fore fractions, followed by 208. Found: [M+H]=654.7.

Example 29

1-(Benzofuran-7-yl)-1-(6-bromo-2-methoxyquinolin-3-yl)-2-(2,6-dimethoxypyridin-4-yl)-4-(dimethylamino)butan-2-ol (209)

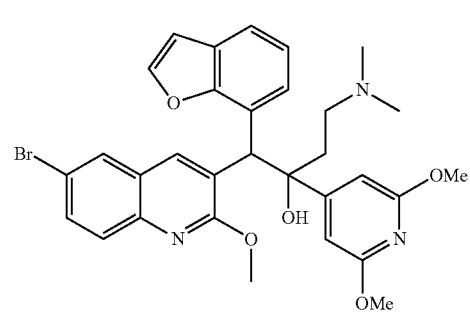
(209)

From coupling of 171 and 6. Column chromatography of the crude product with 0-5% MeOH:DCM gave fore fractions, followed by 209. Found: [M+H]=605.7.

Example 30

1-(6-Bromo-2-methoxyquinolin-3-yl)-2-(2-cyclobutoxy-6-methoxypyridin-4-yl)-1-(2,3-dimethoxypyridin-4-yl)-4-(dimethylamino)butan-2-ol (210)

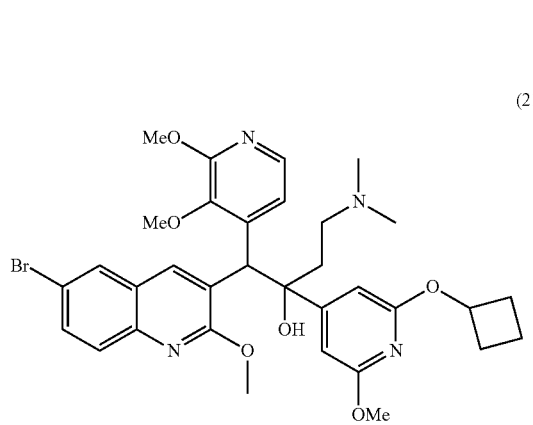

From coupling of 120 and 175. Column chromatography of the crude product with 0-5% MeOH:DCM gave fore fractions, followed by 210. Found: [M+H]=666.7.

Example 31

1-(6-Bromo-2-methoxyquinolin-3-yl)-2-(2,6-dimethoxypyridin-4-yl)-4-(dimethylamino)-1-(2-ethoxy-6-isopropoxypyridin-4-yl)butan-2-ol (211)

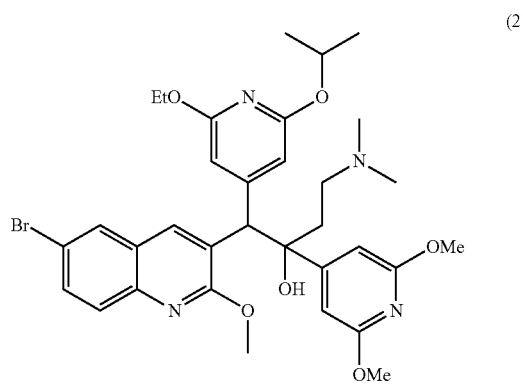

From coupling of 178 and 6. Column chromatography of the crude product with 0-5% MeOH:DCM gave fore fractions, followed by 211. Found: [M+H]=669.0.

Example 32

1-(6-Chloro-2-methoxyquinolin-3-yl)-2-(2,6-diethoxypyridin-4-yl)-4-(dimethylamino)-1-(m-tolyl)butan-2-ol (212)

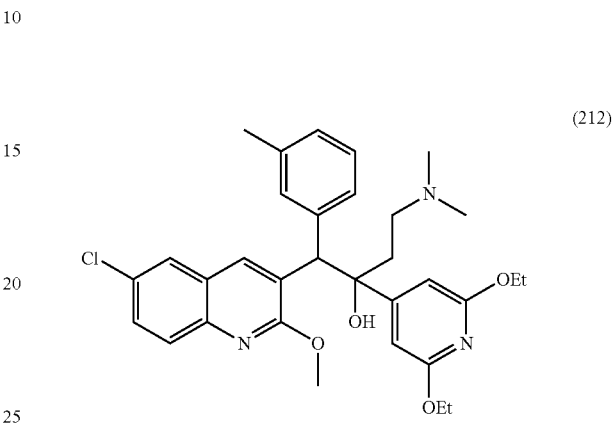

From coupling of 180 and 4. Column chromatography of the crude product with 0-3% MeOH:DCM gave fore fractions, followed by 212. Found: [M+H]=564.0.

Example 33

1-(6-Bromo-2-methoxyquinolin-3-yl)-2-(2,6-dimethoxypyridin-4-yl)-4-(dimethylamino)-1-(2,5-dimethylthiophen-3-yl)butan-2-ol (213)

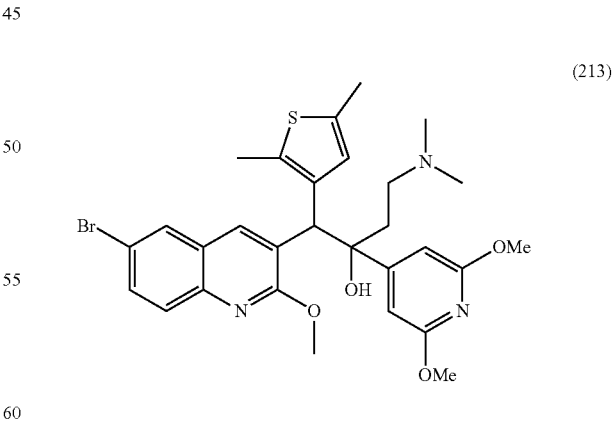

From coupling of 14 and 6. Column chromatography with EtOAc:hexanes (1:3) eluted unreacted 14 while hexanes:EtOAc (1:1) gave 213. Found: [M+H]=600.1.

Example 34

1-(6-Bromo-2-methoxyquinolin-3-yl)-2-(2,6-diethoxypyridin-4-yl)-4-(dimethylamino)-1-(m-tolyl)butan-2-ol (214)

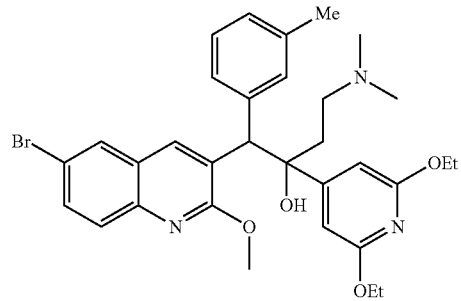
(214)

From coupling of 10 and 4. Column chromatography with EtOAc:hexanes (1:9) gave fore fractions, then elution with EtOAc:hexanes (1:4) gave 214. Found: [M+H]=608.2.

Example 35

1-(6-Bromo-2-methoxyquinolin-3-yl)-2-(2,6-diethoxypyridin-4-yl)-1-(2,3-dimethoxyphenyl)-4-(dimethylamino)butan-2-ol (215)

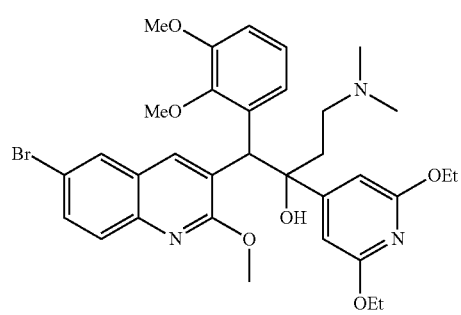
(215)

From coupling of 11 and 4. Column chromatography with EtOAc:hexanes (1:9) gave fore fractions, then elution with EtOAc:hexanes (1:1) gave 215. Found: [M+H]=654.1.

Example 36

1-(6-Bromo-2-methoxyquinolin-3-yl)-2-(2,6-diethoxypyridin-4-yl)-1-(2,3-dimethoxypyridin-4-yl)-4-(dimethylamino)butan-2-ol (216)

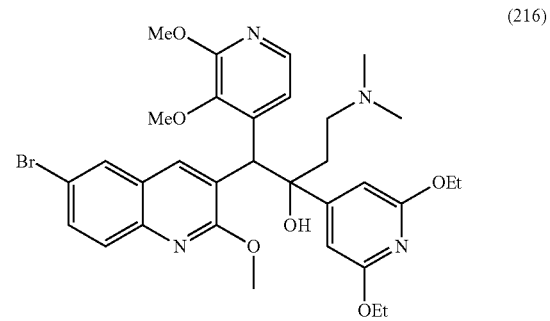
(216)

From coupling of 120 and 4. Column chromatography with EtOAc:hexanes (1:4), then EtOAc gave fore fractions, followed by 216. Found: [M+H]=655.1.

Example 37

1-(6-Bromo-2-methoxyquinolin-3-yl)-1-(2,3-dimethoxyphenyl)-4-(dimethylamino)-2-(2,6-dimethylpyridin-4-yl)butan-2-ol (217)

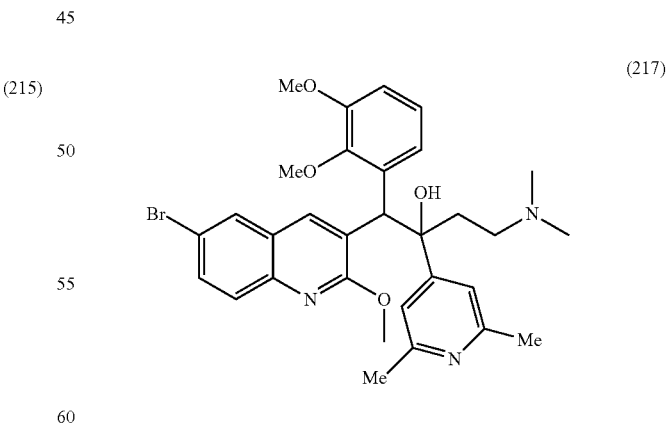
(217)

From coupling of 11 and 283. Column chromatography with MeOH:DCM (0-8%) gave fore fractions, then 217. Found: [M+H]=594.1.

Example 38

1-(6-Bromo-2-methoxyquinolin-3-yl)-2-(2,6-dimethoxypyridin-4-yl)-4-(dimethylamino)-1-(2-methoxypyridin-3-yl)butan-2-ol (218)

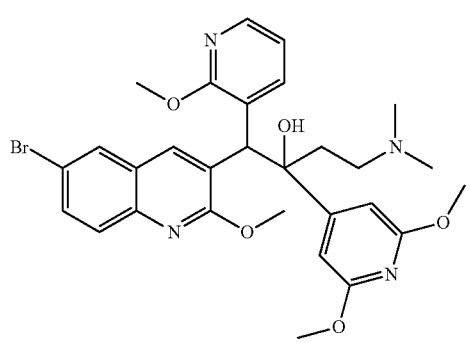
(218)

From coupling of 17 and 6. Column chromatography with EtOAc:hexanes (1:1), then EtOAc gave fore fractions, followed by 218. Found: [M+H]=597.1.

Example 39

1-(6-Bromo-2-methoxyquinolin-3-yl)-2-(2,6-dimethoxypyridin-4-yl)-4-(dimethylamino)-1-(3-fluorophenyl)butan-2-ol (219)

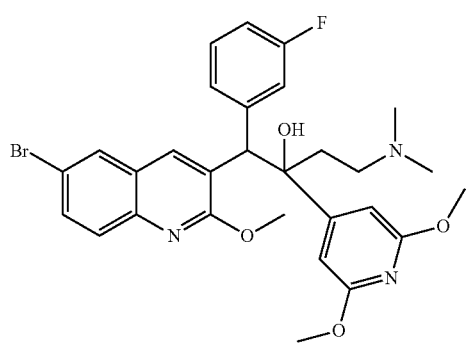
(219)

From coupling of 9 and 6. Column chromatography with EtOAc:hexanes (1:1), then EtOAc gave 219. Found: [M+H]= 584.1.

Example 40

1-(6-Bromo-2-methoxyquinolin-3-yl)-2-(2,3-dihydro-1H-inden-4-yl)-4-(dimethylamino)-1-phenylbutan-2-ol (220)

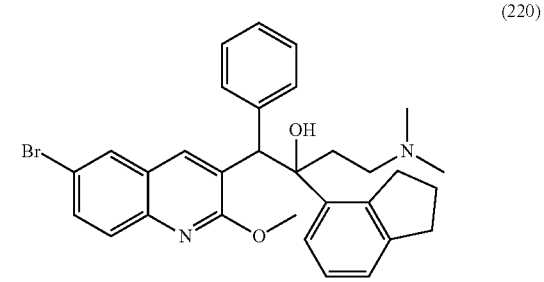 [SMILES: COc1nc2ccc(Br)cc2cc1C(c1ccccc1)C(O)(CCN(C)C)c1cccc2c1CCC2]
(220)

From coupling of 3-benzyl-6-bromo-2-methoxyquinoline and 19. Column chromatography with EtOAc:hexanes (1:1) gave fore fractions, then 220. Found: [M+H]=545.3.

Example 41

1-(6-Bromo-2-methoxyquinolin-3-yl)-1-(2,3-dihydrobenzo[b][1,4]dioxin-5-yl)-2-(2,6-dimethoxypyridin-4-yl)-4-(dimethylamino)butan-2-ol (221)

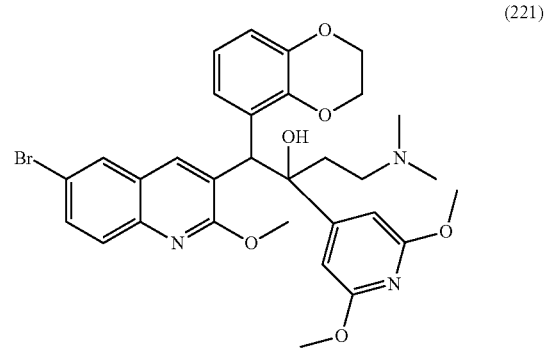 [SMILES: COc1cc(C(O)(CCN(C)C)C(c2cc3cc(Br)ccc3nc2OC)c2cccc3c2OCCO3)cc(OC)n1]
(221)

From coupling of 22 and 6. Column chromatography with EtOAc:hexanes (1:1) gave fore fractions, then 221. Found: [M+H]=624.1.

Example 42

2-(2,6-Dimethoxypyridin-4-yl)-4-(dimethylamino)-1-(6-iodo-2-methoxyquinolin-3-yl)-1-phenylbutan-2-ol (222)

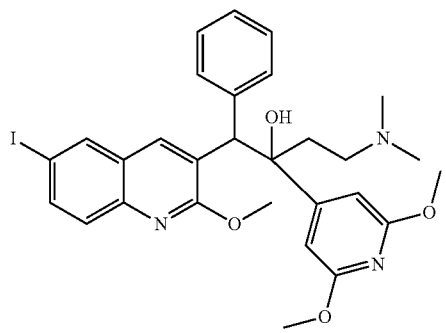
(222)

From coupling of 23 and 6. Column chromatography with EtOAc:hexanes (3:7) gave fore fractions, then 222. Found: [M+H]=614.1.

Example 43

1-(6-Bromo-2-methoxyquinolin-3-yl)-2-(2,6-diethoxypyridin-4-yl)-1-(2,3-dihydrobenzo[b][1,4]dioxin-5-yl)-4-(dimethylamino)butan-2-ol (223)

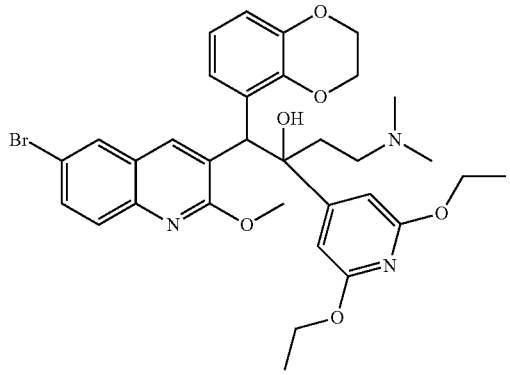
(223)

From coupling of 22 and 4. Column chromatography with EtOAc:hexanes (1:1), then EtOAc gave 223. Found: [M+H]= 652.2.

Example 44

2-(2,6-Bis(ethylthio)pyridin-4-yl)-1-(6-bromo-2-methoxyquinolin-3-yl)-4-(dimethylamino)-1-(2-fluoro-3-methoxyphenyl)butan-2-ol (224)

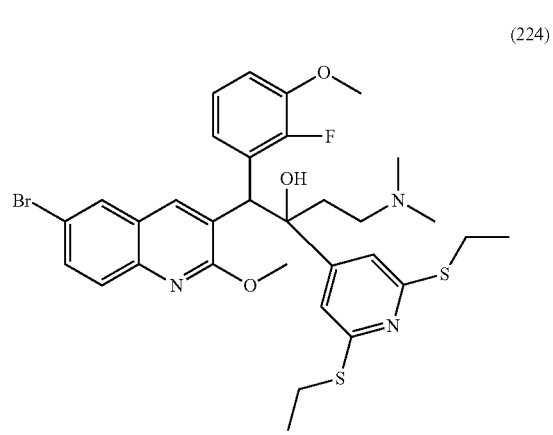 [SMILES: CCSc1cc(C(O)(CCN(C)C)C(c2cc3cc(Br)ccc3nc2OC)c2cccc(OC)c2F)cc(SCC)n1]
(224)

From coupling of 8 and 26. Column chromatography with EtOAc:hexanes (1:1), then EtOAc gave 224. Found: [M+H]= 674.1.

Example 45

2-(2,6-Bis(methylthio)pyridin-4-yl)-1-(6-bromo-2-methoxyquinolin-3-yl)-4-(dimethylamino)-1-(2-fluoro-3-methoxyphenyl)butan-2-ol (225)

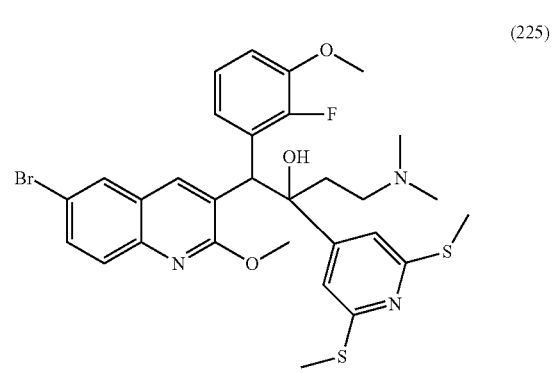 [SMILES: COc1cccc(C(c2cc3cc(Br)ccc3nc2OC)C(O)(CCN(C)C)c2cc(SC)nc(SC)c2)c1F]
(225)

From coupling of 8 and 29. Column chromatography with htUAc:hexanes (1:1), then EtOAc gave fore fractions, followed by 225. Found: [M+H]=646.0.

Example 46

2-(2,6-Bis(methylthio)pyridin-4-yl)-1-(6-bromo-2-methoxyquinolin-3-yl)-1-(2,3-dimethoxypyridin-4-yl)-4-(dimethylamino)butan-2-ol (226)

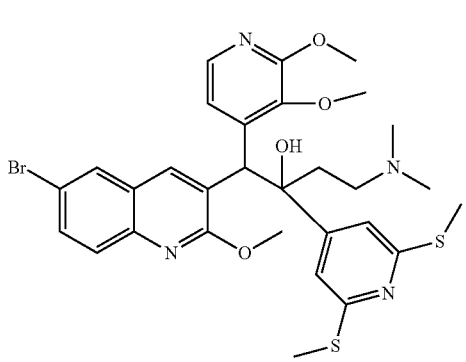
(226)

From coupling of 120 and 29. Column chromatography with EtOAc:hexanes (1:1), then EtOAc gave fore fractions, followed by 226. Found: [M+H]=659.1.

Example 47

1-(6-Bromo-2-methoxyquinolin-3-yl)-2-(2,6-diethoxypyridin-4-yl)-4-(dimethylamino)-1-(2-fluoro-3-methylphenyl)butan-2-ol (227)

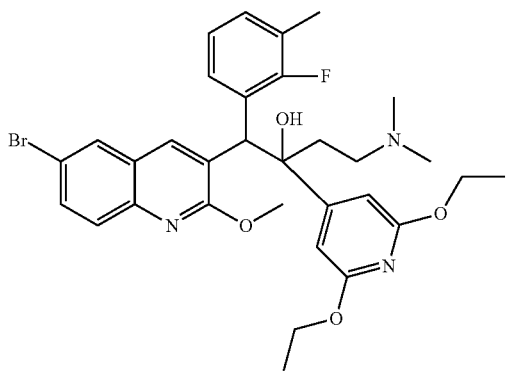
(227)

From coupling of 30 and 4. Column chromatography with EtOAc:hexanes (1:1) gave fore fractions, then 227. Found: [M+H]=626.1.

Example 48

1-(6-Bromo-2-methoxyquinolin-3-yl)-4-(dimethylamino)-1-(2-fluoro-3-methoxyphenyl)-2-(2-methoxy-6-(methylthio)pyridin-4-yl)butan-2-ol (228)

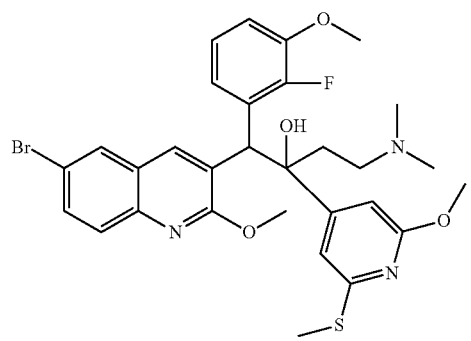
(228)

From coupling of 8 and 33. Column chromatography with EtOAc:hexanes (1:1), then EtOAc gave fore fractions, followed by 228. Found: [M+H]=630.0.

Example 49

1-(6-Bromo-2-methoxyquinolin-3-yl)-2-(2-(difluoromethoxy)-6-methoxypyridin-4-yl)-4-(dimethylamino)-1-(2-fluoro-3-methoxyphenyl)butan-2-ol (229)

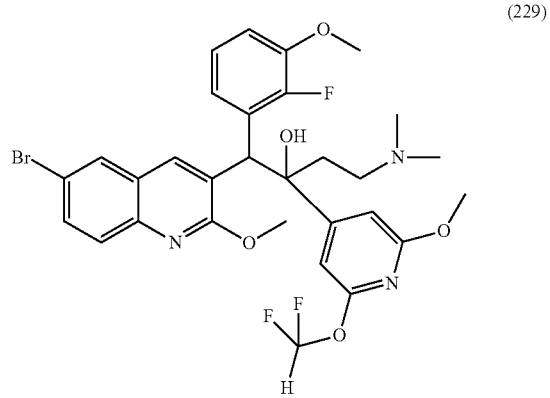 [SMILES: COc1cc(C(O)(CCN(C)C)C(c2cc3cc(Br)ccc3nc2OC)c2cccc(OC)c2F)cc(OC(F)F)n1]
(229)

From coupling of 8 and 37. Column chromatography with EtOAc:hexanes (1:1), then EtOAc gave 229. Found: [M+H]= 650.0.

Example 50

1-(2,6-Bis(methylthio)pyridin-4-yl)-1-(6-bromo-2-methoxyquinolin-3-yl)-2-(2,6-dimethoxypyridin-4-yl)-4-(dimethylamino)butan-2-ol (230)

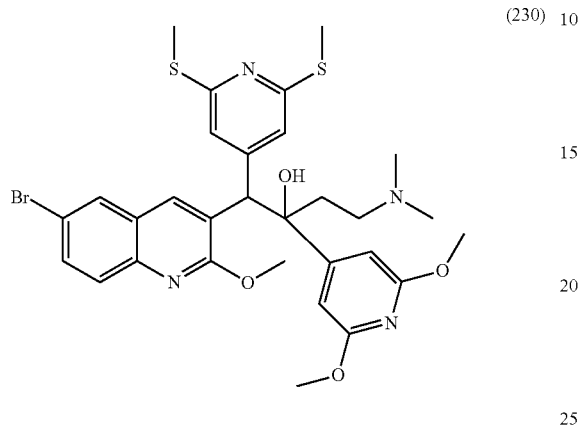

(230)

From coupling of 40 and 6. Column chromatography with EtOAc:hexanes (1:1) gave fore fractions, then 230. Found: [M+H]=658.9.

Example 51

1-(6-Bromo-2-methoxyquinolin-3-yl)-2-(2-(difluoromethoxy)-6-methoxypyridin-4-yl)-1-(2,3-dimethoxypyridin-4-yl)-4-(dimethylamino)butan-2-ol (231)

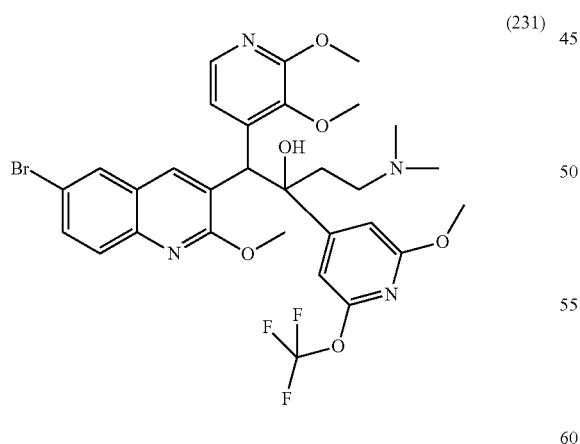

(231)

From coupling of 120 and 37. Column chromatography with EtOAc:hexanes (1:1), then EtOAc gave fore fractions, followed 231. Found: [M+H]=663.0.

Example 52

1-(6-Bromo-2-methoxyquinolin-3-yl)-1-(2,3-dihydro-1H-inden-4-yl)-2-(2,6-dimethoxypyridin-4-yl)-4-(dimethylamino)butan-2-ol (232)

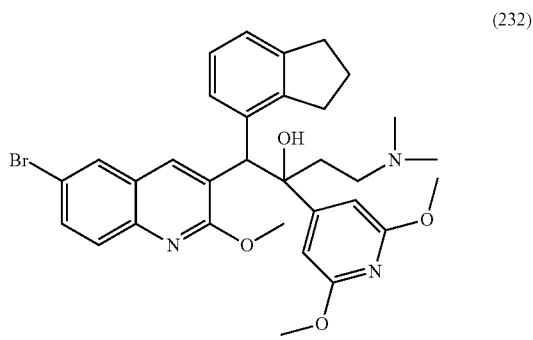 [SMILES: COc1cc(C(O)(CCN(C)C)C(c2cc3cc(Br)ccc3nc2OC)c2cccc3c2CCC3)cc(OC)n1]

(232)

From coupling of 43 and 6. Column chromatography with EtOAc:hexanes (1:1) gave fore fractions, then 232. Found: [M+H]=605.7.

Example 53

1-(6-Bromo-2-methoxyquinolin-3-yl)-2-(2,6-dimethoxypyridin-4-yl)-4-(dimethylamino)-1-(5,6,7,8-tetrahydronaphthalen-1-yl)butan-2-ol (233)

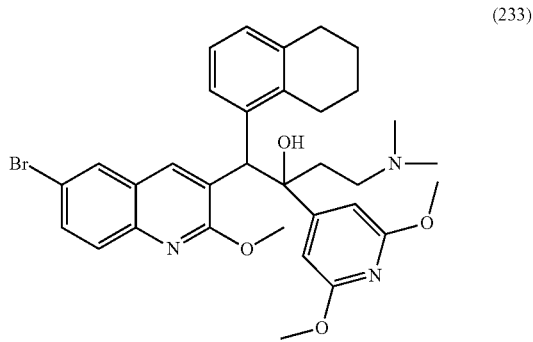 [SMILES: COc1cc(C(O)(CCN(C)C)C(c2cc3cc(Br)ccc3nc2OC)c2cccc3c2CCCC3)cc(OC)n1]

(233)

From coupling of 46 and 6. Column chromatography with EtOAc:hexanes (1:4) gave fore fractions, then 233 Found: [M+H]=619.7.

Example 54

1-(6-Bromo-2-methoxyquinolin-3-yl)-2-(2-(difluoromethoxy)-6-methoxypyridin-4-yl)-4-(dimethylamino)-1-(2-fluoro-3-methylphenyl)butan-2-ol (234)

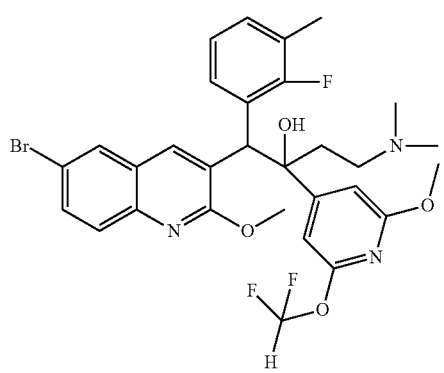

(234)

From coupling of 30 and 37. Column chromatography with EtOAc:hexanes (1:4) gave fore fractions, then 234. Found: [M+H]=633.7.

Example 55

2-(2,6-Bis(methylthio)pyridin-4-yl)-1-(6-bromo-2-methoxyquinolin-3-yl)-4-(dimethylamino)-1-(2-fluoro-3-methylphenyl)butan-2-ol (235)

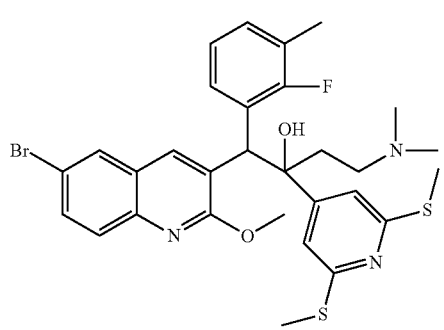

(235)

From coupling of 30 and 29. Column chromatography with EtOAc:hexanes (1:4) gave fore fractions, then 235. Found: [M+H]=629.6.

Example 56

2-(2,6-Bis(methylthio)pyridin-4-yl)-1-(6-bromo-2-methoxyquinolin-3-yl)-1-(2,3-dihydrobenzo[b][1,4]dioxin-5-yl)-4-(dimethylamino)butan-2-ol (236)

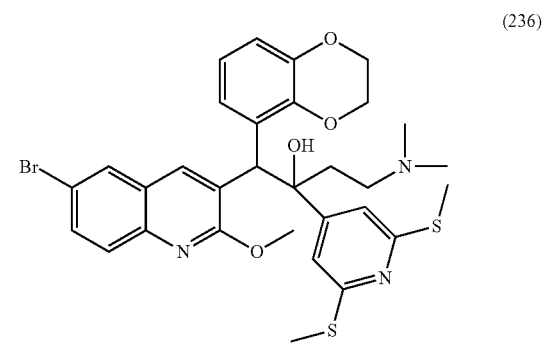

(236)

From coupling of 22 and 29. Column chromatography with EtOAc:hexanes (1:1), then EtOAc gave fore fractions, followed 236. Found: [M+H]=656.0.

Example 57

1-(6-Bromo-2-methoxyquinolin-3-yl)-2-(2,6-dimethoxypyridin-4-yl)-4-(dimethylamino)-1-(2-fluoro-3-methylphenyl)butan-2-ol (237)

(237)

From coupling of 30 and 6. Column chromatography with EtOAc:hexanes (1:1) gave fore fractions, then 237. Found: [M+H]=598.0.

Example 58

1-(6-Bromo-2-methoxyquinolin-3-yl)-2-(2-(difluoromethoxy)-6-methoxypyridin-4-yl)-1-(2,3-dihydrobenzo[b][1,4]dioxin-5-yl)-4-(dimethylamino)butan-2-ol (238)

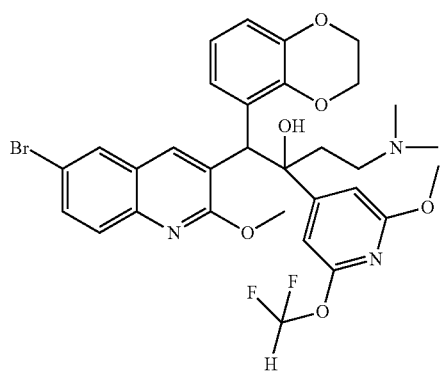

From coupling of 22 and 37. Column chromatography with EtOAc:hexanes (1:1), then EtOAc gave 238. Found: [M+H]=659.9.

Example 59

1-(6-Bromo-2-methoxyquinolin-3-yl)-2-(2,6-diethoxypyridin-4-yl)-1-(6-(diethylamino)pyridin-3-yl)-4-(dimethylamino)butan-2-ol (239)

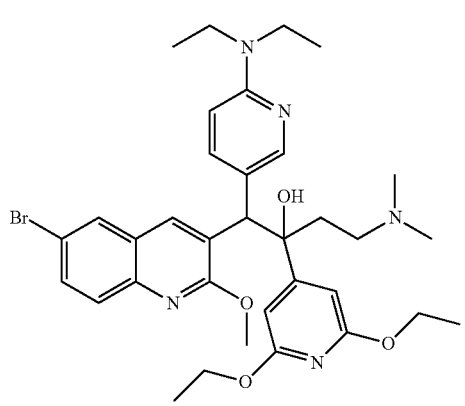

From coupling of 50 and 4. Column chromatography of the crude product using mixtures of hexane/ethyl acetate gave 239. Found: [M+H]=666.1.

Example 60

1-(6-Bromo-2-methoxyquinolin-3-yl)-2-(2,6-dimethoxypyridin-4-yl)-4-(dimethylamino)-1-(3-fluoro-2-methoxypyridin-4-yl)butan-2-ol (240)

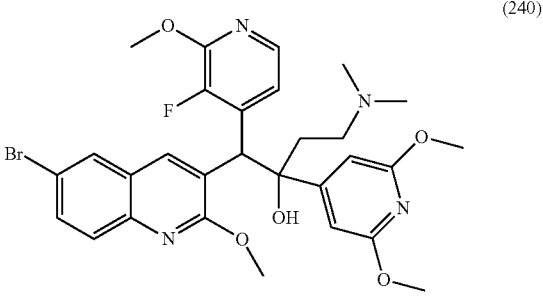 [SMILES: COc1cc(C(O)(CCN(C)C)C(c2cc3cc(Br)ccc3nc2OC)c2ccnc(OC)c2F)cc(OC)n1]

From coupling of 55 and 6. Column chromatography with 9:1 hexane/EtOAc eluted unreacted starting material XX, then chromatography with 1:2 hexane/EtOAc gave 240. Found: [M+H]=614.9.

Example 61

1-(6-Bromo-2-methoxyquinolin-3-yl)-1-(2,3-dimethoxypyridin-4-yl)-4-(dimethylamino)-2-(2,3,6-trimethoxypyridin-4-yl)butan-2-ol (241)

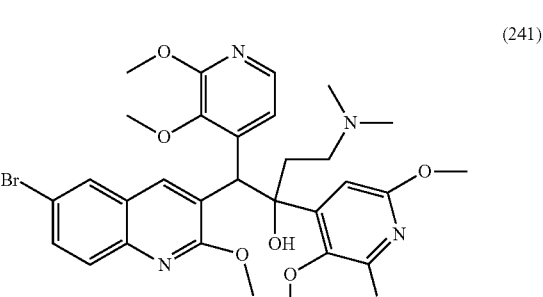

From coupling of 120 and 63. Column chromatography with 1:1 DCM/EtOAc, followed by EtOAc eluted 241. Found: [M+H]=656.6.

Example 62

1-(6-Bromo-2-methoxyquinolin-3-yl)-2-(2,6-dimethoxypyridin-4-yl)-4-(dimethylamino)-1-(3-fluoro-4-methoxyphenyl)butan-2-ol (242)

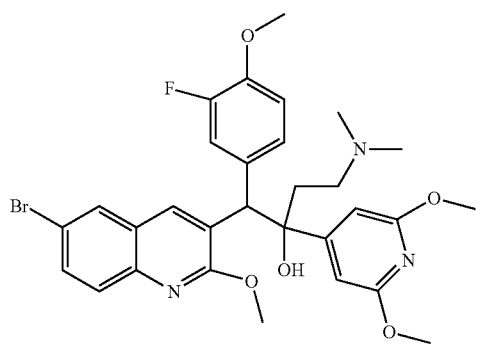

From coupling of 66 and 6. Column chromatography with 9:1 hexane/EtOAc eluted unreacted starting material, then elution with 1:1 hexane/EtOAc eluted 242. Found: [M+H]=613.7.

Example 63

1-(6-Bromo-2-methoxyquinolin-3-yl)-2-(2,6-dimethoxypyridin-4-yl)-4-(dimethylamino)-1-(2,3,6-trimethoxypyridin-4-yl)butan-2-ol (243)

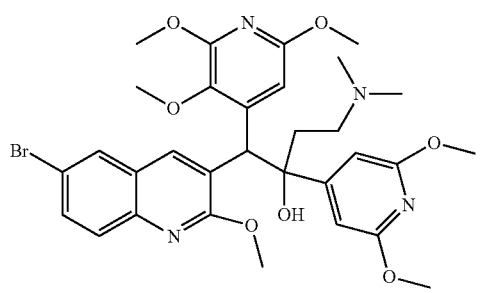

From coupling of 72 and 6. Column chromatography with 2:1 hexane/EtOAc eluted unreacted starting material, then chromatography with 1:1 hexane/EtOAc gave 243. Found: [M+H]=656.7.

Example 64

1-(6-Bromo-2-methoxyquinolin-3-yl)-2-(2,6-dimethoxypyridin-4-yl)-4-(dimethylamino)-1-(2-(dimethylamino)-6-(ethylthio)pyridin-4-yl)butan-2-ol (244)

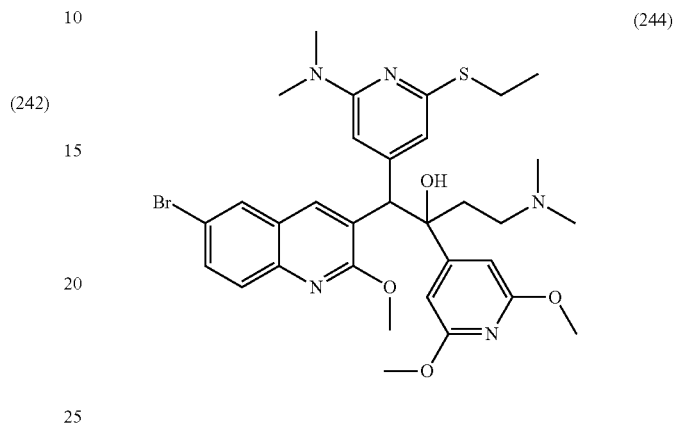

From coupling of 76 and 6. Column chromatography of the crude product, eluting with 10-50% EtOAc/hexane afforded 244 Found: [M+H]=669.7.

Example 65

1-(6-Bromo-2-methoxyquinolin-3-yl)-1-(2,5-dimethoxypyridin-3-yl)-2-(2,6-dimethoxypyridin-4-yl)-4-(dimethylamino)butan-2-ol (245)

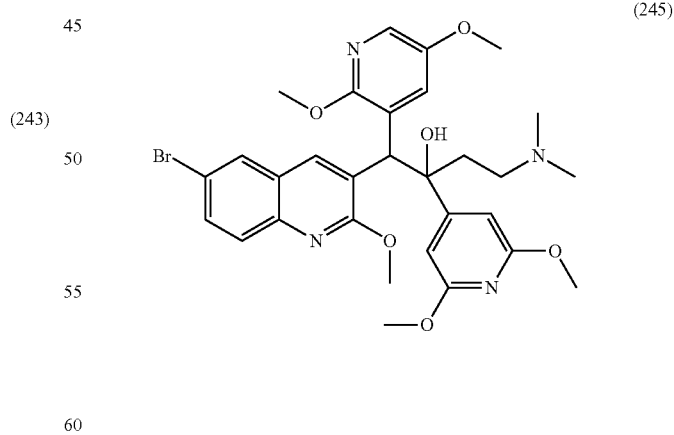

From coupling of 80 and 6. Column chromatography with 1:1 hexane/EtOAc eluted unreacted starting material, then chromatography with 1:3 hexane/EtOAc, then 19:1 EtOAc/MeOH eluted 245. Found: [M+H]=627.0.

Example 66

1-(6-Bromo-2-methoxyquinolin-3-yl)-2-(2,6-dimethoxypyridin-4-yl)-4-(dimethylamino)-1-(2,5,6-trimethoxypyridin-3-yl)butan-2-ol (246)

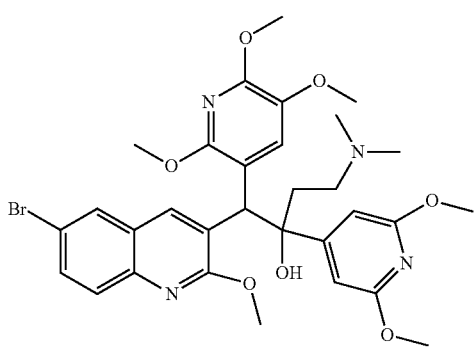

(246)

From coupling of 86 and 6. Column chromatography with 2:1 hexane/EtOAc eluted unreacted starting material, then chromatography with 1:1 hexane/EtOAc gave 246. Found: [M+H]=656.7.

Example 67

1-(6-Bromo-2-methoxyquinolin-3-yl)-2-(2,6-dimethoxypyridin-4-yl)-4-(dimethylamino)-1-(2-(dimethylamino)-6-methoxypyridin-4-yl)butan-2-ol (247)

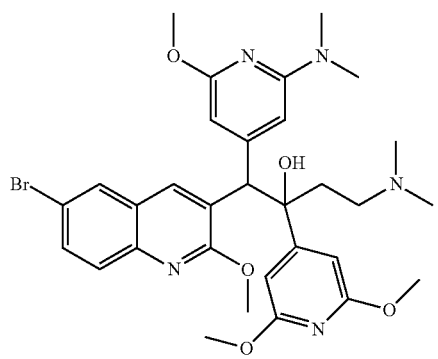

(247)

From coupling of 90 and 6. Column chromatography of the crude product eluting with DCM to remove unreacted starting material followed by mixtures of hexane/EtOAc in increasing eluent strength gave 247. Found: [M+H]=639.7.

Example 68

1-(6-Bromo-2-methoxyquinolin-3-yl)-1-(2,3-dimethoxypyridin-4-yl)-4-(dimethylamino)-2-(2-(dimethylamino)-6-methoxypyridin-4-yl)butan-2-ol (248)

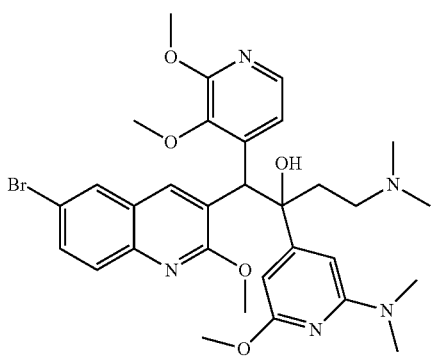

(248)

From coupling of 120 and 93. Repeated flash chromatography of the crude product eluting with DCM to remove unreacted starting material followed by mixtures of hexane/EtOAc in increasing eluent strength gave 248. Found: [M+H]=639.7.

Example 69

1-(6-Bromo-2-methoxyquinolin-3-yl)-2-(2,6-dimethoxypyridin-4-yl)-4-(dimethylamino)-1-(2-(dimethylamino)-6-ethoxypyridin-4-yl)butan-2-ol (249)

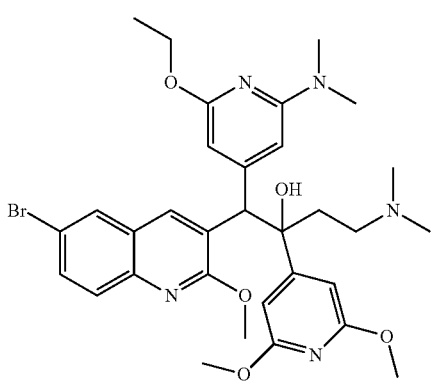

(249)

From coupling of 96 and 6. Repeated flash chromatography of the crude product using mixtures of hexane/EtOAc in increasing eluent strength gave 249. Found: [M+H]=653.7.

Example 70

1-(6-Bromo-2-methoxyquinolin-3-yl)-2-(2,6-dimethoxypyridin-4-yl)-4-(dimethylamino)-1-(5-isopropoxy-2-methoxypyridin-3-yl)butan-2-ol (250)

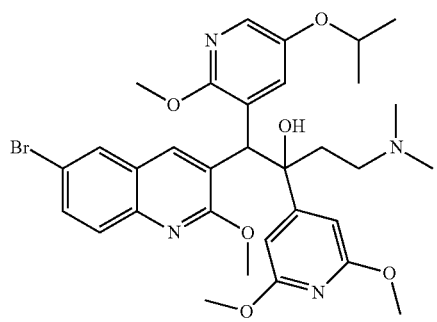

(250)

From coupling of 100 and 6. Column chromatography of the crude product using 0-5% MeOH/DCM gave 250. Found: [M+H]=654.7.

Example 71

1-(6-Bromo-2-methoxyquinolin-3-yl)-1-(4-chloro-2-methoxythiazol-5-yl)-2-(2,6-dimethoxypyridin-4-yl)-4-(dimethylamino)butan-2-ol (251)

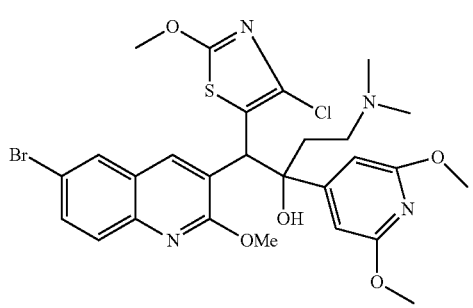

(251)

From coupling of 107 and 6. Column chromatography with 9:1 hexane/EtOAc eluted unreacted starting material, then chromatography with 4:1 hexane/EtOAc followed by 2:1 hexane/EtOAc eluted 251. Found: [M+H]=636.6.

Example 72

3-(1-(2,5-Dimethoxypyridin-3-yl)-2-(2,6-dimethoxypyridin-4-yl)-4-(dimethylamino)-2-hydroxybutyl)-2-methoxyquinoline-6-carbonitrile (252)

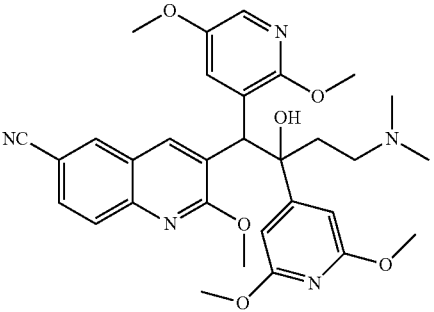

(252)

General Cyanation Procedure

A solution of 245 (0.61 g, 0.969 mmol) in DMF (6 mL, anhydrous) was purged with nitrogen and heated to 55° C. for 10 min. Tri(o-tolyl)phosphine (0.044 g, 0.145 mmol), zinc dust (0.006 g, 0.097 mmol) and tris(dibenzylideneacetone)dipalladium(0) (0.067 g, 0.073 mmol) were then added, and the reaction was again purged with nitrogen and heated for another 10 min at 55° C. Zinc cyanide (0.063 g, 0.533 mmol) was then added and the reaction mixture was heated to 65° C. for 4 hours. The reaction was diluted with water and extracted with EtOAc three times. The organic layer was washed with brine three times, dried and evaporated. Column chromatography with 1:1 hexane/EtOAc followed by 1:3 hexane/EtOAc afforded 252 (0.41 g, 74%) as a foamy solid. Found: [M+H]=573.8.

The following compounds were synthesised using the General Cyanation Procedure. Each coupled product was resolved into its four optical isomers using preparative chiral HPLC.

Example 73

3-(2-(Benzofuran-2-yl)-4-(dimethylamino)-1-(3-fluorophenyl)-2-hydroxybutyl)-2-methoxyquinoline-6-carbonitrile (253)

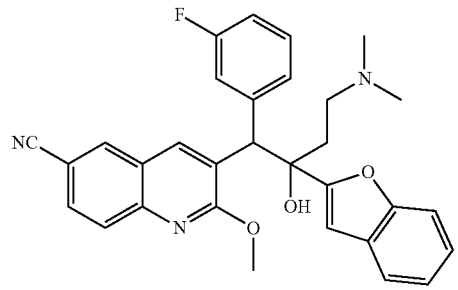

(253)

By cyanation of 186 using the General Cyanation Procedure. The crude product was purified by column chromatography. Elution with 0-6% MeOH:DCM gave 253. Found: [M+H]=510.1.

Example 74

3-(2-(Benzofuran-7-yl)-4-(dimethylamino)-1-(3-fluorophenyl)-2-hydroxybutyl)-2-methoxyquinoline-6-carbonitrile (254)

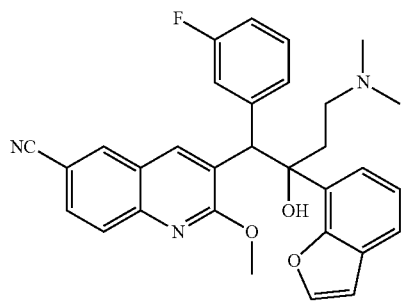 [SMILES: COc1nc2ccc(C#N)cc2cc1C(c1cccc(F)c1)C(O)(CCN(C)C)c1cccc2ccoc12]

By cyanation of 188 using the General Cyanation Procedure. The crude product was purified by column chromatography. Elution with 0-6% MeOH:DCM gave 254. Found: [M+H]=510.2.

Example 75

3-(2-(2,6-Dimethoxypyridin-4-yl)-4-(dimethylamino)-2-hydroxy-1-(5-methylthiophen-2-yl)butyl)-2-methoxyquinoline-6-carbonitrile (255)

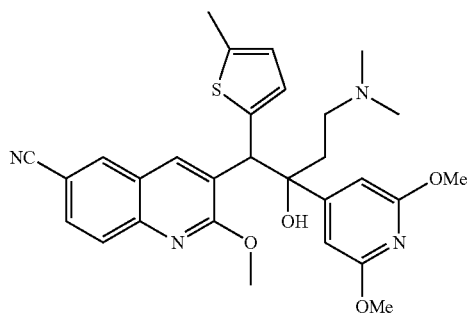

(255)

By cyanation of 191 using the General Cyanation Procedure. The crude product was purified by column chromatography. Elution with 0-6% MeOH:DCM gave 255. Found: [M+H]=533.2.

Example 76

3-(2-(2,6-Dimethoxypyridin-4-yl)-4-(dimethylamino)-2-hydroxy-1-(2-isopropoxy-6-methoxypyridin-4-yl)butyl)-2-methoxyquinoline-6-carbonitrile (256)

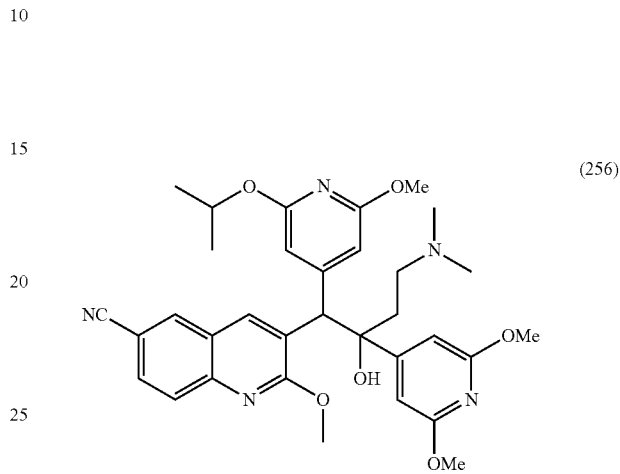

By cyanation of 199 using the General Cyanation Procedure. The crude product was purified by column chromatography. Elution with 0-6% MeOH:DCM gave 256. Found: [M+H]=602.2.

Example 77

3-(2-(Benzofuran-7-yl)-4-(dimethylamino)-2-hydroxy-1-(2-isopropoxy-6-methoxypyridin-4-yl)butyl)-2-methoxyquinoline-6-carbonitrile (257)

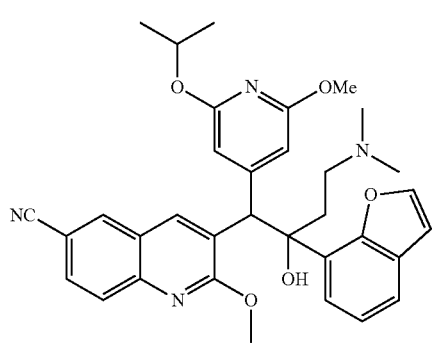

By cyanation of 201 using the General Cyanation Procedure. The crude product was purified by column chromatography. Elution with 0-6% MeOH:DCM gave 257. Found: [M+H]=581.0.

Example 78

3-(2-(2,6-Dimethoxypyridin-4-yl)-2-hydroxy-4-(methylamino)-1-(5-methylthiophen-2-yl)butyl)-2-methoxyquinoline-6-carbonitrile (258)

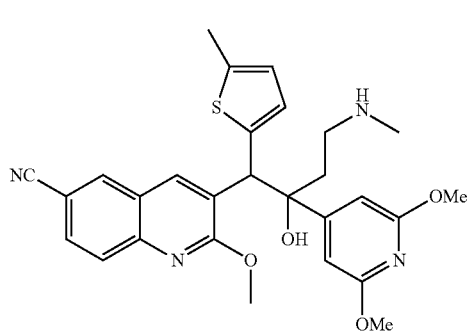

(258)

By cyanation of 111 using the General Cyanation Procedure. The crude product was purified by column chromatography. Elution with 0-10% MeOH:DCM gave 258. Found: M+H]=518.7.

Example 79

3-(2-(2,6-Dimethoxypyridin-4-yl)-4-(dimethylamino)-1-(2-ethoxy-6-isopropoxypyridin-4-yl)-2-hydroxybutyl)-2-methoxyquinoline-6-carbonitrile (259)

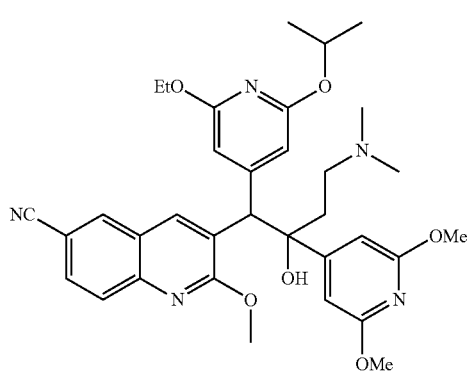

(259)

By cyanation of 211 using the General Cyanation Procedure. The crude product was purified by column chromatography. Elution with 0-5% MeOH:DCM gave 259. Found: [M+H]=615.8.

Example 80

3-(2-(2,6-Dimethoxypyridin-4-yl)-4-(dimethylamino)-1-(3-fluorophenyl)-2-hydroxybutyl)-2-methoxyquinoline-6-carbonitrile (260)

(260)

By cyanation of 219 using the General Cyanation Procedure. Column chromatography with EtOAc:hexanes (1:1) gave fore fractions, then 260. Found: [M+H]=531.2.

Example 81

3-(1-(2,3-Dihydrobenzo[b][1,4]dioxin-5-yl)-2-(2,6-dimethoxypyridin-4-yl)-4-(dimethylamino)-2-hydroxybutyl)-2-methoxyquinoline-6-carbonitrile (261)

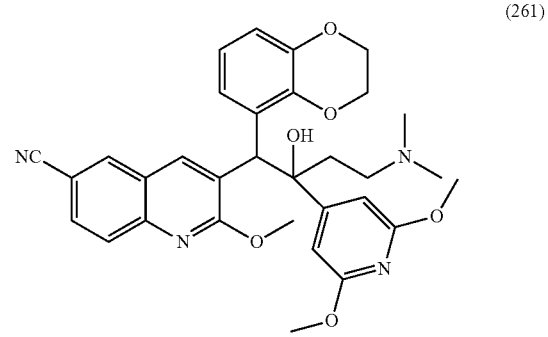 [SMILES: COc1cc(C(O)(CCN(C)C)C(c2cc3cc(C#N)ccc3nc2OC)c2cccc3c2OCCO3)cc(OC)n1]

(261)

By cyanation of 221 using the General Cyanation Procedure. Column chromatography with EtOAc:hexanes (1:1), then EtOAc gave 261. Found: [M+H]=571.0.

Example 82

3-(2-(2-(Difluoromethoxy)-6-methoxypyridin-4-yl)-
4-(dimethylamino)-1-(2-fluoro-3-methoxyphenyl)-2-
hydroxybutyl)-2-methoxyquinoline-6-carbonitrile
(262)

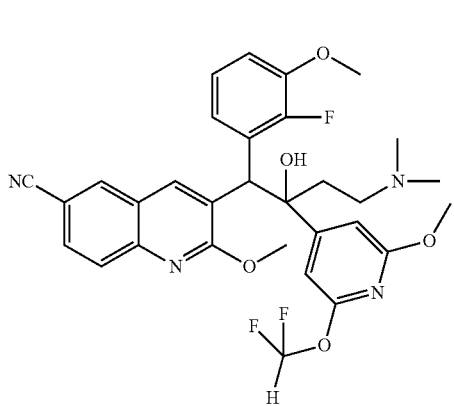

(262)

By cyanation of 229 using the General Cyanation Procedure. Column chromatography with EtOAc:hexanes (1:2), then EtOAc gave fore fractions, followed by 262. Found: [M+H]=597.1.

Example 83

3-(2-(2-(Difluoromethoxy)-6-methoxypyridin-4-yl)-
1-(2,3-dimethoxypyridin-4-yl)-4-(dimethylamino)-2-
hydroxybutyl)-2-methoxyquinoline-6-carbonitrile
(263)

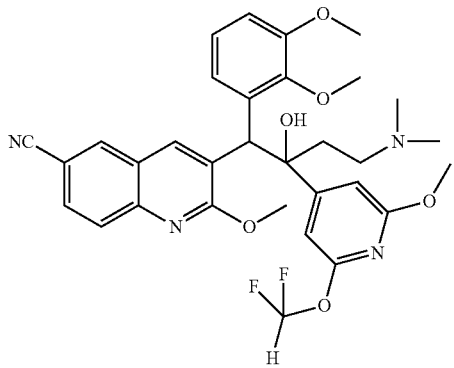

(263)

By cyanation of 231 using the General Cyanation Procedure. Column chromatography with EtOAc:hexanes (1:2), then EtOAc gave fore fractions, followed by 263. Found: [M+H]=610.2.

Example 84

3-(2-(2,6-Diethoxypyridin-4-yl)-1-(2,3-dihydrobenzo[b][1,4]dioxin-5-yl)-4-(dimethylamino)-2-
hydroxybutyl)-2-methoxyquinoline-6-carbonitrile
(264)

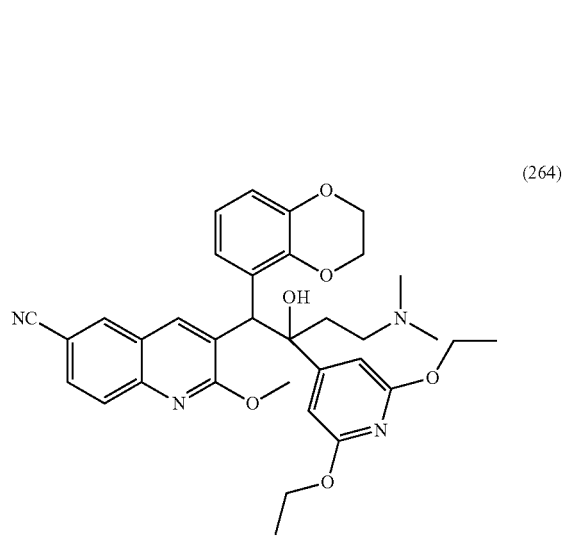 [SMILES: CCOc1cc(C(O)(CCN(C)C)C(c2cc3cc(C#N)ccc3nc2OC)c2cccc3c2OCCO3)cc(OCC)n1]

(264)

By cyanation of 223 using the General Cyanation Procedure. Column chromatography with EtOAc:hexanes (1:1) gave fore fractions, then 264. Found: [M+H]=599.2.

Example 85

3-(1-(2,3-Dihydro-1H-inden-4-yl)-2-(2,6-dimethoxypyridin-4-yl)-4-(dimethylamino)-2-hydroxybutyl)-2-
methoxyquinoline-6-carbonitrile (265)

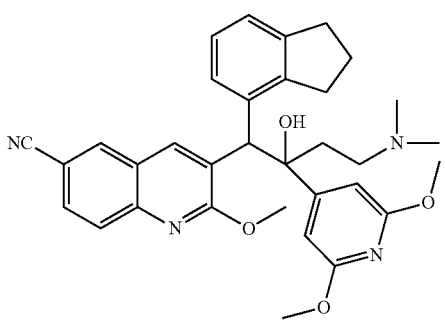

(265)

By cyanation of 232 using the General Cyanation Procedure. Column chromatography with EtOAc:hexanes (1:1) gave fore fractions, then 265. Found: [M+H]=552.9.

Example 86

3-(2-(2,6-Dimethoxypyridin-4-yl)-4-(dimethylamino)-1-(2-fluoro-3-methylphenyl)-2-hydroxybutyl)-2-methoxyquinoline-6-carbonitrile (266)

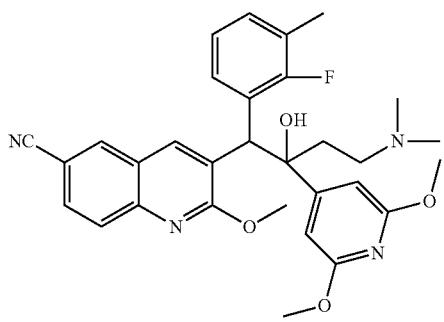
(266)

By cyanation of 237 using the General Cyanation Procedure. Column chromatography with EtOAc:hexanes (1:1) gave fore fractions, then 266. Found: [M+H]=545.1.

Example 87

3-(4-(Dimethylamino)-1-(2-fluoro-3-methoxyphenyl)-2-hydroxy-2-(2-methoxy-6-(methylthio)pyridin-4-yl)butyl)-2-methoxyquinoline-6-carbonitrile (267)

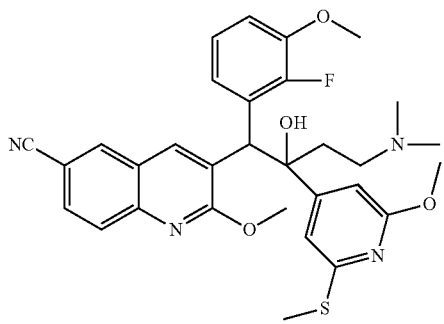
(267)

By cyanation of 228 using the General Cyanation Procedure. Column chromatography with EtOAc:hexanes (1:3) gave fore fractions, then 267. Found: [M+H]=576.8.

Example 88

3-(2-(2-(Difluoromethoxy)-6-methoxypyridin-4-yl)-4-(dimethylamino)-1-(2-fluoro-3-methylphenyl)-2-hydroxybutyl)-2-methoxyquinoline-6-carbonitrile (268)

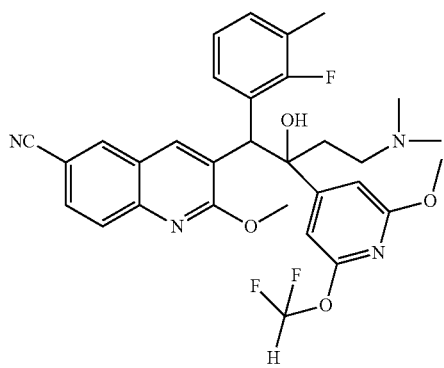
(268)

By cyanation of 234 using the General Cyanation Procedure. Column chromatography with EtOAc:hexanes (2:1) gave fore fractions, then 268. Found: [M+H]=580.8.

Example 89

3-(2-(2,6-Bis(methylthio)pyridin-4-yl)-4-(dimethylamino)-1-(2-fluoro-3-methylphenyl)-2-hydroxybutyl)-2-methoxyquinoline-6-carbonitrile (269)

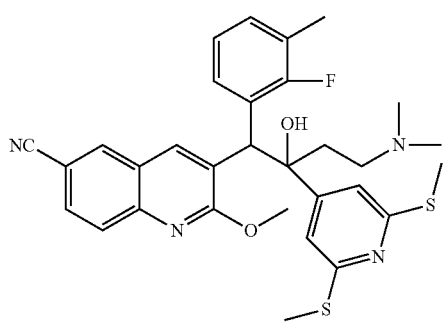
(269)

By cyanation of 235 using the General Cyanation Procedure. Column chromatography with EtOAc:hexanes (2:1) gave fore fractions, then 269. Found: [M+H]=576.7.

141

Example 90

3-(2-(2,6-Bis(methylthio)pyridin-4-yl)-1-(2,3-dihydrobenzo[b][1,4]dioxin-5-yl)-4-(dimethylamino)-2-hydroxybutyl)-2-methoxyquinoline-6-carbonitrile (270)

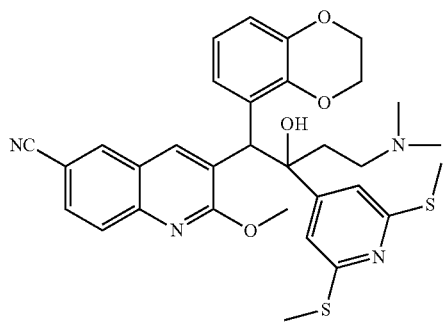

(270)

By cyanation of 236 using the General Cyanation Procedure. Column chromatography with EtOAc:hexanes (1:1), then EtOAc gave 270. Found: [M+H]=602.7.

Example 91

3-(2-(2-(Difluoromethoxy)-6-methoxypyridin-4-yl)-1-(2,3-dihydrobenzo[b][1,4]dioxin-5-yl)-4-(dimethylamino)-2-hydroxybutyl)-2-methoxyquinoline-6-carbonitrile (271)

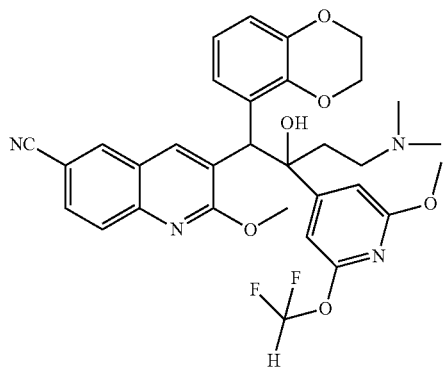

(271)

By cyanation of 238 using the General Cyanation Procedure. Column chromatography with EtOAc:hexanes (2:1), then EtOAc gave fore fractions, followed by 271. Found: [M+H]=606.8.

142

Example 92

3-(2-(2,6-Diethoxypyridin-4-yl)-4-(dimethylamino)-1-(2-fluoro-3-methylphenyl)-2-hydroxybutyl)-2-methoxyquinoline-6-carbonitrile (272)

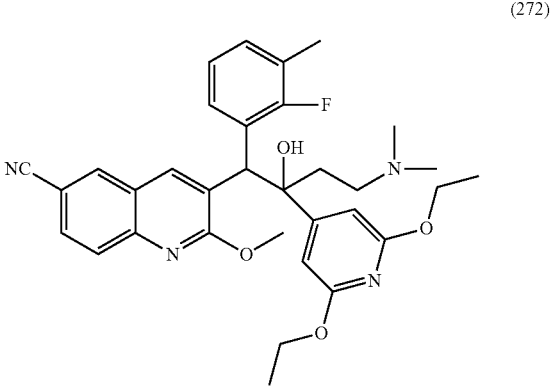 [SMILES: CCOc1cc(C(O)(CCN(C)C)C(c2cc3cc(C#N)ccc3nc2OC)c2cccc(C)c2F)cc(OCC)n1]

(272)

By cyanation of 227 using the General Cyanation Procedure. Column chromatography with EtOAc:hexanes (1:1) gave fore fractions, then 272. Found: [M+H]=573.1.

Example 93

3-(1-(2,3-Dihydrobenzo[b][1,4]dioxin-5-yl)-2-(2,6-dimethoxypyridin-4-yl)-2-hydroxy-4-(methylamino)butyl)-2-methoxyquinoline-6-carbonitrile (273)

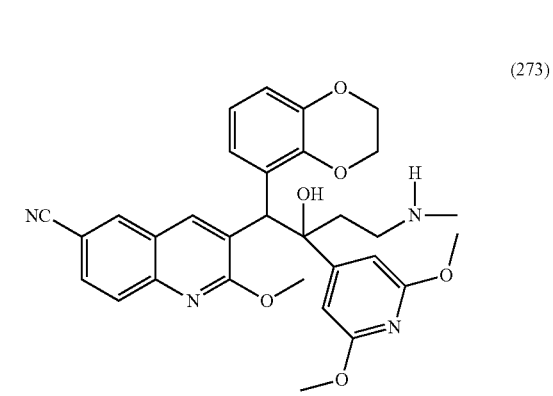 [SMILES: CNCCC(O)(c1cc(OC)nc(OC)c1)C(c1cc2cc(C#N)ccc2nc1OC)c1cccc2c1OCCO2]

(273)

By cyanation of 109 using the General Cyanation Procedure. Column chromatography with EtOAc, then EtOAc:MeOH (4:1) gave 273. Found: [M+H]=557.0.

Example 94

3-(1-(2,3-Dimethoxypyridin-4-yl)-4-(dimethylamino)-2-(2-(dimethylamino)-6-methoxypyridin-4-yl)-2-hydroxybutyl)-2-methoxyquinoline-6-carbonitrile (274)

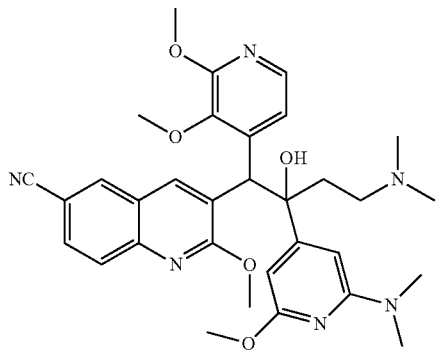

(274)

By cyanation of 248 using the General Cyanation Procedure except that the reaction mixture was heated at 45° C. overnight. Flash chromatography of the crude product using mixtures of hexanes/EtOAc in increasing eluent strength afforded 274 as a bright yellow foam. Found: [M+H]=586.8.

Example 95

3-(2-(2,6-Dimethoxypyridin-4-yl)-4-(dimethylamino)-1-(2-(dimethylamino)-6-ethoxypyridin-4-yl)-2-hydroxybutyl)-2-methoxyquinoline-6-carbonitrile (275)

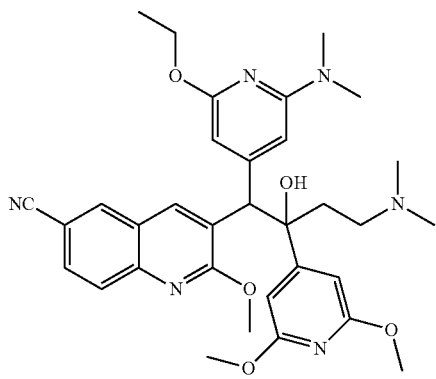

(275)

By cyanation of 249 using the General Cyanation Procedure except that the reaction mixture was heated at 55° C. overnight. Column chromatography of the crude product using mixtures of hexanes/EtOAc in increasing eluent strength gave 275. Found: [M+H]=600.8.

Example 96

3-(2-(2,6-Dimethoxypyridin-4-yl)-4-(dimethylamino)-2-hydroxy-1-(5-isopropoxy-2-methoxypyridin-3-yl)butyl)-2-methoxyquinoline-6-carbonitrile (276)

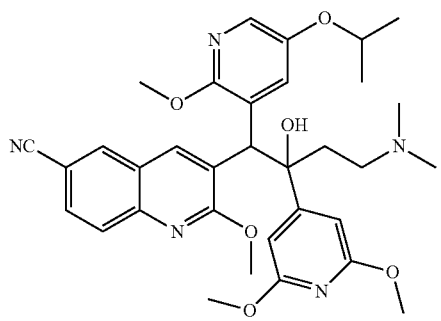

(276)

By cyanation of 250 using the General Cyanation Procedure except that the reaction mixture was heated at 60° C. for 2 hours. Column chromatography of the crude product using mixtures of hexanes/EtOAc in increasing eluent strength gave 276. Found: [M+H]=601.8.

Example 97

3-(2-(2,6-Dimethoxypyridin-4-yl)-1-(3-fluorophenyl)-2-hydroxy-4-(methylamino)butyl)-2-methoxyquinoline-6-carbonitrile (277)

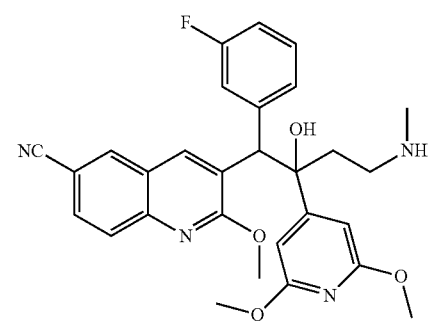

(277)

By cyanation of 102 using the General Cyanation Procedure except that the reaction mixture was heated at 40° C. overnight. Column chromatography of the crude product using mixtures of hexanes/EtOAc in increasing eluent strength and finally 5% MeOH in EtOAc gave 277. Found: [M+H]=516.8.

Example 98

3-(2-(2,6-Dimethoxypyridin-4-yl)-4-(dimethyl-amino)-2-hydroxy-1-(2,5,6-trimethoxypyridin-3-yl)butyl)-2-methoxyquinoline-6-carbonitrile (278)

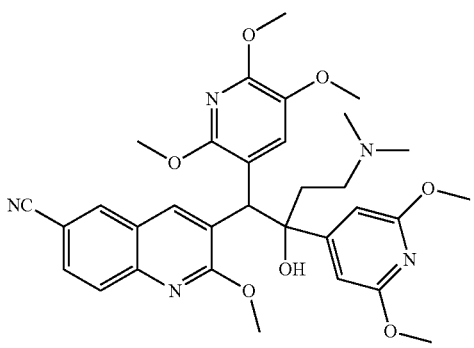

(278)

By cyanation of 246 using the General Cyanation Procedure. Column chromatography of the crude product using a mixture of 1:1 hexanes/EtOAc gave 278. Found: [M+H]= 603.8.

Example 99

Activity Against Replicating M. tuberculosis $H_{37}$Rv

Representative compounds were evaluated for Minimum Inhibitory Concentration (MIC) versus M. tuberculosis $H_{37}$Rv (ATCC 27294) using the microplate Alamar Blue assay (MABA) using 7H12 media (Collins, L., and S. G. Franzblau. 1997. Microplate alamar blue assay versus BACTEC 460 system for high-throughput screening of compounds against Mycobacterium tuberculosis and Mycobacterium avium. Antimicrob Agents Chemother 41:1004-9).

Cultures were incubated in 200 ml medium in 96-well plates for 7 days at 37° C. Alamar Blue and Tween 80 were added and incubation continued for 24 hours at 37° C. Fluorescence was determined at excitation/emission wavelengths of 530/590 nm, respectively. The MIC was defined as the lowest concentration effecting a reduction in fluorescence of 90% relative to controls.

MIC data for representative compounds of the invention are provided in Table 1:

TABLE 1

| Example | M. tuberculosis MIC (µg/ml) | cLogP | MWt |
|---|---|---|---|
| 1 | <0.02 | 6.3 | 580.51 |
| 2 | 0.07 | 6.64 | 545.47 |
| 3 | 0.47 | 5.59 | 584.48 |
| 4 | 0.02 | 5.55 | 580.51 |
| 5 | 0.02 | 6.86 | 642.56 |
| 7 | 0.03 | 5.61 | 606.51 |
| 9 | <0.02 | 4.77 | 627.53 |
| 10 | 0.03 | 5.61 | 606.51 |
| 11 | <0.02 | 5.94 | 586.54 |
| 12 | <0.01 | 7.41 | 634.56 |
| 13 | <0.02 | 5.8 | 614.5 |
| 14 | 0.06 | 6.64 | 545.47 |
| 15 | 0.02 | 7.11 | 561.53 |
| 16 | <0.02 | 6.64 | 642.56 |
| 17 | <0.01 | 6.33 | 628.53 |
| 18 | <0.01 | 5.61 | 655.58 |
| 19 | <0.01 | 6.36 | 655.58 |
| 20 | <0.02 | 5.3 | 641.56 |
| 21 | <0.02 | 7.19 | 634.56 |
| 22 | <0.02 | 6.89 | 620.54 |
| 23 | <0.02 | 6.13 | 669.61 |
| 24 | <0.02 | 6.88 | 669.61 |
| 25 | 0.01 | 7.13 | 608.57 |
| 26 | 0.01 | 6.58 | 655.58 |
| 27 | 0.01 | 6.71 | 598.1 |
| 28 | 0.01 | 5.83 | 655.58 |
| 29 | <0.004 | 6.36 | 606.51 |
| 30 | <0.004 | 5.68 | 667.6 |
| 31 | <0.01 | 6.88 | 669.61 |
| 32 | 0.02 | 7.2 | 564.11 |
| 33 | <0.02 | 6.39 | 600.57 |
| 34 | 0.04 | 7.35 | 608.57 |
| 35 | <0.02 | 6.11 | 654.59 |
| 36 | <0.02 | 5.83 | 655.58 |
| 37 | 0.08 | 4.83 | 594.54 |
| 38 | <0.02 | 4.72 | 597.5 |
| 39 | <0.02 | 5.94 | 584.48 |
| 40 | 0.07 | 7.09 | 545.51 |
| 41 | 0.02 | 5.72 | 624.52 |
| 42 | <0.02 | 6.06 | 613.49 |
| 43 | 0.07 | 6.78 | 652.58 |
| 44 | <0.02 | 7.5 | 674.69 |
| 45 | <0.02 | 6.4 | 646.63 |
| 46 | <0.02 | 5.43 | 659.65 |
| 47 | <0.02 | 7.49 | 626.56 |
| 48 | <0.02 | 6.14 | 630.57 |
| 49 | 0.04 | 6.24 | 650.48 |
| 50 | <0.01 | 6.18 | 659.66 |
| 51 | <0.004 | 5.21 | 663.51 |
| 52 | 0.01 | 6.81 | 606.55 |
| 53 | <0.004 | 7.37 | 620.58 |
| 54 | 0.01 | 6.88 | 634.48 |
| 55 | <0.004 | 7.1 | 630.63 |
| 56 | 0.01 | 7.4 | 684.71 |
| 57 | <0.01 | 6.44 | 598.5 |
| 58 | <0.01 | 6.17 | 660.5 |
| 59 | <0.02 | 7.13 | 666.65 |
| 60 | <0.02 | 5.10 | 615.49 |
| 61 | 0.02 | 4.80 | 657.55 |
| 62 | 0.01 | 5.80 | 614.5 |
| 63 | 0.01 | 5.15 | 657.55 |
| 64 | 0.01 | 6.68 | 670.66 |
| 65 | <0.02 | 5.12 | 627.53 |
| 66 | <0.01 | 5.15 | 657.55 |
| 67 | 0.01 | 5.83 | 640.57 |
| 68 | 0.01 | 5.08 | 640.57 |
| 69 | <0.004 | 6.36 | 654.59 |
| 70 | <0.004 | 5.96 | 655.58 |
| 71 | 0.03 | 5.68 | 637.97 |
| 72 | <0.01 | 3.76 | 573.64 |
| 73 | 0.08 | 5.42 | 509.57 |
| 74 | 0.04 | 5.42 | 509.57 |
| 75 | 0.19 | 4.59 | 532.65 |
| 76 | <0.02 | 5 | 601.69 |
| 77 | <0.02 | 5.84 | 580.67 |
| 78 | 0.09 | 4.01 | 518.63 |
| 79 | 0.01 | 5.53 | 615.72 |
| 80 | 0.03 | 4.58 | 530.39 |
| 81 | 0.02 | 4.36 | 570.64 |
| 82 | <0.02 | 4.89 | 596.6 |
| 83 | <0.02 | 3.86 | 609.62 |
| 84 | 0.03 | 5.42 | 598.69 |
| 85 | 0.02 | 5.45 | 552.66 |
| 86 | <0.02 | 5.08 | 544.63 |
| 87 | 0.02 | 4.79 | 576.68 |
| 88 | 0.01 | 5.53 | 580.6 |
| 89 | 0.02 | 5.74 | 576.75 |
| 90 | 0.01 | 5.02 | 602.77 |

TABLE 1-continued

| Example | *M. tuberculosis* MIC (μg/ml) | cLogP | MWt |
|---|---|---|---|
| 91 | 0.02 | 4.81 | 606.62 |
| 92 | <0.02 | 6.14 | 572.67 |
| 93 | 0.01 | 3.78 | 556.62 |
| 94 | 0.06 | 3.73 | 586.68 |
| 95 | 0.03 | 5.01 | 600.71 |
| 96 | <0.004 | 4.6 | 601.7 |
| 97 | 0.01 | 4 | 516.57 |
| 98 | <0.01 | 3.79 | 603.67 |

The invention is further described in the following numbered paragraphs:

1. A compound of formula (I):

(I)

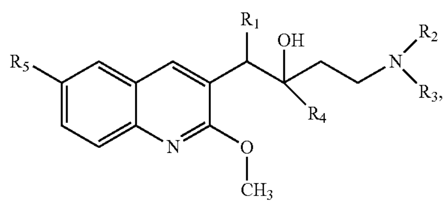

including any stereochemically isomeric form thereof, wherein:

$R_1$ is -phenyl, optionally mono- or bi-substituted independently with lower alkyl, halogen or alkoxy, 5- or 6-membered heteroaryl, optionally mono-, bi- or tri-substituted independently with lower alkyl, halogen, alkoxy, —$SCH_3$, $SCH_2CH_3$, —$N(CH_2CH_3)_2$ or —$N(CH_3)_2$, benzofuranyl, 2,3-dihydrobenzo[b][1,4]dioxin-5-yl, 2,3-dihydro-1H-inden-4-yl or 5,6,7,8-tetrahydro naphthalene-1-yl;

$R_2$ and $R_3$, independently of each other, are hydrogen or lower alkyl; $R_4$ is -phenyl, optionally mono- or bi-substituted independently with halogen or lower alkyl, 5- or 6-membered heteroaryl, optionally mono-, bi- or tri-substituted independently with alkoxy, —O-cycloalkyl, —S-loweralkyl, difluoromethoxy or —$N(CH_3)_2$, benzofuranyl, benzo[b]thiophenyl or 2,3-dihydro-1H-indenyl; and $R_5$ is halogen or cyano, or a pharmaceutically acceptable salt thereof.

2. The compound according to paragraph 1, wherein $R_1$ is unsubstituted phenyl.

3. The compound according to paragraph 1, wherein $R_1$ is phenyl mono- or bi-substituted independently with lower alkyl, halogen or alkoxy.

4. The compound according to paragraph 1, wherein $R_1$ is an unsubstituted 5- or 6-membered heteroaryl.

5. The compound according to paragraph 1, wherein $R_1$ is pyridinyl.

6. The compound according to paragraph 1, wherein $R_1$ is a 5- or 6-membered heteroaryl mono-, bi- or tri-substituted independently with lower alkyl, halogen, alkoxy, —$SCH_3$, —$SCH_2CH_3$, —$N(CH_2CH_3)_2$ or —N—$(CH_3)_2$.

7. The compound according to paragraph 1, wherein $R_1$ pyridinyl mono-, bi- or tri-substituted independently with lower alkyl, halogen, alkoxy, —$SCH_3$, —$SCH_2CH_3$, —$N(CH_2CH_3)_2$ or —N—$(CH_3)_2$.

8. The compound according to paragraph 1, wherein $R_1$ is pyridinyl mono- or bi-substituted independently with lower alkyl, halogen, alkoxy, —$SCH_3$, —$SCH_2CH_3$, —$N(CH_2CH_3)_2$ or —N—$(CH_3)_2$.

9. The compound according to paragraph 1, wherein $R_1$ is benzofuranyl, 2,3-dihydrobenzo[b][1,4]dioxin-5-yl, 2,3-dihydro-1H-inden-4-yl or 5,6,7,8-tetrahydro naphthalene-1-yl.

10. The compound according to paragraph 1, wherein $R_2$ and $R_3$, independently of each other, are hydrogen or methyl.

11. The compound according to paragraph 1, wherein both $R_2$ and $R_3$ are methyl.

12. The compound according to paragraph 1, wherein $R_4$ is unsubstituted phenyl.

13. The compound according to paragraph 1, wherein $R_4$ is phenyl mono- or bi-substituted independently with halogen or lower alkyl.

14. The compound according to paragraph 1, wherein $R_4$ is an unsubstituted 5- or 6-membered heteroaryl.

15. The compound according to paragraph 1, wherein $R_4$ is pyridinyl.

16. The compound according to paragraph 1, wherein $R_4$ is a 5- or 6-membered heteroaryl mono-, bi- or tri-substituted independently with alkoxy, —O-cycloalkyl, —S-loweralkyl, difluoromethoxy or —$N(CH_3)_2$.

17. The compound according to paragraph 1, wherein $R_4$ is pyridinyl mono-, bi- or tri-substituted independently with alkoxy, —O-cycloalkyl, —S-loweralkyl, difluoromethoxy or —$N(CH_3)_2$.

18. The compound according to paragraph 1, wherein $R_4$ is pyridinyl mono- or bi-substituted independently with alkoxy, —O-cycloalkyl, —S-loweralkyl, difluoromethoxy or —$N(CH_3)_2$.

19. The compound according to paragraph 1, wherein $R_4$ is benzofuranyl, benzo[b]thiophenyl or 2,3-dihydro-1H-indenyl.

20. The compound according to paragraph 1, wherein $R_5$ is halogen.

21. The compound according to paragraph 1, wherein $R_5$ is bromine, chlorine or iodine.

22. The compound according to paragraph 1, wherein $R_5$ is bromine.

23. The compound according to paragraph 1, wherein $R_5$ is cyano.

24. The compound according to paragraph 1, wherein said compound is:

1-(6-Bromo-2-methoxyquinolin-3-yl)-2-(2,6-dimethoxypyridin-4-yl)-4-(dimethylamino)-1-(m-tolyl)butan-2-ol;

2-(Benzofuran-7-yl)-1-(6-bromo-2-methoxyquinolin-3-yl)-4-(dimethylamino)-1-phenylbutan-2-ol;

1-(6-Bromo-2-methoxyquinolin-3-yl)-1-(5,6-dimethoxypyridin-3-yl)-4-(dimethylamino)-2-(3-fluorophenyl)butan-2-ol;

1-(6-Bromo-2-methoxyquinolin-3-yl)-1-(2,3-dimethoxypyridin-4-yl)-4-(dimethylamino)-2-(m-tolyl)butan-2-ol;

1-(6-Bromo-2-methoxyquinolin-3-yl)-2-(2,6-diethoxypyridin-4-yl)-4-(dimethylamino)-1-(2-fluoro-3-methoxyphenyl)butan-2-ol;

2-(Benzofuran-2-yl)-1-(6-bromo-2-methoxyquinolin-3-yl)-4-(dimethylamino)-1-(3-fluorophenyl)butan-2-ol;

2-(Benzofuran-2-yl)-1-(6-bromo-2-methoxyquinolin-3-yl)-1-(2,3-dimethoxypyridin-4-yl)-4-(dimethylamino)butan-2-ol;

2-(Benzofuran-7-yl)-1-(6-bromo-2-methoxyquinolin-3-yl)-4-(dimethylamino)-1-(3-fluorophenyl)butan-2-ol;

1-(6-Bromo-2-methoxyquinolin-3-yl)-1-(2,3-dimethoxypyridin-4-yl)-2-(2,6-dimethoxypyridin-4-yl)-4-(dimethylamino)butan-2-ol;
2-(Benzofuran-5-yl)-1-(6-bromo-2-methoxyquinolin-3-yl)-1-(2,3-dimethoxypyridin-4-yl)-4-(dimethylamino)butan-2-ol;
1-(6-Bromo-2-methoxyquinolin-3-yl)-2-(2,6-dimethoxypyridin-4-yl)-4-(dimethylamino)-1-(5-methylthiophen-2-yl)butan-2-ol;
2-(Benzofuran-7-yl)-1-(6-bromo-2-methoxyquinolin-3-yl)-1-(2,6-diethoxypyridin-4-yl)-4-(dimethylamino)butan-2-ol;
1-(6-Bromo-2-methoxyquinolin-3-yl)-2-(2,6-dimethoxypyridin-4-yl)-4-(dimethylamino)-1-(2-fluoro-3-methoxyphenyl)butan-2-ol;
2-(Benzofuran-4-yl)-1-(6-bromo-2-methoxyquinolin-3-yl)-4-(dimethylamino)-1-phenylbutan-2-ol;
2-(Benzo[b]thiophen-7-yl)-1-(6-bromo-2-methoxyquinolin-3-yl)-4-(dimethylamino)-1-phenylbutan-2-ol;
1-(6-Bromo-2-methoxyquinolin-3-yl)-4-(dimethylamino)-1-(2-fluoro-3-methoxyphenyl)-2-(2-isopropoxy-6-methoxypyridin-4-yl)butan-2-ol;
1-(6-Bromo-2-methoxyquinolin-3-yl)-4-(dimethylamino)-2-(2-ethoxy-6-methoxypyridin-4-yl)-1-(2-fluoro-3-methoxyphenyl)butan-2-ol;
1-(6-Bromo-2-methoxyquinolin-3-yl)-1-(2,3-dimethoxypyridin-4-yl)-4-(dimethylamino)-2-(2-isopropoxy-6-methoxypyridin-4-yl)butan-2-ol;
1-(6-Bromo-2-methoxyquinolin-3-yl)-2-(2,6-dimethoxypyridin-4-yl)-4-(dimethylamino)-1-(2-isopropoxy-6-methoxypyridin-4-yl)butan-2-ol;
1-(6-Bromo-2-methoxyquinolin-3-yl)-1-(2,3-dimethoxypyridin-4-yl)-4-(dimethylamino)-2-(2-ethoxy-6-methoxypyridin-4-yl)butan-2-ol;
2-(Benzofuran-7-yl)-1-(6-bromo-2-methoxyquinolin-3-yl)-4-(dimethylamino)-1-(2-isopropoxy-6-methoxypyridin-4-yl)butan-2-ol;
2-(Benzofuran-7-yl)-1-(6-bromo-2-methoxyquinolin-3-yl)-4-(dimethylamino)-1-(2-ethoxy-6-methoxypyridin-4-yl)butan-2-ol;
1-(6-Bromo-2-methoxyquinolin-3-yl)-1-(2,3-dimethoxypyridin-4-yl)-4-(dimethylamino)-2-(2-ethoxy-6-isopropoxypyridin-4-yl)butan-2-ol;
1-(6-Bromo-2-methoxyquinolin-3-yl)-1-(2,6-dimethoxypyridin-4-yl)-4-(dimethylamino)-2-(2-ethoxy-6-isopropoxypyridin-4-yl)butan-2-ol;
1-(6-Bromo-2-methoxyquinolin-3-yl)-4-(dimethylamino)-2-(2-isopropoxy-6-methoxypyridin-4-yl)-1-(m-tolyl)butan-2-ol;
1-(6-Bromo-2-methoxyquinolin-3-yl)-2-(2,6-dimethoxypyridin-4-yl)-4-(dimethylamino)-1-(2-methoxy-6-propoxypyridin-4-yl)butan-2-ol;
1-(6-Chloro-2-methoxyquinolin-3-yl)-2-(2,6-diethoxypyridin-4-yl)-4-(dimethylamino)-1-(2-fluoro-3-methoxyphenyl)butan-2-ol;
1-(6-Bromo-2-methoxyquinolin-3-yl)-1-(2,3-dimethoxypyridin-4-yl)-4-(dimethylamino)-2-(2-methoxy-6-propoxypyridin-4-yl)butan-2-ol;
1-(Benzofuran-7-yl)-1-(6-bromo-2-methoxyquinolin-3-yl)-2-(2,6-dimethoxypyridin-4-yl)-4-(dimethylamino)butan-2-ol;
1-(6-Bromo-2-methoxyquinolin-3-yl)-2-(2-cyclobutoxy-6-methoxypyridin-4-yl)-1-(2,3-dimethoxypyridin-4-yl)-4-(dimethylamino)butan-2-ol;
1-(6-Bromo-2-methoxyquinolin-3-yl)-2-(2,6-dimethoxypyridin-4-yl)-4-(dimethylamino)-1-(2-ethoxy-6-isopropoxypyridin-4-yl)butan-2-ol;
1-(6-Chloro-2-methoxyquinolin-3-yl)-2-(2,6-diethoxypyridin-4-yl)-4-(dimethylamino)-1-(m-tolyl)butan-2-ol;
1-(6-Bromo-2-methoxyquinolin-3-yl)-2-(2,6-dimethoxypyridin-4-yl)-4-(dimethylamino)-1-(2,5-dimethylthiophen-3-yl)butan-2-ol;
1-(6-Bromo-2-methoxyquinolin-3-yl)-2-(2,6-diethoxypyridin-4-yl)-4-(dimethylamino)-1-(m-tolyl)butan-2-ol;
1-(6-Bromo-2-methoxyquinolin-3-yl)-2-(2,6-diethoxypyridin-4-yl)-1-(2,3-dimethoxyphenyl)-4-(dimethylamino)butan-2-ol;
1-(6-Bromo-2-methoxyquinolin-3-yl)-2-(2,6-diethoxypyridin-4-yl)-1-(2,3-dimethoxypyridin-4-yl)-4-(dimethylamino)butan-2-ol;
1-(6-Bromo-2-methoxyquinolin-3-yl)-1-(2,3-dimethoxyphenyl)-4-(dimethylamino)-2-(2,6-dimethylpyridin-4-yl)butan-2-ol;
1-(6-Bromo-2-methoxyquinolin-3-yl)-2-(2,6-dimethoxypyridin-4-yl)-4-(dimethylamino)-1-(2-methoxypyridin-3-yl)butan-2-ol;
1-(6-Bromo-2-methoxyquinolin-3-yl)-2-(2,6-dimethoxypyridin-4-yl)-4-(dimethylamino)-1-(3-fluorophenyl)butan-2-ol;
1-(6-Bromo-2-methoxyquinolin-3-yl)-2-(2,3-dihydro-1H-inden-4-yl)-4-(dimethylamino)-1-phenylbutan-2-ol;
1-(6-Bromo-2-methoxyquinolin-3-yl)-1-(2,3-dihydrobenzo[b][1,4]dioxin-5-yl)-2-(2,6-dimethoxypyridin-4-yl)-4-(dimethylamino)butan-2-ol;
2-(2,6-Dimethoxypyridin-4-yl)-4-(dimethylamino)-1-(6-iodo-2-methoxyquinolin-3-yl)-1-phenylbutan-2-ol;
1-(6-Bromo-2-methoxyquinolin-3-yl)-2-(2,6-diethoxypyridin-4-yl)-1-(2,3-dihydrobenzo[b][1,4]dioxin-5-yl)-4-(dimethylamino)butan-2-ol;
2-(2,6-Bis(ethylthio)pyridin-4-yl)-1-(6-bromo-2-methoxyquinolin-3-yl)-4-(dimethylamino)-1-(2-fluoro-3-methoxyphenyl)butan-2-ol;
2-(2,6-Bis(methylthio)pyridin-4-yl)-1-(6-bromo-2-methoxyquinolin-3-yl)-4-(dimethylamino)-1-(2-fluoro-3-methoxyphenyl)butan-2-ol;
2-(2,6-Bis(methylthio)pyridin-4-yl)-1-(6-bromo-2-methoxyquinolin-3-yl)-1-(2,3-dimethoxypyridin-4-yl)-4-(dimethylamino)butan-2-ol;
1-(6-Bromo-2-methoxyquinolin-3-yl)-2-(2,6-diethoxypyridin-4-yl)-4-(dimethylamino)-1-(2-fluoro-3-methylphenyl)butan-2-ol;
1-(6-Bromo-2-methoxyquinolin-3-yl)-4-(dimethylamino)-1-(2-fluoro-3-methoxyphenyl)-2-(2-methoxy-6-(methylthio)pyridin-4-yl)butan-2-ol;
1-(6-Bromo-2-methoxyquinolin-3-yl)-2-(2-(difluoromethoxy)-6-methoxypyridin-4-yl)-4-(dimethylamino)-1-(2-fluoro-3-methoxyphenyl)butan-2-ol;
1-(2,6-Bis(methylthio)pyridin-4-yl)-1-(6-bromo-2-methoxyquinolin-3-yl)-2-(2,6-dimethoxypyridin-4-yl)-4-(dimethylamino)butan-2-ol;
1-(6-Bromo-2-methoxyquinolin-3-yl)-2-(2-(difluoromethoxy)-6-methoxypyridin-4-yl)-1-(2,3-dimethoxypyridin-4-yl)-4-(dimethylamino)butan-2-ol;
1-(6-Bromo-2-methoxyquinolin-3-yl)-1-(2,3-dihydro-1H-inden-4-yl)-2-(2,6-dimethoxypyridin-4-yl)-4-(dimethylamino)butan-2-ol;
1-(6-Bromo-2-methoxyquinolin-3-yl)-2-(2,6-dimethoxypyridin-4-yl)-4-(dimethylamino)-1-(5,6,7,8-tetrahydronaphthalen-1-yl)butan-2-ol;
1-(6-Bromo-2-methoxyquinolin-3-yl)-2-(2-(difluoromethoxy)-6-methoxypyridin-4-yl)-4-(dimethylamino)-1-(2-fluoro-3-methylphenyl)butan-2-ol;

2-(2,6-Bis(methylthio)pyridin-4-yl)-1-(6-bromo-2-methoxyquinolin-3-yl)-4-(dimethylamino)-1-(2-fluoro-3-methylphenyl)butan-2-ol;

2-(2,6-Bis(methylthio)pyridin-4-yl)-1-(6-bromo-2-methoxyquinolin-3-yl)-1-(2,3-dihydrobenzo[b][1,4]dioxin-5-yl)-4-(dimethylamino)butan-2-ol;

1-(6-Bromo-2-methoxyquinolin-3-yl)-2-(2,6-dimethoxypyridin-4-yl)-4-(dimethylamino)-1-(2-fluoro-3-methylphenyl)butan-2-ol;

1-(6-Bromo-2-methoxyquinolin-3-yl)-2-(2-(difluoromethoxy)-6-methoxypyridin-4-yl)-1-(2,3-dihydrobenzo[b][1,4]dioxin-5-yl)-4-(dimethylamino)butan-2-ol;

1-(6-Bromo-2-methoxyquinolin-3-yl)-2-(2,6-diethoxypyridin-4-yl)-1-(6-(diethylamino)pyridin-3-yl)-4-(dimethylamino)butan-2-ol;

1-(6-Bromo-2-methoxyquinolin-3-yl)-2-(2,6-dimethoxypyridin-4-yl)-4-(dimethylamino)-1-(3-fluoro-2-methoxypyridin-4-yl)butan-2-ol;

1-(6-Bromo-2-methoxyquinolin-3-yl)-1-(2,3-dimethoxypyridin-4-yl)-4-(dimethylamino)-2-(2,3,6-trimethoxypyridin-4-yl)butan-2-ol;

1-(6-Bromo-2-methoxyquinolin-3-yl)-2-(2,6-dimethoxypyridin-4-yl)-4-(dimethylamino)-1-(3-fluoro-4-methoxyphenyl)butan-2-ol;

1-(6-Bromo-2-methoxyquinolin-3-yl)-2-(2,6-dimethoxypyridin-4-yl)-4-(dimethylamino)-1-(2,3,6-trimethoxypyridin-4-yl)butan-2-ol;

1-(6-Bromo-2-methoxyquinolin-3-yl)-2-(2,6-dimethoxypyridin-4-yl)-4-(dimethylamino)-1-(2-(dimethylamino)-6-(ethylthio)pyridin-4-yl)butan-2-ol;

1-(6-Bromo-2-methoxyquinolin-3-yl)-1-(2,5-dimethoxypyridin-3-yl)-2-(2,6-dimethoxypyridin-4-yl)-4-(dimethylamino)butan-2-ol;

1-(6-Bromo-2-methoxyquinolin-3-yl)-2-(2,6-dimethoxypyridin-4-yl)-4-(dimethylamino)-1-(2,5,6-trimethoxypyridin-3-yl)butan-2-ol;

1-(6-Bromo-2-methoxyquinolin-3-yl)-2-(2,6-dimethoxypyridin-4-yl)-4-(dimethylamino)-1-(2-(dimethylamino)-6-methoxypyridin-4-yl)butan-2-ol;

1-(6-Bromo-2-methoxyquinolin-3-yl)-1-(2,3-dimethoxypyridin-4-yl)-4-(dimethylamino)-2-(2-(dimethylamino)-6-methoxypyridin-4-yl)butan-2-ol;

1-(6-Bromo-2-methoxyquinolin-3-yl)-2-(2,6-dimethoxypyridin-4-yl)-4-(dimethylamino)-1-(2-(dimethylamino)-6-ethoxypyridin-4-yl)butan-2-ol;

1-(6-Bromo-2-methoxyquinolin-3-yl)-2-(2,6-dimethoxypyridin-4-yl)-4-(dimethylamino)-1-(5-isopropoxy-2-methoxypyridin-3-yl)butan-2-ol;

1-(6-Bromo-2-methoxyquinolin-3-yl)-1-(4-chloro-2-methoxythiazol-5-yl)-2-(2,6-dimethoxypyridin-4-yl)-4-(dimethylamino)butan-2-ol;

3-(1-(2,5-Dimethoxypyridin-3-yl)-2-(2,6-dimethoxypyridin-4-yl)-4-(dimethylamino)-2-hydroxybutyl)-2-methoxyquinoline-6-carbonitrile;

3-(2-(Benzofuran-2-yl)-4-(dimethylamino)-1-(3-fluorophenyl)-2-hydroxybutyl)-2-methoxyquinoline-6-carbonitrile;

3-(2-(Benzofuran-7-yl)-4-(dimethylamino)-1-(3-fluorophenyl)-2-hydroxybutyl)-2-methoxyquinoline-6-carbonitrile;

3-(2-(2,6-Dimethoxypyridin-4-yl)-4-(dimethylamino)-2-hydroxy-1-(5-methylthiophen-2-yl)butyl)-2-methoxyquinoline-6-carbonitrile;

3-(2-(2,6-Dimethoxypyridin-4-yl)-4-(dimethylamino)-2-hydroxy-1-(2-isopropoxy-6-methoxypyridin-4-yl)butyl)-2-methoxyquinoline-6-carbonitrile;

3-(2-(Benzofuran-7-yl)-4-(dimethylamino)-2-hydroxy-1-(2-isopropoxy-6-methoxypyridin-4-yl)butyl)-2-methoxyquinoline-6-carbonitrile;

3-(2-(2,6-Dimethoxypyridin-4-yl)-2-hydroxy-4-(methylamino)-1-(5-methylthiophen-2-yl)butyl)-2-methoxyquinoline-6-carbonitrile;

3-(2-(2,6-Dimethoxypyridin-4-yl)-4-(dimethylamino)-1-(2-ethoxy-6-isopropoxypyridin-4-yl)-2-hydroxybutyl)-2-methoxyquinoline-6-carbonitrile;

3-(2-(2,6-Dimethoxypyridin-4-yl)-4-(dimethylamino)-1-(3-fluorophenyl)-2-hydroxybutyl)-2-methoxyquinoline-6-carbonitrile;

3-(2-(2,3-Dihydrobenzo[b][1,4]dioxin-5-yl)-2-(2,6-dimethoxypyridin-4-yl)-4-(dimethylamino)-2-hydroxybutyl)-2-methoxyquinoline-6-carbonitrile;

3-(2-(2-(Difluoromethoxy)-6-methoxypyridin-4-yl)-4-(dimethylamino)-1-(2-fluoro-3-methoxyphenyl)-2-hydroxybutyl)-2-methoxyquinoline-6-carbonitrile;

3-(2-(2-(Difluoromethoxy)-6-methoxypyridin-4-yl)-1-(2,3-dimethoxypyridin-4-yl)-4-(dimethylamino)-2-hydroxybutyl)-2-methoxyquinoline-6-carbonitrile;

3-(2-(2,6-Diethoxypyridin-4-yl)-1-(2,3-dihydrobenzo[b][1,4]dioxin-5-yl)-4-(dimethylamino)-2-hydroxybutyl)-2-methoxyquinoline-6-carbonitrile;

3-(1-(2,3-Dihydro-1H-inden-4-yl)-2-(2,6-dimethoxypyridin-4-yl)-4-(dimethylamino)-2-hydroxybutyl)-2-methoxyquinoline-6-carbonitrile;

3-(2-(2,6-Dimethoxypyridin-4-yl)-4-(dimethylamino)-1-(2-fluoro-3-methylphenyl)-2-hydroxybutyl)-2-methoxyquinoline-6-carbonitrile;

3-(4-(Dimethylamino)-1-(2-fluoro-3-methoxyphenyl)-2-hydroxy-2-(2-methoxy-6-(methylthio)pyridin-4-yl)butyl)-2-methoxyquinoline-6-carbonitrile;

3-(2-(2-(Difluoromethoxy)-6-methoxypyridin-4-yl)-4-(dimethylamino)-1-(2-fluoro-3-methylphenyl)-2-hydroxybutyl)-2-methoxyquinoline-6-carbonitrile;

3-(2-(2,6-Bis(methylthio)pyridin-4-yl)-4-(dimethylamino)-1-(2-fluoro-3-methylphenyl)-2-hydroxybutyl)-2-methoxyquinoline-6-carbonitrile;

3-(2-(2,6-Bis(methylthio)pyridin-4-yl)-1-(2,3-dihydrobenzo[b][1,4]dioxin-5-yl)-4-(dimethylamino)-2-hydroxybutyl)-2-methoxyquinoline-6-carbonitrile;

3-(2-(2-(Difluoromethoxy)-6-methoxypyridin-4-yl)-1-(2,3-dihydrobenzo[b][1,4]dioxin-5-yl)-4-(dimethylamino)-2-hydroxybutyl)-2-methoxyquinoline-6-carbonitrile;

3-(2-(2,6-Diethoxypyridin-4-yl)-4-(dimethylamino)-1-(2-fluoro-3-methylphenyl)-2-hydroxybutyl)-2-methoxyquinoline-6-carbonitrile;

3-(2-(2,3-Dihydrobenzo[b][1,4]dioxin-5-yl)-2-(2,6-dimethoxypyridin-4-yl)-2-hydroxy-4-(methylamino)butyl)-2-methoxyquinoline-6-carbonitrile;

3-(2-(2,3-Dimethoxypyridin-4-yl)-4-(dimethylamino)-2-(2-(dimethylamino)-6-methoxypyridin-4-yl)-2-hydroxybutyl)-2-methoxyquinoline-6-carbonitrile;

3-(2-(2,6-Dimethoxypyridin-4-yl)-4-(dimethylamino)-1-(2-(dimethylamino)-6-ethoxypyridin-4-yl)-2-hydroxybutyl)-2-methoxyquinoline-6-carbonitrile;

3-(2-(2,6-Dimethoxypyridin-4-yl)-4-(dimethylamino)-2-hydroxy-1-(5-isopropoxy-2-methoxypyridin-3-yl)butyl)-2-methoxyquinoline-6-carbonitrile;

3-(2-(2,6-Dimethoxypyridin-4-yl)-1-(3-fluorophenyl)-2-hydroxy-4-(methylamino)butyl)-2-methoxyquinoline-6-carbonitrile; or 3-(2-(2,6-Dimethoxypyridin-4-yl)-4-(dimethylamino)-2-hydroxy-1-(2,5,6-trimethoxypyridin-3-yl)butyl)-2-methoxyquinoline-6-carbonitrile.

25. A pharmaceutical composition, comprising a therapeutically effective amount of a compound according to paragraph 1, or a pharmaceutically acceptable salt thereof, and a pharmaceutically acceptable carrier.

26. A pharmaceutical composition, comprising a therapeutically effective amount of a compound according to paragraph 24, or a pharmaceutically acceptable salt thereof, and a pharmaceutically acceptable carrier.

27. A method for the treatment of tuberculosis, comprising the step of administering to a patient in need thereof a therapeutically effective amount of a compound according to paragraph 1, or a pharmaceutically acceptable salt thereof, and a pharmaceutically acceptable carrier.

28. A method for the treatment of tuberculosis, comprising the step of administering to a patient in need thereof a therapeutically effective amount of a compound according to paragraph 24, or a pharmaceutically acceptable salt thereof, and a pharmaceutically acceptable carrier.

It is to be understood that the invention is not limited to the particular embodiments of the invention described above, as variations of the particular embodiments may be made and still fall within the scope of the appended claims.

The invention claimed is:
1. A compound of formula (I):

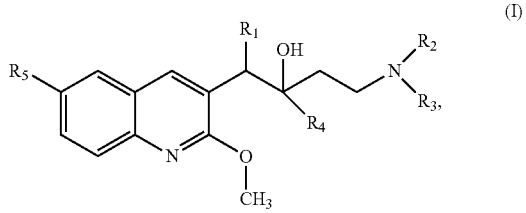

(I)

including any stereochemically isomeric form thereof, wherein:
$R_1$ is -phenyl, optionally mono- or bi-substituted independently with lower alkyl, halogen or alkoxy,
5- or 6-membered heteroaryl, optionally mono-, bi- or tri-substituted independently with lower alkyl, halogen, alkoxy, —$SCH_3$, —$SCH_2CH_3$, —$N(CH_2CH_3)_2$ or —$N(CH_3)_2$,
benzofuranyl,
2,3-dihydrobenzo[b][1,4]dioxin-5-yl,
2,3-dihydro-1H-inden-4-yl or
5,6,7,8-tetrahydro naphthalene-1-yl;
$R_2$ and $R_3$, independently of each other, are hydrogen or methyl;
$R_4$ is
5- or 6-membered heteroaryl mono-, bi- or tri-substituted independently with alkoxy, —O-cycloalkyl, —S-loweralkyl, difluoromethoxy or —$N(CH_3)_2$,
benzofuranyl,
benzo[b]thiophenyl or
2,3-dihydro-1H-indenyl; and
$R_5$ is bromine or cyano,
or a pharmaceutically acceptable salt thereof.

2. The compound according to claim 1, wherein $R_1$ is unsubstituted phenyl.

3. The compound according to claim 1, wherein $R_1$ is phenyl mono- or bi-substituted independently with lower alkyl, halogen or alkoxy.

4. The compound according to claim 1, wherein $R_1$ is an unsubstituted 5- or 6-membered heteroaryl.

5. The compound according to claim 1, wherein $R_1$ pyridinyl.

6. The compound according to claim 1, wherein $R_1$ is a 5- or 6-membered heteroaryl mono-, bi- or tri-substituted independently with lower alkyl, halogen, alkoxy, —$SCH_3$, —$SCH_2CH_3$, —$N(CH_2CH_3)_2$ or —$N$—$(CH_3)_2$.

7. The compound according to claim 1, wherein $R_1$ pyridinyl mono-, bi- or tri-substituted independently with lower alkyl, halogen, alkoxy, —$SCH_3$, —$SCH_2CH_3$, —$N(CH_2CH_3)_2$ or —$N$—$(CH_3)_2$.

8. The compound according to claim 1, wherein $R_1$ pyridinyl mono- or bi-substituted independently with lower alkyl, halogen, alkoxy, —$SCH_3$, —$SCH_2CH_3$, —$N(CH_2CH_3)_2$ or —$N$—$(CH_3)_2$.

9. The compound according to claim 1, wherein $R_1$ is benzofuranyl, 2,3-dihydrobenzo[b][1,4]dioxin-5-yl, 2,3-dihydro-1H-inden-4-yl or 5,6,7,8-tetrahydro naphthalene-1-yl.

10. The compound according to claim 1, wherein $R_4$ is a 5- or 6-membered heteroaryl mono-, bi- or tri-substituted independently with alkoxy, —O-cycloalkyl, —S-loweralkyl, difluoromethoxy or —$N(CH_3)_2$.

11. The compound according to claim 1, wherein $R_4$ is pyridinyl mono-, bi- or tri-substituted independently with alkoxy, —O-cycloalkyl, —S-loweralkyl, difluoromethoxy or —$N(CH_3)_2$.

12. The compound according to claim 1, wherein $R_4$ is pyridinyl mono- or bi-substituted independently with alkoxy, —O-cycloalkyl, —S-loweralkyl, difluoromethoxy or —$N(CH_3)_2$.

13. The compound according to claim 1, wherein $R_4$ is benzofuranyl, benzo[b]thiophenyl or 2,3-dihydro-1H-indenyl.

14. A pharmaceutical composition, comprising a therapeutically effective amount of a compound according to claim 1, or a pharmaceutically acceptable salt thereof, and a pharmaceutically acceptable carrier.

15. A method for the treatment of tuberculosis, comprising the step of administering to a patient in need thereof a therapeutically effective amount of a compound according to claim 1, or a pharmaceutically acceptable salt thereof, and a pharmaceutically acceptable carrier.

* * * * *